(12) United States Patent
Cai et al.

(10) Patent No.: US 9,187,758 B2
(45) Date of Patent: Nov. 17, 2015

(54) OPTIMIZED NON-CANONICAL ZINC FINGER PROTEINS

(75) Inventors: Qihua C. Cai, Westfield, IN (US); Vipula K. Shukla, Indianapolis, IN (US); Joseph F. Petolino, Zionsville, IN (US); Lisa W. Baker, Carmel, IN (US); Robbi J. Garrison, Fillmore, IN (US); Ryan C. Blue, Fishers, IN (US); Jon C. Mitchell, Zionsville, IN (US); Nicole L. Arnold, Carmel, IN (US); Sarah E. Worden, Fillmore, IN (US); Jeffrey Miller, Pleasanton, CA (US); Fyodor Urnov, Point Richmond, CA (US)

(73) Assignees: Sangamo BioSciences, Inc., Richmond, CA (US); Dow AgroSciences LLC, Indianapolis, IN (US)

(*) Notice: Subject to any disclaimer, the term of this patent is extended or adjusted under 35 U.S.C. 154(b) by 1308 days.

(21) Appl. No.: 12/001,939

(22) Filed: Dec. 13, 2007

(65) Prior Publication Data
US 2008/0182332 A1 Jul. 31, 2008

Related U.S. Application Data

(60) Provisional application No. 60/874,911, filed on Dec. 14, 2006, provisional application No. 60/932,497, filed on May 30, 2007.

(51) Int. Cl.
C12N 15/82 (2006.01)
C07K 19/00 (2006.01)
C12N 15/62 (2006.01)

(52) U.S. Cl.
CPC ........ *C12N 15/8243* (2013.01); *C12N 15/8213* (2013.01); *C07K 2319/81* (2013.01)

(58) Field of Classification Search
None
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 6,007,988 A | 12/1999 | Choo et al. | |
| 6,140,081 A | 10/2000 | Barbas | |
| 6,453,242 B1 | 9/2002 | Eisenberg et al. | |
| 6,479,626 B1 | 11/2002 | Kim et al. | |
| 6,506,559 B1 | 1/2003 | Driver et al. | |
| 6,534,261 B1 | 3/2003 | Cox, III et al. | |
| 6,794,136 B1 | 9/2004 | Eisenberg et al. | |
| 2003/0104526 A1* | 6/2003 | Liu | 435/69.1 |
| 2003/0108880 A1 | 6/2003 | Rebar et al. | |
| 2003/0119023 A1 | 6/2003 | Choo et al. | |
| 2003/0232410 A1 | 12/2003 | Liljedahl et al. | |
| 2005/0026157 A1 | 2/2005 | Baltimore et al. | |
| 2005/0064474 A1* | 3/2005 | Urnov et al. | 435/6 |
| 2005/0208489 A1 | 9/2005 | Carroll et al. | |
| 2005/0267061 A1 | 12/2005 | Martin | |
| 2006/0188987 A1 | 8/2006 | Guschin et al. | |
| 2006/0246567 A1 | 11/2006 | Rebar et al. | |
| 2006/0246588 A1 | 11/2006 | Rebar et al. | |
| 2007/0134796 A1 | 6/2007 | Holmes et al. | |

FOREIGN PATENT DOCUMENTS

| | | |
|---|---|---|
| WO | WO 02/057293 A2 | 7/2002 |
| WO | WO 03/080809 A2 | 10/2003 |
| WO | WO 2005/014791 A2 | 2/2005 |
| WO | WO 2005014794 A2 * | 2/2005 |
| WO | WO 2005028630 A2 * | 3/2005 |
| WO | WO 2005078079 A1 * | 8/2005 |
| WO | WO 2005/084190 A2 | 9/2005 |
| WO | WO 2006/029296 A2 | 3/2006 |

OTHER PUBLICATIONS

Stevenson-Paulik et al. Generation of phytate-free seeds in Arabidopsis through disruption of inositol polyphosphate kinaes. Proceedings of the National Academy of Sciences of the USA, vol. 102, No. 35, pp. 12612-12617, Aug. 2005.*

Krizek et al 1991 (Journal of the American Chemical Society, vol. 113, pp. 4518-4523).*

Beerli, et al., "Engineering Polydactyl Zinc-Finger Transcription Factors," *Nature Biotechnology* 20:135-141 (2002).

Bibikova, et al., "Stimulation of Homologous Recombination Through Targeted Cleavage by Chimeric Nucleases," *Mol Cell Biol* 21:289-297 (2001).

Choo, et al., "Advances in Zinc Finger Engineering," *Curr. Opin. Struct. Biol.* 10:411-416 (2000).

Isalan et al., "A Rapid, Generally Applicable Method to Engineer Zinc Fingers Illustrated by Targeting the HIV-1 Promoter," *Nat Biotechnol* 19:656-660 (2001).

Jiang, et al., "A Novel Family of Cys-Cys, His-Cys Zinc Finger Transcription Factors Expressed in Developing Nervous System and Pituitary Gland," *J. Biol Chem* 271:10723-10730 (1996).

Pabo, et al., "Design and Selection of Novel Cys2-His2 Zinc Finger Proteins," *Ann. Rev. Biochem.* 70:313-340 (2001).

Segal, et al., "Custom DNA-Binding Proteins Come of Age: Polydactyl Zinc-Finger Proteins," *Curr. Opin. Biotechnol.* 12:632-637 (2001).

(Continued)

*Primary Examiner* — David T Fox
*Assistant Examiner* — Matthew Keogh
(74) *Attorney, Agent, or Firm* — Dahna S. Pasternak; Pasternak Patent Law

(57) ABSTRACT

Disclosed herein are zinc fingers comprising CCHC zinc coordinating residues. Also described are zinc finger proteins and fusion proteins comprising these CCHC zinc fingers as well as polynucleotides encoding these proteins. Methods of using these proteins for gene editing and gene regulation are also described.

18 Claims, 52 Drawing Sheets

(56) References Cited

OTHER PUBLICATIONS

Smith, et al., "Requirements for Double-Strand Cleavage by Chimeric Restriction Enzymes With Zinc Finger DNA-Recognition Domains," *Nucleic Acids Res.* 28:3361-3369 (2000).

Umov, et al., "Highly Efficient Endogenous Human Gene Correction Using Designed Zinc-Finger Nucleases," *Nature* 435:646-651 (2005).

Database UniProt, Database Accession No. Q9Y2K1, "Zinc Finger and BTB Domain-Containing Protein 1," (2003).

Kelly, et al., "POZ for Effect—POZ-ZF Transcription Factors in Cancer and Development," *Trends in Cell Biology* 16(11): 578-587 (2006).

Yang, et al., "Structural Characteristic and Special Expression Pattern During Development of a Novel Gene BSG2 Containing BTB and Zinc Finger Domain," *Chinese Journal of Biochemistry and Molecular Biology* 20:725-731 (2004).

Boudarra, et al., "An Alternative Internal Splicing Site Defines New Ikaros Isoforms in Pleurodeles Waltl," *Developmental and Comparative Immunology* 26(7): 659-673 (2002).

Colasanti, et al., "The Maize Indeterminate Flowering Time Regulator Defines a Highly Conserved Zinc Finger Protein Family in Higher Plants," *Bmc Genomics* 7(1): 158 (2006).

Database Uniprot, Database Accession No. Q92794, "Histone Acetyltransferase," (1998).

Holbert, et al., "The Human Monocytic Leukemia Zinc Finger Histone Acetyltransferase Domain Contains DNA-Binding Activity Implicated in Chromatin Targeting," *Journal of Biological Chemistry* 282(50):36603-36613 (2007).

Houchens, et al., "The dhfr Ori-Beta-Binding Protein RIP60 Contains 15 Zinc Fingers: DNA Binding and Looping by the Central Three Fingers and an Assocaited Proline-Rich Region," *Nucleic Acids Research* 28(2):570-581 (2000).

Kozaki, et al., "The Maize ID1 Flowering Time Regulator Is a Zinc Finger Protein With Novel DNA Binding Properties," *Nucleic Acids Research* 32(5):1710-1720 (2004).

Liippo, et al., "The Evolutionarily Conserved Avian Aiolos Gene Encodes Alternative Isoforms," *European Journal of Immunology* 29(9):2651-2657 (1999).

\* cited by examiner

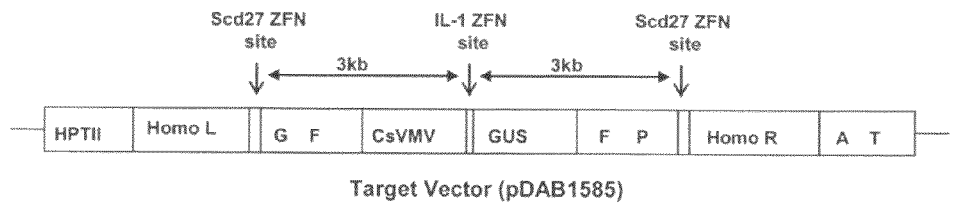
Figure 4
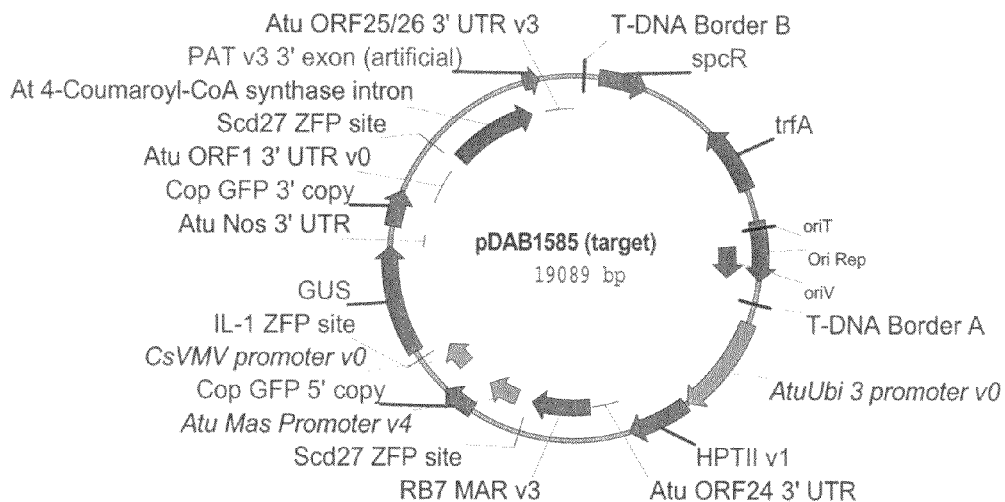
Figure 5: Schematic Representation of Plasmid pDAB1585 - Target Vector for Tobacco

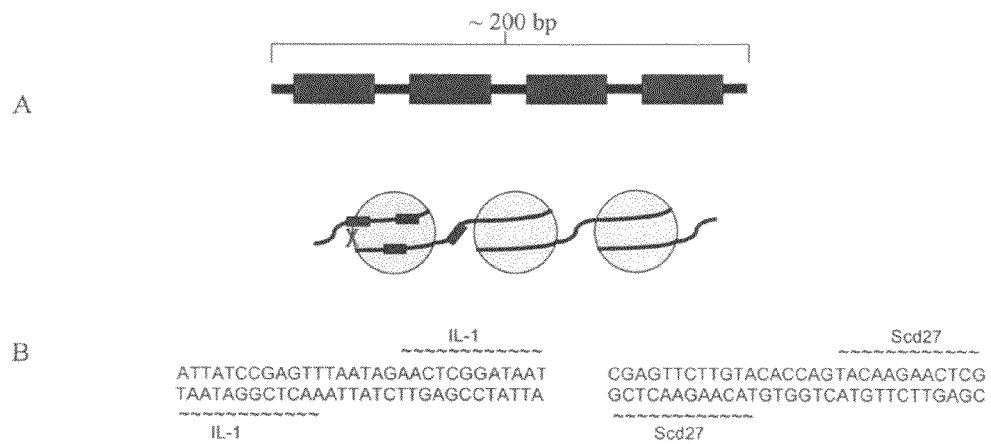
Figure 6: Zinc Finger Nuclease Binding Sequences and the Target Site Design for tobacco
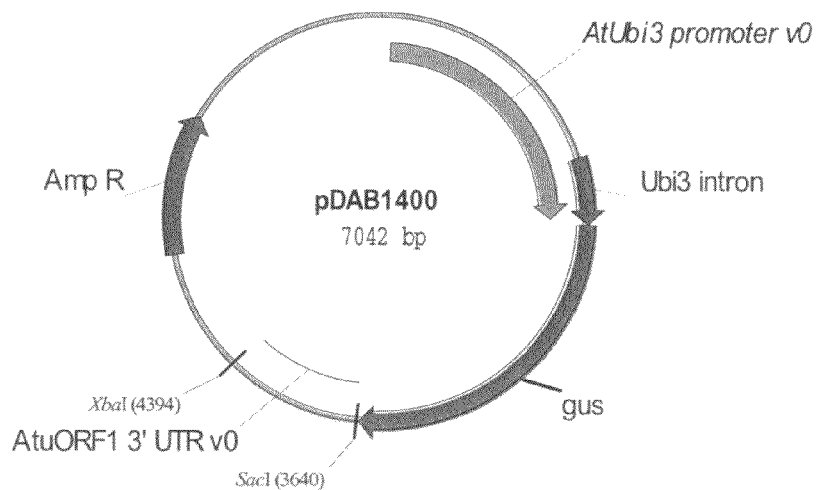
Figure 7: Schematic representation of plasmid pDAB1400

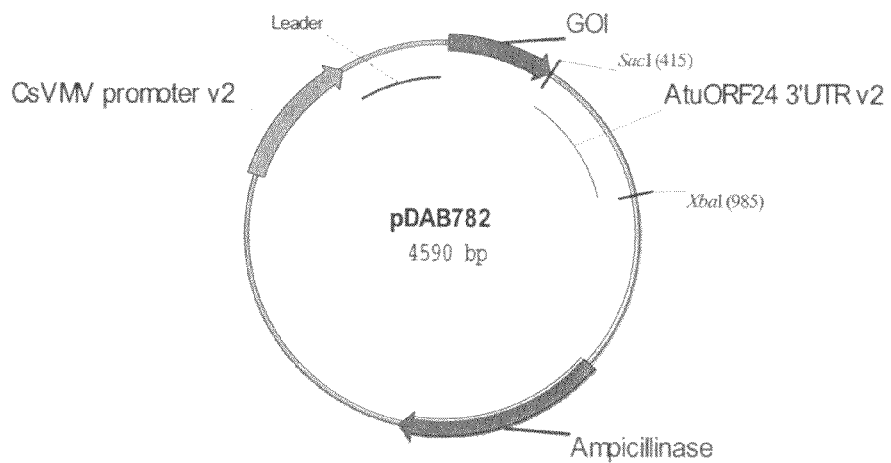
Figure 8: Schematic representation of plasmid pDAB782
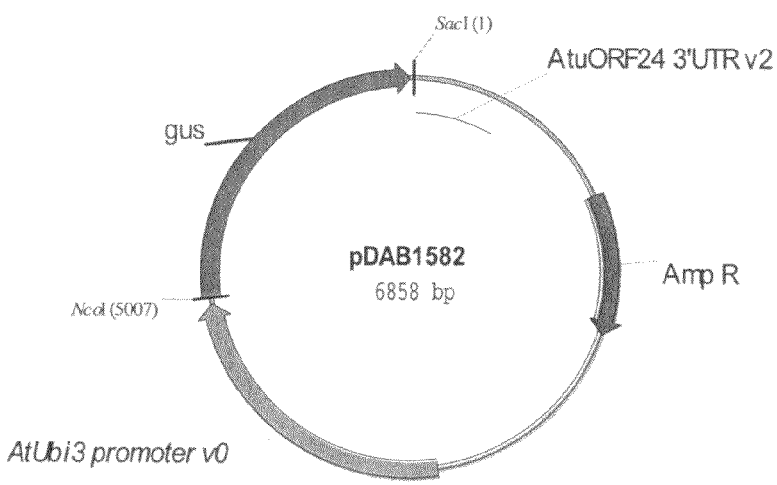
Figure 9: Schematic representation of plasmid pDAB1582

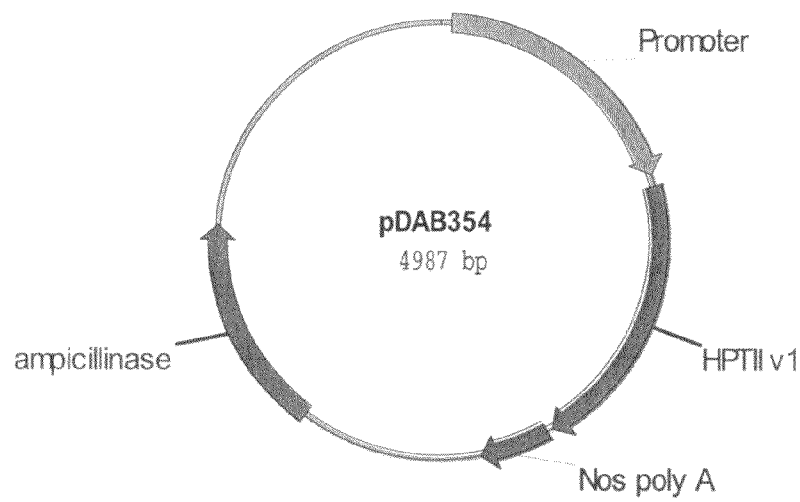
Figure 10: Schematic representation of plasmid pDAB354
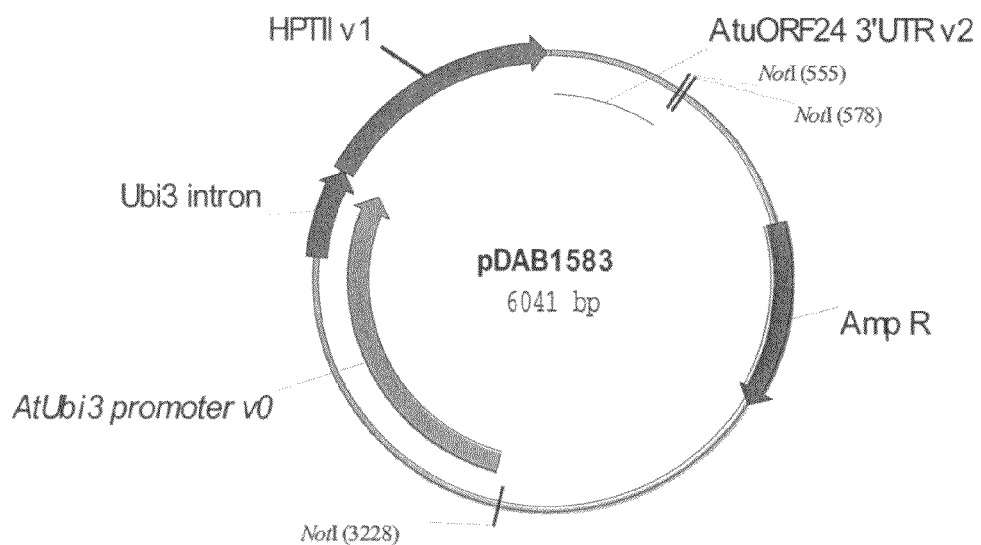
Figure 11: Schematic representation of plasmid pDAB1583

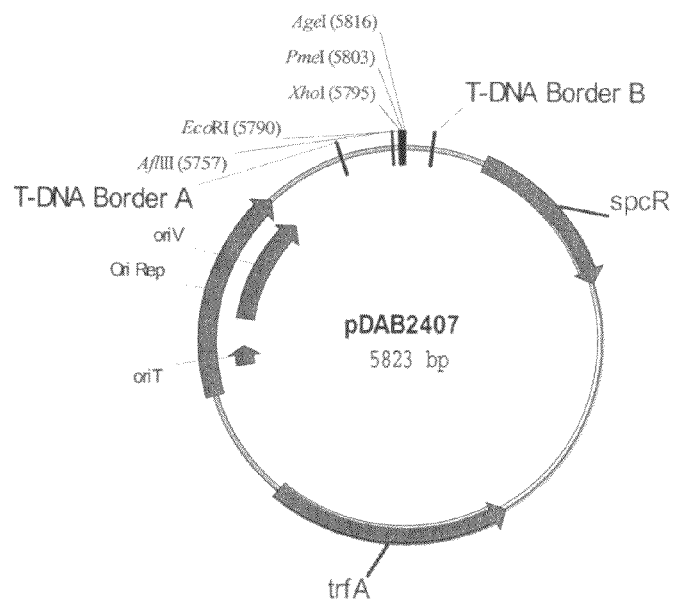
Figure 12: Schematic representation of plasmid pDAB2407
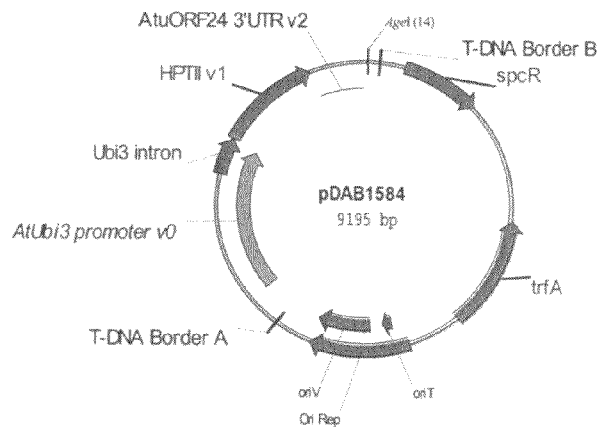
Figure 13: Schematic representation of plasmid pDAB1584

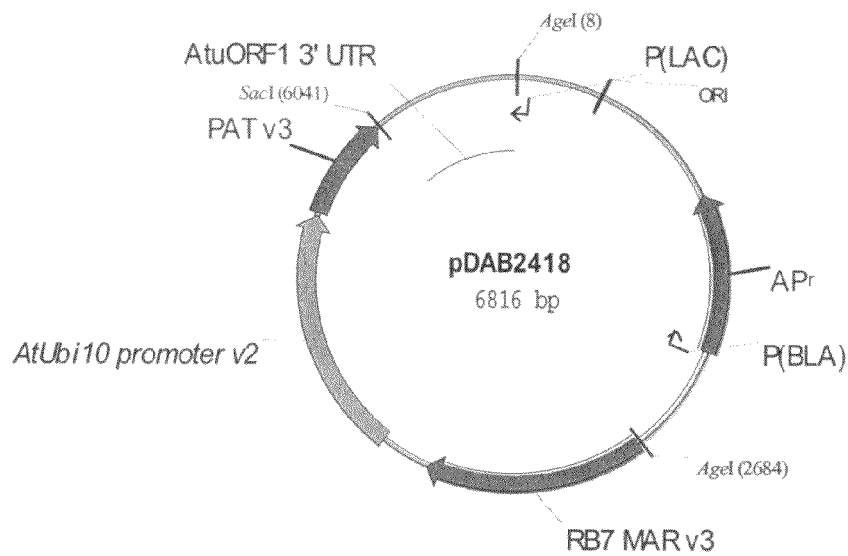
Figure 14: Schematic representation of plasmid pDAB2418
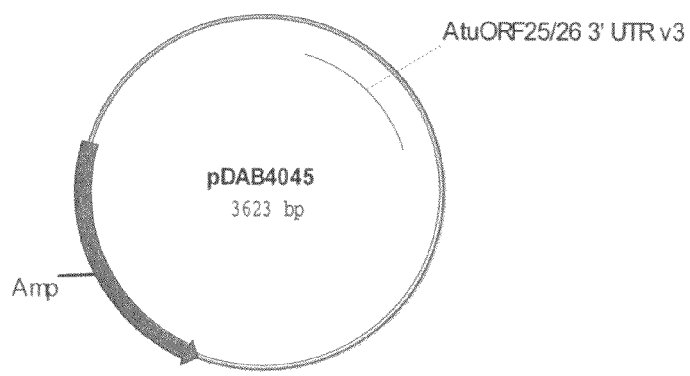
Figure 15: Schematic representation of plasmid pDAB4045

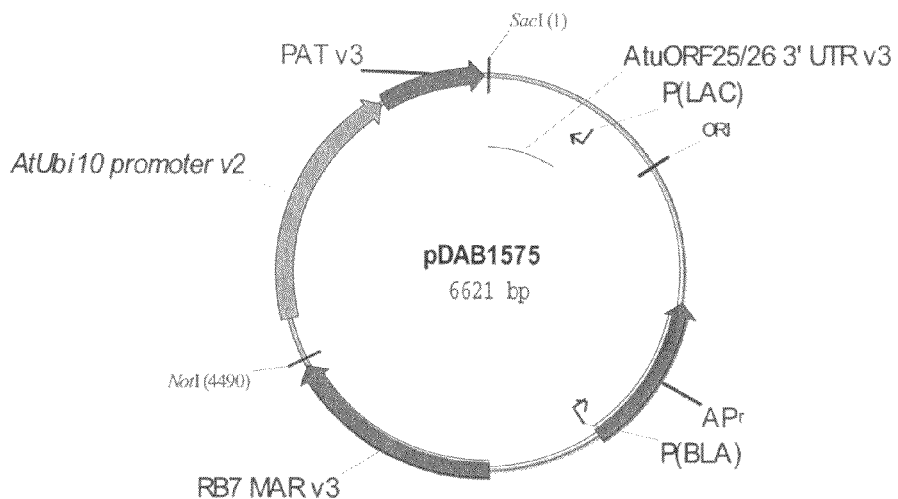
Figure 16: Schematic representation of plasmid pDAB1575
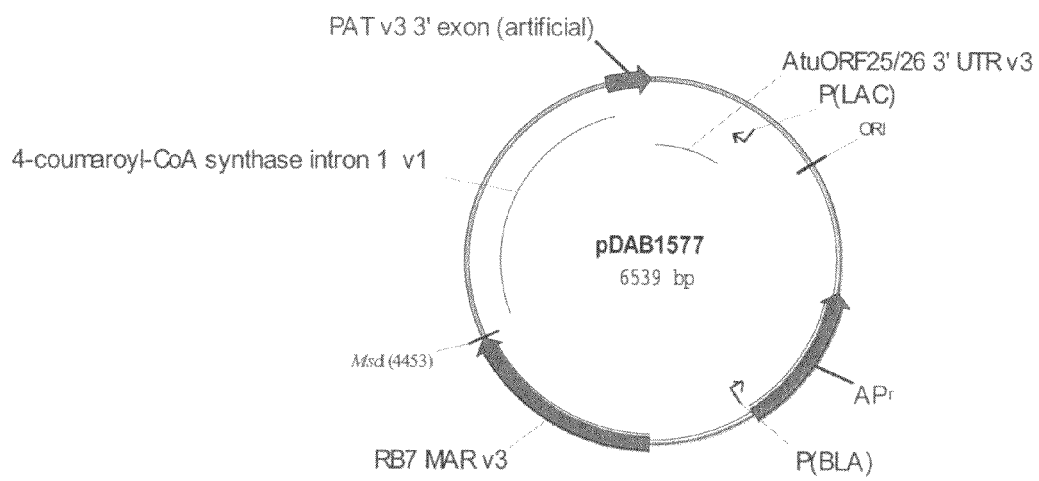
Figure 17: Schematic representation of plasmid pDAB1577

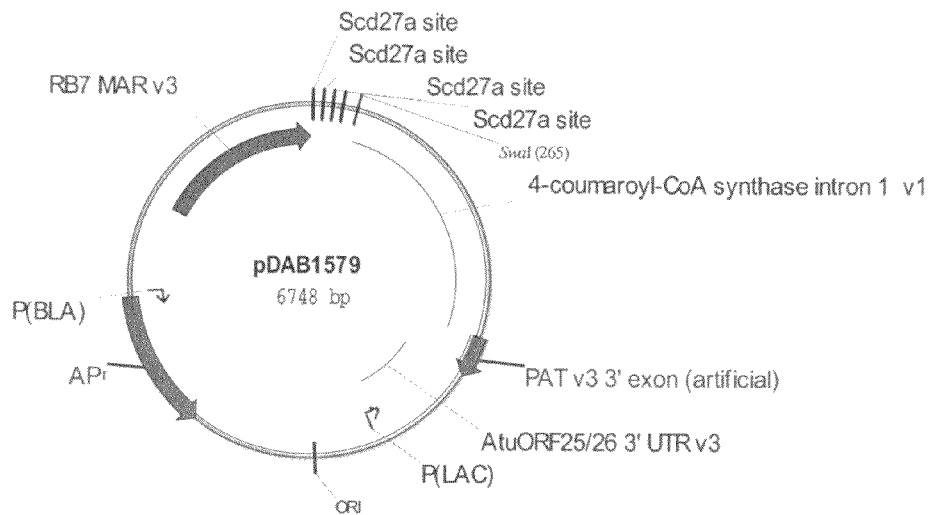
Figure 18: Schematic representation of plasmid pDAB1579
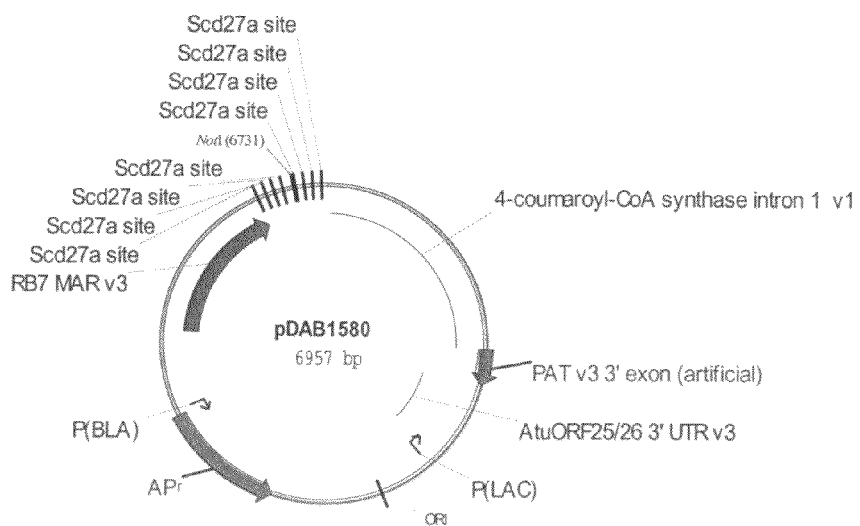
Figure 19: Schematic representation of plasmid pDAB1580

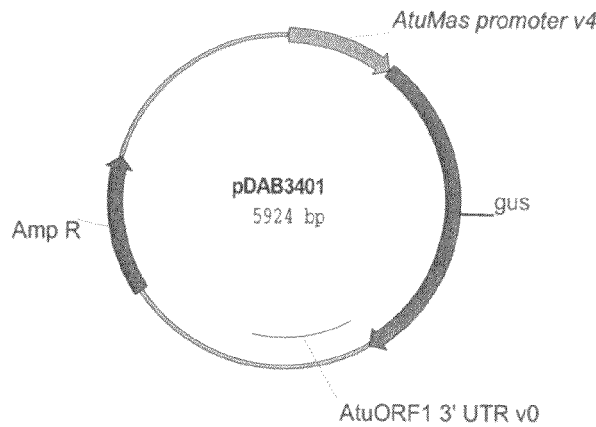
Figure 20: Schematic representation of plasmid pDAB3401
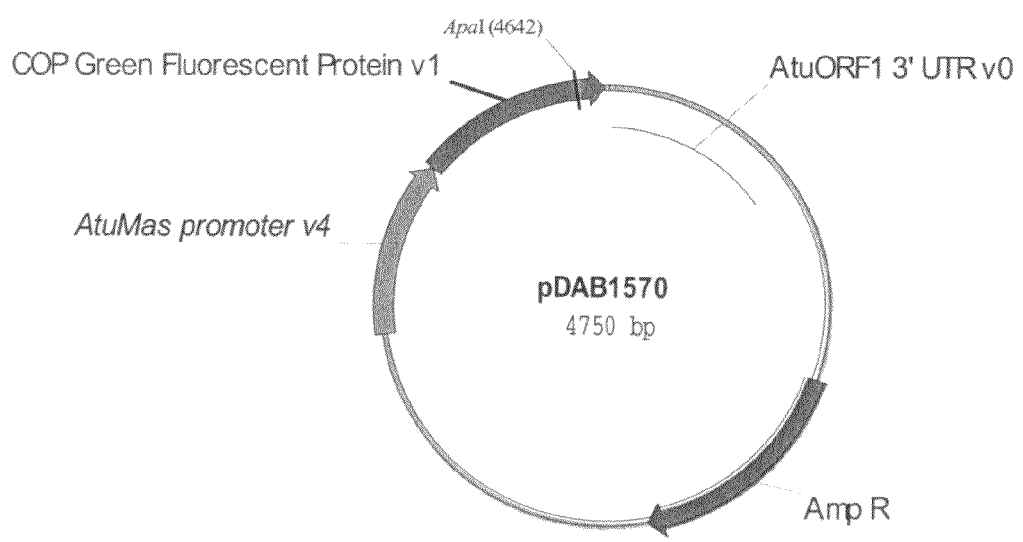
Figure 21: Schematic representation of plasmid pDAB1570

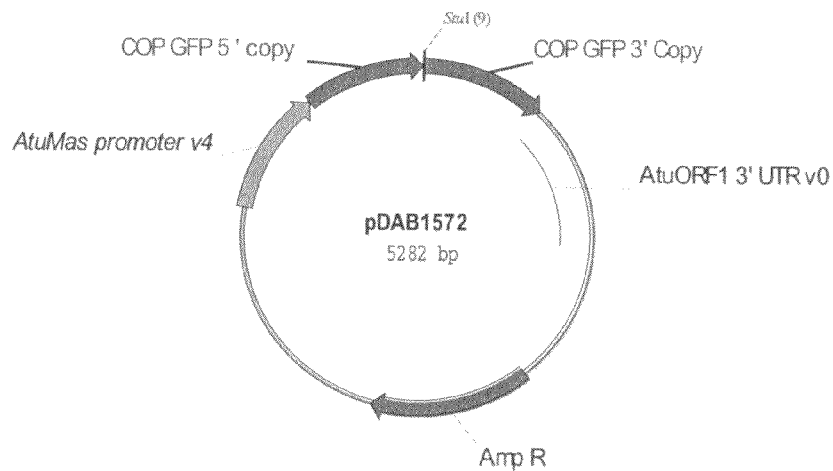
Figure 22: Schematic representation of plasmid pDAB1572
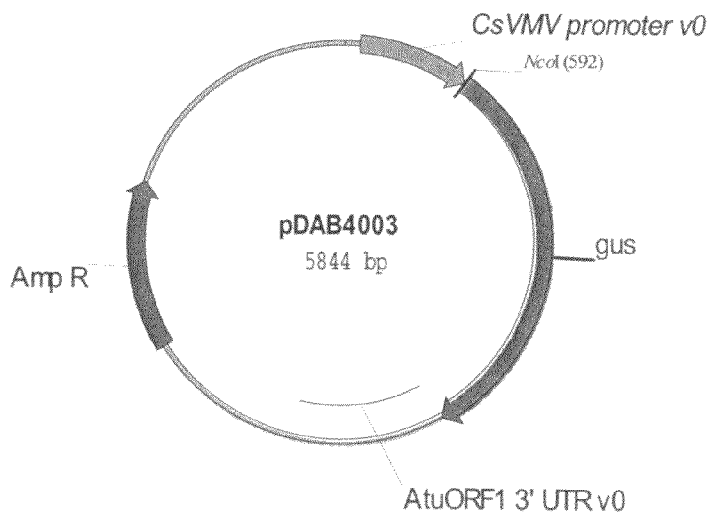
Figure 23. Schematic representation of plasmid pDAB4003

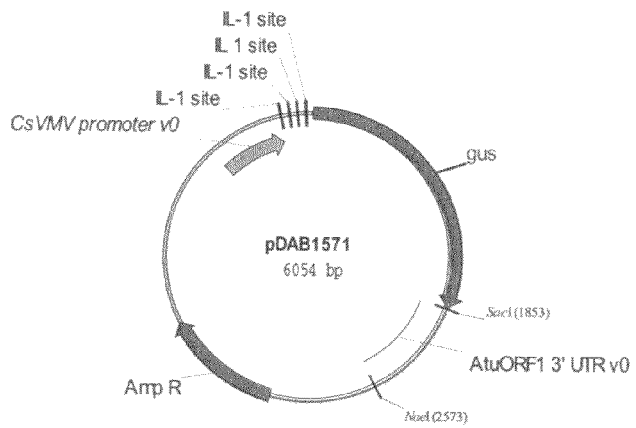
Figure 24. Schematic representation of plasmid pDAB1571
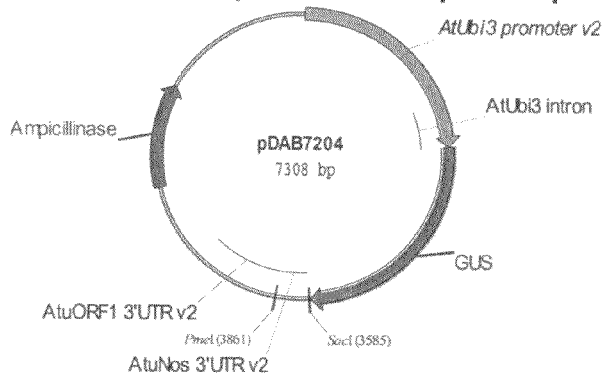
Figure 25. Schematic representation of plasmid pDAB7204
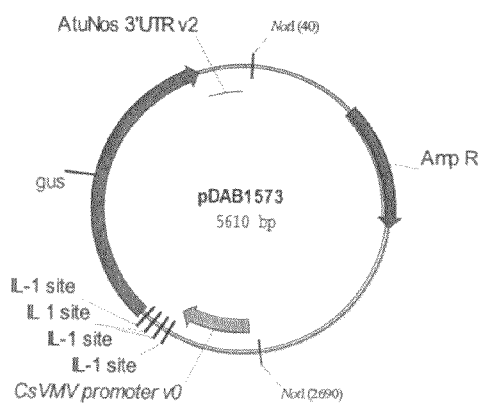
Figure 26. Schematic representation of plasmid pDAB1573

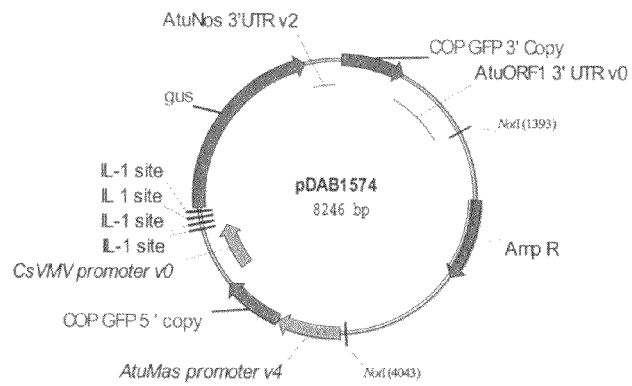
Figure 27: Schematic representation of plasmid pDAB1574
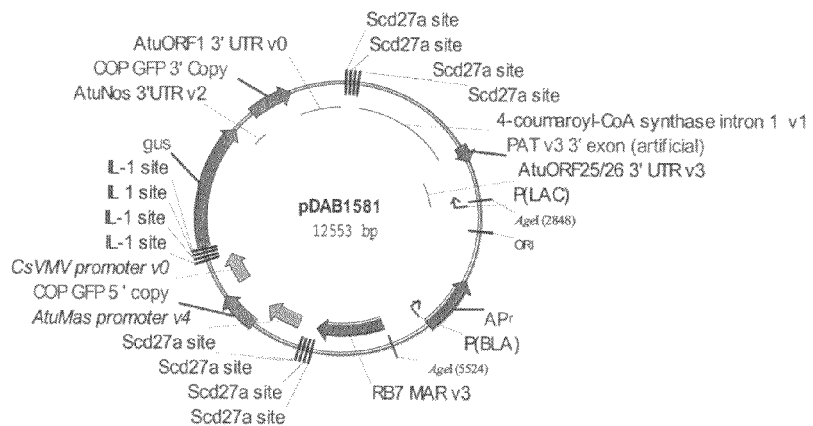
Figure 28: Schematic representation of plasmid pDAB1581
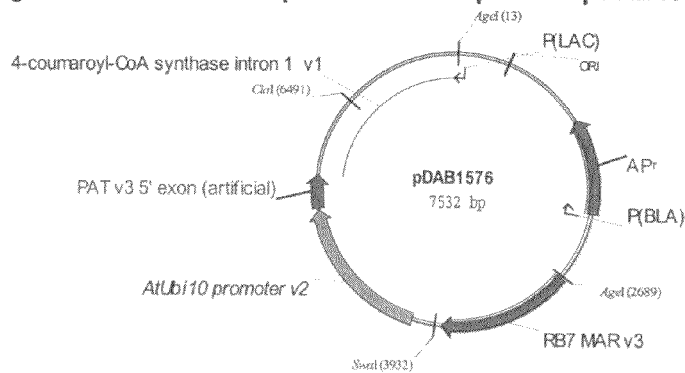
Figure 29: Schematic representation of plasmid pDAB1576

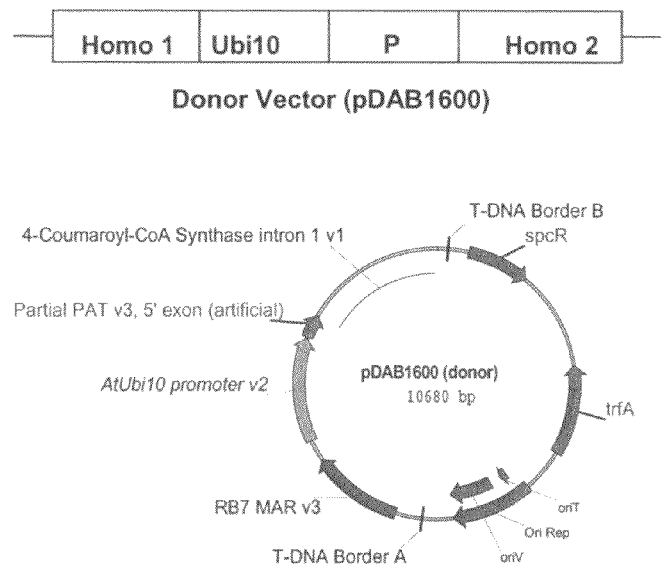
Figure 30: Schematic representation of plasmid pDAB1600. Donor DNA Vector for tobacco
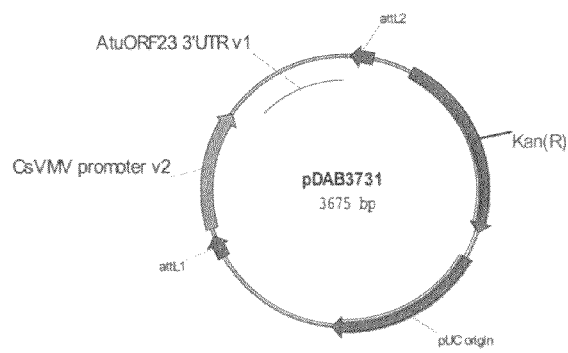
Figure 31: Schematic representation of plasmid pDAB3731

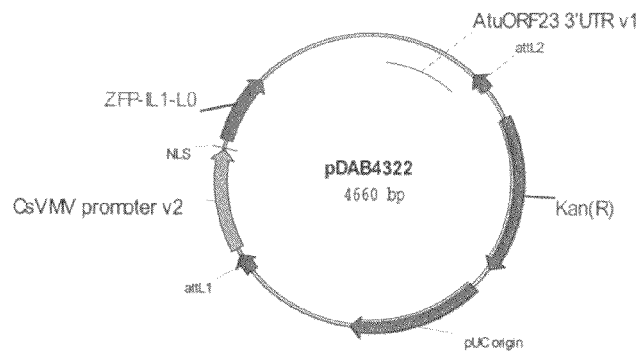
Figure 32: Schematic representation of plasmid pDAB4322
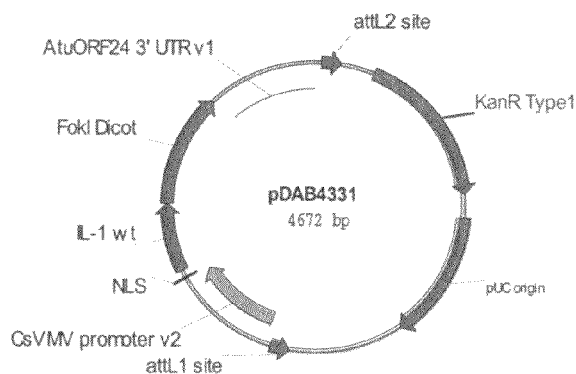
Figure 33: Schematic representation of plasmid pDAB4331
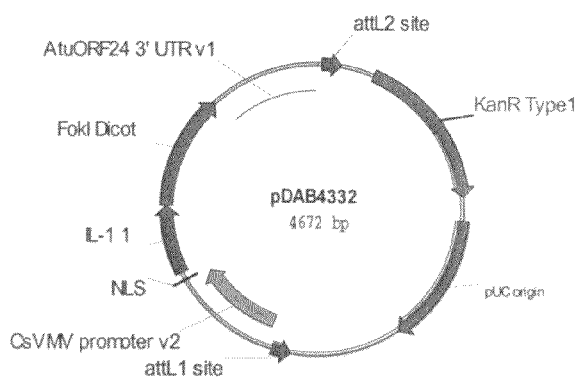
Figure 34: Schematic representation of plasmid pDAB4332

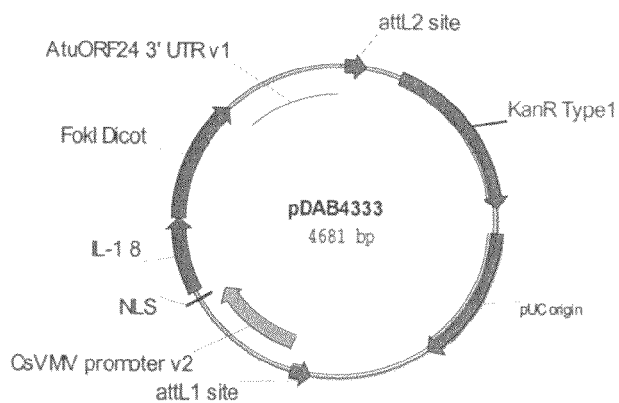
Figure 35: Schematic representation of plasmid pDAB4333
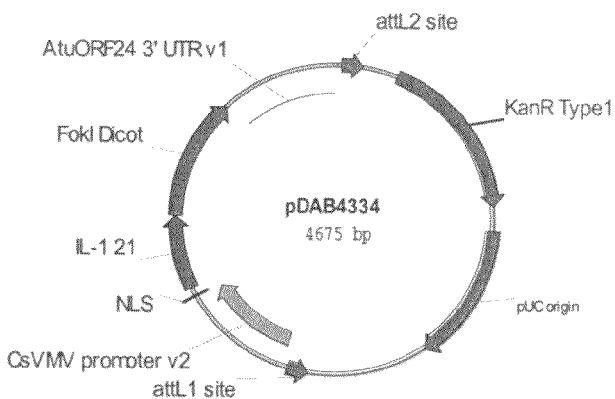
Figure 36: Schematic representation of plasmid pDAB4334

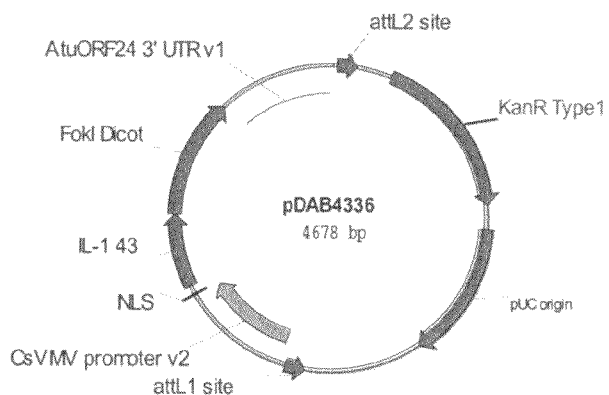
Figure 37: Schematic representation of plasmid pDAB4336
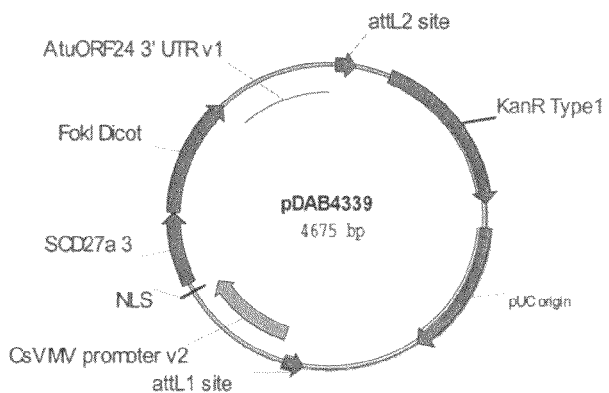
Figure 38: Schematic representation of plasmid pDAB4339

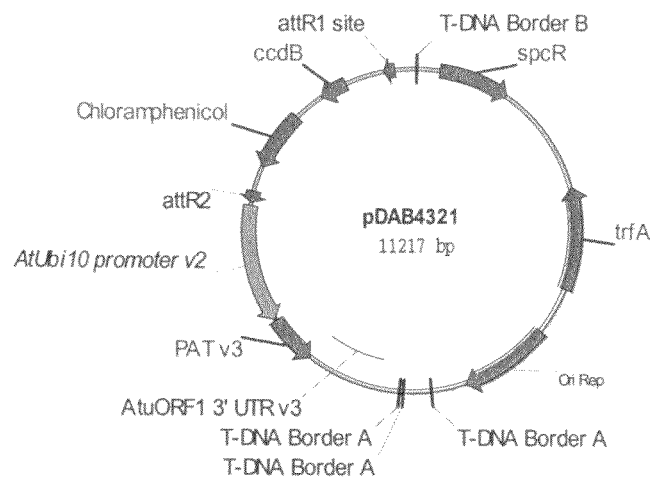
Figure 39: Schematic representation of plasmid pDAB4321
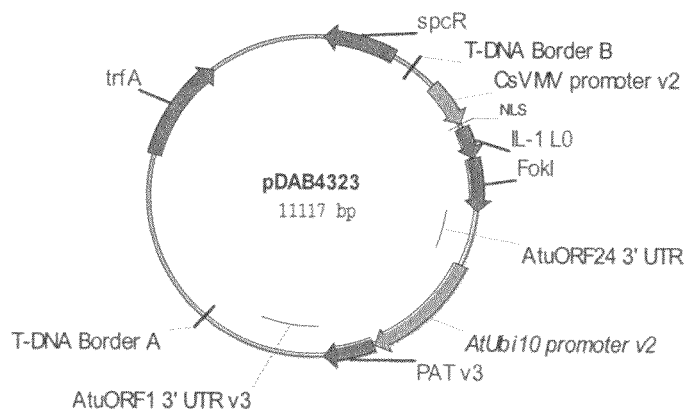
Figure 40: Schematic representation of plasmid pDAB4323

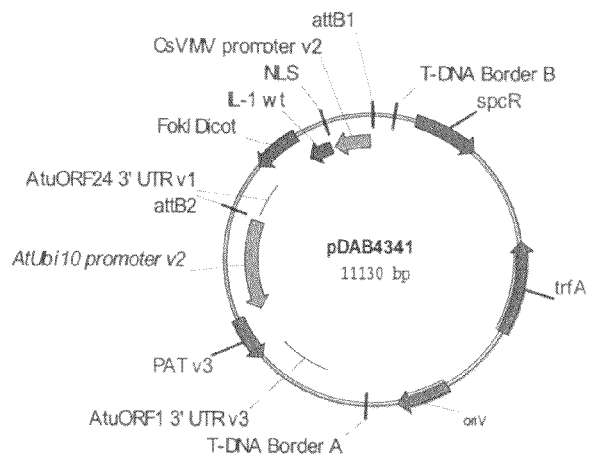
Figure 41: Schematic representation of plasmid pDAB4341
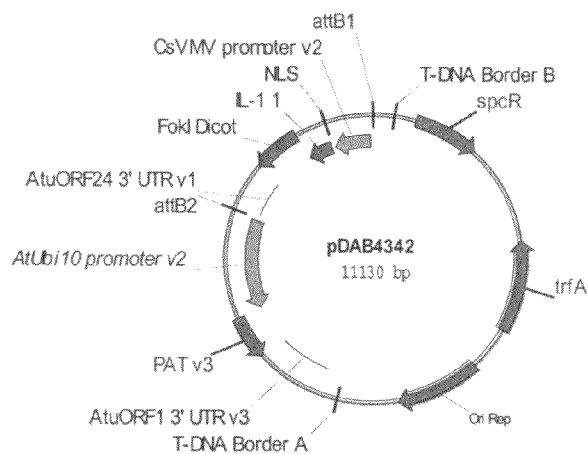
Figure 42: Schematic representation of plasmid pDAB4342

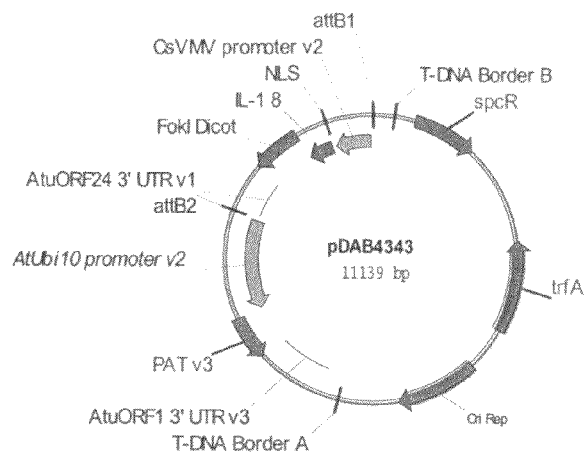
Figure 43: Schematic representation of plasmid pDAB4343
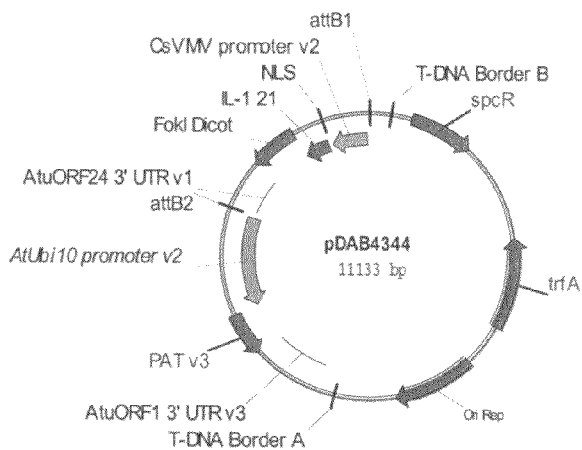
Figure 44: Schematic representation of plasmid pDAB4344

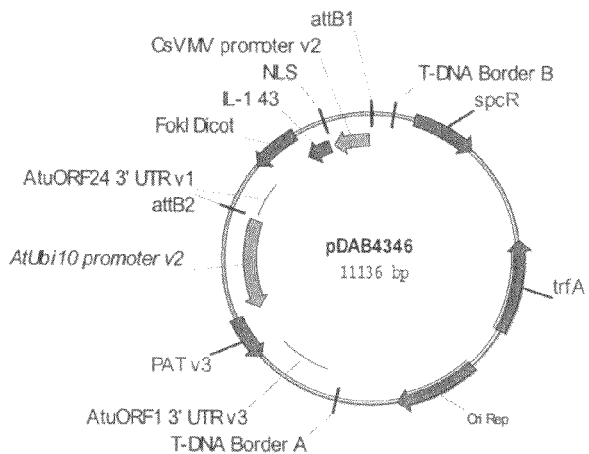
Figure 45: Schematic representation of plasmid pDAB4346
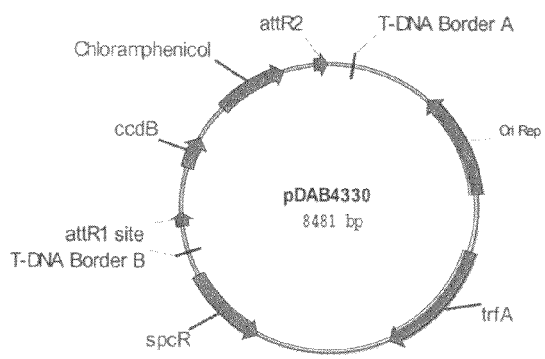
Figure 46: Schematic representation of plasmid pDAB4330
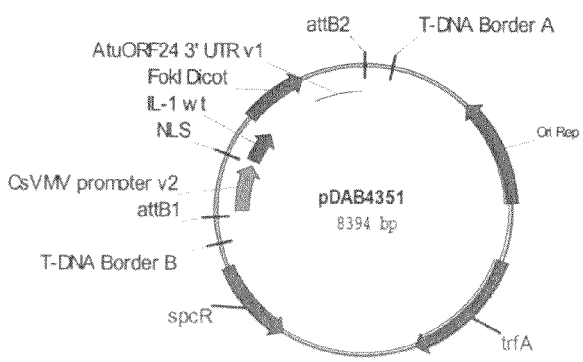
Figure 47: Schematic representation of plasmid pDAB4351

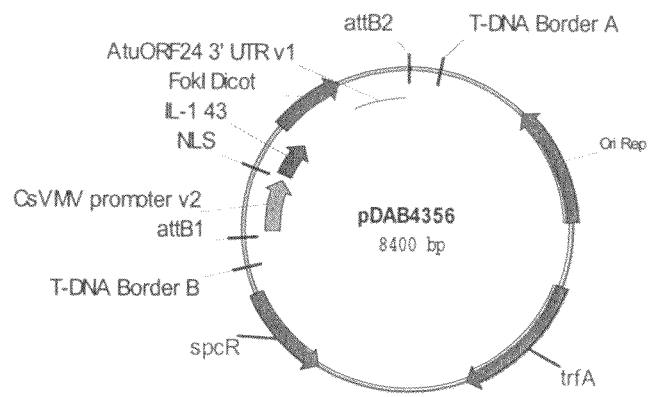
Figure 48: Schematic representation of plasmid pDAB4356
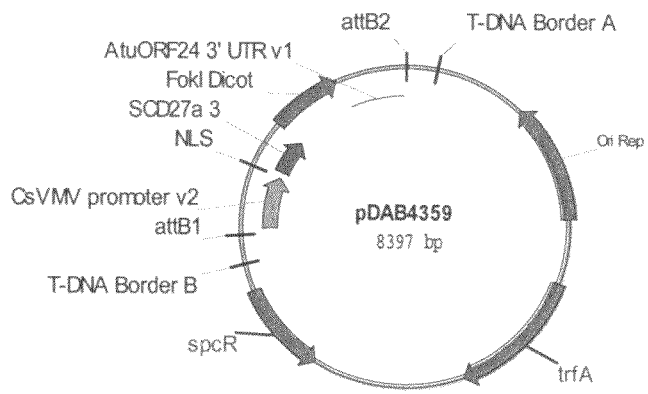
Figure 49: Schematic representation of plasmid pDAB4359

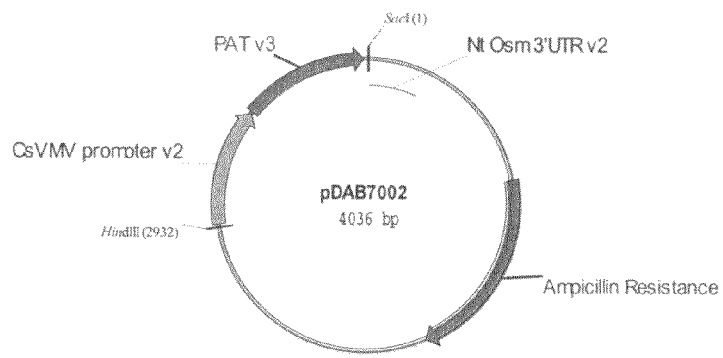
Figure 50: Schematic representation of plasmid pDAB7002
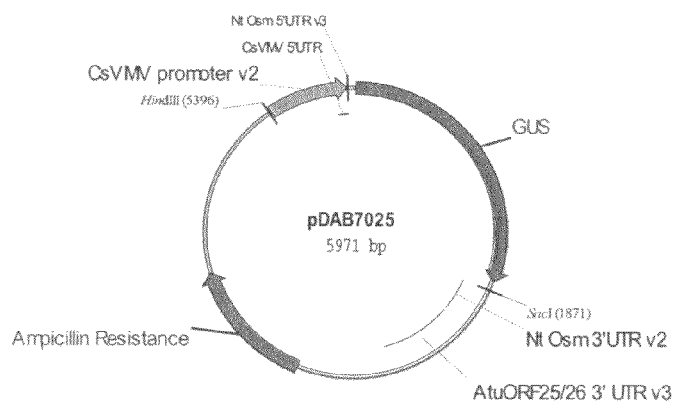
Figure 51: Schematic representation of plasmid pDAB7025
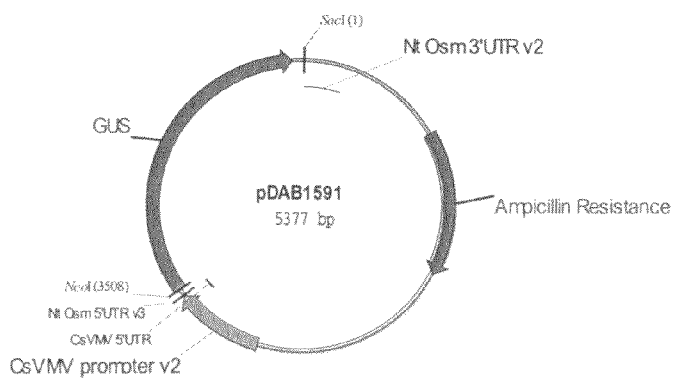
Figure 52: Schematic representation of plasmid pDAB1591

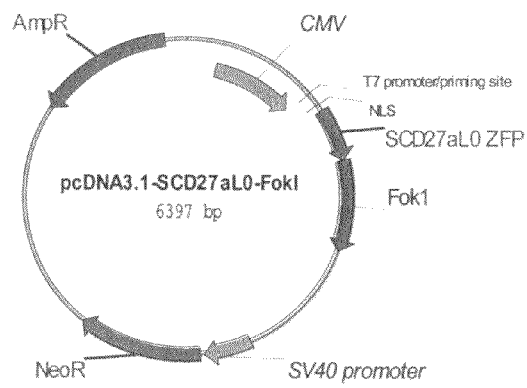
Figure 53: Schematic representation of plasmid pCDNA3.1-SCD27a-L0-FokI
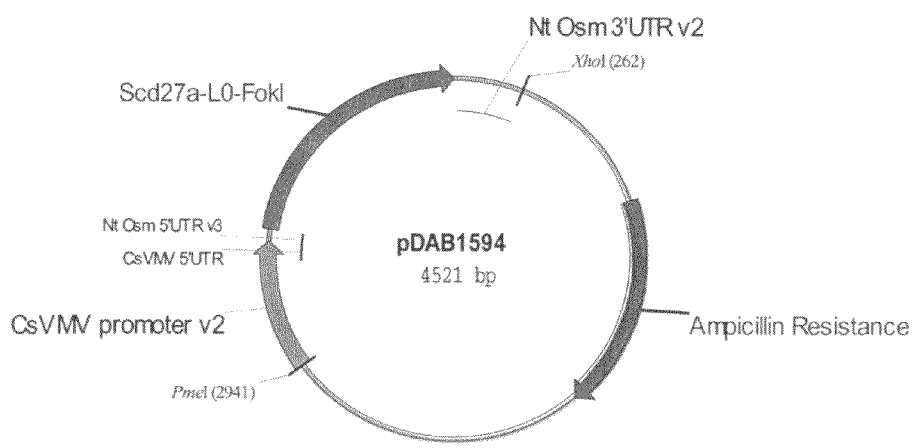
Figure 54: Schematic representation of plasmid pDAB1594

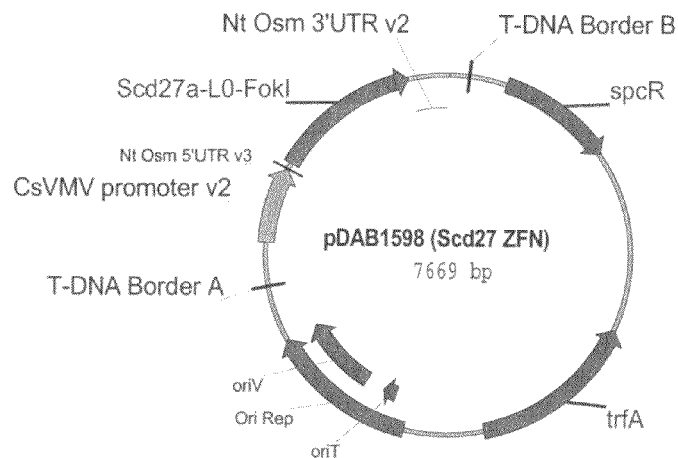
Figure 55: Schematic representation of plasmid pDAB1598 - Zinc Finger-Fok1 Fusion Protein Gene Expression Vectors
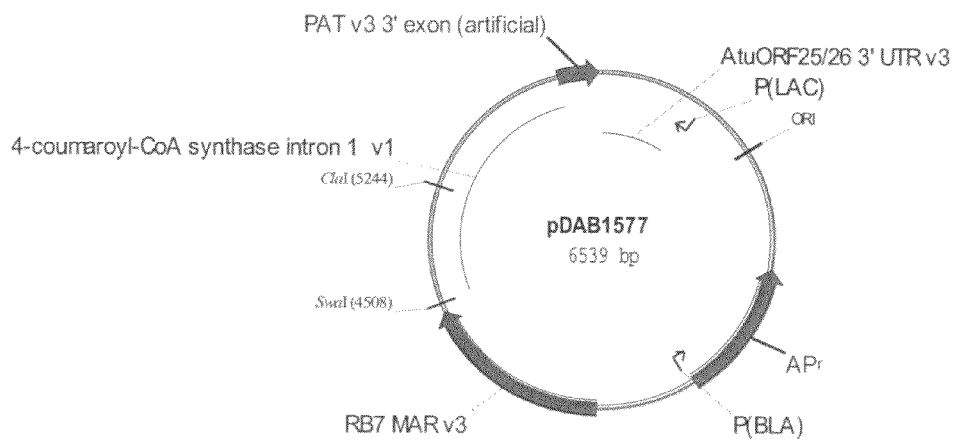
Figure 56: Schematic representation of plasmid pDAB1577

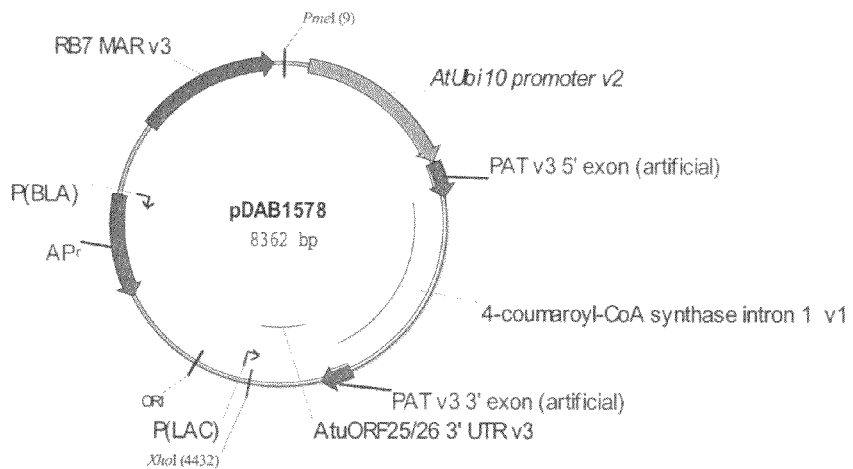
Figure 57: Schematic representation of plasmid pDAB1578
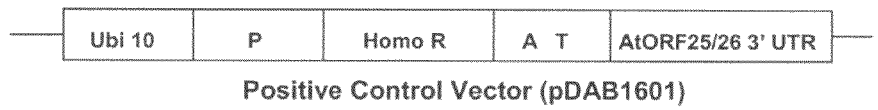
Positive Control Vector (pDAB1601)
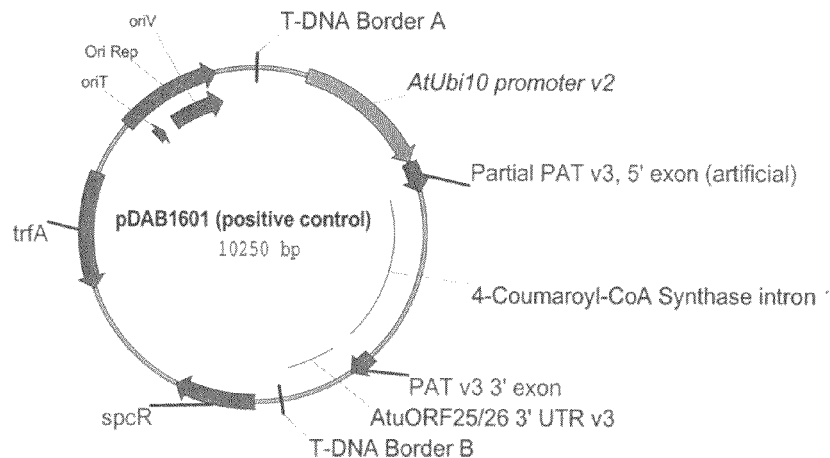
Figure 58: Schematic representation of plasmid pDAB1601 - PAT Gene Control Vector

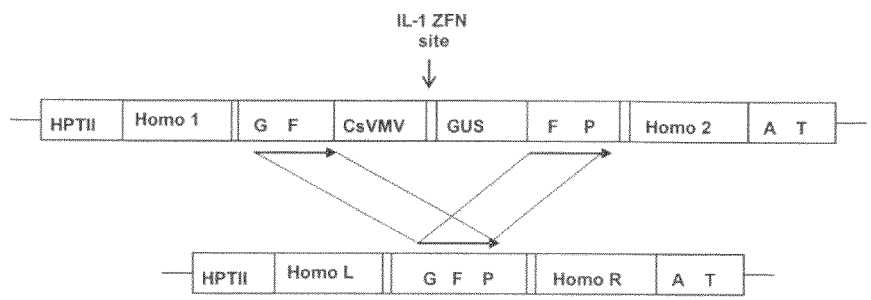
Figure 59: Predicted Intra-Chromosomal Homologous Recombination Stimulated by IL-1-Fok1 Fusion Protein.
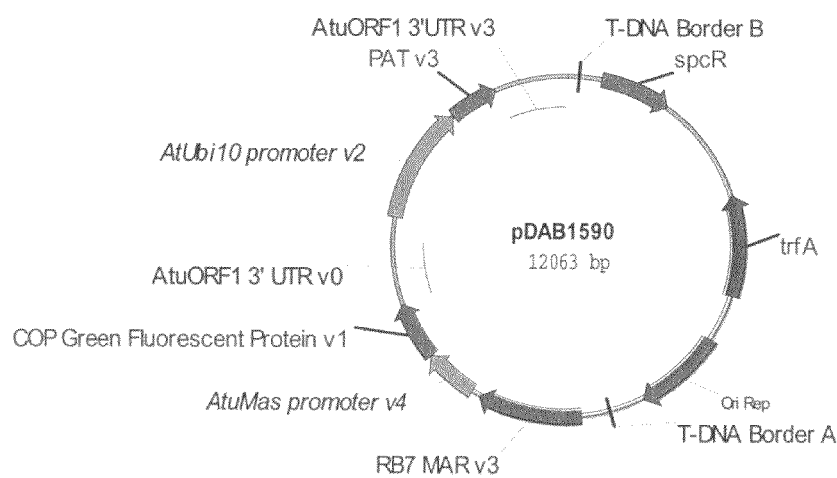

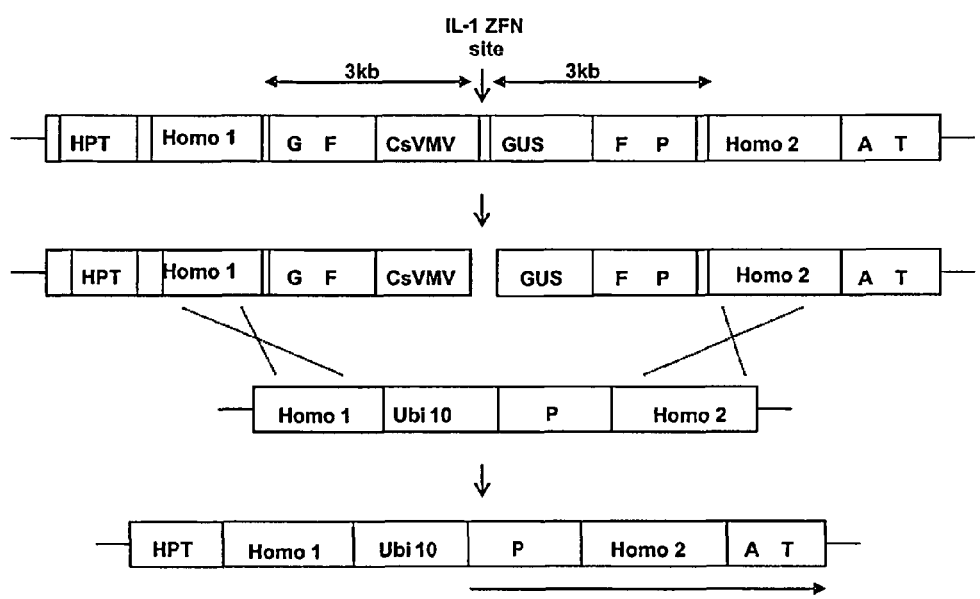
Figure 61: Predicted Inter-Chromosomal Homologous Recombination Stimulated by IL-1 Zinc Finger-Fok1 Fusion Protein.

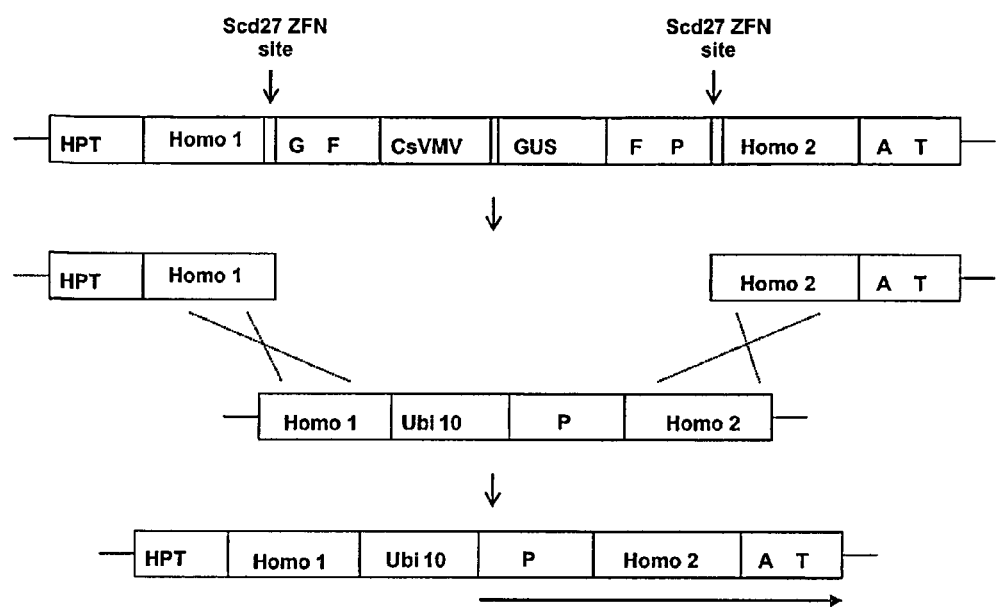
Figure 62: Predicted Inter-Chromosomal Homologous Recombination Stimulated by Scd27 Zinc Finger-Fok1 Fusion Protein.

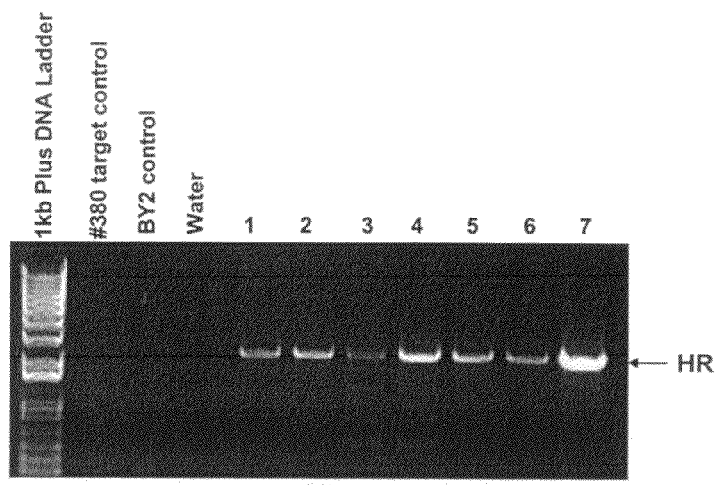

Figure 63: PCR Analysis of the Recombinants. 1-5: HR events from the transformation of BY2-380 with C3H IL-1-FokI fusion protein gene. 6-7: HR events from the transformation of BY2-380 with C3H SCD27-FokI fusion protein gene.

Figure 64: Maize IPP2K gene sequence.

```
   1    ATGGAGATGG ATGGGGTTCT GCAAGCCGCG GATGCCAAGG ACTGGGTTTA
  51    CAAGGGGGAA GGCGCCGCGA ATCTCATCCT CAGCTACACC GGCTCGTCGC
 101    CCTCCATGGT AAGCGCTGAG TAGGTTCTTA CTGAGCGTGC ACGCATCGAT
 151    CACTTGACTT TAGGGGCTCA ATGTGTGATT CACGGGTGCC GCGGCGCCAT
 201    TCGAGCTCCA GATCCAGTAC CGCTCGAGCA AGTGATAAAA CATGGAGCAG
 251    GGACGATCAC GTGGTCACTT GAAAATTACG TGAGGTCCGG GGCGACGATG
 301    TACGGCGCGG CGAACTCTCA AACACTCACA CAACCAAAAC CGCTTCGTGT
 351    TCGTCTTTGT TCCAAGCGAC TGTGTGAGTG TTTGAGAGTT CGCCAGCGCG
 401    ACATCGCCCG ATCTGACAAA TTAAGCTTTC GTTGCTTTTC CATGATTGTG
 451    CATTTTGTGA GCATGCACTG AATACTATGA TGGATATGTT TGGAGGAAGC
 501    ATTATTCCAA TTTGATGATA AGGGTGTTAT TTACACTTGT TTTCAGCTTG
 551    GCAAGGTACT GCGGCTCAAG AAGATTCTAA AAAACAAGTC GCAGCGGGCA
 601    CCGAGTTGTA TTGTATTCTC AAGTCATGAG CAACTCCTGT GGGGCCATAT
 651    CCCAGAACTG GTTGAGTCGG TCAAACAAGA TTGCTTGGCT CAAGCCTATG
 701    CAGTGCATGT TATGAGCCAA CACCTGGGTG CCAATCATGT CGATGGTGGG
 751    GTATGGTTCA GATTCAGTTC ATTTATGTCC TGTTATTGTG ATTTTGATTG
 801    GTAACATATT GACAACCTCG ACACTTGGGA TCAGATTCAG TTCACTTATG
 851    GAAGAAATTG GAGAATTGTT ATAATTTATC TATAATCACC CCTACTGAAA
 901    TAGAAATAAC ATGGCATCAA TGTGCATGCT ATTGGATTTT GACACGAATA
 951    TGCTTTATTC TATCATATGT TGGTAATTCC AGCAGGCAGC AGGCACTACT
1001    CTTTGGATCC ACGTGACTTG ACAAAGAAAT CATGCCATCT TTCCACAATG
1051    CAGGTCCGTG TACGTGTTTC TAGGGATTTT CTGGAGCTTG TCGAAAAGAA
1101    TGTTCTTAGC AGCCGTCCTG CTGGGAGAGT AAATGCAAGT TCAATTGATA
1151    ACACTGCTGA TGCCGCTCTT CTAATAGCAG ACCACTCTTT ATTTTCTGG
```

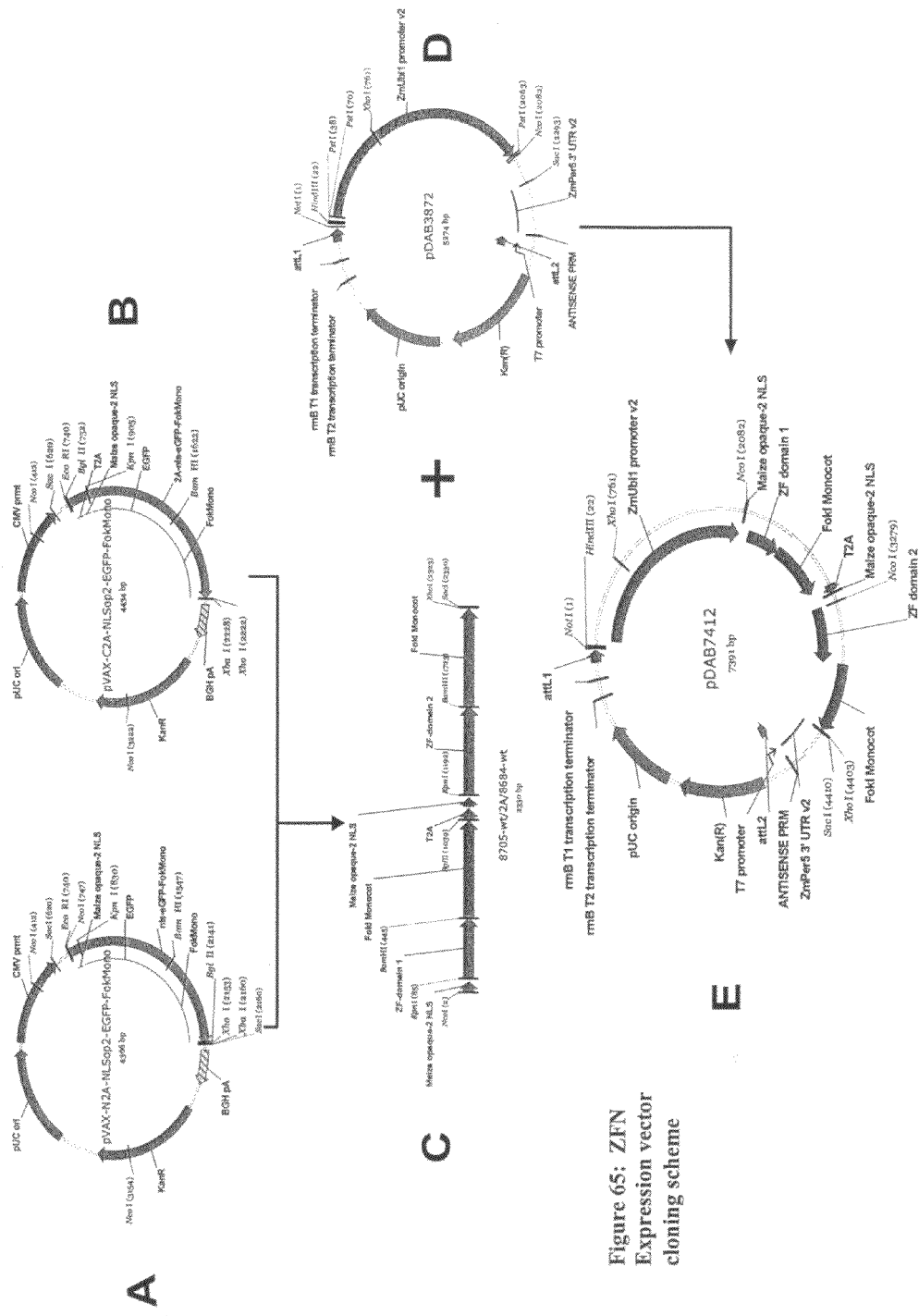
Figure 65: ZFN Expression vector cloning scheme

Figure 66: Binding and cleavage of ZFNs to the maize IPP2K gene.

```
           8705 binding site
    caactcctgtggggccatatc ccagaactggttgagtcggtcaaacaaga
    gttgaggacaccccggtatag ggtcttgaccaactcagccagtttgttct
                                  8684 binding site
                                  8685
                                  8686
```

Figure 67: ZFN-mediated deletion.

```
wild type    AAGTCATGAGCAACTCCTGTGGGGCCATATCCCAGAACTGGTTGAGTCGGTCAAACAAG
clone 127    AAGTCATGAGCAACTCCTGTGGGGCCA------AGAACTGGTTGAGTCGGTCAAACAAG
```

Figure 68: ZFN-mediated deletions.

```
wild type    AAGTCATGAGCAACTCCTGTGGGGCCATATCCCAGAACTGGTTGAGTCGGTCAAACAAG
experim.     AAGTCATGAGCAACTCCTGTGGGGCC::A::::AGAACTGGTTGAGTCGGTCAAACAAG
             AAGTCATGAGCAACTCCTGTGGGGCCATA::::AGAACTGGTTGAGTCGGTCAAACAAG
             AAGTCATGAGCAACTCCTGTGGGGCCATA:::::GAACTGGTTGAGTCGGTCAAACAAG
             AAGTCATGAGCAACTCCTGTGGGGCCATA::CAGAACTGGTTGAGTCGGTCAAACAAG
             AAGTCATGAGCAACTCCTGTGGGGCCATA::CAGAACTGGTTGAGTCGGTCAAACAAG
             AAGTCATGAGCAACTCCTGTGGGGCCATA:CCAGAACTGGTTGAGTCGGTCAAACAAG
             AAGTCATGAGCAACTCCTGTGGGG::::::CCAGAACTGGTTGAGTCGGTCAAACAAG
             AAGTCATGAGCAACTCCTGTGGGGCCATAT::CAGAACTGGTTGAGTCGGTCAAACAAG
             AAGTCATGAGCAACTCCTGTGGGGCCATA::::GAACTGGTTGAGTCGGTCAAACAAG
             AAGTCATGAGCAACTCCTGTGGGGCCATA::::GAACTGGTTGAGTCGGTCAAACAAG
          AAGTCATGAGCAACTCCTGGTGGGGCCATA::CAGAACTGGTTGAGTCGGTCAAACAAG
             AAGTCATGAGCAACTCCTGTGGGGCCATA::::GAACTGGTTGAGTCGGTCAAACAAG
             AAG:CATGAGCAACTCCTGTGGGGCCATA::::GAACTGGTTGAGTCGGTCAAACAAG
             AAGTCATGAGCAACTCCTGTGGGGCCATA::CAGAACTGGTTGAGTCGGTCAAACAAG
             AAGTCATGAGCAACTCCTGTGGGGCCATAT::CAGAACTGGTTGAGTCGGTCAAACAAG
             AAGTCATGAGCAACTCCTGTGGGGCCATA::::GAACTGGTTGAGTCGGTCAAACAAG
             AAGTCATGAGCAACTCCTGTGGGGCC::A:::CAGAACTGGTTGAGTCGGTCAAACAAG
             AAGTCATGAGCAACTCCTGTGGGGCCATA::::GAACTGGTTGAGTCGGTCAAACAAG
             AAGTCATGAGCAACTCCTGTGGGGCCATA::::GAACTGGTTGAGTCGGTCAAACAAG
             AAGTCATGAGCAACTCCTGTGGGGCCATA::CCAGAACTGGTTGAGTCGGTCAAACAAG
             AAGTCATGAGCAACTCCTGTGGGGCCATA::::GAACTGGTTGAGTCGGTCAAACAAG
             AAGTCATGAGCAACTCCTGTGGGGCCATA::::GAACTGGTTGAGTCGGTCAAACAAG
             AAGTCATGAGCAACTCCTGTGGGGCCATA::CAGAACTGGTTGAGTCGGTCAAACAAG
             AAGTCATGAGCAACTCCTGTGGGGCCATA::::GAACTGGTTGAGTCGGTCAAACAAG
             AAGTCATGAGCAACTCCTGTGGGGCCATAT::AGAACTGGTTGAGTCGGTCAAACAAG
             AAGTCATGAGCAACTCCTGTGGGGCCATA::::GAACTGGTTGAGTCGGTCAAACAAG
             AAGTCATGAGCAACTCCTGTGGGGCCATA::::GAACTGGTTGAGTCGGTCAAACAAG
             AAGTCATGAGCAACTCCTGTGGGGCCATA::::AGAACTGGTTGAGTCGGTCAAACAAG
             AAGTCATGAGCAACTCCTGTGGGGCCATAT:::AGAACTGGTTGAGTCGGTCAAACAAG
             AAGTCATGAGCAACTCCTGTGGGGCCATA::CAGAACTGGTTGAGTCGGTCAAACAAG
             AAGTCATGAGCAACTCCTGTGGGGCCATA::CCAGAACTGGTTGAGTCGGTCAAACAAG
```

Figure 70. Plasmid Construction pDAB7471.
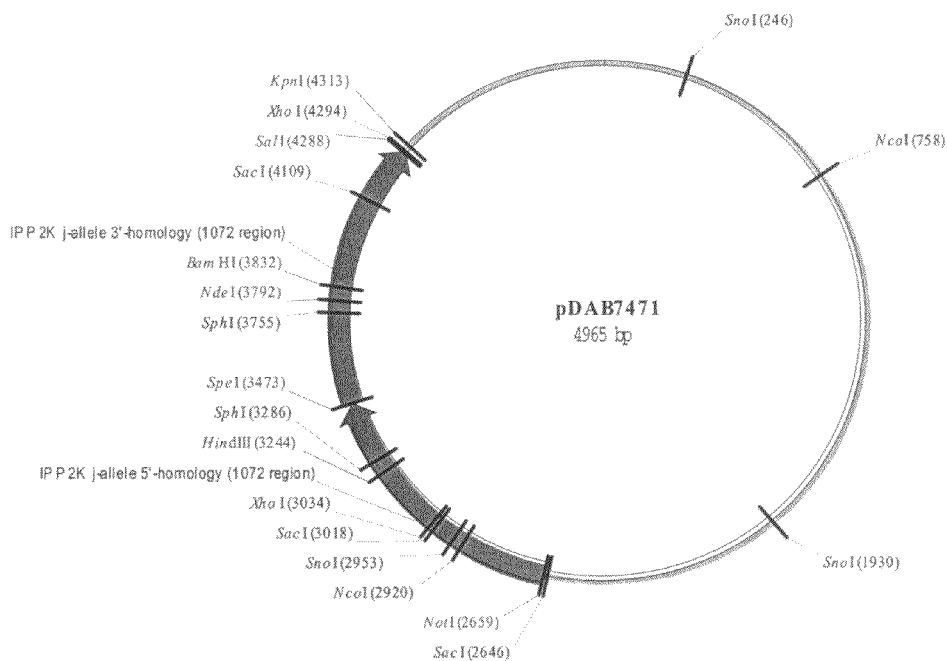

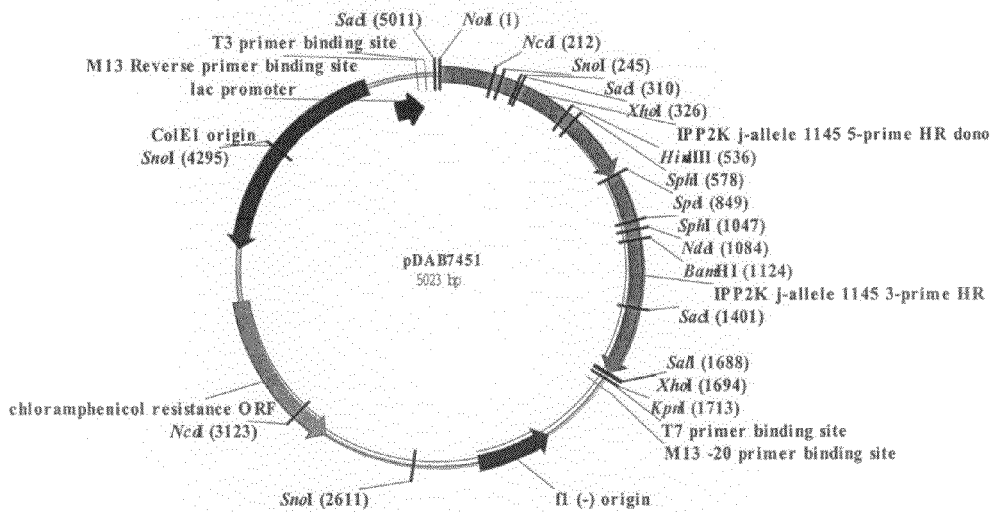
Figure 71: Plasmid Construction pDAB7451.
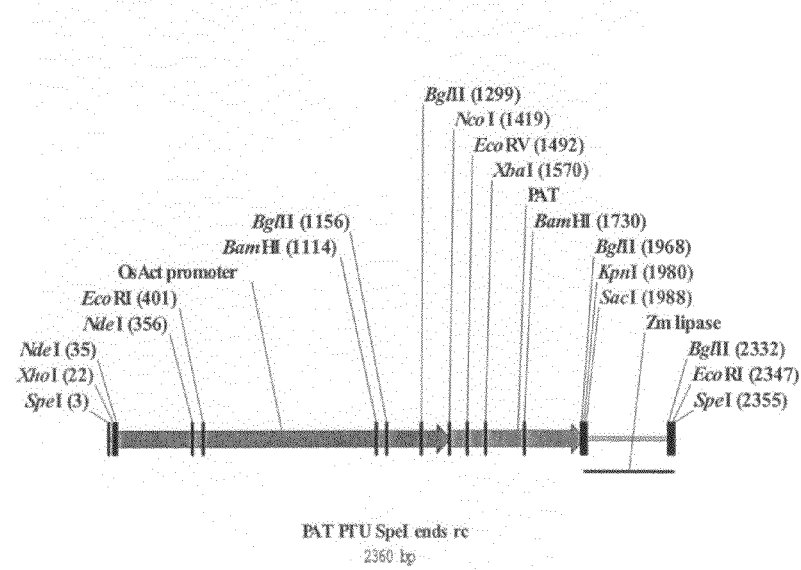
Figure 72. Autonomous herbicide-tolerance gene expression cassette.

Figure 74. Plasmid Construction pDAB7452.

Figure 75. Non-autonomous herbicide-tolerance gene expression cassette.

Figure 76. Plasmid Construction pDAB7423.

Figure 77. Plasmid Construction pDAB7454.

Figure 78. Plasmid Construction pDAB 7424.

Figure 79. Plasmid Construction pDAB 7425.

Figure 80. Plasmid Construction pDAB 7426.

Figure 81. Plasmid Construction pDAB 7427.

Figure 82
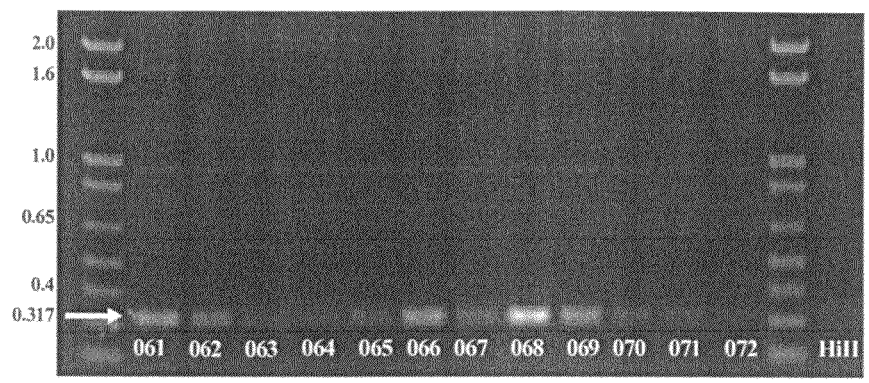
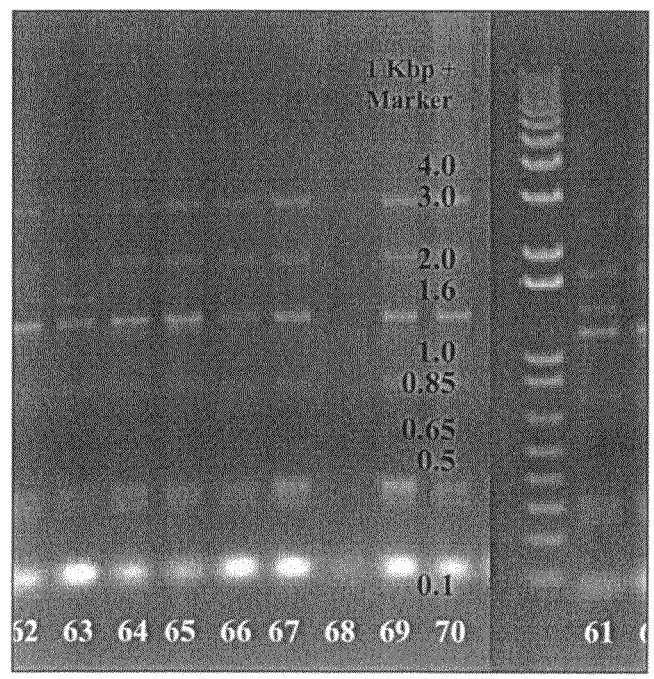
Figure 83

Figure 87: Position-1 5'-homology flank sequence (SEQ ID NO:1)

```
GCGGCCGCGT CTCACCGCGG CTTGGGGATT GGATACGGAG CTAGTTAACC
AGCAGAGCTA GATAGCAGAC GCAGATCGCT TGCTTCTCTG GTTTGATTTT
TGGAGTCACC ATTTCTGTTT GGTTCGTGTG CCTCAGTGTC TGACAGCAGC
AGATCCTCGA TGGAGATGGA TGGGGTTCTG CAAGCCGCGG ATGCCAAGGA
CTGGGTTTAC AAGGGGGAAG GCGCCGCGAA TCTCATCCTC AGCTACACCG
GCACGTCGCC CTCCATGGTA AGCGCTGAGT AGGTTCTTAC TGAGTGTGCA
CGCATCGATC ACTTGACTTT AGGGGCTCAA TGTGTGATTC ACGGGTGCCG
CCATTCGAGC TCCAGATCCA GTATCGCTCG AGCAAGTGAT AAAACATGGA
GCAGGGACGA TCACGTGGTC ACTTGAAAAT TATGTGAGGT CCGGGGCGAC
GATGTACGGC GCGGCGAACT CTCAAACACT CACACAGCCA AAACCGCTTC
GTGTTCGTCT TTGTTCCAAG CGACCGTGTG GTGTGTTTGT AGTAGTTCGC
CGGCGCCGCA CATCGTCGCC CCGGATCTGA CAAATTAAGC TTTCGTTGCT
TTTCCACGAT TGTGCATTTT CTGAGCATGC ACTGAATACT ATGATGGATA
TGTTTGGAGG AAGCATTATT CCAATTTGAT GATAATGGTG TTATTTACAC
TTGTTTTCAG CTTGGCAAGG TACTGCGGCT CAAGAAGATT CTAAAAAACA
AGTTGCAGCG GGCACCAAGT TGTATTGCCT TCTCAAGTCA TGAGCAACTC
CTGTGGGGCC ATATCACTAG T
```

Figure 88: Position-1 3'-homology flank sequence (SEQ ID NO:4)

```
ACTAGTCCAG AACTGGTTGA GTCGGTCAAA CAAGATTGCT TGGCTCAAGC
CTATGCAGTG CATGTTATGA GCCAACACCT GGGTGCCAAT CATGTCGATG
GTGGGGTATG GTTCAGATTC AGTTCATTTA TGTCCTGTTA TTGTGATTTT
GATTGGTAAC ATATTGACAA CCTCGACACT TGGGATCAGA TTCAGTTCAC
TTATGGAAGA AATTGGAGAA TTGTGATAAT TTATCTATAA TCACCCCTAC
TGAAATAGAA ATAACATGAC ATCAATGTGC ATGCTATTGG ATTTTGACAC
GAATATGCTT TATTCTATCA TATGTTGGTA ATTCCAGCAG GCAGCAGGCA
CTACTCTTTG GATCCACGTG ACTTGACAAA GAAATCATGC CATCTTTCCA
CAATGCAGGT CCGTGTACGT GTTTCTAGGG ATTTTCTGGA GCTTGTCGAA
AAGAATGTTC TTAGCAGCCG TCCTGCTGGG AGAGTAAATG CAAGTTCAAT
TGATAACACT GCTGATGCCG CTCTTCTAAT AGCAGACCAC TCTTTATTTT
CTGGTACGTA CTCTATCCCT CTTCTTACCA TAATCTGAAT CTTGTTAAGG
TTTAAAATAT ATGATTGATT AAGTAAAATC CAGAGCTCTA TTCATATCTC
ACGCACTGAT GTTTTGATGA AACGCTTGCA GCAAGACGGT TGCCTGTTAT
TTCTATTTGC ATTAGACAAA CAGTCACCTT TGTTTATAAA GGTCTTTGAA
TTTGCAGTTC TTATAGGTTT AAGTTTGCAA CTGTTACTTA CAACAGCCCA
ATGGGTAGCA TCAAGGTCGA C
```

Figure 89: Position-2 5'-homology flank sequence (SEQ ID NO:139)

```
GCGGCCGCTA GATAGCAGAT GCAGATTGCT TGCTTCTCTG GTTTGATTTT
TGGAGTCACC ATTTCTGTTT GGTTCGTGTG CCTCAGTGTC TGACAGCAGC
AGATCCTCGA TGGAGATGGA TGGGGTTCTG CAAGCCGCGG ATGCCAAGGA
CTGGGTTTAC AAGGGGGAAG GCGCCGCGAA TCTCATCCTC AGCTACACCG
GCACGTCGCC CTCCATGGTA AGCGCTGAGT AGGTTCTTAC TGAGTGTGCA
CGCATCGATC ACTTGACTTT AGGGGCTCAA TGTGTGATTC ACGGGTGCCG
CCATTCGAGC TCCAGATCCA GTATCGCTCG AGCAAGTGAT AAAACATGGA
GCAGGGACGA TCACGTGGTC ACTTGAAAAT TATGTGAGGT CCGGGGCGAC
GATGTACGGC GCGGCGAACT CTCAAACACT CACACAGCCA AAACCGCTTC
GTGTTCGTCT TTGTTCCAAG CGACCGTGTG GTGTGTTTGT AGTAGTTCGC
CGGCGCCGCA CATCGTCGCC CCGGATCTGA CAAATTAAGC TTTCGTTGCT
TTTCCACGAT TGTGCATTTT CTGAGCATGC ACTGAATACT ATGATGGATA
TGTTTGGAGG AAGCATTATT CCAATTTGAT GATAATGGTG TTATTTACAC
TTGTTTTCAG CTTGGCAAGG TACTGCGGCT CAAGAAGATT CTAAAAAACA
AGTTGCAGCG GGCACCAAGT TGTATTGCCT TCTCAAGTCA TGAGCAACTC
CTGTGGGGCC ATATCCCAGA ACTGGTTGAG TCGGTCAAAC AAGATTGCTT
GGCTCAAGCC TATGCAGTGC ATGTTATGAG CCAACACCTG GGTGCCAATA
CTAGT
```

Figure 90: Position-2 3'-homology flank sequence (SEQ ID NO:140)

```
ACTAGTCATG TCGATGGTGG GGTATGGTTC AGATTCAGTT CATTTATGTC
CTGTTATTGT GATTTTGATT GGTAACATAT TGACAACCTC GACACTTGGG
ATCAGATTCA GTTCACTTAT GGAAGAAATT GGAGAATTGT GATAATTTAT
CTATAATCAC CCCTACTGAA ATAGAAATAA CATGACATCA ATGTGCATGC
TATTGGATTT TGACACGAAT ATGCTTTATT CTATCATATG TTGGTAATTC
CAGCAGGCAG CAGGCACTAC TCTTTGGATC CACGTGACTT GACAAAGAAA
TCATGCCATC TTTCCACAAT GCAGGTCCGT GTACGTGTTT CTAGGGATTT
TCTGGAGCTT GTCGAAAAGA ATGTTCTTAG CAGCCGTCCT GCTGGGAGAG
TAAATGCAAG TTCAATTGAT AACACTGCTG ATGCCGCTCT TCTAATAGCA
GACCACTCTT TATTTTCTGG TACGTACTCT ATCCCTCTTC TTACCATAAT
CTGAATCTTG TTAAGGTTTA AAATATACGA TTGATTAAGT AAAATCCAGA
GCTCTATTCA TATCTCACGC ACTGATGTTT TGATGAAACG CTTGCAGCAA
GACGGTTGCC TGTTATTTCT ATTTGCATTA GACAAACAGT CACCTTTGTT
TATAAAGGTC TTTGAATTTG CAGTTCTTAT AGGTTTAAGT TTGCAACTGT
TACTTACAAC AGCCCAATGG GTAGCATCAA GATTGTTTTT TTCAGTGATT
CATAACTTAA CTCTTGGTTA AACCGCTAGA ACATGGTTGG TGTCTTAAAA
TGCAACTGGT CCTGAGGCCG TAACCTGAAA TCATTGTACG TCGAC
```

Figure 91: Upstream (5'-) IPP2K genomic sequence of the ZFN targeted regions (SEQ ID NO:141)

```
TGGACGGAGC GAGAGCCAGA ATTCGACGCT GGCGGCGGCG CGTCGCCAAT
ACGCAGCGCG GATGTGGAGC CACATGCAAA CGTGTGTCCG CCCGCGTGGC
GTCCACTCTC CCTCCACGTT TCGGCGTCCT CGTCGCCTTC CTGGGAAATC
TCCAGCTACT GCCCACTGCC CCTTCCCTTC AGTCCCTTTC CCCGGGCTGT
GGTACCAGTA CTAGTACCAG CATCTCTTCA GGCTCCACCA AGCGCAGACA
CCGCAGCAGC GGCAGCAGCA CGATCCGGTG ACCCCCGCC GCGTCCAGCC
TGCTCCTCCG GTGATCGCCG GACTGGCGGG GTAGGAACCA GCGGAGCGCA
GCCCGCCTCC TTCCGCTGGT AAGAGTGACG CCCGCCCGCT CCTCCCTTCG
CTCGCTTCCT TGCTCTTCCG ATTCTGGCGT ACCAGTCTCA CCGCGGCTTG
GGGATTTGAT GCGGAGCTAG TTAACCAGCA GAGC
```

Figure 92: Downstream (3'-) IPP2K genomic sequence of the ZFN targeted regions (SEQ ID NO:142)

```
ATTGTTTTTT TCAGTGATTC ATAACTTAAC TCTTGGTTAA ACCGCTAGAA
CATGGTTGGT GTCTTAAAAT GCAACTGGTC CTGAGGCCGT AACCTGAAAT
CATTGTACTT TTCTCTCATT TCTTTAGATA TTTCCAAAAC TCTACATTAG
ATGATTTATG TTTGCTTACT TAGTCTTTCT TAATCTCAGG CAATCCTAAG
GGTAGCAGCT GCATAGCTGT AGAGATAAAG GTACTTTGCA AGCTTCCTCT
TTTATTCTTA TTTTTCATTT CTTATGTATA TTTCTCCTCA ACCATTTGAC
TTCTTTTCGG CATGCTCTAC CTTGCAGGCC AAATGTGGGT TTCTGCCATC
ATCAGAATAT ATATCAGAAG ATAATACTAT CAAGAAACTA GTAACGAGAT
ATAAGATGCA TCAGCACCTC AAATTTTATC AGGGTGAGGT GTGTAGATTG
GAATGCTTGA TGCCTTGATC CAAGATAAAA TTCCACTCTC TTTTGCGCAC
TTAAAAAACA TCCATCGATG ATACAAACTT GATCAAAATA CCTTAAGGCT
TGTTATTTAC GGCACTGTTG TAATATTATA CCGTCTCTTG CTTTTTGACA
TCAGGTTGAT TCCCAATACA TTCTTGCACA CATTTCAGAT ATCGAAGACT
AGTGAGTACA ATCCTCTTGA TCTATTTTCT GGGTCAAAAG AGAGAATATG
CATGGCCATC AAGTCCCTTT TCTCAACTC
```

OPTIMIZED NON-CANONICAL ZINC FINGER PROTEINS

CROSS-REFERENCE TO RELATED APPLICATIONS

The present application claims the benefit of U.S. Provisional Application No. 60/874,911, filed Dec. 14, 2006 and U.S. Provisional Application No. 60/932,497 filed May 30, 2007, both of which disclosures are hereby incorporated by reference in their entireties herein.

TECHNICAL FIELD

The present disclosure is in the fields of genome engineering, gene targeting, targeted chromosomal integration, protein expression and epigenome editing.

BACKGROUND

Sequence-specific binding of proteins to DNA, RNA, protein and other molecules is involved in a number of cellular processes such as, for example, transcription, replication, chromatin structure, recombination, DNA repair, RNA processing and translation. The binding specificity of cellular binding proteins that participate in protein-DNA, protein-RNA and protein-protein interactions contributes to development, differentiation and homeostasis.

Zinc finger proteins (ZFPs) are proteins that can bind to DNA in a sequence-specific manner. Zinc fingers were first identified in the transcription factor TFIIIA from the oocytes of the African clawed toad, *Xenopus laevis*. A single zinc finger domain of this class of ZFPs is about 30 amino acids in length, and several structural studies have demonstrated that it contains a beta turn (containing two conserved cysteine residues) and an alpha helix (containing two conserved histidine residues), which are held in a particular conformation through coordination of a zinc atom by the two cysteines and the two histidines. This class of ZFPs is also known as C2H2 ZFPs. Additional classes of ZFPs have also been suggested. See, e.g., Jiang et al. (1996) J. Biol. Chem. 271:10723-10730 for a discussion of Cys-Cys-His-Cys (C3H) ZFPs. To date, over 10,000 zinc finger sequences have been identified in several thousand known or putative transcription factors. Zinc finger domains are involved not only in DNA recognition, but also in RNA binding and in protein-protein binding. Current estimates are that this class of molecules will constitute about 2% of all human genes.

Most zinc finger proteins have conserved cysteine and histidine residues that tetrahedrally-coordinate the single zinc atom in each finger domain. In particular, most ZFPs are characterized by finger components of the general sequence: -Cys-$(X)_{2-4}$-Cys-$(X)_{12}$-His-$(X)_{3-5}$-His- (SEQ ID NO: 1), in which X represents any amino acid (the $C_2H_2$ ZFPs). The zinc-coordinating sequences of this most widely represented class contain two cysteines and two histidines with particular spacings. The folded structure of each finger contains an antiparallel β-turn, a finger tip region and a short amphipathic α-helix. The metal coordinating ligands bind to the zinc ion and, in the case of zif268-type zinc fingers, the short amphipathic α-helix binds in the major groove of DNA. In addition, the structure of the zinc finger is stabilized by certain conserved hydrophobic amino acid residues (e.g., the residue directly preceding the first conserved Cys and the residue at position +4 of the helical segment of the finger) and by zinc coordination through the conserved cysteine and histidine residues.

Canonical (C2H2) zinc finger proteins having alterations in positions making direct base contacts, 'supporting' or 'buttressing' residues immediately adjacent to the base-contacting positions, and positions capable of contacting the phosphate backbone of the DNA have been described. See, e.g., U.S. Pat. Nos. 6,007,988; 6,013,453; 6,140,081; 6,866,997; 6,746,838; 6,140,081; 6,610,512; 7,101,972; 6,453,242; 6,785,613; 7,013,219; PCT WO 98/53059; Choo et al. (2000) Curr. Opin. Struct. Biol. 10:411-416; Segal et al. (2000) Curr. Opin. Chem. Biol. 4:34-39.

In addition, zinc finger proteins containing zinc fingers with modified zinc coordinating residues have also been described (see, e.g., U.S. Patent Application Nos. 20030108880, 20060246567 and 20060246588; the disclosures of which are incorporated by reference). However, while zinc finger proteins containing these non-canonical zinc fingers retain gene transcription regulatory function, their ability to act as zinc finger nucleases (ZFNs) is in some cases diminished relative to zinc finger proteins consisting exclusively of canonical, C2H2 zinc fingers.

Thus, there remains a need, particularly in the construction of zinc finger nucleases, for additional engineered zinc finger binding proteins containing zinc fingers having optimized non-canonical zinc coordinating regions.

SUMMARY

The present disclosure provides zinc finger DNA-binding domains with alterations in at least one zinc coordinating residue. In particular, described herein are CCHC zinc fingers. These CCHC zinc fingers can further comprise additional alterations (substitutions, insertions and/or deletions), in the vicinity of the zinc coordinating residues, for example in the residues surrounding the C-terminal-most zinc coordinating residue of the zinc finger. Zinc finger polypeptides and fusion proteins comprising one or more these CCHC zinc fingers, polynucleotides encoding these zinc fingers and fusion proteins and methods of using these zinc finger polypeptides and/or fusion proteins are also described.

Thus, the present disclosure encompasses, but is not limited to, the following numbered embodiments:

1. A zinc finger protein comprising a non-canonical (non-$C_2H_2$) zinc finger, wherein the non-canonical zinc finger has a helical portion involved in DNA binding and wherein the zinc-coordinating region of the helical portion comprises the amino acid sequence $HX_1X_2RCX_L$ (SEQ ID NO:2); and wherein the zinc finger protein is engineered to bind to a target sequence.

2. The zinc finger protein of embodiment 1, wherein $X_1$ is A and $X_2$ is Q.

3. The zinc finger protein of embodiment 1, wherein $X_1$ is K and $X_2$ is E.

4. The zinc finger protein of embodiment 1, wherein $X_1$ is T and $X_2$ is R.

5. The zinc finger protein of embodiment 1, wherein $X_L$ is G.

6. A zinc finger protein comprising two or more zinc fingers, wherein at least one zinc finger comprises the sequence Cys-$(X^A)_{2-4}$-Cys-$(X^B)_{12}$-His-$(X^C)_{3-5}$-Cys-$(X^D)_{1-10}$ (SEQ ID NO:3), where $X^A$, $X^B$, $X^C$ and $X^D$ can be any amino acid.

7. The zinc finger protein of any of embodiments 1 to 6, comprising any of the sequences shown in any of Tables 1, 2, 3 or 4.

8. The zinc finger protein of any of embodiments 6 or 7, wherein $X^D$ comprises the sequence QLV or QKP.

9. The zinc finger protein of embodiment 8, wherein the sequence QLV or QKP are the 3 C-terminal amino acid residues of the zinc finger.

10. The zinc finger protein of any of embodiments 6 to 9, wherein $X^D$ comprises 1, 2 or 3 Gly (G) residues.

11. A zinc finger protein comprising a plurality of zinc fingers, wherein at least one of the zinc fingers comprises a CCHC zinc finger according to any of embodiments 1 to 10.

12. The zinc finger protein of embodiment 11, wherein the zinc finger protein comprises 3, 4, 5 or 6 zinc fingers.

13. The zinc finger protein of embodiment 11 or 12, wherein finger 2 comprises the CCHC zinc finger.

14. The zinc finger protein of any of embodiments 11 to 13, wherein the C-terminal zinc finger comprises the CCHC finger.

15. The zinc finger protein of any of embodiments 11 to 14, wherein at least two zinc fingers comprise the CCHC zinc finger.

16. The zinc finger protein of any of embodiments 11 to 15, wherein the zinc finger protein comprises any of the sequences shown in Table 8 and is engineered to bind to a target sequence in an IPP2-K gene.

17. A fusion protein comprising a zinc finger protein of any of embodiments 1 to 16 and one or more functional domains.

18. A fusion protein comprising:
 (a) a cleavage half-domain,
 (b) the zinc finger protein of any of embodiments 1 to 16, and
 (c) a ZC linker interposed between the cleavage half-domain and the zinc finger protein.

19. The fusion protein of embodiment 18, wherein the length of the ZC linker is 5 amino acids.

20. The fusion protein of embodiment 19, wherein the amino acid sequence of the ZC linker is GLRGS (SEQ ID NO:4).

21. The fusion protein of embodiment 18, wherein the length of the ZC linker is 6 amino acids.

22. The fusion protein of embodiment 21, wherein the amino acid sequence of the ZC linker is GGLRGS (SEQ ID NO:5).

23. A polynucleotide encoding a zinc finger protein according to any of embodiments 1 to 16 or a fusion protein according to any of embodiments 17 to 22.

24. A method for targeted cleavage of cellular chromatin in a plant cell, the method comprising expressing, in the cell, a pair of fusion proteins according to any of embodiments 18 to 22; wherein:
 (a) the target sequences of the fusion proteins are within ten nucleotides of each other; and
 (b) the fusion proteins dimerize and cleave DNA located between the target sequences.

25. A method of targeted genetic recombination in a host plant cell, the method comprising:
 (a) expressing, in the host cell, a pair of fusion proteins according to any of embodiments 18 to 22, wherein the target sequences of the fusion proteins are present in a chosen host target locus; and
 (b) identifying a recombinant host cell which exhibits a sequence alteration in the host target locus.

26. The method of either of embodiment 24 or 25, wherein the sequence alteration is a mutation selected from the group consisting of a deletion of genetic material, an insertion of genetic material, a substitution of genetic material and any combination thereof.

27. The method of any of embodiments 24 to 26, further comprising introducing an exogenous polynucleotide into the host cell.

28. The method of embodiment 27, wherein the exogenous polynucleotide comprises sequences homologous to the host target locus.

29. The method of any of embodiments 24 to 28, wherein the plant is selected from the group consisting of a monocotyledon, a dicotyledon, gymnosperms and eukaryotic algae.

30. The method of embodiment 29, wherein the plant is selected from the group consisting of maize, rice, wheat, potato, soybean, tomato, tobacco, members of the *Brassica* family, and *Arabidopsis*.

31. The method of any of embodiments 24 to 29 wherein the plant is a tree.

32. The method of any of embodiments 24 to 31, wherein the target sequences are in an IPP2K gene.

33. A method for reducing the level of phytic acid in seeds, the method comprising inactivating or altering an IPP2-K gene according to embodiment 32.

34. A method for making phosphorous more metabolically available in seed, the method comprising inactivating or altering an IPP2-K gene according to embodiment 32.

35. A plant cell comprising a zinc finger protein according to any of embodiments 1 to 16, a fusion protein according to any of embodiments 17 to 22 or a polynucleotide according to embodiment 23.

36. The plant cell of embodiment 35, wherein the cell is a seed.

37. The plant cell of embodiment 36, wherein seed is a corn seed.

38. The plant cell of any of embodiments 35 to 37, wherein IPP2-K is partially or fully inactivated.

39. The plant cell of embodiment 38, wherein the levels of phytic acid in the seed are reduced.

40. The plant cell of embodiments 35 to 39, wherein metabolically available levels of phosphorous in the cell are increased.

BRIEF DESCRIPTION OF THE DRAWINGS

FIG. 4 is a linear schematic representation of plasmid pDAB1585, a target vector for tobacco.

FIG. 5 is a schematic representation of plasmid pDAB1585, a target vector for tobacco.

FIGS. 6A and 6B depict zinc finger nucleases (ZFN). FIG. 6A is a schematic depicting ZFN binding. FIG. 6B shows the sequence (SEQ ID NOs:200-201) of the target sequence.

FIG. 7 is a schematic representation of plasmid pDAB1400.

FIG. 8 is a schematic representation of plasmid pDAB782.

FIG. 9 is a schematic representation of plasmid pDAB1582.

FIG. 10 is a schematic representation of plasmid pDAB354.

FIG. 11 is a schematic representation of plasmid pDAB1583.

FIG. 12 is a schematic representation of plasmid pDAB2407.

FIG. 13 is a schematic representation of plasmid pDAB1584.

FIG. 14 is a schematic representation of plasmid pDAB2418.

FIG. 15 is a schematic representation of plasmid pDAB4045.

FIG. 16 is a schematic representation of plasmid pDAB1575.

FIG. 17 is a schematic representation of plasmid pDAB1577.

FIG. 18 is a schematic representation of plasmid pDAB1579.

FIG. 19 is a schematic representation of plasmid pDAB1580.

FIG. 20 is a schematic representation of plasmid pDAB3401.

FIG. 21 is a schematic representation of plasmid pDAB1570.

FIG. 22 is a schematic representation of plasmid pDAB1572.

FIG. 23 is a schematic representation of plasmid pDAB4003.

FIG. 24 is a schematic representation of plasmid pDAB1571.

FIG. 25 is a schematic representation of plasmid pDAB7204.

FIG. 26 is a schematic representation of plasmid pDAB1573.

FIG. 27 is a schematic representation of plasmid pDAB1574.

FIG. 28 is a schematic representation of plasmid pDAB1581.

FIG. 29 is a schematic representation of plasmid pDAB1576.

FIG. 30 are schematic representations of plasmid pDAB1600.

FIG. 31 is a schematic representation of plasmid pDAB3731.

FIG. 32 is a schematic representation of plasmid pDAB4322.

FIG. 33 is a schematic representation of plasmid pDAB4331.

FIG. 34 is a schematic representation of plasmid pDAB4332.

FIG. 35 is a schematic representation of plasmid pDAB4333.

FIG. 36 is a schematic representation of plasmid pDAB4334.

FIG. 37 is a schematic representation of plasmid pDAB4336.

FIG. 38 is a schematic representation of plasmid pDAB4339.

FIG. 39 is a schematic representation of plasmid pDAB4321.

FIG. 40 is a schematic representation of plasmid pDAB4323.

FIG. 41 is a schematic representation of plasmid pDAB4341.

FIG. 42 is a schematic representation of plasmid pDAB4342.

FIG. 43 is a schematic representation of plasmid pDAB4343.

FIG. 44 is a schematic representation of plasmid pDAB4344.

FIG. 45 is a schematic representation of plasmid pDAB4346.

FIG. 46 is a schematic representation of plasmid pDAB4330.

FIG. 47 is a schematic representation of plasmid pDAB4351.

FIG. 48 is a schematic representation of plasmid pDAB4356.

FIG. 49 is a schematic representation of plasmid pDAB4359.

FIG. 50 is a schematic representation of plasmid pDAB7002.

FIG. 51 is a schematic representation of plasmid pDAB7025.

FIG. 52 is a schematic representation of plasmid pDAB1591.

FIG. 53 is a schematic representation of plasmid pcDNA3.1-SCD27a-L0-FokI, the DNA template used for PCR amplification of Scd27 ZFN.

FIG. 54 is a schematic representation of plasmid pDAB1594.

FIG. 55 is a schematic representation of plasmid pDAB1598.

FIG. 56 is a schematic representation of plasmid pDAB1577.

FIG. 57 is a schematic representation of plasmid pDAB1578.

FIG. 58 is a schematic representation of plasmid pDAB1601, the PAT gene control vector.

FIG. 59 is a schematic depicting predicted intrachromosomal homologous recombination stimulated by IL-1-FokI fusion protein.

FIG. 60 is a schematic representation of plasmid pDAB1590, a positive GFP-expressing control.

FIG. 61 is a schematic depicting predicted inter-chromosomal homologous recombination stimulated by IL-1 zinc finger-FokI fusion protein.

FIG. 62 is a schematic depicting predicted inter-chromosomal homologous recombination stimulated by Scd27 Zinc Finger-FokI fusion protein.

FIG. 63 is a gel depicting PCR Analysis of the Recombinants. First 4 lanes on the left are labeled above the gel. Lanes labeled 1-5 show HR events from the transformation of BY2-380 with C3H IL-1-FokI fusion protein gene and lanes labeled 6-7 show HR events from the transformation of BY2-380 with C3H SCD27-FokI fusion protein gene.

FIG. 64 shows a maize IPP2K gene sequence (SEQ ID NO:6), derived from HiII cell culture, and which served as a design template for the engineering of ZFNs targeted to maize IPP2K.

FIG. 65, panels A to E, depict a ZFN Expression vector cloning scheme. A stepwise cloning strategy was used to generate ZFN expression constructs. Individual ZFN-encoding genes were cloned into vectors pVAX-N2A-NLSop2-EGFP-FokMono (A) and pVAX-C2A-NLSop2-EGFP-FokMono (B) to create a dual-protein cassette (C). This cassette was ligated into pDAB3872 (D) to generate a final plasmid (E) for expression of the ZFN heterodimer.

FIG. 66 depicts ZFN binding in a maize IPP2K gene. Two ZFN proteins are required to carry out double-stranded cleavage of DNA. The sequence surrounding the cleavage site (indicated with a downward arrow) is shown (SEQ ID NO:7). One protein (8075) was bound to sequence CTGTGGGGC-CAT (top strand) (SEQ ID NO:8), where another protein (8684, 8685, or 8686) bound to downstream sequence (CTGACCAACTCAGCCAG, bottom strand) (SEQ ID NO:9).

FIG. 67 depicts sequences of wild-type (top sequence, SEQ ID NO:10) and ZFN clone 127 (bottom sequence, SEQ ID NO:11). The cleavage target for this ZFN is highlighted in a gray box.

FIG. 68 shows an alignment of multiple deletions resulting from non-homologous end joining (NHEJ) of a ZFN-mediated dsDNA break in the maize IPP2K gene as detecting by 454 sequencing (SEQ ID NOs:173-197). The cleavage target for this ZFN is highlighted in a gray box.

FIG. 70 depicts plasmid pDAB7471, constructed as described in Example 18B.

FIG. 71 depicts plasmid pDAB7451, constructed as described in Example 18C.

FIG. 72 is a schematic depicting an exemplary autonomous herbicide-tolerance gene expression cassette. This construction comprises a complete promoter-transcriptional unit (PTU) containing a promoter, herbicide tolerance gene and poly adenylation (polyA) termination sequence as described in Example 18D.

FIG. 82 depicts amplification of donor-DNA specific sequences from genomic DNA. The presence of a 317 bp product is diagnostic for the presence of donor DNA containing the PAT gene inserted into the genome of maize calli lines #61-72 as described in Example 20C. HiII indicates a wild-type negative control.

FIG. 83 depicts amplification of the 5'-boundary between donor-DNA and maize genomic sequences specific for IPP2K. Secondary PCR products derived from targeted integration of donor into the IPP2K gene were diagnosed by the presence of DNA fragments of 1.65 Kbp as described in Example 21A. HiII indicates a wild-type negative control.

FIG. 87 depicts the sequence of the position-1 5'-homology flank (SEQ ID NO:171).

FIG. 88 depicts the sequence of the position-1 3'-homology flank (SEQ ID NO:172).

FIG. 89 depicts the sequence of the position-2 5'-homology flank (SEQ ID NO:139).

FIG. 90 depicts the sequence of the position-2 3'-homology flank (SEQ ID NO:140).

FIG. 91 depicts the sequence of an upstream (5'-) IPP2K genomic sequence of the ZFN targeted regions (SEQ ID NO:141).

FIG. 92 depicts the sequence of a downstream (3'-) IPP2K genomic sequence of the ZFN targeted regions (SEQ ID NO: 142).

DETAILED DESCRIPTION

Figure 1:
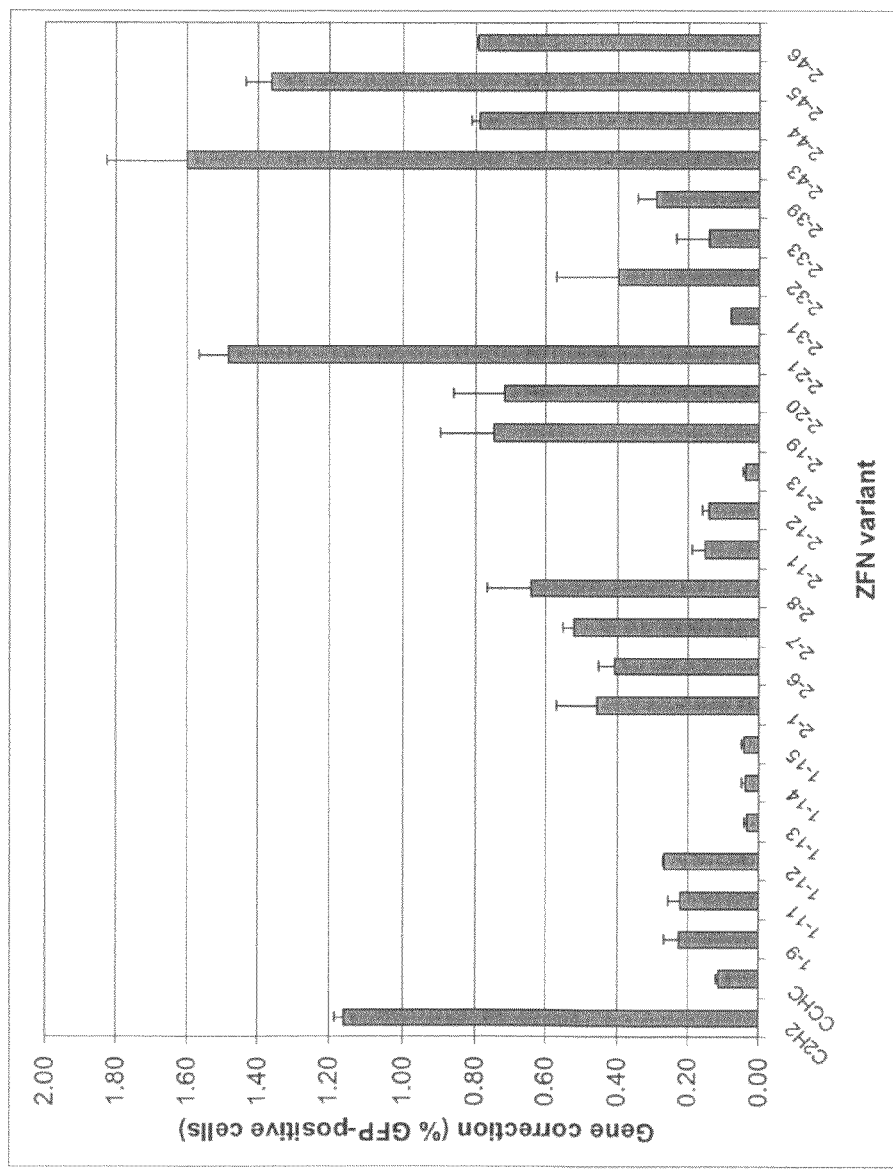
FIG. 1 is a graph depicting gene correction rates, as measured by the percentage of cells expressing GFP, in a GFP cell reporter assay system as described in U.S. Patent No. 2005/0064474 and below. The ZFN variants are designated "X-Y," where "X" refers to the Table number and "Y" refers to the number given the zinc finger in the particularly selected table. For instance, "2-21" refers to a ZFN having a finger comprising the sequence shown in Table 2 in the row numbered 21, namely HAQRCGLRGSQLV (SEQ ID NO:53).

Disclosed herein are compositions comprising zinc finger binding polypeptides (ZFPs) containing non-canonical zinc fingers of the format Cys-Cys-His-Cys. Inasmuch as zinc coordination provides the principal folding energy for zinc fingers, adjustment of zinc coordinating residues provides a ready means for modifying finger stability and structure, which impacts on a variety of important functional features of zinc finger proteins, including, for example, cellular half life, interactions with other cellular factors, DNA binding specificity and affinity, and relative orientation of functional domains.

Zinc finger proteins comprising non-canonical zinc fingers such as those disclosed in U.S. Patent Application Nos. 20030108880; 20060246567; and 20060246588 have been shown to bind DNA and alter transcription. However, when incorporated into zinc finger nucleases (ZFNs, see, for example US Patent Application Publication No. 2005/0064474), these previously described non-canonical zinc finger proteins can sometimes exhibit sub-optimal activity in cleaving the target DNA.

Described herein are zinc finger proteins comprising one or more CCHC zinc fingers, in which specific sequences surrounding the C-terminal pair of zinc coordinating residues have been altered. Also described herein are fusion proteins, for example zinc finger nucleases (ZFNs), comprising these optimized non-canonical zinc fingers, wherein the ZFNs cleave the target DNA at rates comparable to cleavage achieved using ZFNs comprising canonical (CCHH) zinc fingers.

Fusion polypeptides, as disclosed herein, can enhance or suppress transcription of a gene, and/or cleave a target sequence. Polynucleotides encoding optimized non-canonical zinc fingers, and polynucleotides encoding fusion proteins comprising one or more optimized non-canonical zinc fingers are also provided. Additionally provided are pharmaceutical compositions comprising a therapeutically effective amount of any of the zinc finger-nucleotide binding polypeptides described herein or functional fragments thereof; or a therapeutically effective amount of a nucleotide sequence that encodes any of the modified zinc finger-nucleotide binding polypeptides or functional fragments thereof, in combination with a pharmaceutically acceptable carrier. Further provided are agricultural compositions comprising an agronomically effective amount of any of the zinc finger-nucleotide binding polypeptides described herein or functional fragments thereof; or an agronomically effective amount of a nucleotide sequence that encodes any of the modified zinc finger-nucleotide binding polypeptides or functional fragments thereof, in combination with an agriculturally acceptable carrier. Also provided are screening methods for obtaining a modified zinc finger-nucleotide binding polypeptide which binds to a genomic sequence.

Genomic sequences include those present in chromosomes, episomes, organellar genomes (e.g., mitochondria, chloroplasts), artificial chromosomes and any other type of nucleic acid present in a cell such as, for example, amplified sequences, double minute chromosomes and the genomes of endogenous or infecting bacteria and viruses. Genomic sequences can be normal (i.e., wild-type) or mutant; mutant sequences can comprise, for example, insertions, deletions, substitutions, translocations, rearrangements, and/or point mutations. A genomic sequence can also comprise one of a number of different alleles.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261; and 6,785,613; see, also WO 98/53058; WO 98/53059; WO 98/53060; WO 02/016536 and WO 03/016496; and U.S. Pat. Nos. 6,746,838; 6,866,997; and 7,030,215.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; U.S. Pat. No. 6,733,970; U.S. Pat. No. RE39,229; and WO 95/19431; WO 96/06166; WO 98/53057; WO 98/54311; WO 00/27878; WO 01/60970 WO 01/88197 and WO 02/099084.

A "non-canonical" zinc finger protein is a protein comprising a non-canonical (non-C2H2) zinc finger. A non-canonical zinc finger thus comprises a substitution, addition and/or deletion of at least one amino acid, compared to a naturally occurring C2H2 zinc finger protein. Non-limiting examples of non-canonical zinc fingers include those comprising zinc coordinating residues (from amino to carboxy) of Cys-Cys-His-Cys (e.g., C3H).

A "homologous sequence" refers to a first sequence which shares a degree of sequence identity with a second sequence, and whose sequence may be identical to that of the second sequence. A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). An exemplary method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GENBANK™+EMBL+DDBJ+PDB+GENBANK™ CDS translations+Swiss protein+Spupdate+PIR. Details of these programs can be found on the internet. With respect to sequences described herein, the range of desired degrees of sequence identity is approximately 35% to 100% and any integer value therebetween. Typically the percent identities between sequences are at least 35%-40%; 40%-45%; 45%-50%; 50%-60%; 60%-70%; 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (e.g., double-strand cleavage activity).

The terms "cleavage domain" and "cleavage half-domain" includes wild-type domains and portions or mutants of cleavage domains or cleavage half-domains that retains the ability to multimerize (e.g., dimerize) to form a functional cleavage domain.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, an *Agrogacterium tumefacians* T-strand, a plasmid or episome introduced into a cell, or a chromosome that is not normally present in the cell. Exogenous nucleic acids or polynucleotides can, however, contain sequences that are homologous or identical to endogenous sequences. With respect to a particular endogenous genomic region, an "exogenous sequence" refers to a nucleotide sequence that is not present at that region. Such an exogenous sequence may be present at another endogenous chromosomal location or it may not be present in the genome at all. Thus, an exogenous polynucleotide can contain both exogenous and endogenous sequences: for example, a transgene flanked by sequences homologous to a genomic region. Such exogenous nucleic acids are used in methods for targeted integration and targeted recombination as described infra. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, for example, covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 25,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Zinc Finger Binding Domains

Described herein are non-canonical zinc finger binding domains and polynucleotides encoding these zinc finger binding domains. In certain embodiments, the non-canonical zinc finger binding domains described herein are C3H zinc fingers, in which one of the two conserved zinc-coordinating histidine residues is converted to cysteine. In additional embodiments, the C-terminal-most histidine residue is converted to a cysteine residue, generating a "CCHC protein."

A zinc finger binding domain can comprise one or more zinc fingers (e.g., 2, 3, 4, 5, 6, 7, 8, 9 or more zinc fingers), and can be engineered to bind to any target sequence (e.g., a genomic sequence). Zinc finger binding domains may bind to DNA, RNA and/or protein. Typically, a single zinc finger domain is about 30 amino acids in length. Zinc fingers include both canonical $C_2H_2$ zinc fingers (i.e., those in which the zinc ion is coordinated by two cysteine and two histidine residues) and non-canonical zinc fingers including, for example, $C_3H$ zinc fingers (those in which the zinc ion is coordinated by three cysteine residues and one histidine residue). See also U.S. Patent Application Nos. 20030108880, 20060246567 and 20060246588; the disclosures of which are incorporated by reference.

Structural studies have demonstrated that a canonical zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines. The non-canonical zinc fingers disclosed herein retain this beta-beta-alpha structure.

The non-canonical zinc fingers described herein may be naturally occurring zinc finger binding domains. However, more typically, non-canonical zinc fingers as described herein include one or more zinc finger components in which at least one of the zinc-coordinating cysteine or histidine residues has been replaced with one or more amino acids. For example, in certain embodiments, the C-terminal His residue of a canonical zinc finger binding module is replaced with a Cys residue.

The CCHC zinc fingers described herein can also comprise one or more alterations (with respect to the sequence of a naturally-occurring C2H2 zinc finger) in the sequence of amino acids residues other than the zinc coordinating residues. Such alterations can comprise substitutions, deletions, and/or insertions. Amino acids may be altered anywhere in the zinc finger. Non-limiting examples of alterations include: (1) substitutions of single residues surrounding the altered zinc-coordinating residue; (2) addition of extra residues before or after the altered zinc-coordinating residue, (e.g., in cases in which the C-terminal-most His residue is converted to Cys, addition of extra amino acid residues may facilitate zinc coordination by compensating for the shorter cysteine side chain); and/or (3) substitution of residues located between the His and Cys residues of a naturally-occurring CCHC zinc finger into the corresponding region of a non-canonical CCHC zinc finger.

In certain embodiments, the zinc finger proteins described herein include at least one zinc finger comprising a non-canonical (non-$C_2H_2$) zinc finger, wherein the non-canonical zinc finger has a helical portion involved in DNA binding and wherein the zinc-coordinating region of the helical portion comprises the amino acid sequence $HX_1X_2RCX_L$ (SEQ ID NO:2); and wherein the zinc finger protein is engineered to bind to a target sequence. In certain embodiments, $X_1$ is A or K or T; $X_2$ is Q or E or R; and $X_L$ is G.

In other embodiments, the non-canonical zinc fingers described herein have the general structure: Cys-$(X^A)_{2-4}$-Cys-$(X^B)_{12}$-His-$(X^C)_{3-5}$-Cys-$(X^D)_{1-10}$ (SEQ ID NO:3), where $X^A$, $X^B$, $X^C$ and $X^D$ represent any amino acid. In embodiments in which $X^C$ comprises 3 residues (i) at least one of these residues is altered as compared to a canonical CCHC zinc finger; and/or (ii) $X^D$ comprises at least one deletion, substitution or insertion as compared to a canonical CCHH zinc finger. In certain embodiments, $X^D$ comprises the sequence QLV or QKP. In other embodiments $X^D$ comprises one or more (e.g., 1, 2, 3, 4, 5, 6, 7, 8, 9, or 10) Gly (G) residues.

Partial amino acid sequence (including and C-terminal to the 3$^{rd}$ zinc coordinating residue) of exemplary non-canonical zinc fingers are shown in Tables 1, 2, 3 and 4. In all Tables, the two C-terminal-most (i.e., the third and fourth) zinc coordinating residues (H and C) are underlined. The alterations (e.g., substitutions, insertions, deletions) as compared to the sequence of the "wild-type" non-canonical finger (Row 2 of Tables 1 and 3) are shown in double underlining.

TABLE 1

| | | |
|---|---|---|
| C2H2 | HTKIHLRGSQLV (wild type canonical) (SEQ ID NO: 12) | |
| 1 = C3H | HTKICLRGSQLV (wild-type altered to non-canonical) (SEQ ID NO: 13) | |
| 2 | HTKGCLRGSQLV (SEQ ID NO: 14) | |
| 3 | HTKACLRGSQLV (SEQ ID NO: 15) | |
| 4 | HTKVCLRGSQLV (SEQ ID NO: 16) | |
| 5 | HTKLCLRGSQLV (SEQ ID NO: 17) | |
| 6 | HTKSCLRGSQLV (SEQ ID NO: 18) | |
| 7 | HTKNCLRGSQLV (SEQ ID NO: 19) | |
| 8 | HTKKCLRGSQLV (SEQ ID NO: 20) | |
| 9 | HTKRCLRGSQLV (SEQ ID NO: 21) | |
| 10 | HTKIGGCLRGSQLV (SEQ ID NO: 22) | |
| 11 | HTKICGLRGSQLV (SEQ ID NO: 23) | |
| 12 | HTKICGGLRGSQLV (SEQ ID NO: 24) | |
| 13 | HTKIGCGLRGSQLV (SEQ ID NO: 25) | |
| 14 | HTKIGCGGLRGSQLV (SEQ ID NO: 26) | |
| 15 | HLKGNCLRGSQLV (SEQ ID NO: 27) | |
| 16 | HLKGNCPAGSQLV (SEQ ID NO: 28) | |
| 17 | HSEGGCLRGSQLV (SEQ ID NO: 29) | |
| 18 | HSEGGCPGGSQLV (SEQ ID NO: 30) | |
| 19 | HSSSNCLRGSQLV (SEQ ID NO: 31) | |
| 20 | HSSSNCTIGSQLV (SEQ ID NO: 32) | |

TABLE 2

| 1  | HTKICGGGLRGSQLV   | (SEQ ID NO: 33) |
| 2  | HTKIGCGGGLRGSQLV  | (SEQ ID NO: 34) |
| 3  | HTKIGGCLRGSQLV    | (SEQ ID NO: 35) |
| 4  | HTKIGGCGLRGSQLV   | (SEQ ID NO: 36) |
| 5  | HTKIGGCGGLRGSQLV  | (SEQ ID NO: 37) |
| 6  | HTKRCGLRGSQLV     | (SEQ ID NO: 38) |
| 7  | HTKRCGGLRGSQLV    | (SEQ ID NO: 39) |
| 8  | HTKRCGGGLRGSQLV   | (SEQ ID NO: 40) |
| 9  | HTKRGCLRGSQLV     | (SEQ ID NO: 41) |
| 10 | HTKRGCGLRGSQLV    | (SEQ ID NO: 42) |
| 11 | HTKRGCGGLRGSQLV   | (SEQ ID NO: 43) |
| 12 | HTKRGCGGGLRGSQLV  | (SEQ ID NO: 44) |
| 13 | HTKRGGCLRGSQLV    | (SEQ ID NO: 45) |
| 14 | HTKRGGCGLRGSQLV   | (SEQ ID NO: 46) |
| 15 | HTKRGGCGGLRGSQLV  | (SEQ ID NO: 47) |
| 16 | HLKGNCGLRGSQLV    | (SEQ ID NO: 48) |
| 17 | HLKGNCGGLRGSQLV   | (SEQ ID NO: 49) |
| 18 | HLKGNCGGGLRGSQLV  | (SEQ ID NO: 50) |
| 19 | HKERCGLRGSQLV     | (SEQ ID NO: 51) |
| 20 | HTRRCGLRGSQLV     | (SEQ ID NO: 52) |
| 21 | HAQRCGLRGSQLV     | (SEQ ID NO: 53) |
| 22 | HKKFYCGLRGSQLV    | (SEQ ID NO: 54) |
| 23 | HKKHYCGLRGSQLV    | (SEQ ID NO: 55) |
| 24 | HKKYTCGLRGSQLV    | (SEQ ID NO: 56) |
| 25 | HKKYYCGLRGSQLV    | (SEQ ID NO: 57) |
| 26 | HKQYYCGLRGSQLV    | (SEQ ID NO: 58) |
| 27 | HLLKKCGLRGSQLV    | (SEQ ID NO: 59) |
| 28 | HQKFPCGLRGSQLV    | (SEQ ID NO: 60) |
| 29 | HQKKLCGLRGSQLV    | (SEQ ID NO: 61) |
| 30 | HQIRGCGLRGSQLV    | (SEQ ID NO: 62) |
| 31 | HIKRQSCGLRGSQLV   | (SEQ ID NO: 63) |
| 32 | HIRRYTCGLRGSQLV   | (SEQ ID NO: 64) |
| 33 | HISSKKCGLRGSQLV   | (SEQ ID NO: 65) |
| 34 | HKIQKACGLRGSQLV   | (SEQ ID NO: 66) |
| 35 | HKRIYTCGLRGSQLV   | (SEQ ID NO: 67) |
| 36 | HLKGQNCGLRGSQLV   | (SEQ ID NO: 68) |
| 37 | HLKKDGCGLRGSQLV   | (SEQ ID NO: 69) |
| 38 | HLKYTPCGLRGSQLV   | (SEQ ID NO: 70) |
| 39 | HTKRCGRGSQLV      | (SEQ ID NO: 71) |
| 40 | HTKIGCGGRGSQLV    | (SEQ ID NO: 72) |

TABLE 2-continued

| 41 | HLKGNCGRGSQLV   | (SEQ ID NO: 73) |
| 42 | HLKGNCGGGSQLV   | (SEQ ID NO: 74) |
| 43 | HIRTCTGSQKP     | (SEQ ID NO: 75) |
| 44 | HIRTCGTGSQKP    | (SEQ ID NO: 76) |
| 45 | HIRTGCTGSQKP    | (SEQ ID NO: 77) |
| 46 | HIRTGCGTGSQKP   | (SEQ ID NO: 78) |
| 47 | HIRRCTGSQKP     | (SEQ ID NO: 79) |
| 48 | HIRRGCTGSQKP    | (SEQ ID NO: 80) |

TABLE 3

| wt | HTKIHTGSQKP  | (SEQ ID NO: 81) |
| 1a | HTKICTGSQKP  | (SEQ ID NO: 82) |
| 2a | HTKRCTGSQKP  | (SEQ ID NO: 83) |
| 3a | HAQRCTGSQKP  | (SEQ ID NO: 84) |
| 4a | HTKICGTGSQKP | (SEQ ID NO: 85) |
| 5a | HTKRCGTGSQKP | (SEQ ID NO: 86) |
| 6a | HAQRCGTGSQKP | (SEQ ID NO: 87) |

TABLE 4

| wt  | HTKIHLRGSQLV | (SEQ ID NO: 88) |
| 7a  | HAQRCGG      | (SEQ ID NO: 89) |
| 8a  | HAQRCGGG     | (SEQ ID NO: 90) |
| 9a  | HTKICGGG     | (SEQ ID NO: 91) |
| 10a | HTKRCGGG     | (SEQ ID NO: 92) |
| 11a | HAQRCG       | (SEQ ID NO: 93) |

As noted above, a ZFP can include any number of zinc finger binding domains, for example at least 3 zinc fingers. Furthermore, one, more than one, or all of the zinc fingers may be non-canonical zinc fingers as described herein.

In certain embodiments, the C-terminal-most finger of a multi-finger zinc finger protein comprises a canonical zinc finger. In other embodiments, the C-terminal-most finger of a multi-finger zinc finger protein comprises a CCHC finger as described herein, for example a CCHC finger comprising one or more amino acid insertions C-terminal to the C-terminal-most zinc-coordinating Cys residue. See Examples 1-5 describing 4-fingered zinc finger proteins in which finger 2 (F2) and/or finger 4 (F4) are non-canonical zinc fingers as described herein.

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection (e.g., methods in which a plurality of different zinc finger sequences are screened against a single target nucleotide sequence). Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261. Additional design methods are disclosed, for example, in U.S. Pat. Nos. 6,746,838; 6,785,613; 6,866,997; and 7,030,215. Enhancement of binding specificity for zinc finger binding domains has been described, for example, in co-owned U.S. Pat. No. 6,794,136.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the zinc finger motifs do not bind to overlapping subsites, a six-nucleotide target sequence is bound by a two-finger binding domain; a nine-nucleotide target sequence is bound by a three-finger binding domain, etc. Binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain. See, for example, U.S. Pat. Nos. 6,479,626; 6,903,185 and 7,153,949 and U.S. Patent Application Publication No. 2003/0119023; the disclosures of which are incorporated by reference.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linker sequences between certain of the zinc fingers may increase the affinity and/or specificity of binding by the binding domain. See, for example, U.S. Pat. No. 6,479,626 and U.S. Patent Application Publication No. 2003/0119023; the disclosures of which are incorporated by reference. Accordingly, multi-finger zinc finger binding domains can also be characterized with respect to the presence and location of non-canonical inter-finger linkers. Use of longer inter-finger linkers can also facilitate the binding of a zinc finger protein to target sites comprising non-contiguous nucleotides. As a result, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites.

A target subsite is a nucleotide sequence (generally 3 or 4 nucleotides) that is bound by a single zinc finger. However, it is not necessary for a target site to be a multiple of three nucleotides. For example, in cases in which cross-strand interactions occur (see, e.g., U.S. Pat. Nos. 6,453,242 and 6,794,136), one or more of the individual zinc fingers of a multi-finger binding domain can bind to overlapping quadruplet subsites. See also U.S. Pat. Nos. 6,746,838 and 6,866,997. To provide but one example, a three-finger binding domain can bind to a 10-nucleotide target site comprising three overlapping 4-nucleotide subsites.

Selection of a sequence in cellular chromatin for binding by a zinc finger domain (e.g., a target site) can be accomplished, for example, according to the methods disclosed in co-owned U.S. Pat. No. 6,453,242 (Sep. 17, 2002), which also discloses methods for designing ZFPs to bind to a selected sequence. It will be clear to those skilled in the art that simple visual inspection of a nucleotide sequence can also be used for selection of a target site. Accordingly, any means for target site selection can be used in the methods described herein.

Multi-finger zinc finger proteins can be constructed by joining individual zinc fingers obtained, for example, by design or selection. Alternatively, binding modules consisting of two zinc fingers can be joined to one another, using either canonical or longer, non-canonical inter-finger linkers (see above) to generate four- and six-finger proteins. Such two finger modules can be obtained, for example, by selecting for two adjacent fingers, which bind a particular six-nucleotide target sequence, in the context of a multi-finger protein (generally three fingers). See, for example, WO 98/53057 and U.S. Patent Application Publication No. 2003/0119023; the disclosures of which are incorporated by reference. Alternatively, two-finger modules can be constructed by assembly of individual zinc fingers.

Thus, the zinc finger domains described herein can be used individually or in various combinations to construct multi-finger zinc finger proteins that bind to any target site.

Distance between sequences (e.g., target sites) refers to the number of nucleotides or nucleotide pairs intervening between two sequences, as measured from the edges of the sequences nearest each other.

In embodiments using ZFNs, for example in which cleavage depends on the binding of two zinc finger domain/cleavage half-domain fusion molecules to separate target sites, the two target sites can be on opposite DNA strands. In other embodiments, both target sites are on the same DNA strand. See, for example, WO 2005/084190; the disclosure of which is incorporated by reference.

Polynucleotides encoding zinc fingers or zinc finger proteins are also within the scope of the present disclosure. These polynucleotides can be constructed using standard techniques and inserted into a vector, and the vector can be introduced into a cell (see below for additional disclosure regarding vectors and methods for introducing polynucleotides into cells) such that the encoded protein is expressed in the cell.

Fusion Proteins

Fusion proteins comprising one or more non-canonical zinc finger components described herein are also provided.

Fusion molecules are constructed by methods of cloning and biochemical conjugation that are well known to those of skill in the art. Fusion molecules comprise a CCHC-containing ZFP and, for example, a cleavage domain, a cleavage half-domain, a transcriptional activation domain, a transcriptional repression domain, a component of a chromatin remodeling complex, an insulator domain, a functional fragment of any of these domains; and/or any combinations of two or more functional domains or fragments thereof.

In certain embodiments, fusion molecules comprise a modified plant zinc finger protein and at least two functional domains (e.g., an insulator domain or a methyl binding protein domain and, additionally, a transcriptional activation or repression domain).

Fusion molecules also optionally comprise a nuclear localization signal (such as, for example, that from the SV40 T-antigen or the maize Opaque-2 NLS) and an epitope tag (such as, for example, FLAG or hemagglutinin). Fusion proteins (and nucleic acids encoding them) are designed such that the translational reading frame is preserved among the components of the fusion.

Methods for design and construction of fusion proteins (and polynucleotides encoding same) are known to those of skill in the art. For example, methods for the design and construction of fusion protein comprising zinc finger proteins (and polynucleotides encoding same) are described in co-owned U.S. Pat. Nos. 6,453,242 and 6,534,261.

Polynucleotides encoding such fusion proteins are also within the scope of the present disclosure. These polynucleotides can be constructed using standard techniques and inserted into a vector and the vector can be introduced into a cell (see below for additional disclosure regarding vectors and methods for introducing polynucleotides into cells).

An exemplary functional domain for fusing with a ZFP DNA-binding domain, to be used for repressing gene expression, is a KRAB repression domain from the human KOX-1 protein (see, e.g., Thiesen et al., New Biologist 2, 363-374 (1990); Margolin et al., Proc. Natl. Acad. Sci. USA 91, 4509-4513 (1994); Pengue et al., Nucl. Acids Res. 22:2908-2914 (1994); Witzgall et al., Proc. Natl. Acad. Sci. USA 91, 4514-4518 (1994). The KOX domain is also suitable for use as a repression domain. Another suitable repression domain is methyl binding domain protein 2B (MBD-2B) (see, also Hendrich et al. (1999) *Mamm Genome* 10:906-912 for description of MBD proteins). Another useful repression domain is that associated with the v-ErbA protein. See, for example, Damm, et al. (1989) *Nature* 339:593-597; Evans (1989) *Int. J. Cancer Suppl.* 4:26-28; Pain et al. (1990) *New Biol.* 2:284-294; Sap et al. (1989) *Nature* 340:242-244; Zenke et al. (1988) *Cell* 52:107-119; and Zenke et al. (1990) *Cell* 61:1035-1049. Additional exemplary repression domains include, but are not limited to, thyroid hormone receptor (TR), SID, MBD1, MBD2, MBD3, MBD4, MBD-like proteins, members of the DNMT family (e.g., DNMT1, DNMT3A, DNMT3B), Rb, MeCP1 and MeCP2. See, for example, Zhang et al. (2000) *Ann Rev Physiol* 62:439-466; Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Suitable domains for achieving activation include the HSV VP16 activation domain (see, e.g., Hagmann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-4968 (1992)).

Additional exemplary activation domains include, but are not limited to, p300, CBP, PCAF, SRC1 PvALF, and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

Additional functional domains are disclosed, for example, in co-owned U.S. Pat. No. 6,933,113. Further, insulator domains, chromatin remodeling proteins such as ISWI-containing domains, and methyl binding domain proteins suitable for use in fusion molecules are described, for example, in co-owned International Publications WO 01/83793 and WO 02/26960.

In other embodiments, the fusion protein is a zinc finger nuclease (ZFN) comprising one or more CCHC zinc fingers as described herein and a cleavage domain (or cleavage half-domain). The zinc fingers can be engineered to recognize a target sequence in any genomic region of choice and, when introduced into a cell, will result in binding of the fusion protein(s) to its (their) binding site(s) and cleavage within or near said genomic region. Such cleavage can result in alteration of the nucleotide sequence of the genomic region (e.g., mutation) following non-homologous end joining. Alternatively, if an exogenous polynucleotide containing sequences homologous to the genomic region is also present in such a cell, homologous recombination occurs at a high rate between the genomic region and the exogenous polynucleotide, following targeted cleavage by the ZFNs. Homologous recombination can result in targeted sequence replacement or targeted integration of exogenous sequences, depending on the nucleotide sequence of the exogenous polynucleotide.

The non-canonical zinc fingers described herein provide improved cleavage function when incorporated into ZFNs. As described in the Examples, 4-fingered ZFNs containing at least one CCHC finger as described herein cleave at least as well as nucleases containing exclusively CCHH fingers. In certain embodiments, when the C-terminal finger comprises a non-canonical CCHC zinc finger, the residues between the third and fourth zinc-coordinating residues (i.e., between the C-terminal His and Cys residues) are different than those present in a canonical CCHH zinc finger, and one or more glycine residues (e.g., 1, 2, 3, 4, 5 or more) are inserted after the C-terminal Cys residue.

The cleavage domain portion of the ZFNs disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases,* Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, providing the cleavage half-domain requires dimerization for cleavage activity. In general, two fusion proteins are required for targeted cleavage of genomic DNA if the fusion proteins comprise cleavage half-domains. Alternatively, a single protein comprising two cleavage half-domains can be used. The two cleavage half-domains can be derived from the same endonuclease, or each cleavage half-domain can be derived from a different endonuclease. In addition, the target sites for the two fusion proteins are disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotide pairs or by 15-18 nucleotide pairs. In additional embodiments, the target sites are within ten nucleotide pairs of each other. However any integral number of nucleotides or nucleotide pairs can intervene between two target sites (e.g., from 2 to 50 nucleotides or more). In general, the point of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using ZFNs comprising zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure and, for example, in US Patent Application Publication No. 2005/0064474; the disclosure of which is incorporated by reference.

In additional embodiments, a FokI cleavage half-domain may include one or more mutations at any amino acid residue which affects dimerization. Such mutations can be useful for preventing one of a pair of ZFP/FokI fusions from undergoing homodimerization which can lead to cleavage at undesired sequences. For example, amino acid residues at positions 446, 447, 479, 483, 484, 486, 487, 490, 491, 496, 498, 499, 500, 531, 534, 537, and 538 of FokI are all close enough to the dimerization interface to influence dimerization. Accordingly, amino acid sequence alterations at one or more of the aforementioned positions can be used to alter the dimerization properties of the cleavage half-domain. Such changes can be introduced, for example, by constructing a library containing (or encoding) different amino acid residues at these positions and selecting variants with the desired properties, or by rationally designing individual mutants. In addition to preventing homodimerization, it is also possible that some of these mutations may increase the cleavage efficiency, compared to that obtained with two wild-type cleavage half-domains.

Thus, for targeted cleavage using a pair of ZFP/FokI fusions, one or both of the fusion proteins can comprise one or more amino acid alterations that inhibit self-dimerization, but allow heterodimerization of the two fusion proteins to occur such that cleavage occurs at the desired target site. In certain embodiments, alterations are present in both fusion proteins, and the alterations have additive effects; i.e., homodimerization of either fusion, leading to aberrant cleavage, is minimized or abolished, while heterodimerization of the two fusion proteins is facilitated compared to that obtained with wild-type cleavage half-domains.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

Cleavage half-domains may also be provided in separate molecules. For example, two fusion polypeptides may be expressed in a cell, wherein each polypeptide comprises a binding domain and a cleavage half-domain. The cleavage half-domains can have the same amino acid sequence or different amino acid sequences, so long as they function to cleave the DNA. Further, the binding domains bind to target sequences which are typically disposed in such a way that, upon binding of the fusion polypeptides, the two cleavage half-domains are presented in a spatial orientation to each other that allows reconstitution of a cleavage domain (e.g., by dimerization of the half-domains), thereby positioning the half-domains relative to each other to form a functional cleavage domain, resulting in cleavage of cellular chromatin in a region of interest. Generally, cleavage by the reconstituted cleavage domain occurs at a site located between the two target sequences. One or both of the proteins can be engineered to bind to its target site.

Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

In certain embodiments, the components of a ZFN are arranged such that the zinc finger domain is nearest the amino terminus of the fusion protein, and the cleavage half-domain is nearest the carboxy-terminus. This mirrors the relative orientation of the cleavage domain in naturally-occurring dimerizing cleavage domains such as those derived from the Fok I enzyme, in which the DNA-binding domain is nearest the amino terminus and the cleavage half-domain is nearest the carboxy terminus. In these embodiments, dimerization of the cleavage half-domains to form a functional nuclease is brought about by binding of the fusion proteins to sites on opposite DNA strands, with the 5' ends of the binding sites being proximal to each other.

In this orientation, the C-terminal-most zinc finger is proximal to the FokI cleavage half-domain. It has previously been determined that non-canonical zinc finger proteins bind their DNA targets most efficiently when a CCHC-type zinc finger is present as the C-terminal-most finger. It is therefore possible that the presence of previously-described CCHC-type zinc fingers in proximity to the FokI cleavage half-domain inhibited its function. If this is the case, the presently-disclosed optimized CCHC zinc fingers apparently do not exhibit this postulated inhibitory activity.

In additional embodiments, the components of the fusion proteins (e.g., ZFP-Fok I fusions) are arranged such that the cleavage half-domain is nearest the amino terminus of the fusion protein, and the zinc finger domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger domain nearest the carboxy terminus located to the 5' side of the binding site of the second fusion protein containing the zinc finger domain nearest the amino terminus. See also WO 2005/084190; the disclosure of which is incorporated by reference.

The amino acid sequence between the zinc finger domain and the cleavage domain (or cleavage half-domain) is denoted the "ZC linker." The ZC linker is to be distinguished from the inter-finger linkers discussed above. See, e.g., U.S. Patent Publications 20050064474A1 and 20030232410, and International Patent Publication WO 2005/084190; the disclosures of which are incorporated by reference, for details on obtaining ZC linkers that optimize cleavage.

Expression Vectors

A nucleic acid encoding one or more ZFPs or ZFP fusion proteins (e.g., ZFNs) can be cloned into a vector for transformation into prokaryotic or eukaryotic cells for replication and/or expression. Vectors can be prokaryotic or eukaryotic vectors, including but not limited to, plasmids, shuttle vectors, insect vectors, binary vectors (see, e.g., U.S. Pat. No. 4,940,838; Horsch et al (1984) *Science* 233:496-498, and Fraley et al (1983) *Proc. Nat'l. Acad. Sci. USA* 80:4803) and the like. A nucleic acid encoding a ZFP can also be cloned into an expression vector, for administration to a plant cell.

To express the fusion proteins, sequences encoding the ZFPs or ZFP fusions are typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; 3$^{rd}$ ed., 2001); Kriegler, *Gene Transfer and Expression: A Laboratory Manual* (1990); and *Current Protocols in Molecular Biology* (Ausubel et al., supra. Bacterial expression systems for expressing the ZFP are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The promoter used to direct expression of a ZFP-encoding nucleic acid depends on the particular application. For example, a strong constitutive promoter suited to the host cell is typically used for expression and purification of ZFPs.

In contrast, when a ZFP is administered in vivo for plant gene regulation (see, "Nucleic Acid Delivery to Plant Cells" section below), either a constitutive or an inducible promoter is used, depending on the particular use of the ZFP. Non-limiting examples of plant promoters include promoter sequences derived from *A. thaliana* ubiguitin-3 (ubi-3) (Callis, et al., 1990, J. Biol. Chem. 265-12486-12493); *A. tumifaciens* mannopine synthase (Δmas) (Petolino et al., U.S. Pat. No. 6,730,824); and/or Cassava Vein Mosaic Virus (CsVMV) (Verdaguer et al., 1996, Plant Molecular Biology 31:1129-1139). See, also, Examples.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the ZFP, and signals required, e.g., for efficient polyadenylation of the transcript, transcriptional termination, ribosome binding sites, or translation termination. Additional elements of the cassette may include, e.g., enhancers, and heterologous splicing signals.

The particular expression vector used to transport the genetic information into the cell is selected with regard to the intended use of the ZFP, e.g., expression in plants, animals, bacteria, fungus, protozoa, etc. (see expression vectors described below). Standard bacterial and animal expression vectors are known in the art and are described in detail, for example, U.S. Patent Publication 20050064474A1 and International Patent Publications WO05/084190, WO05/014791 and WO03/080809; the disclosures of which are incorporated by reference.

Standard transfection methods can be used to produce bacterial, mammalian, yeast or insect cell lines that express large quantities of protein, which can then be purified using standard techniques (see, e.g., Colley et al., *J. Biol. Chem.* 264: 17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds., 1983).

Any of the well known procedures for introducing foreign nucleotide sequences into such host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Nucleic Acid Delivery to Plant Cells

As noted above, DNA constructs may be introduced into (e.g., into the genome of) a desired plant host by a variety of conventional techniques. For reviews of such techniques see, for example, Weissbach & Weissbach *Methods for Plant*

Molecular Biology (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced into a plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) *Science* 233:496-498, and Fraley et al (1983) *Proc. Nat'l. Acad. Sci. USA* 80:4803.

In addition, gene transfer may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al (1985) *Science* 227:1229-1231). Generally, the *Agrobacterium* transformation system is used to engineer dicotyledonous plants (Bevan et al (1982) *Ann. Rev. Genet* 16:357-384; Rogers et al (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al (1984) *EMBO J* 3:3039-3041; Hooykass-Van Slogteren et al (1984) *Nature* 311:763-764; Grimsley et al (1987) *Nature* 325:1677-179; Boulton et al (1989) *Plant Mol. Biol.* 12:31-40; and Gould et al (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

The disclosed methods and compositions can be used to insert exogenous sequences into a predetermined location in a plant cell genome. This is useful inasmuch as expression of an introduced transgene into a plant genome depends critically on its integration site. Accordingly, genes encoding, e.g., nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In certain embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Glycine, Gossypium, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna*, and *Zea*.

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the amount of mRNA has increased, it can be assumed that the corresponding endogenous gene is being expressed at a greater rate than before. Other methods of measuring gene and/or CYP74B activity can be used. Different types of enzymatic assays can be used, depending on the substrate used and the method of detecting the increase or decrease of a reaction product or by-product. In addition, the levels of and/or CYP74B protein expressed can be measured immunochemically, i.e., ELISA, RIA, EIA and other antibody based assays well known to those of skill in the art, such as by electrophoretic detection assays (either with staining or western blotting). The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

ZFPs and expression vectors encoding ZFPs can be administered directly to the plant for targeted cleavage and/or recombination.

Administration of effective amounts is by any of the routes normally used for introducing ZFP into ultimate contact with the plant cell to be treated. The ZFPs are administered in any suitable manner. Suitable methods of administering such compositions are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of pharmaceutical compositions that are available (see, e.g., *Remington's Pharmaceutical Sciences*, 17$^{th}$ ed. 1985)).

Applications

Zinc finger proteins comprising one or more non-canonical zinc fingers as described herein are useful for all genome regulation and editing applications for which canonical C2H2 ZFPs are currently used, including but not limited to: gene activation; gene repression; genome editing (cleavage, targeted insertion, replacement or deletion); and epigenome editing (via the targeting of covalent modifications of histones or of DNA).

ZFNs comprising non-canonical zinc fingers as disclosed herein can be used to cleave DNA at a region of interest in cellular chromatin (e.g., at a desired or predetermined site in a genome, for example, in a gene, either mutant or wild-type). For such targeted DNA cleavage, a zinc finger binding domain is engineered to bind a target site at or near the predetermined cleavage site, and a fusion protein comprising the engineered zinc finger binding domain and a cleavage domain is expressed in a cell. Upon binding of the zinc finger portion of the fusion protein to the target site, the DNA is cleaved near the target site by the cleavage domain. The exact site of cleavage can depend on the length of the ZC linker.

Alternatively, two ZFNs, each comprising a zinc finger binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two zinc finger binding domains. One or both of the zinc finger binding domains can be engineered.

For targeted cleavage using a zinc finger binding domain-cleavage domain fusion polypeptide, the binding site can encompass the cleavage site, or the near edge of the binding site can be 1, 2, 3, 4, 5, 6, 10, 25, 50 or more nucleotides (or any integral value between 1 and 50 nucleotides) from the cleavage site. The exact location of the binding site, with respect to the cleavage site, will depend upon the particular cleavage domain, and the length of the ZC linker. For methods in which two fusion polypeptides, each comprising a zinc finger binding domain and a cleavage half-domain, are used, the binding sites generally straddle the cleavage site. Thus the near edge of the first binding site can be 1, 2, 3, 4, 5, 6, 10, 25 or more nucleotides (or any integral value between 1 and 50 nucleotides) on one side of the cleavage site, and the near edge of the second binding site can be 1, 2, 3, 4, 5, 6, 10, 25 or more nucleotides (or any integral value between 1 and 50 nucleotides) on the other side of the cleavage site. Methods for mapping cleavage sites in vitro and in vivo are known to those of skill in the art.

Once introduced into, or expressed in, the target cell, the fusion protein binds to the target sequence and cleaves at or near the target sequence. The exact site of cleavage depends on the nature of the cleavage domain and/or the presence and/or nature of linker sequences between the binding and cleavage domains. In cases where two ZFNs, each comprising a cleavage half-domain, are used, the distance between the near edges of the binding sites can be 1, 2, 3, 4, 5, 6, 7, 8, 9, 10, 25 or more nucleotides (or any integral value between 1 and 50 nucleotides). Optimal levels of cleavage can also depend on both the distance between the binding sites of the two ZFNs (see, for example, Smith et al. (2000) *Nucleic Acids Res.* 28:3361-3369; Bibikova et al. (2001) *Mol. Cell. Biol.* 21:289-297) and the length of the ZC linker in each ZFN. See, also, U.S. Patent Publication 20050064474A1 and International Patent Publications WO05/084190, WO05/014791 and WO03/080809, the disclosures of which are incorporated by reference.

Two ZFNs, each comprising a cleavage half-domain, can bind in the region of interest in the same or opposite polarity, and their binding sites (i.e., target sites) can be separated by any number of nucleotides, e.g., from 0 to 50 nucleotide pairs or any integral value therebetween. In certain embodiments, the binding sites for two fusion proteins, each comprising a zinc finger binding domain and a cleavage half-domain, can be located between 5 and 18 nucleotide pairs apart, for example, 5-8 nucleotide pairs apart, or 15-18 nucleotide pairs apart, or 6 nucleotide pairs apart, or 16 nucleotide pairs apart, or within 10 nucleotide pairs of each other, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for many applications, including targeted recombination and targeted mutagenesis, cleavage within a range of nucleotides is generally sufficient, and cleavage between particular base pairs is not required.

As noted above, a fusion protein(s) can be expressed in a cell following the introduction, into the cell, of polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

In certain embodiments, targeted cleavage in a genomic region by a ZFN results in alteration of the nucleotide sequence of the region, following repair of the cleavage event by non-homologous end joining (NHEJ).

In other embodiments, targeted cleavage in a genomic region by a ZFN can also be part of a procedure in which a genomic sequence (e.g., a region of interest in cellular chromatin) is replaced with a homologous non-identical sequence (i.e., by targeted recombination) via homology-dependent mechanisms (e.g., insertion of a donor sequence comprising an exogenous sequence together with one or more sequences that are either identical, or homologous but non-identical, with a predetermined genomic sequence (i.e., a target site)). Because double-stranded breaks in cellular DNA stimulate cellular repair mechanisms several thousand-fold in the vicinity of the cleavage site, targeted cleavage with ZFNs as described herein allows for the alteration or replacement (via homology-directed repair) of sequences at virtually any site in the genome.

Targeted replacement of a selected genomic sequence requires, in addition to the ZFNs described herein, the introduction of an exogenous (donor) polynucleotide. The donor polynucleotide can be introduced into the cell prior to, concurrently with, or subsequent to, expression of the ZFNs. The donor polynucleotide contains sufficient homology to a genomic sequence to support homologous recombination (or homology-directed repair) between it and the genomic sequence to which it bears homology. Approximately 25, 50 100, 200, 500, 750, 1,000, 1,500, 2,000 nucleotides or more of sequence homology (or any integral value between 10 and 2,000 nucleotides, or more) will support homologous recombination. Donor polynucleotides can range in length from 10 to 5,000 nucleotides (or any integral value of nucleotides therebetween) or longer.

It will be readily apparent that the nucleotide sequence of the donor polynucleotide is typically not identical to that of the genomic sequence that it replaces. For example, the sequence of the donor polynucleotide can contain one or more substitutions, insertions, deletions, inversions or rearrangements with respect to the genomic sequence, so long as sufficient homology with chromosomal sequences is present. Such sequence changes can be of any size and can be as small as a single nucleotide pair. Alternatively, a donor polynucleotide can contain a non-homologous sequence (i.e., an exogenous sequence, to be distinguished from an exogenous polynucleotide) flanked by two regions of homology. Additionally, donor polynucleotides can comprise a vector molecule containing sequences that are not homologous to the region of interest in cellular chromatin. Generally, the homologous region(s) of a donor polynucleotide will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

To simplify assays (e.g., hybridization, PCR, restriction enzyme digestion) for determining successful insertion of sequences from the donor polynucleotide, certain sequence differences may be present in the donor sequence as compared to the genomic sequence. Preferably, if located in a coding region, such nucleotide sequence differences will not change the amino acid sequence, or will make silent amino acid changes (i.e., changes which do not affect the structure or function of the protein). The donor polynucleotide can optionally contain changes in sequences corresponding to the zinc finger domain binding sites in the region of interest, to prevent cleavage of donor sequences that have been introduced into cellular chromatin by homologous recombination.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by bacteria or viruses (e.g., *Agrobacterium*, *Rhizobium* sp. NGR234, *Sinorhizoboium meliloti*, *Mesorhizobium loti*, tobacco mosaic virus, potato virus X, cauliflower mosaic virus and cassava vein mosaic virus. See, e.g., Chung et al. (2006) *Trends Plant Sci.* 11(1):1-4.

For alteration of a chromosomal sequence, it is not necessary for the entire sequence of the donor to be copied into the chromosome, as long as enough of the donor sequence is copied to effect the desired sequence alteration.

The efficiency of insertion of donor sequences by homologous recombination is inversely related to the distance, in the cellular DNA, between the double-stranded break and the site at which recombination is desired. In other words, higher homologous recombination efficiencies are observed when the double-stranded break is closer to the site at which recombination is desired. In cases in which a precise site of recombination is not predetermined (e.g., the desired recombination event can occur over an interval of genomic sequence), the length and sequence of the donor nucleic acid, together with the site(s) of cleavage, are selected to obtain the desired recombination event. In cases in which the desired event is designed to change the sequence of a single nucleotide pair in a genomic sequence, cellular chromatin is cleaved within 10,000 nucleotides on either side of that nucleotide pair. In certain embodiments, cleavage occurs within 1,000, 500, 200, 100, 90, 80, 70, 60, 50, 40, 30, 20, 10, 5, or 2 nucleotides, or any integral value between 2 and 1,000 nucleotides, on either side of the nucleotide pair whose sequence is to be changed.

Targeted insertion of exogenous sequences into a genomic region is accomplished by targeted cleavage in the genomic region using ZFNs, in concert with provision of an exogenous (donor) polynucleotide containing the exogenous sequences.

The donor polynucleotide also typically contains sequences flanking the exogenous sequence, which contains sufficient homology to the genomic region to support homology-directed repair of the double-strand break in the genomic sequence, thereby inserting the exogenous sequence into the genomic region. Therefore, the donor nucleic acid can be of any size sufficient to support integration of the exogenous sequence by homology-dependent repair mechanisms (e.g., homologous recombination). Without wishing to be bound by any particular theory, the regions of homology flanking the exogenous sequence are thought to provide the broken chromosome ends with a template for re-synthesis of the genetic information at the site of the double-stranded break.

Targeted integration of exogenous sequences, as described above, can be used to insert a marker gene at a chosen chromosomal location. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Exemplary marker genes thus include, but are not limited to, β-glucuronidase (GUS), phosphinothricin N-acetyl transferase (PAT, BAR), neomycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase. In certain embodiments, targeted integration is used to insert a RNA expression construct, e.g., sequences responsible for regulated expression of micro RNA or siRNA. Promoters, enhancers and additional transcription regulatory sequences can also be incorporated in a RNA expression construct.

Further increases in efficiency of targeted recombination, in cells comprising a zinc finger/nuclease fusion molecule and a donor DNA molecule, are achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding the protein into the cell or by introducing into the cell an engineered ZFP which activates expression of the gene encoding the protein. Cell-cycle arrest is also achieved by inhibiting the activity of cyclins and CDKs, for example, using RNAi methods (e.g., U.S. Pat. No. 6,506,559) or by introducing into the cell an engineered ZFP which represses expression of one or more genes involved in cell-cycle progression such as, for example, cyclin and/or CDK genes. See, e.g., co-owned U.S. Pat. No. 6,534,261 for methods for the synthesis of engineered zinc finger proteins for regulation of gene expression.

As described above, the disclosed methods and compositions for targeted cleavage can be used to induce mutations in a genomic sequence. Targeted cleavage can also be used to create gene knock-outs (e.g., for functional genomics or target validation) and to facilitate targeted insertion of a sequence into a genome (i.e., gene knock-in). Insertion can be by means of replacements of chromosomal sequences through homologous recombination or by targeted integration, in which a new sequence (i.e., a sequence not present in the region of interest), flanked by sequences homologous to the region of interest in the chromosome, is inserted at a predetermined target site. The same methods can also be used to replace a wild-type sequence with a mutant sequence, or to convert one allele to a different allele.

Targeted cleavage of infecting or integrated plant pathogens can be used to treat pathogenic infections in a plant host, for example, by cleaving the genome of the pathogen such that its pathogenicity is reduced or eliminated. Additionally, targeted cleavage of genes encoding receptors for plant viruses can be used to block expression of such receptors, thereby preventing viral infection and/or viral spread in the plant.

Exemplary plant pathogens include, but are not limited to, plant viruses such as Alfamoviruses, Alphacryptoviruses, Badnaviruses, Betacryptoviruses, Bigeminiviruses, Bromoviruses, Bymoviruses, Capilloviruses, Carlaviruses, Carmoviruses, Caulimoviruses, Closteroviruses, Comoviruses, Cucumoviruses, Cytorhabdoviruses, Dianthoviruses, Enamoviruses, Fabaviruses, Fijiviruses, Furoviruses, Hordeiviruses, Hybrigeminiviruses, Idaeoviruses, Ilarviruses, Ipomoviruses, Luteoviruses, Machlomoviruses, Macluraviruses, Marafiviruses, Monogeminiviruses, Nanaviruses, Necroviruses, Nepoviruses, Nucleorhabdoviruses, Oryzaviruses, Ourmiaviruses, Phytoreoviruses, Potexviruses, Potyviruses, Rymoviruses, satellite RNAs, satelliviruses, Sequiviruses, Sobemoviruses, Tenuiviruses, Tobamoviruses, Tobraviruses, Tombusviruses, Tospoviruses, Trichoviruses, Tymoviruses, Umbraviruses, Varicosaviruses and Waikaviruses; fungal pathogens such as smuts (e.g. Ustilaginales), rusts (Uredinales), ergots (Clavicepts pupurea) and mildew; molds (Oomycetes) such as *Phytophthora infestans* (potato blight); bacterial pathogens such as *Erwinia* (e.g., *E. herbicola*), *Pseudomonas* (e.g., *P. aeruginosa*, *P. syringae*, *P. fluorescense* and *P. putida*), *Ralstonia* (e.g., *R. solanacearum*), *Agrobacterium* and *Xanthomonas*; roundworms (*Nematoda*); and *Phytomyxea* (*Polymyxa* and *Plasmodiophora*).

The disclosed methods for targeted recombination can be used to replace any genomic sequence with a homologous, non-identical sequence. For example, a mutant genomic sequence can be replaced by its wild-type counterpart, thereby providing methods for treatment of plant diseases; providing resistance to plant pathogens; increasing crop yields, etc. In like fashion, one allele of a gene can be replaced by a different allele using the methods of targeted recombination disclosed herein.

In many of these cases, a region of interest comprises a mutation, and the donor polynucleotide comprises the corresponding wild-type sequence. Similarly, a wild-type genomic sequence can be replaced by a mutant sequence, if such is desirable. Indeed, any pathology dependent upon a particular genomic sequence, in any fashion, can be corrected or alleviated using the methods and compositions disclosed herein.

Targeted cleavage and targeted recombination can also be used to alter non-coding sequences (e.g., regulatory sequences such as promoters, enhancers, initiators, terminators, splice sites) to alter the levels of expression of a gene product. Such methods can be used, for example, for therapeutic purposes, alterations in cellular physiology and biochemistry, functional genomics and/or target validation studies.

The methods and compositions described herein can also be used for activation and repression of gene expression using fusions between a non-canonical zinc finger binding domain and a functional domain. Such methods are disclosed, for example, in co-owned U.S. Pat. Nos. 6,534,261; 6,824,978 and 6,933,113; the disclosures of which are incorporated by reference. Additional repression methods include the use of antisense oligonucleotides and/or small interfering RNA (siRNA or RNAi) targeted to the sequence of the gene to be repressed.

In additional embodiments, one or more fusions between a zinc finger binding domain and a recombinase (or functional fragment thereof) can be used, in addition to or instead of the zinc finger-cleavage domain fusions disclosed herein, to facilitate targeted recombination. See, for example, co-owned U.S. Pat. No. 6,534,261 and Akopian et al. (2003) *Proc. Natl. Acad. Sci. USA* 100:8688-8691.

In additional embodiments, the disclosed methods and compositions are used to provide fusions of ZFP binding domains with transcriptional activation or repression domains that require dimerization (either homodimerization or heterodimerization) for their activity. In these cases, a fusion polypeptide comprises a zinc finger binding domain and a functional domain monomer (e.g., a monomer from a dimeric transcriptional activation or repression domain). Binding of two such fusion polypeptides to properly situated target sites allows dimerization so as to reconstitute a functional transcription activation or repression domain.

EXAMPLES

The present invention is further defined in the following Examples, in which all parts and percentages are by weight and degrees are Celsius, unless otherwise stated. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

ZFN Expression Vectors

Expression vectors comprising sequences encoding 4-fingered ZFNs (designated "5-8" and "5-9") as described in Examples 2 and 14 of U.S. Patent Publication 2005/0064474, the disclosure of which is incorporated by reference (See Example 2 of that application) were modified as follows. Briefly, the 5-8 and 5-9 ZFN (comprising 4 zinc finger domains fused to the nuclease domain of the type IIS restriction enzyme FokI (amino acids 384-579 of the sequence of Wah et al. (1998) *Proc. Natl. Acad. Sci. USA* 95:10564-10569) via a four amino acid ZC linker) were modified to a CCHC structure. Additional modifications (substitutions and insertions) were also made to residues between the C-terminal His and Cys zinc coordinating structures and/or C-terminal to the C-terminal Cys to finger 2 and/or finger 4.

Example 2

Gene Correction of eGFP in Reporter Cell Lines

The ability of ZFNs comprising CCHC zinc fingers as described herein to facilitate homologous recombination was tested in the GFP system described in Urnov (2005) *Nature* 435(7042):646-51 and U.S. Patent Publication No. 20050064474 (e.g., Examples 6-11). Briefly, 50 ng of each ZFN and 500 ng of the promoter-less GFP donor (Urnov (2005) *Nature*) were transfected into 500,000 reporter cells, using 2 uL of LIPOFECTAMINE™ 2000 per sample, as per the Invitrogen LIPOFECTAMINE™ 2000 protocol.

Vinblastine was added 24 hours post-transfection at a 0.2 uM final concentration, and was removed 72 hours post-transfection.

The cells were assayed for GFP expression 5 days post-transfection by measuring 40,000 cells per transfection on the Guava bench top FACS analyzer.

As shown in FIG. 1, most ZFNs comprising altered CCHC zinc fingers as shown in Tables 1 and 2 above facilitate homologous recombination at the reporter (GFP) locus, resulting in GFP expression at levels above unmodified CCHC zinc fingers and several performed comparably to ZFNs comprising CCHH zinc fingers. The optimal performing variant when positioned in finger 4 (F4) comprised the following sequence (including and C-terminal to the His zinc coordinating residue): HAQRCGLRGSQLV (SEQ ID NO:53) (the zinc finger in Table 2 designated #21 and shown in FIG. 1 as "2-21"). The optimal performing variant when positioned in finger 2 (F2) comprised the following sequence (including and C-terminal to the His zinc coordinating residue): HIRTCTGSQKP (SEQ ID NO:75) (the zinc finger in Table 2 designated #43 and shown in FIG. 1 as "2-43").

Example 3

Editing of a Chromosomal IL2Rγ Gene by Targeted Recombination

ZFNs as described herein were also assayed in the endogenous IL2Rγ assay described in Urnov (2005) *Nature* 435 (7042):646-51 and Example 2 of U.S. Patent Publication No. 20050064474. Briefly, two and a half micrograms each ZFN expression construct were transfected into 500,000 K562 cells using a NUCLEOFACTOR™ (Amaxa). Genomic DNA was harvested and gene disruption was assayed at the endogenous IL2Rγ locus using the Surveyor endonuclease kit.

Figure 2:
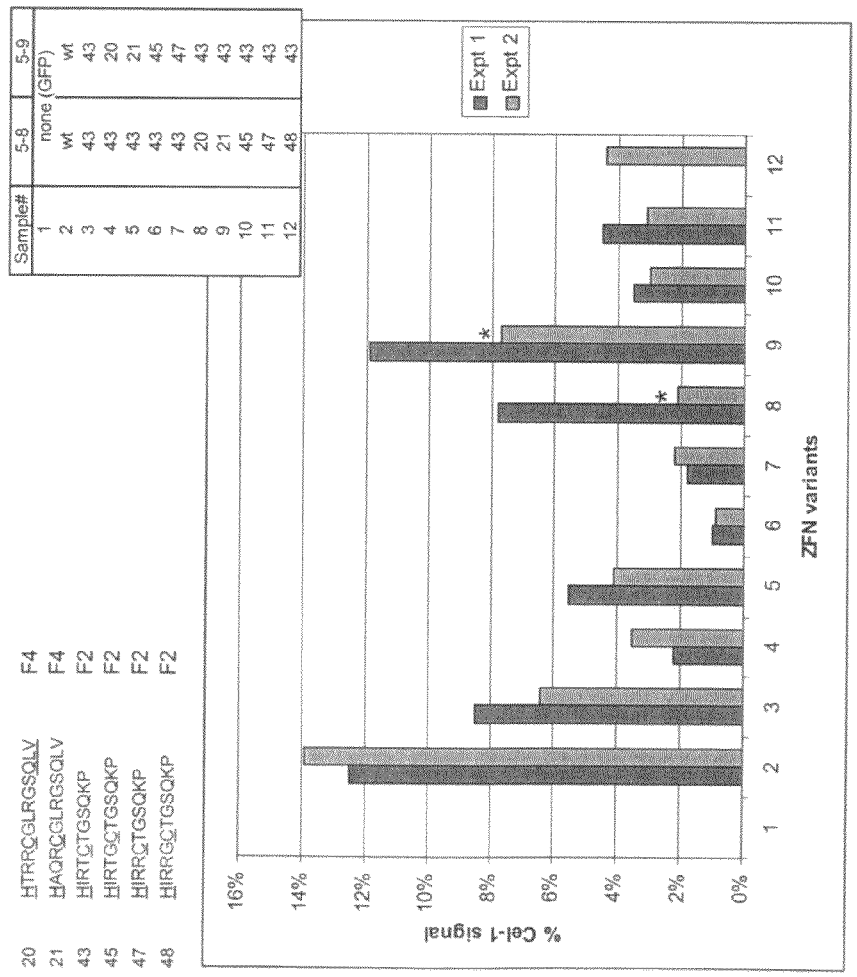
FIG. 2 is a graph depicting percentage of Cel-1 signal resulting from cleavage using various pairs of ZFN variants. The results of two experiments are shown for each pair of ZFNs by reference to sample number. The pairs of variants used for each sample are shown in the box on the upper right corner, where "wt 5-8" and "wt 5-9" refer to canonical ZFN pairs disclosed in Example 14 (Table 17) of U.S. Patent Application No. 2005/0064474. In samples 3-12, the C-terminal region of the recognition helices of finger 2 or finger 4 of the canonical ZFN 5-8 or 5-9 are replaced with non-canonical sequences. Partial sequence of the non-canonical ZFN variants designated 20 (SEQ ID NO:52), 21 (SEQ ID NO:53), 43 (SEQ ID NO:75), 45 (SEC) ID NO:77), 47 (SEQ ID NO:79) and 48 (SEQ ID NO:80) in samples 3-12 and the finger position of these variants within the 4-fingered ZFN are shown in the top left corner above the graph. The asterix above the bar depicting results from experiment 2 for samples 8 and 9 indicates background in the lane, resulting in an underestimation of ZFN efficiency.

ZFNs are shown in the upper left of FIG. 2. In particular, altered zinc finger 20 refers to a CCHC zinc finger comprising the sequence HTRRCGLRGSQLV (SEQ ID NO:52); zinc finger 21 comprises the sequence HAQRCGLRGSQLV (SEQ ID NO:53); zinc finger 43 comprises the sequence HIRTCTGSQKP (SEQ ID NO:75); zinc finger 45 comprises the sequence HIRTGCTGSQKP (SEQ ID NO:77); zinc finger 47 comprises the sequence HIRRCTGSQKP (SEQ ID NO:79); and zinc finger 48 comprises the sequence HIRRGCTGSQKP (SEQ ID NO:80). Zinc fingers 20 and 21 were used in finger 4 of the 4-fingered ZFNs and zinc fingers 43, 45, 47, and 48 were used in finger 2 of the 4-fingered ZFNs.

The pairs of ZFNs tested are shown in FIG. 2 above and to the right of the graph and in Table 5:

TABLE 5

| Sample # | 5-8 ZFN | 5-9 ZFN |
| --- | --- | --- |
| 1 | None (GFP) | |
| 2 | wild type (CCHH) | wild type (CCHH) |
| 3 | 43 (finger 2) | 43 (finger 2) |
| 4 | 43 (finger 2) | 20 (finger 4) |
| 5 | 43 (finger 2) | 21 (finger 4) |
| 6 | 43 (finger 2) | 45 (finger 2) |
| 7 | 43 (finger 2) | 47 (finger 2) |
| 8 | 20 (finger 4) | 43 (finger 2) |
| 9 | 21 (finger 4) | 43 (finger 2) |
| 10 | 45 (finger 2) | 43 (finger 2) |
| 11 | 47 (finger 2) | 43 (finger 2) |
| 12 | 48 (finger 2) | 43 (finger 2) |

To determine if mutations had been induced at the cleavage site, the amplification product was analyzed using a Cel-1 assay, in which the amplification product is denatured and renatured, followed by treatment with the mismatch-specific Cel-1 nuclease. See, for example, Oleykowski et al. (1998) *Nucleic Acids res.* 26:4597-4602; Qui et al. (2004) *BioTechniques* 36:702-707; Yeung et al. (2005) *BioTechniques* 38:749-758.

Results of two experiments are shown for each sample in FIG. 2. Experiment #2 for samples 8 and 9 had significant background noise in the lanes which reduced the apparent efficacy of these ZFNs.

As shown in FIG. 2, certain CCHC variants are essentially equivalent to the wild-type C2H2 ZFNs. Zinc finger 21 at finger 4 (samples 5 and 9) produced better results than zinc finger 20 at finger 4 (samples 4 and 8). In Finger 2, zinc finger 43 produced the best results.

Example 4

Gene Correction of eGFP in Reporter Cell Lines

Based on the results shown in FIGS. 1 and 2, CCHC zinc fingers shown in Tables 3 and 4 above (designated 1a through 10a) were produced. These zinc fingers were incorporated into the 5-8 and 5-9 ZFNs and tested in the GFP gene correction assay described in Example 2 above. The ZFN pairs tested in each sample are shown below each bar, where the zinc finger numbers 20, 21, 43, 45, 47 and 48 are those described in Example 3 and CCHC zinc fingers 1a through 10a comprise the sequence shown in Tables 3 and 4 above. Zinc fingers 20, 21, 7a, 8a, 9a and 10a were used in Finger 4; zinc fingers 43, 45, 47, 48, 1a, 2a, 3a, 4a, 5a, and 6a were used in Finger 2.

Figure 3:
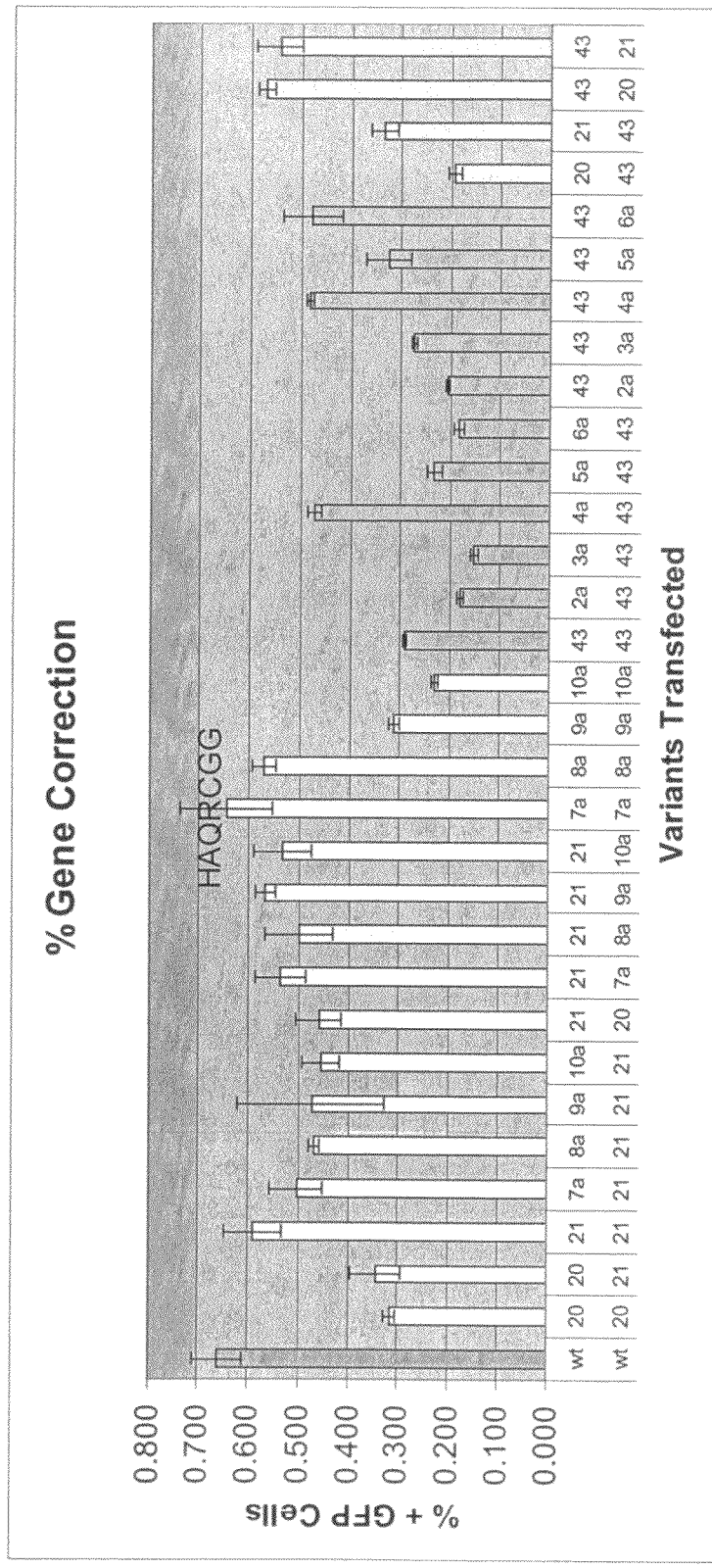
FIG. 3 is a graph depicting gene correction rates in the GFP cell reporter assay system described in U.S. Patent No. 2005/0064474 and herein. The ZFN pairs tested in each sample are shown below each bar, where the zinc finger numbers 20, 21, 43, 45, 47 and 48 are those described in Example 3 and CCHC zinc fingers 1a through 10a comprise the sequence shown in Tables 3 and 4. Zinc fingers 20, 21, 7a (comprising the amino acid sequence HAQRCGG, SEQ ID NO:89), 8a, 9a and 10a were used in Finger 4; zinc fingers 43, 45, 47, 48, 1a, 2a, 3a, 4a, 5a, and 6a were used in Finger 2.

Results are shown in FIG. 3. The top row beneath each bar refers to the zinc finger incorporated into ZFN 5-8 and the bottom row beneath each bar refers to the zinc finger incorporated into ZFN 5-9. For example, the $2^{nd}$ bar from the left on the graph of FIG. 3 refers to a sample transfected with 5-8 and 5-9 ZFNs in which F4 of both ZFNs comprises the sequence of zinc finger 20. As shown, many of the ZFNs comprising CCHC zinc fingers performed comparable to wild type (CCHH) ZFNs.

Example 5

Design and Generation of Target Vector

A. Overall Structure of the Target Sequence

The target construct for tobacco (a dicot) included the following 7 components as shown in FIGS. 4 and 5: i) a hygromycin phosphotransferase (HPT) expression cassette comprising an *A. thaliana* ubiquitin-3 (ubi-3) promoter (Callis, et al., 1990, J. Biol. Chem. 265-12486-12493) driving the *E. coli* HPT gene (Waldron et al., 1985, Plant Mol. Biol. 18:189-200) terminated by an *A. tumifaciens* open reading frame-24 (orf-24) 3' untranslated region (UTR) (Gelvin et al., 1987, EP222493); ii) homologous sequence-1, comprising the *N. tabacum* RB7 matrix attachment region (MAR) (Thompson et al., 1997, WO9727207); iii) a 5' Green Fluorescent Protein (GFP) gene fragment (Evrogen Joint Stock Company, Moscow, Russia) driven by a modified *A. tumifaciens* mannopine synthase (Δmas) promoter (Petolino et al., U.S. Pat. No. 6,730,824); iv) a β-glucuronidase (GUS) expression cassette comprising a Cassava Vein Mosaic Virus (CsVMV) promoter (Verdaguer et al., 1996, Plant Molecular Biology 31:1129-1139) driving a GUS gene (Jefferson, 1987, Plant Mol. Biol. Rep. 5:387-405) terminated by the *A. tumifaciens* nopaline synthase (nos) 3'UTR (DePicker et al., 1982, J. Mol. Appl. Genet. 1:561-573); v) a 3' GFP gene fragment (Evrogen Joint Stock Company, Moscow, Russia) terminated by an *A. tumifaciens* orf-1 3' UTR (Huang et al., J. Bacteriol. 172: 1814-1822); vi) homologous sequence-2, comprising *A. thaliana* 4-coumaroyl-CoA synthase (4-CoAS) intron-1 (Locus At3g21320, GENBANK™ NC 003074) and; vii) a *S. viridochromogenes* phosphinothricin phosphotransferase (PAT) (Wohlleben et al., 1988, Gene 70:25-37) 3' gene fragment terminated by *A. tumifaciens* ORF-25/26 3' UTR (Gelvin et al., 1987, EP222493).

A zinc finger-FokI fusion protein binding site (IL-1-L0-Fok1) (Urnov et al., 2005, US 2005/0064474) was inserted downstream of the CsVMV promoter (Verdaguer et al., 1996, Plant Molecular Biology 31:1129-1139) and fused with the GUS coding sequence (Jefferson, 1987, Plant Mol. Biol. Rep. 5:387-405) at the N-terminal. Two copies of a second zinc finger-Fok1 fusion protein binding site (Scd27-L0-Fok1) (Urnov et al., 2005, US 2005/0064474) flanked the 5' and 3' GFP gene fragments (Evrogen Joint Stock Company, Moscow, Russia). Each binding site contained four tandem repeats of the recognition sequence of the particular zinc finger-Fok1 fusion protein so that each binding site was ~200 bp in size (FIG. 6A). This was designed to ensure that the recognition sequences would be accessible to the zinc finger-Fok1 fusion protein in the complex chromatin environment. Each recognition sequence included an inverted repeat sequence to which a single zinc finger-Fok1 fusion protein bound as a homodimer and cleaved the double stranded DNA (FIG. 6B). The 5' and 3' GFP gene fragments overlapped by 540 bp providing homology within the target sequence and a stop codon was inserted at the 3' end of the 5' GFP fragment to ensure no functional GFP translation from the target sequence.

The transformation vector comprising the target sequence was generated through a multiple-step cloning process as described below.

B. Construction of the HPT Binary Vector (pDAB1584)

The vector pDAB1400, which contained a GUS expression cassette, comprising an *A. thaliana* ubi-3 promoter (Callis, et al., 1990, J. Biol. Chem. 265-12486-12493) driving the GUS gene (Jefferson, 1987, Plant Mol. Biol. Rep. 5:387-405) terminated by *A. tumifaciens* orf-1 UTR (Huang et al., J. Bacteriol. 172:1814-1822), was used as the starting base construct (FIG. 7).

To avoid any unnecessary repeated regulatory elements in the target construct, the *A. tumifaciens* orf-1 UTR (Huang et al., J. Bacteriol. 172:1814-1822) in pDAB1400 was replaced with an *A. tumifaciens* orf-24 UTR (Gelvin et al., 1987, EP222493), which was excised from pDAB782 (FIG. 8) as a SacI/XbaI fragment and cloned into the same sites in pDAB1400. The resulting construct contained an *A. thaliana* ubi-3 promoter (Callis, et al., 1990, J. Biol. Chem. 265-12486-12493) driving the GUS gene (Jefferson, 1987, Plant Mol. Biol. Rep. 5:387-405) terminated by an *A. tumifaciens* orf-24 UTR (Gelvin et al., 1987, EP222493) and was named pDAB1582 (FIG. 9).

The HPT coding sequence (Waldron et al., 1985, Plant Mol. Biol. 18:189-200) was PCR amplified from pDAB354 plasmid (FIG. 10) using the primers P1 and P2. A BbsI site was added at the 5' end of primer P1 and the SacI site was retained at the 3' end of primer P2. The HPTII PCR fragment was digested with BbsI/SacI and cloned into pDAB1582 digested with NcoI-SacI to replace the GUS gene with the HPT gene from the PCR fragment. The resulting plasmid was named pDAB1583 (FIG. 11).

The *A. thaliana* ubi-3/HPT/*A. tumifaciens* orf-24 fragment was then excised from pDAB1583 by NotI digestion and treated with T4 DNA polymerase to generate blunt-ends. The blunt-end-treated HPT expression cassette was cloned into pDAB2407 (FIG. 12), a binary base vector, at the PmeI site resulting in plasmid pDAB1584 (FIG. 13).

C. Construction of the Vector Comprising the Homologous Sequences and the Scd27 Zinc Finger-Fok1 Fusion Protein Binding Site (pDAB1580)

The *A. tumefaciens* orf-1 UTR (Huang et al., J. Bacteriol. 172:1814-1822) in pDAB2418 (FIG. 14) was replaced with the *A. tumefaciens* orf25/26 UTR (Gelvin et al., 1987, EP222493) to avoid repeated regulatory sequences in the target vector. To make the UTR swap, the *A. tumefaciens* orf25/26 UTR (Gelvin et al., 1987, EP222493) was PCR amplified from the pDAB4045 plasmid (FIG. 15) using primers P3 and P4. SmaI and AgeI sites were added to the 3' end of PCR fragment, and the SacI site was retained at the 5' end. The pDAB2418 plasmid DNA, which contained a PAT gene expression cassette comprising the *A. thaliana* ubiquitin-10 (ubi-10) promoter (Callis, et al., 1990, J. Biol. Chem. 265-12486-12493) driving the PAT gene (Wohlleben et al., 1988, Gene 70:25-37) terminated by the *A. tumefaciens* orf-1 UTR (Huang et al., J. Bacteriol. 172:1814-1822) and a *N. tabacum* RB7 MAR sequence (Thompson et al., 1997, WO9727207), was digested with SacI and AgeI and the two largest fragments were recovered. These fragments were ligated with the *A. tumefaciens* orf25/26 UTR (Gelvin et al., 1987, EP222493) PCR product digested with SacI and AgeI. The resulting plasmid was named pDAB1575 (FIG. 16). The *N. tabacum* RB7 MAR (Thompson et al., 1997, WO9727207) serves as homologous sequence-1 in the target vector.

Intron-1 of *A. thaliana* 4-CoAS (Locus At3g21320, GEN-BANK™ NC 003074) was selected to serve as homologous sequence-2 in the target vector. The PAT gene (Wohlleben et al., 1988, Gene 70:25-37) coding sequence was analyzed and the 299/300 bp downstream of the start codon was identified as the site for inserting the intron so that the appropriate 5' and 3' splicing sites would be formed. The full-length intron was then fused with 253 bp of 3' partial PAT coding sequence by DNA synthesis (Picoscript Ltd., LLP, Houston, Tex.). NotI and SacI sites were added to the 5' and 3' end of the DNA fragment, respectively. The synthesized DNA fragment was then digested with NotI/SacI and inserted into pDAB1575 at the same sites to replace the full-length PAT coding sequence. The resulting construct was named pDAB 1577 (FIG. 17).

A 241 bp DNA fragment containing 4 tandem repeats of Scd27-L0-Fok1 recognition sites (FIG. 6) was synthesized (Picoscript Ltd., LLP, Houston, Tex.) with a SmaI site added to both 5' and 3' ends of the fragment. The synthesized zinc finger-Fok1 binding site-containing fragment was then digested with SmaI and inserted into pDAB1577 at MscI site. The resulting vector was named pDAB1579 (FIG. 18). A second SmaI-digested zinc finger-Fok1 binding site-containing fragment was then inserted into pDAB1579 at the SwaI site. The resulting construct was named pDAB1580 (FIG. 19). This vector contains homologous sequences 1 and 2 (*N. tabacum* RB7 MAR and *A. thaliana* 4-CoAS intron1, respectively) and two synthesized Scd27 zinc finger-Fok1 binding sites, each containing 4 tandem repeats of Scd27-L0-Fok1 recognition sites.

D. Construction of the Vector Containing Two Partially Duplicated Non-Functional GFP Fragments (pDAB1572)

The GFP gene, CopGFP, was purchased from Evrogen Joint Stock Company (Moscow, Russia) and the full-length coding sequence was PCR amplified using primers P5 and P6. BbsI and SacI sites were added to the 5' and 3' ends of the PCR product, respectively. The CopGFP PCR product was then digested with BbsI/SacI and cloned into pDAB3401 (FIG. 20) comprising the modified *A. tumifaciens* Δmas promoter (Petolino et al., U.S. Pat. No. 6,730,824) driving the GUS gene (Jefferson, 1987, Plant Mol. Biol. Rep. 5:387-405) and terminated by *A. tumifaciens* orf-1 3' UTR (Huang et al., J. Bacteriol. 172:1814-1822) at the NcoI/SacI sites to replace the GUS gene. The resulting vector was named pDAB1570 (FIG. 21).

To make the two partially duplicated, non-functional GFP fragments, a DNA fragment containing the majority of the coding sequence of CopGFP with a 47 bp deletion at the 5' end was PCR amplified using primers P9 and P10. An ApaI site was added to both the 5' and 3' ends and an additional StuI site was added to the 5' end downstream of the ApaI site. The PCR product was then digested with ApaI and inserted into pDAB1570 at the ApaI site, thereby creating two non-functional GFP fragments in the same vector with a 540 bp duplicated sequence. The resultant construct was named pDAB1572 (FIG. 22).

E. Construction of the Vector Containing the IL-1 Zinc Finger-Fok1 Fusion Protein Binding Site/GUS Gene Fusion (pDAB1573)

A 233 bp DNA fragment containing 4 tandem repeats of IL-1_L0-Fok1 recognition site (FIG. 6) was synthesized by Picoscript Ltd., LLP, (Houston, Tex.) with NcoI and AflIII sites added to the 5' and 3' ends, respectively. The synthesized fragment was then digested with NcoI/AflIII and inserted into pDAB4003 (FIG. 23), which contained a GUS gene (Jefferson, 1987, Plant Mol. Biol. Rep. 5:387-405) driven by a CsVMV promoter (Verdaguer et al., 1996, Plant Molecular Biology 31:1129-1139) terminated by *A. tumefaciens* orf-1 3' UTR (Huang et al., J. Bacteriol. 172:1814-1822) at NcoI site. An N-terminal fusion between IL-1_Lo-Fok1 binding site and GUS coding sequence was then generated. The resulting vector was named pDAB1571 (FIG. 24).

To avoid repeat 3' UTR elements in the target vector, the *A. tumefaciens* nos 3' UTR (DePicker et al., 1982, J. Mol. Appl. Genet. 1:561-573) was excised from pDAB7204 (FIG. 25) as a SacI/PmeI fragment and cloned into pDAB1571, which was digested with SacI/NaeI, to replace the *A. tumefaciens* orf-1 3' UTR (Huang et al., J. Bacteriol. 172:1814-1822). The resulting plasmid was named pDAB1573 (FIG. 26).

F. Construction of the Final Target Vector (pDAB1585)

To make to final target vector, the GUS expression cassette with the IL-1-Fok1 fusion protein target site insertion was excised from pDAB1573 by NotI digestion, blunt-end treated and inserted into pDAB1572 at StuI site. The resulting intermediate vector was named pDAB1574 (FIG. 27). The entire cassette containing the modified Δmas promoter (Petolino et al., U.S. Pat. No. 6,730,824), a 5' partially duplicated GFP sequence (Evrogen Joint Stock Company, Moscow, Russia), the CsVMV promoter (Verdaguer et al., 1996, Plant Molecular Biology 31:1129-1139), an IL-1-Fok1 fusion protein target sequence, the GUS gene (Jefferson, 1987, Plant Mol. Biol. Rep. 5:387-405) coding region, an *A. tumefaciens* nos 3' UTR (DePicker et al., 1982, J. Mol. Appl. Genet. 1:561-573), a 3' partially duplicated GFP (Evrogen Joint Stock Company, Moscow, Russia) and *A. tumefaciens* orf-1 3' UTR (Huang et al., J. Bacteriol. 172:1814-1822) was excised from pDAB1574 and inserted into pDAB1580 at the NotI site. The resulting plasmid was named pDAB1581 (FIG. 28). The AgeI fragment of pDAB1581 was then inserted into pDAB1584 at AgeI site thereby creating the final target construct, pDAB1585 (FIGS. 4 and 5).

Example 6

Generation of Transgenic Cell Lines with Integrated Target Sequences

A tobacco cell suspension culture, referred to as BY2, was used into which target sequences of Example 5 were stably integrated via *Agrobacterium* transformation. The base cell line, BY2, was obtained from Jun Ueki of Japan Tobacco, Iwata, Shizuoka, Japan. This culture proliferates as 5-10µ diameter cells in 100-150 cell clusters with a doubling time of roughly 18 hours. BY2 cell suspension cultures were maintained in media containing LS basal salts (PhytoTechnology Labs L689), 170 mg/L $KH_2PO_4$, 30 g/L sucrose, 0.2 mg/L 2,4-D and 0.6 mg/L thiamine-HCL at a pH of 6.0. The BY2 cells were sub-cultured every 7 days by adding 50 mL of LS-based medium to 0.25 mL PCV. The BY2 cell suspension culture was maintained in 250-mL flasks on a rotary shaker at 25° C. and 125 RPM.

In order to generate transgenic BY2 cell culture with integrated target sequences, a flask of a four-day post sub-culture tobacco suspension was divided into 10-12 four mL aliquots which were co-cultivated in 100×25 mm Petri dishes with 100 µL *Agrobacterium* strain LBA4404 harboring pDAB1585 grown overnight to an $OD_{600}$~1.5. Dishes were wrapped with parafilm and incubated at 25° C. without shaking for 3 days after which excess liquid was removed and replaced with 11 mL of LS-based basal medium containing 500 mg/L carbenicillin.

Following re-suspension of the tobacco cells, 1 mL suspension was dispensed onto 100×25 mm plates of appropriate base medium containing 500 mg/L carbenicillin and 200 mg/L hygromycin solidified with 8 g/L TC agar, and incubated unwrapped at 28° C. in the dark. This resulted in 122-144 selection plates for a single treatment. Individual hygromycin-resistant isolates appeared 10-14 days after plating and were transferred to individual 60×20 mm plates (one isolate per plate) where they were maintained as callus on a 14-day subculture schedule until needed for analysis and subsequent re-transformation experiments.

Example 7

Screening and Characterization of Target Transgenic Events

The hygromycin-resistant transgenic events generated from the transformation of target vector into BY2 tobacco cell cultures, as described in Example 6 were analyzed as follows.

The initial analyses conducted for screening these transgenic events included GUS expression analysis to indicate the accessibility of the target sequence, PCR analysis of the partial and full-length target sequence to confirm the presence and intactness of target vector and Southern blot analysis to determine the copy number of the integrated target sequence. A subset of the transgenic events that showed GUS expression contained one single copy of full length target sequence; these were selected for re-establishing suspension cultures to generate the target lines for subsequent re-transformation. These re-established target lines were also subjected further characterization, which included more thorough Southern blot analysis, sequencing confirmation of the entire target insert and flanking genomic sequence analysis.

Transgenic tobacco callus tissue or suspension cultures initiated from the selected events were analyzed for GUS activity by incubating 50 mg samples in 150 µL of assay buffer for 24-48 hours at 37° C. The assay buffer consisted of 0.2 M sodium phosphate pH 8.0, 0.1 mM each of potassium ferricyanide and potassium ferrocyanide, 1.0 mM sodium EDTA, 0.5 mg/mL 5-bromo-4-chloro-3-indoyl-β-glucuronide and 0.6% (v/v) Triton X-100 (Jefferson, 1987, Plant Mol. Biol. Rep. 5:387-405). The appearance of blue colored regions was used as the indicator of GUS gene expression, which indicated that the target sequence insertion was transcriptionally active and thus accessible in the local genomic environment.

The GUS expressing transgenic events were assayed by PCR using the primer pair P15/P16 which led to amplification of a 10 kb DNA fragment extending from the 3' UTR of the HTP expression cassette at the 5' end of target sequence to the 3' UTR of the partial PAT gene cassette at the 3' end of the target sequence. Since all of the events were obtained under hygromycin selection, it was assumed that the HPT expression cassette was intact in all of the target events. Therefore, only the 3' UTR of the HPT expression cassette was covered in the full length PCR analysis. A subset of events were also PCR assayed using the primer pairs P15/P17 and P18/P19 to determine the intactness of the 5' and 3' ends of the target sequence, respectively. All target events confirmed with PCR analysis were further assayed by Southern blot analysis to determine the copy number of the integrated target sequence.

Southern blot analysis was carried out for all target events that passed the screening of GUS expression and full-length PCR. Ten fig of genomic DNA was digested with NsiI, which was a unique cutter within the target sequence. The digested genomic DNA was separated on a 0.8% agarose gel and transferred onto a nylon membrane. After cross-linking, the transferred DNA on the membrane was hybridized with an HPT gene probe to determine the copy number of the 5' end of target sequence. The same blot was then stripped and re-hybridized with a PAT gene probe to determine the copy number of the 3' end of the target sequence.

Multiple events that showed GUS expression and contained a single copy of full-length target sequence were selected for further characterization, which included more thorough Southern blot analysis, entire target sequence confirmation and flanking genomic sequence analysis. One event, referred to as BY2-380, was selected based on the molecular characterization. Suspension culture was re-established from this event for subsequent re-transformation with vectors comprising donor DNA and non-C2H2 zinc finger-Fok1 fusion protein genes.

To ensure the suspension culture established from the target event BY2-380 contained the intact target sequence as expected, the major target sequence from the 3'UTR of the HPT expression cassette at the 5' end of the target sequence to the 3' UTR of the partial PAT gene cassette at the 3' end of the target sequence was PCR amplified using the primer pair P15/P16 and cloned into pCR2.1 TOPO vector (Invitrogen, Carlsbad, Calif.). The PCR products inserted in the TOPO vector were sequenced by Lark technology, Inc. (Houston, Tex.). The sequence results indicated that the BY2-380 had complete target sequences as expected.

The BY2-380 cell line was further analyzed to obtain the flanking genomic sequences using the Universal GenomeWalker Kit (Clontech, Mountain View, Calif.). Brief, 2.5 µg of genomic DNA was digested with three blunt-end restriction enzymes, EcoRV, DraI and StuI in separate reactions. The digested DNA was purified through phenol/chloroform extraction and ligated with BD GenomeWalker Adaptor. Nested PCR amplification was performed with the ligation as template and primer P20 (walking upstream of the 5' end of target sequence insertion) and P21 (walking downstream of the 3' end of target sequence insertion) for the primary PCR reaction, and primer P22 (walking upstream of the 5' end of target sequence insertion) and P23 (walking downstream of the 3' end of target sequence insertion) for the secondary nested PCR reaction. The amplified fragments from the secondary PCR reactions were cloned into pCR2.1 TOPO or pCR Blunt II TOPO vector (Invitrogen, Carlsbad, Calif.) and sequenced using a Dye Terminator Cycle Sequencing Kit (Beckman Coulter, Fullerton, Calif.). The flanking genomic sequences were obtained from the BY2-380 target line through this process. Primers were then designed based on the flanking genomic sequences and used to amplify the entire target sequence.

The amplified fragments obtained from this target line was of expected size. Both ends of the amplified fragments were confirmed by sequencing.

Example 8

Design and Generation of Donor DNA Vector

The donor DNA construct included homologous sequence-1 (*N. tabacum* RB7 MAR) (Thompson et al., 1997, WO9727207), a full-length *A. thaliana* ubi10 promoter (Callis, et al., 1990, J. Biol. Chem. 265-12486-12493), 299 bp of 5' partial PAT gene coding sequence (Wohlleben et al., 1988, Gene 70:25-37) and homologous sequence-2 (*A. thaliana* 4-CoAS intron-1) (Locus At3g21320, GENBANK™ NC 003074). Both homologous sequence-1 and sequence-2 in the donor vector were identical to the corresponding homologous sequence-1 and sequence-2 in the target vector (pDAB1585).

To construct the donor vector, the 299 bp of 5' partial PAT coding sequence was fused with the full-length *A. thaliana* 4-CoAS intron-1 (Locus At3g21320, GENBANK™ NC 003074) through DNA synthesis by Picoscript Ltd., LLP, (Houston, Tex.). NcoI and XhoI sites were added to the 5' and 3' end of the fragment, respectively. This synthesized DNA fragment was then digested with NcoI/XhoI and inserted into pDAB 1575 at the same sites to replace the full-length PAT gene coding sequence and its 3' UTR. The resulting construct was named pDAB 1576 (FIG. 29).

pDAB1576 was then digested with AgeI and the entire fragment containing the 5' partial PAT expression cassette flanked by homologous sequence-1 and homologous sequence-2 was inserted into pDAB2407, the binary base vector, at the same site. The resultant construct was named pDAB1600 (FIG. 30) and was the binary version of the donor vector for plant cell re-transformation.

Example 9

Design and Generation of Zinc Finger Nuclease Expression Vectors

The zinc finger-Fok1 fusion protein gene was driven by a CsVMV promoter and 5' UTR (Verdaguer et al., 1996, Plant Molecular Biology 31:1129-1139). Also included in the cassette were an *A. tumifaciens* open reading frame-24 (orf-24) 3' untranslated region (UTR) (Gelvin et al., 1987, EP222493).

To make these vectors, the C2H2 controls and their C3H variants of IL-1-Fok1 and Scd27-Fok1 coding sequences described in Examples 1 to 4 above were PCR amplified from their original designs with BbsI or NcoI and SacI sites added to the 5' and 3' end of the PCR fragments, respectively and cloned into the pDAB3731 (FIG. 31) digested with NcoI-SacI. The resultant plasmids were named pDAB4322 (FIG. 32), pDAB4331 (FIG. 33), pDAB4332 (FIG. 34), pDAB4333 (FIG. 35) pDAB4334 (FIG. 36), pDAB4336 (FIG. 37), and pDAB4339 (FIG. 38). All of these vectors contained the attL1 and attL2 sites flanking the ZFN expression cassette and were compatible with Gateway™ cloning system (Invitrogen, Carlsbad, Calif.).

Two sets of binary version vectors were constructed for the IL-1-FokI fusion protein. One contained the PAT selectable marker gene and the other did not contain the PAT selectable marker gene. For SCd27-FokI fusion protein, only the binary version of vector without the PAT selectable marker gene was constructed. To make the binary vectors with PAT selectable marker gene, the IL-1-FokI fusion protein expression cassette in pDAB4322, pDAB4331, pDAB4332, pDAB4333, pDAB4334, and pDAB4336 were cloned into pDAB4321 (FIG. 39) through LR recombination reaction using the LR Clonase™ Enzyme Mix (Invitrogen, Carlsbad, Calif.). The resultant plasmid were named pDAB4323 (FIG. 40), pDAB4341 (FIG. 41), pDAB4342 (FIG. 42), pDAB4343 (FIG. 43), pDAB4344 (FIG. 44), pDAB4346 (FIG. 45). To make the binary vectors without the PAT selectable marker gene, the C2H2 IL-1-FokI, C3H IL-1-FokI and Scd27-FokI expression cassette in the pDAB4331, pDAB4336 and pDAB4339, respectively, were cloned into pDAB4330 (FIG. 46) through LR recombination reaction using the LR Clonase™ Enzyme Mix (Invitrogen, Carlsbad, Calif.). The resultant plasmid were named pDAB4351 (FIG. 47), pDAB4356 (FIG. 48) and pDAB4359 (FIG. 49), respectively.

To make the C2H2 control of SCD27-FokI, the HindIII/SacI fragment comprising CsVMV promoter and 5'UTR driving PAT in pDAB7002 (FIG. 50) was replaced with a fragment comprising CsVMV promoter and 5' UTR and *N. tabacum* 5' UTR driving GUS, which was excised from pDAB7025 (FIG. 51) with HindIII/SacI. The resultant plasmid was named as pDAB1591 (FIG. 52). The Scd27-L0-Fok1 coding sequences were PCR amplified from their original vectors pCDNA3.1-SCD27a-L0-FokI (FIG. 53) using primer pair P13/P14. BbsI and SacI sites were added to the 5' and 3' end of the PCR fragments, respectively. The PAT gene in pDAB1591 was replaced with the zinc finger fusion protein gene PCR fragment through SacI/NcoI cloning. The resultant plasmid was named pDAB1594 (FIG. 54). The binary version of this vector was constructed by excising the zinc finger fusion protein gene expression cassette from pDAB1594 as a PmeI/XhoI fragments, filling in the ends and cloning into pDAB2407 at the PmeI site. The resultant plasmid was named pDAB1598 (FIG. 55). The details of all binary vectors used for plant transformation is summarized in Table 6.

TABLE 6

Zinc Finger Nuclease Expression Vectors

| Vector | ZFN | Type of ZFP | Finger Position of Zinc finger | Amino Acid Sequence | SEQ ID NO: |
|---|---|---|---|---|---|
| pDAB4323 | IL 1-FokI | C2H2 | F4 | C...C...HTKIH | 94 |
| pDAB4341 | IL 1-FokI. | C2H2 | F4 | C...C...HTKIH | 95 |
| pDAB4342 | IL 1-FokI* | C3H | F4 | C...C...HTKIC | 96 |
| pDAB4343 | IL 1-FokI* | C3H | F4 | C...C...HTKRCGGG | 97 |
| pDAB4344 | IL 1-FokI* | C3H | F4 | C...C...HAQRCG | 98 |
| pDAB4346 | IL 1-FokI* | C3H | F2 | C...C...HIRTGC | 99 |
| pDAB4351 | IL 1-FokI* | C2H2 | F4 | C...C...HTKIH | 100 |
| pDAB4356 | IL 1-FokI* | C3H | F2 | C...C...HIRTGC | 101 |
| pDAB1598 | Scd27-FokI | C2H2 | F4 | C...C...HTKIH | 102 |
| pDAB4359 | Scd27-FokI* | C3H | F4 | C...C...HAQRCGG | 103 |

*FokI domain was plant codon biased.

Example 10

Design and Generation of Positive Control Vector

To estimate the illegitimate recombination frequency and serve as a positive control, a vector containing the PAT gene expression cassette was used. In order to be comparable with the final recombinants, the *A. thaliana* 4-CoAS intron-1 (Locus At3g21320, GENBANK™ NC 003074) was inserted at the 299/300 bp of the PAT coding sequence (Wohlleben et al., 1988, Gene 70:25-37). To make this construct, the 2559 bp SwaI/ClaI fragment from pDAB 1576 was ligated with the backbone fragment of pDAB 1577 (FIG. 56) which was digested with the same restriction enzymes. The resulting vector contained the PAT gene expression cassette with the 1743 bp of *A. thaliana* 4-CoAS intron-1 (Locus At3g21320, GENBANK™ NC 003074) (Locus At3g21320, GENBANK™ NC 003074) insertion in the middle of PAT coding sequence (Wohlleben et al., 1988, Gene 70:25-37). This vector was named pDAB 1578 (FIG. 57).

To make the binary version of pDAB 1578, the PAT gene expression cassette with the *A. thaliana* intron-1 (Locus At3g21320, GENBANK™ NC 003074) was excised from pDAB 1578 with PmeI/XhoI. After the 3' end of the fragment was blunt-end treated, it was inserted into pDAB2407, the binary base vector, at the PmeI site. The resulting vector was named pDAB1601 (FIG. 58) which comprised the PAT gene (Wohlleben et al., 1988, Gene 70:25-37) containing *A. thaliana* 4-CoAS intron-1 (Locus At3g21320, GENBANK™ NC 003074) sequence driven by the *A. thaliana* ubi10 promoter (Callis, et al., 1990, J. Biol. Chem. 265-12486-12493) and terminated by the *A. tumefaciens* orf25/26 3' UTR (Gelvin et al., 1987, EP222493).

Example 11

Demonstration of Intra-Chromosomal Homologous Recombination by Re-transformation of Target Cell Cultures with C3H Zinc Finger Nuclease Genes To validate the functionality of C3H zinc finger nucleases in stimulating intra-chromosomal homologous recombination, two nonfunctional GFP fragments with 540 bp overlap sequences were included in the target vector as shown in FIG. 59. In between these two fragments was a GUS gene expression cassette. The IL-1-Fok1 fusion protein binding sequence was fused with the GUS coding sequence at its N-terminal. Without being bound by one theory, it was hypothesized that in the presence of IL-1-Fok1 fusion protein, the IL-1 ZFN binding sequences would be recognized and a double stranded DNA break would be induced, which would stimulate the endogenous DNA repair process. Without the presence of donor DNA, the two partially homologous GFP fragments would undergo an intra-chromosomal homologous recombination process and a functional GFP gene would be reconstituted.

The BY2-380 transgenic cell line which contains a single, full-length integrated copy of the target sequence was used to re-initiate suspension cultures by placing~250-500 mg of callus tissue into 40-50 mL of LS-based basal medium containing 100 mg/L hygromycin and sub-culturing every 7 days as described above. Prior to re-transformation, the suspension cultures were transferred to basal medium without hygromycin for two passages, at least.

*Agrobacterium*-mediated transformation of the target cell cultures was performed as described above. For each experiment, 8 co-cultivation plates were generated as follows: one plate comprised cells co-cultivated with 300 μL of base *Agrobacterium* strain LBA4404; one plate comprised cells co-cultivated with 300 μL of an *Agrobacterium* strain harboring pDAB1590 (functional GFP construct); six plates each comprised cells co-cultivated with 300 μL of an *Agrobacterium* strain harboring pDAB4323, pDAB4341, pDAB4342, pDAB4343, pDAB4344, and pDAB4346, respectively. Following co-cultivation using the methods described above, the cells were plated out on eight plates containing the LS-based basal medium supplemented with 500 mg/L carbenicillin without selection reagent. Apparent expression of the constituted functional GFP gene resulted in visible fluorescence around 5-8 days after transformation). The number of green fluorescent loci per field was counted by viewing 5 'random' microscope fields per plate, 8 plates per constructs in each experiment, and averaged from 6 independent experiments.

As summarized in Table 7, an average of 9.50 and 7.57 green fluorescent loci per field were observed from two C3H zinc finger nucleases, pDAB4346 and pDAB4343, respectively. These two C3H designs of IL-1-FokI performed better than their C2H2 controls, pDAB4341 (6.37 loci per field) and pDAB4323 (5.53 loci per field). Meanwhile, in comparison with the C2H2 controls, the function of other two C3H variants of IL-1-FokI fusion protein, pDAB4344 (4.39 loci per field) and pDAB4342 (0.25 loci per field) was significantly impaired, in particular the pDAB4342, in which the C3H conversion was made simply by replacing the second cysteine with histidine in the fourth finger. No appreciable fluorescence beyond slight background was observed in the negative controls transformed with the base *Agrobacterium* strain, LBA4404.

TABLE 7

Constitution of functional GFP through IL-1-Fok1 zinc finger fusion protein-stimulated intra-chromosomal homologous recombination

| Vector | Type of ZFP | GFP expression | Tukey Test** |
|---|---|---|---|
| pDAB4346 | C3H | 9.50 | A |
| pDAB4343 | C3H | 7.57 | B |
| pDAB4341 | C2H2 | 6.37 | C |
| pDAB4323* | C2H2 | 5.53 | D |
| pDAB4344 | C3H | 4.39 | E |
| pDAB4342 | C3H | 0.25 | F |

*contains non-plant codon biased FokI domain
**Means not connected by the same letter are significantly different at the 0.05 level Example 12

Demonstration of Inter-Chromosomal Homologous Recombination by Re-transformation of Target Cell Cultures with C3H Zinc Finger Nuclease Genes and Donor DNA Sequences To validate the functionality of C3H zinc finger-Fok1 fusion protein in simulating inter-chromosomal homologous recombination in the exemplary tobacco system, two strategies were developed and tested.

In strategy 1, the binding site for the zinc finger-Fok1 fusion protein (IL-1-L0-Fok1), was included in the middle of the target construct (FIG. 61). In this strategy, the binding site was flanked by ~3 kb of non-homologous sequences on both sides followed by homologous sequence-1 (*N. tabacum* RB7 MAR) and homologous sequence-2 (*A. thaliana* 4-CoAS intron-1) upstream and downstream, respectively. As demonstrated previously (e.g., U.S. Patent Publication No. 20050064474) in the presence of C2H2 IL-1 zinc finger-Fok1 fusion protein, the IL-1-L0-Fok1 binding sequences was recognized and a double stranded DNA break was induced at this specific site, which stimulated the endogenous DNA repair process. In the presence of donor DNA, which contained homologous sequences identical to that in the target sequence, the 5' partial PAT gene along with its promoter, replaced the entire ~6 kb DNA fragment between the homologous sequences in the target through homologous recombination. Through this process, the two partial PAT gene sequences, with the *A. thaliana* 4-CoAS intron-1 interposed between, reconstituted a functional PAT gene, resulting in PAT expression and an herbicide resistance phenotype.

In strategy 2, two zinc finger-Fok1 binding sites (Scd27-L0-FokI) were included in the target vector: one directly downstream of the *N. tabacum* RB7 MAR and the other directly upstream of the *A. thaliana* 4-CoAS intron1 (FIG. 62). In between the two zinc finger-Fok1 fusion protein binding sites were ~6 kb of sequence, which included the 5' GFP fragment, a GUS expression cassette and the 3' GFP fragment. As demonstrated previously (e.g., U.S. Patent Publication No. 20050064474), in the presence of Scd27 zinc finger-Fok1 fusion protein, the two binding sequences recognized and double stranded DNA breaks were induced at both locations, which removed the ~6 kb DNA fragment in between these two binding sequences, and stimulated the endogenous DNA repair process. Similar to the strategy 1, in the presence of donor DNA, which contained homologous sequences identical to that in the target sequence, the 5' partial PAT gene along with its promoter, was inserted into the target sequence through homologous recombination at the site where the double strand DNA breaks were induced. Through this process, the two partial PAT gene sequences, with the *A. thaliana* 4-CoAS intron-1 interposed between, reconstituted a functional PAT gene, resulting in PAT expression and an herbicide resistance phenotype.

*Agrobacterium*-mediated transformation of the BY2-380 target cell culture was performed as described above. For each experiment, 12 co-cultivation plates were generated as follows: one plate comprised cells co-cultivated with 50 µL of an *Agrobacterium* strain harboring pDAB1600 (donor DNA) and 250 µL *Agrobacterium* base strain, LBA4404; one plate comprised cells co-cultivated with 50 µL of an *Agrobacterium* strain harboring pDAB1601 (PAT selectable marker) and 250 µL *Agrobacterium* base strain, LBA4404; two plates comprised cells co-cultivated with 50 µL of an *Agrobacterium* strain harboring pDAB1600 (donor DNA) and 250 µL of an *Agrobacterium* strain harboring pDAB4351 (C2H2 IL-1 ZFP-Fok1); three plates comprised cells co-cultivated with 50 µL of an *Agrobacterium* strain harboring pDAB1600 (donor DNA) and 250 µL of an *Agrobacterium* strain harboring pDAB4356 (C3H IL-1 ZFP-Fok1); two plates comprised cells co-cultivated with 50 µL of an *Agrobacterium* strain harboring pDAB1600 (donor DNA) and 250 µL of an *Agrobacterium* strain harboring pDAB1598 (C2H2 Scd 27a ZFP-Fok1); three plates comprised cells co-cultivated with 50 µL of an *Agrobacterium* strain harboring pDAB1600 (donor DNA) and 250 µL of an *Agrobacterium* strain harboring pDAB4359 (C3H Scd27a ZFP-Fok1). Following co-cultivation using the methods described above, the cells were plated out on the LS-based basal medium containing 500 mg/L carbenicillin and 15 mg/L Bialaphos®. Individual Bialaphos®-resistant isolates appeared 2-4 weeks after plating and were transferred to individual 60×20 mm plates (one isolate per plate) where they were maintained as callus on a 14-day subculture schedule until needed for analysis.

Multiple Bialaphos®-resistant isolates were obtained from both C3H IL-1 zinc finger nuclease (pDAB4356) and C3H Scd27 zinc finger nuclease (pDAB4359). These isolates were analyzed by PCR using primer pair P24/25, which amplified a DNA fragment spanning the reconstituted PAT gene. Primer P24 was homologous to the 5' end of the PAT coding sequence in the donor DNA and primer P25 was homologous to the 3' end of the PAT coding sequence in the target DNA. A 2.3 kb PCR fragment would result if the two partial PAT coding sequences were joined through homologous recombination. As shown in FIG. 63, a 2.3 kb PCR product was obtained from multiple isolates analyzed. These isolates were obtained from both the co-transformation of C3H IL-1 zinc finger-Fok1 fusion protein gene/donor DNA and C3H Scd27 zinc finger-Fok1 fusion protein gene/donor DNA. The 2.3 kb PCR products from multiple independent isolates representative of those derived from both C3H IL-1 zinc finger-Fok1 and C3H Scd27 zinc finger-Fok1 fusion protein gene transformations were purified from agarose gels and cloned into the pCR2.1 TOPO vector (Invitrogen, Carlsbad, Calif.). The 2.3 kb PCR product inserted in the TOPO vector was then sequenced using the Dye Terminator Cycle Sequencing Kit (Beckman Coulter). The sequencing results confirmed that all of the PCR products cloned in the TOPO vector contained the recombined sequence as predicted, including the 5' and 3' partial PAT gene sequences with the intervening *A. thaliana* 4-CoAS intron-1. These results confirmed the predicted interchromosomal recombination for both strategies tested and exemplified gene targeting via the expression of C3H zinc finger-Fok1 fusion protein genes.

Example 13

Identification of Target Gene Sequences in Maize Cell Culture

A. Sequence Identification

In this example, DNA sequences for an endogenous maize gene of known function were selected as targets for genome editing using engineered zinc-finger nucleases. The genomic structure and sequence of this gene, referred to as IPP2-K, which is derived from proprietary maize inbred line 5XH751, has been described in WO2006/029296; the disclosure of which is incorporated by reference.

In particular, the IPP2-K genomic sequence was used to query the TIGR maize genome database (available on the internet) using BLAST algorithms. Several additional genomic fragments were identified with segments of overlapping homology to IPP2-K, including, but not limited to, accessions AZM515213 and TC311535. Based on the sequence of these accessions as well as the IPP2-K sequence, multiple short oligonucleotides were designed for use as PCR primers using the Primer3 program (Rozen, S. and Skaletsky, H. J. (2000) *Primer3 on the WWW for general users and for biologist programmers*. In: Krawetz S, Misener S (eds.) Bioinformatics Methods and Protocols: Methods in Molecular Biology. Humana Press, Totowa, N.J., pp 365-386; also available on the internet). These primers include, but are not limited to, the following forward orientation oligonucleotides:

```
                                       (SEQ ID NO: 104)
1.    5'-ATGGAGATGGATGGGGTTCTGCAAGCCGC-3'

(SEQ ID NO: 161)
2.    5'-CTTGGCAAGGTACTGCGGCTCAAGAAGATTC-3'

(SEQ ID NO: 162)
3.    5'-ATGAAGAAAGACAGGGAATGAAGGAC-3'

(SEQ ID NO: 163)
4.    5'-ATGAAGAAAGACAGGGAATGAAGGACCGCCAC-3'

(SEQ ID NO: 164)
5.    5'-CATGGAGGGCGACGAGCCGGTGTAGCTG-3'

(SEQ ID NO: 165)
6.    5'-ATCGACATGATTGGCACCCAGGTGTTG-3'
```

In addition, the primers include, but are not limited to, the following reverse orientation oligonucleotides:

```
                                       (SEQ ID NO: 166)
7.    5'-TTTCGACAAGCTCCAGAAAATCCCTAGAAAC-3'

(SEQ ID NO: 167)
8.    5'-ACAAGCTCCAGAAAATCCCTAGAAACAC-3'

(SEQ ID NO: 168)
9.    5'-TTCGACAAGCTCCAGAAAATCCCTAGAAACAC-3'

(SEQ ID NO: 169)
10.   5'-TGCTAAGAACATTCTTTTCGACAAGCTCC-3'

(SEQ ID NO: 170)
11.   5'-GAACATTCTTTTCGACAAGCTCCAGAAAATCC-3'
```

All oligonucleotide primers were synthesized by and purchased from Integrated DNA Technologies (IDT, Coralville, Iowa).

B. Hi II Maize Cell Culture

To obtain immature embryos for callus culture initiation, $F_1$ crosses between greenhouse-grown Hi-II parents A and B (Armstrong, C., Green, C. and Phillips, R. (1991) Maize Genet. Coop. News Lett. 65: 92-93) were performed. Embryos of approximately 1.0-1.2 mm in size (~9-10 days after pollination), were harvested from healthy ears and surface sterilized by scrubbing with Liqui-Nox® soap, immersed in 70% ethanol for 2-3 minutes, then immersed in 20% commercial bleach (0.1% sodium hypochlorite) for 30 minutes.

Ears were rinsed in sterile, distilled water, and the immature zygotic embryos were aseptically excised and cultured on 15Ag10 medium (N6 Medium (Chu C. C., Wang C. C., Sun C. S., Hsu C., Yin K. C., Chu C. Y., and Bi F. Y. (1975) Sci. Sinica 18:659-668), 1.0 mg/L 2,4-D, 20 g/L sucrose, 100 mg/L casein hydrolysate (enzymatic digest), 25 mM L-proline, 10 mg/L $AgNO_3$, 2.5 g/L Gelrite, pH 5.8) for 2-3 weeks with the scutellum facing away from the medium. Tissues showing the expected morphology (Welter, M E, Clayton, D S, Miller, M A, Petolino, J F. (1995) Plant Cell Rep: 14:725-729) were selectively transferred at biweekly intervals onto fresh 15Ag10 medium for approximately 6 weeks, then transferred to 4 medium (N6 Medium, 1.0 mg/L 2,4-D, 20 g/L sucrose, 100 mg/L casein hydrolysate (enzymatic digest), 6 mM L-proline, 2.5 g/L Gelrite, pH 5.8) at bi-weekly intervals for approximately 2 months.

To initiate embryogenic suspension cultures, approximately 3 ml packed cell volume (PCV) of callus tissue originating from a single embryo was added to approximately 30 ml of H9CP+ liquid medium (MS basal salt mixture (Murashige T., & Skoog F. (1962) Physiol. Plant. 15:473-497), modified MS Vitamins containing 10-fold less nicotinic acid and 5-fold higher thiamine-HCl, 2.0 mg/L 2,4-D, 2.0 mg/L α-naphthaleneacetic acid (NAA), 30 g/L sucrose, 200 mg/L casein hydrolysate (acid digest), 100 mg/L myo-inositol, 6 mM L-proline, 5% v/v coconut water (added just before subculture), pH 6.0). Suspension cultures were maintained under dark conditions in 125 ml Erlenmeyer flasks in a temperature-controlled shaker set at 125 rpm at 28° C. During cell line establishment (2-3 months), suspensions were subcultured every 3.5 days by adding 3 ml PCV of cells and 7 ml of conditioned medium to 20 ml of fresh H9CP+ liquid medium using a wide-bore pipette. Upon reaching maturity, as evidenced by growth doubling, suspensions were scaled-up and maintained in 500 ml flasks whereby 12 ml PCV of cells and 28 ml conditioned medium was transferred into 80 ml H9CP+ medium. Upon complete establishment of the suspension culture, aliquots were cryopreserved for future use. See, WO 2005/107437.

C. DNA Isolation and Amplification

Maize HiII cell cultures as described above were grown in 250 ml flasks in standard GN6 medium (N6 medium, 2.0 mg/L 2,4-D, 30 g/L sucrose, 2.5 g/L Gelrite, pH 5.8) and genomic DNA was extracted using the Qiagen (Valencia, Calif.) Plant DNeasy extraction kit as per the manufacturer's recommendations. PCR amplification reactions using the primers described above in all possible combinations was carried out under the following conditions: 25 ul reaction volume containing 20 ng gDNA template, 20 pmol each primer, 1% DMSO and 10 units Accuprime™ Pf polymerase (Invitrogen, Carlsbad, Calif.) in the enzyme manufacturer's buffer. Amplification products ranging in size from 500 bp to 2 kb resulted from amplification cycles consisting of 95° C.-1', (95° C.-30", 57-62° C.-30", 72° C.-1')×30, 72° C.-5', 4° C.-hold. The amplified fragments were directly cloned into vector pCR2.1 (Invitrogen, Carlsbad, Calif.) using the TA cloning kit from Invitrogen (Carlsbad, Calif.) as per the manufacturer's recommendations.

D. Sequence Analysis

Previous analysis of the IPP2-K gene in maize inbred 5XH751 and HiII cell culture had indicated the presence of 2-3 distinct genes comprising a small gene family (Sun et al., in press, Plant Physiology; WO2006029296). Therefore, isolated cloned fragments were sequenced with the CEQ Dye Terminator Cycle Sequencing Kit from Beckman Coulter (Fullerton, Calif.) as per the manufacturer's recommendations. Sequence analysis of multiple clones revealed that 2 distinct gene fragments, derived from 2 distinct and previously characterized loci of the maize genome, had been isolated from HiII cells.

Comparison of the 2 sequences isolated from HiII cultured cells indicated that, in predicted coding regions, small differences such as single nucleotide polymorphisms (SNPs) exist between the 2 paralogs, whereas the intronic and non-coding regions vary significantly at the nucleotide level. These differences between the 2 paralogs are noted because they highlight regions of sequence that may be discriminated by a sequence-dependent DNA binding protein such as a zinc-finger domain. One skilled in the art may design zinc-finger DNA binding domains that bind to one gene sequence and not another, highly similar gene sequence. Partial gene sequence of 1.2 kb corresponding to the paralog of interest (FIG. 66) was selected as template for zinc-finger nuclease protein design and subsequently subjected to zinc-finger DNA binding domain analysis described above.

Example 14

Design of IPP2-K Zinc-Finger DNA Binding Domains

Using target sites identified for IPP2-K, recognition helices were selected for IPP2-K zinc fingers. The zinc finger designs are shown below in Table 8:

TABLE 8

IPP2-K Zinc finger Designs

| ZFN Name | F1 | F2 | F3 | F4 | F5 | F6 |
|---|---|---|---|---|---|---|
| IPP2-K-1072a1 | DRSALSR (SEQ ID NO: 105) | RNDDRKK (SEQ ID NO: 106) | RSDNLST (SEQ ID NO: 107) | HSHARIK (SEQ ID NO: 108) | RSDVLSE (SEQ ID NO: 109) | QSGNLAR (SEQ ID NO: 110) |
| IPP2-K-1072b1 | DRSALSR (SEQ ID NO: 105) | RNDDRKK (SEQ ID NO: 106) | RSDNLAR (SEQ ID NO: 111) | TSGSLTR (SEQ ID NO: 112) | RSDVLSE (SEQ ID NO: 109) | QSGNLAR (SEQ ID NO: 110) |
| IPP2-K-1072c1 | DRSALSR (SEQ ID NO: 105) | RNDDRKK (SEQ ID NO: 106) | TSGNLTR (SEQ ID NO: 113) | TSGSLTR (SEQ ID NO: 112) | RSDVLSE (SEQ ID NO: 109) | QSGNLAR (SEQ ID NO: 110) |
| IPP2-K-r1065a1 | RSDHLSE (SEQ ID NO: 114) | QSATRKK (SEQ ID NO: 115) | ERGTLAR (SEQ ID NO: 116) | RSDALTQ (SEQ ID NO: 117) | NONE | NONE |
| IPP2-K-r1149a2 | RSDSLSA (SEQ ID NO: 118) | RSAALAR (SEQ ID NO: 119) | RSDNLSE (SEQ ID NO: 120) | ASKTRTN (SEQ ID NO: 121) | DRSHLAR (SEQ ID NO: 122) | NONE |
| IPP2-K-1156a2 | RSDHLST (SEQ ID NO: 123) | QSGSLTR (SEQ ID NO: 124) | RSDHLSE (SEQ ID NO: 114) | QNHHRIN (SEQ ID NO: 125) | TGSNLTR (SEQ ID NO: 126) | DRSALAR (SEQ ID NO: 127) |

Target sites of the zinc finger designs are shown below in Table 9:

TABLE 9

Target Sites of IPP2-K Zinc Fingers
Target sites of the zinc finger designs are shown below in Table 9:

| ZFN Name | Target Site (5' to 3') |
|---|---|
| IPP2-K-1072a1 | GAACTGGTTGAGTCGGTC (SEQ ID NO: 128) |
| IPP2-K-1072b1 | GAACTGGTTGAGTCGGTC (SEQ ID NO: 129) |
| IPP2-K-1072c1 | GAACTGGTTGAGTCGGTC (SEQ ID NO: 129) |
| IPP2-K-r1065a1 | ATGGCCCCACAG (SEQ ID NO: 130) |
| IPP2-K-r1149a2 | GGCACCCAGGTGTTG (SEQ ID NO: 131) |
| IPP2-K-1156a2 | GTCGATGGTGGGGTATGG (SEQ ID NO: 132) |

The IPP2-K designs were incorporated into zinc finger expression vectors encoding a protein having a CCHC structure. See, Tables 1 through 4 above. The non-canonical zinc finger-encoding sequences were then fused to the nuclease domain of the type IIS restriction enzyme FokI (amino acids 384-579 of the sequence of Wah et al. (1998) *Proc. Natl. Acad. Sci. USA* 95:10564-10569 via a four amino acid ZC linker) to form IPP2-K ZFNs.

Example 15

Gene Correction Using IPP2-K Zinc-Finger Nucleases

The ability of IPP2-K ZFNs as described herein to facilitate homologous recombination was tested in the GFP system described in Urnov (2005) *Nature* 435(7042):646-51 and U.S. Patent Publication No. 20050064474 (e.g., Examples 6-11). Briefly, 50 ng of each ZFN and 500 ng of the promoterless GFP donor (Urnov (2005) *Nature*) were transfected into 500,000 reporter cells, using 2 uL of LIPOFECTAMINE™ 2000 per sample, as per the Invitrogen LIPOFECTAMINE™ 2000 protocol.

Vinblastine was added 24 hours post-transfection at a 0.2 uM final concentration, and was removed 72 hours post-transfection.

Figure 69:
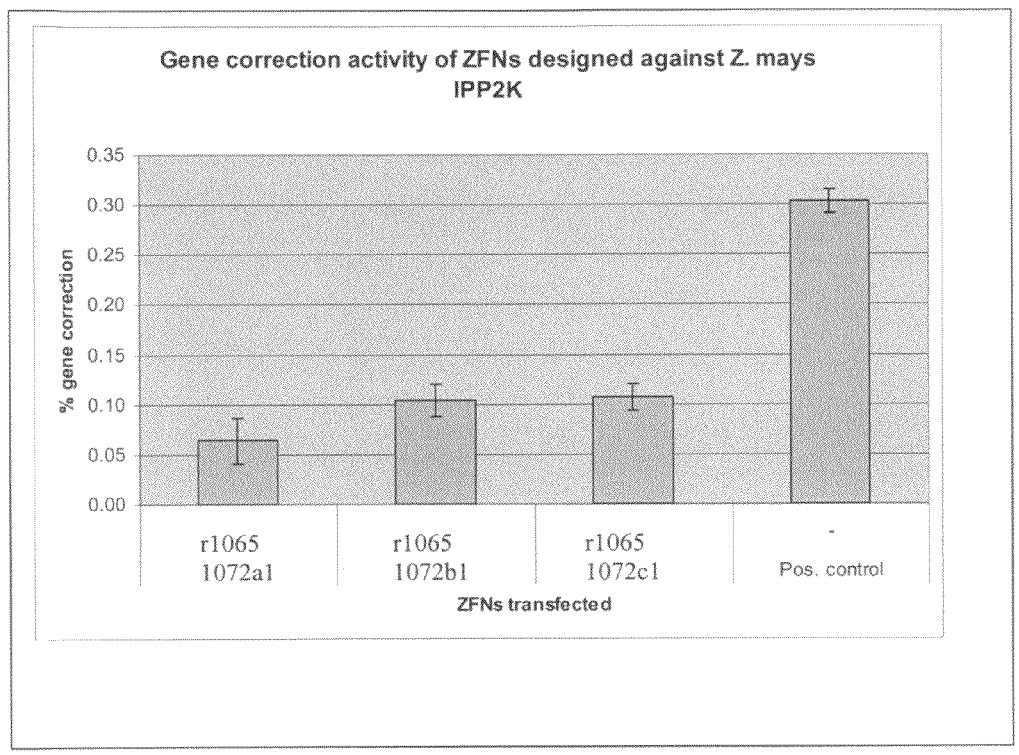
FIG. 69 is a graph depicting gene correction rates in the GFP cell reporter assay system described in U.S. Patent No. 2005/0064474 and herein. The ZFN pairs tested in each sample are shown below each bar.

The cells were assayed for GFP expression 5 days post-transfection by measuring 40,000 cells per transfection on the Guava benchtop FACS analyzer. Results are shown in FIG. 69.

Example 16

Expression C3H1 ZFNs in Maize HiII Cells

A. Vector Design

Plasmid vectors for the expression of ZFN proteins in maize cells were constructed. In order to optimize the expression and relative stoichiometry of the 2 distinct proteins required to form a functional zinc-finger nuclease heterodimer, an expression strategy was adopted that results in insertion of the open reading frames of both ZFNs monomers on a single vector, driven by a single promoter. This strategy exploits the functionality of a 2A sequence (Mattion, N. M., Harnish, E. C., Crowley, J. C. & Reilly, P. A. (1996) J. Virol. 70, 8124-8127) derived from the Thesoa asigna virus, a maize nuclear localization (NLS) signal from the opaque-2 gene (op-2) (Maddaloni, M., Di Fonzo, N., Hartings, H., Lazzaroni, N., Salaminil, F., Thompson, R., & Motto M. (1989) Nucleic Acids Research Vol. 17(18):7532), and a promoter derived from the maize ubiquitin-1 gene (Christensen A. H., Sharrock R. A., & Quail P. H. (1992) Plant Mol Biol. 18(4):675-89). A stepwise modular cloning scheme was devised to develop these expression vectors for any given pair of ZFN-encoding genes selected from the library archive or synthesized de novo.

First, a pVAX vector (see, for example U.S. Patent Publication 2005-0267061; the disclosure of which is incorporated by reference) was modified to encompass the N-terminal expression domain as shown in FIG. 65, panels A to E. Features of this modified plasmid (pVAX-N2A-NLSop2-EGFP-FokMono) (FIG. 65A) include a redesigned and synthesized segment encoding a NLS derived from maize op-2 (RKRKESNRESARRSRYRK, SEQ ID NO:133), and a redesigned and synthesized segment encoding the FokI nuclease domain utilizing the maize codon-bias. Additionally, a single nucleotide insertion (C) downstream of the unique XhoI site created an extra SacI site for cloning convenience.

Second, a pVAX vector (see, for example U.S. Patent Publication 2005-0267061) was also modified to encompass the C-terminal expression domain. Features of this modified plasmid (pVAX-C2A-NLSop2-EGFP-FokMono) (FIG. 65B) include a redesigned and synthesized segment encoding a NLS derived from maize op-2 (RKRKESNRE-SARRSRYRK, SEQ ID NO:133), and a redesigned and synthesized segment encoding the FokI nuclease domain utilizing the maize codon-bias. Additionally, the 2A sequence from Thosea asigna virus (EGRGSLLTCGDVEENPGP, SEQ ID NO:134) was introduced at the N-terminus of the ZFN ORF for the purpose of subsequent linking of the 2 protein encoding domains.

The gene cassettes encoding the ORFs of individual zinc-finger proteins were cloned into either the N2A or C2A vector via ligation using the restriction enzymes KpnI and BamHI to create compatible ends. Next, the BglII/XhoI fragment from the C2A vector was inserted into the N2A vector via the same restriction sites, yielding an intermediate construct that contains a cassette including 2 ZFN-encoding domains flanked by NcoI and SacI restriction sites.

Finally, the NcoI/SacI cassette from this intermediate construction (FIG. 65C), containing both ZFN genes, was excised via restriction using those enzymes and ligated into the plasmid backbone pDAB3872 (FIG. 65D). The resulting plasmids include the ZFN genes plus the relevant promoter and terminator sequences, plus selectable markers for plasmid maintenance.

In the final constructions, an example of which is shown in FIG. 65E, the ZFN expression cassette (including promoter and terminator elements) is flanked by attL sites for convenient manipulation using the Gateway system from Invitrogen (Carlsbad, Calif.). Each of the ZFN constructs generated using this cloning scheme were transformed into *E. coli* DH5a cells (Invitrogen, Carlsbad, Calif.) and subsequently maintained under the appropriate selection.

B. DNA Delivery and Transient Expression

Plasmid preparations of ZFN expression vectors constructed as described in FIG. 65E were generated from 2 L cultures of *E. coli* cells grown in LB media plus antibiotics using an Endonuclease-free Gigaprep kit from Qiagen (Valencia, Calif.) as per the manufacturer's recommendations. Plasmid DNA was delivered directly to maize HiII culture cells using a variety of methods.

In one example, maize cells were subjected to DNA delivery via Whiskers™. Approximately 24 hours prior to DNA delivery, 3 ml PCV of HiII maize suspension cells plus 7 ml of conditioned medium was subcultured into 20 ml of GN6 liquid medium (GN6 medium lacking Gelrite) in a 125 ml Erlenmeyer flask, and placed on a shaker at 125 rpm at 28° C. for 24 hours. 2 mL PCV was removed and added to 12 ml GN6 S/M osmotic medium (N6 Medium, 2.0 mg/L 2,4-D, 30 g/L sucrose, 45.5 g/L sorbitol, 45.5 g/L mannitol, 100 mg/L myo-inositol, pH 6.0) in a 125 mL Erlenmeyer flask. The flask was incubated in the dark for 30-35 minutes at 28° C. with moderate agitation (125 rpm). During this time a 50 mg/ml suspension of silicon carbide whiskers (Advanced Composite Materials, Inc., Eureka Springs, Ak.) was prepared by adding the appropriate volume of GN6 S/M liquid medium to pre-weighed sterile whiskers. Following incubation in GN6 S/M, the contents of each flask were poured into a 15 mL conical centrifuge tube.

After the cells settled, all but 1 mL of GN6 S/M liquid was drawn off and collected in the 125 mL flask for future use. The pre-wetted suspension of whiskers was vortexed for 60 seconds on maximum speed, 160 μL was added to the centrifuge tube using a wide-bore, filtered pipet tip, and 20 μg DNA was added. The tube was 'finger vortexed,' and immediately placed in a Caulk 'Vari-Mix II' dental amalgamator, modified to hold a 17×100 mm culture tube, and then agitated for 60 seconds on medium speed. After agitation, the cocktail of cells, media, whiskers and DNA was returned to the Erlenmeyer flask along with 18 ml of additional GN6 liquid medium. The cells were allowed to recover on a shaker at 125 RPM for 2 hours at 28° C. in the dark.

Approximately 5-6 mL of dispersed suspension was filtered onto Whatman #4 filter paper (5.5 cm) using a glass cell collector unit connected to a house vacuum line such that 5-6 filters were obtained per sample. Filters were placed onto 60×20 mm plates of GN6 medium and cultured at 28° C. under dark conditions. After 24, 48, or 72 hours, the cells from 2-5 filter papers were scraped off, collected into a tube, placed on dry ice, and then frozen at −80° C.

In another example of DNA delivery, the purified endonuclease-free plasmid preparations were delivered directly to maize cells using micro-projectile bombardment techniques adapted from the instrument manufacturer's protocol. All bombardments were conducted with the Biolistic PDS-1000/He™ system (Bio-Rad Laboratories, Hercules, Calif.). For particle coating, 3 mg of 1.0 micron diameter gold particles were washed once with 100% ethanol, twice with sterile distilled water and resuspended in 50 μl water in a siliconized Eppendorf tube. Five micrograms of plasmid DNA, 20 μl spermidine (0.1 M) and 50 μl calcium chloride (2.5 M) were added to the gold suspension. The mixture was incubated at room temperature for 10 min, pelleted at 10K rpm for 10 s, resuspended in 60 μl cold 100% ethanol and 8-9 μl was distributed onto each macrocarrier. To prepare the cells for bombardment, cell clusters were removed from liquid culture 3 days post-subculture and placed on a circle 2.5 cm in diameter of osmotic medium consisting of growth media plus 0.256 M each of mannitol and sorbitol in a Petri dish. The cells were incubated in osmoticum for 4 h prior to bombardment. Bombardment took place in the instrument described above using by placing the tissue on the middle shelf under conditions of 1100 psi and 27 in of Hg vacuum and following the operational manual. At a time point of 24 hours post-treatment, the bombarded cell clusters were harvested, frozen in liquid $N_2$ and stored at −80° C.

Another example of DNA delivery and transient expression of ZFNs in maize cells involved the utilization of protoplast preparations. Using methods modified from Mitchell and Petolino (1991) *J. Plant. Physiol.* 137: 530-536 and Lyznik et al. (1995) *Plant J.* 8(2): 177-186), protoplasts were prepared from HiII maize cell culture. Suspension cultures were harvested 48 hours post-subculture (mid-log growth) by centrifugation at 1000 rpm for 5 minutes. Culture medium was removed and 5 ml packed PCV was gently washed in 10 ml W5 medium (154 mM NaCl$_2$; 125 mM CaCl$_2$H$_2$O; 5 mM KCl$_2$; 5 mM glucose; pH 5.8).

Washed cells were collected via centrifugation at 100 rpm for 5 minutes and subsequently incubated in an enzymatic cocktail containing 3% Cellulase Y-C+0.3% pectolyase Y23 (Karlan Research Products Corp., Cottonwood, Ariz.) in 25 ml of filter sterilized K3 medium (2.5 g KNO$_3$; 250 mg NH$_4$NO$_3$; 900 mg CaCl$_2$ (dihydrate); 250 mg Mg$_2$SO$_4$; 250 mg NH$_4$SO$_4$; 150 mg NaPO$_4$ (monobasic); 250 mg xylose; 10 ml ferrous sulfate/chealate stock (F318); 1 ml B5 micronutrient (1000× stock-750 mg potassium iodide; 250 mg molybdic acid (sodium salt) dehydrate; 25 mg cobalt chloride; 25 mg cupric sulfate); 10 ml K3 Vitamins (100× stock-1 g myo-inositol; 10 mg pyridoxine HCl; 100 mg thiamine HCl; 10 mg nicotinc acid);+0.6M mannitol; pH=5.8]. Cells were incubated at 25° C. for 5-6 hours with gentle agitation (50 rpm) in order to digest the secondary plant cell wall.

Upon degradation of the cell wall, the enzyme-cell mixture was filtered through a 100 micron cell strainer and the flow-through, containing protoplasts and cell debris, was washed with an equal volume of K3+0.6M mannitol medium. The protoplasts were centrifuged at 800 rpm for 5 minutes, the supernatant was discarded and the washing was repeated. The protoplast pellet was washed resuspended in 20 ml K3+0.6M mannitol+9% Ficoll 400 solution. Ten ml of this solution was dispensed into 2 sterile plastic tubes and 2 ml of TM medium (19.52 g MES; 36.45 g mannitol; 40 ml 2M CaCl$_2$H$_2$O stock; pH=5.5)) was gently overlaid on the suspension, forming a discontinuous gradient.

Viable protoplasts were separated from non-viable protoplast, cell debris and intact suspension cells via centrifugation at 800 rpm for 5 minutes. The distinct protoplast band formed at the gradient interface was removed with a pipette and washed with 10 ml fresh TM solution, followed by centrifugation at 800 rpm for 5 minutes. The resulting protoplast pellet was re-suspended in 1 ml of TM medium and the number of viable protoplasts was quantitated with 25 mg/mg fluorescein diacetate (FDA) staining in a hemocytometer. The protoplast solution was adjusted to a final concentration to 1×10$^7$ protoplasts/ml in TM medium.

Approximately 1×10$^6$ protoplasts (100 μl) were transferred to a 2 ml Eppendorf tube containing 10-80 μg purified plasmid DNA. 100 μl of a 40% PEG-3350 (Sigma Chemical Co., St. Louis, Mo.) solution was added drop-wise and the suspension was gently mixed. The protoplast/DNA mixture was incubated for 30 minutes at room temperature, followed by a drop-wise dilution with 1 ml GN6 growth medium. The diluted protoplasts were incubated in this medium for 24 hours at 25° C. and subsequently harvested, frozen in liquid $N_2$ and stored at −80° C.

Example 17

In Vivo ZFN Functionality

Functionality of a ZFN in this example is understood to include (but not be limited to) the ability of a ZFN to express in cells of a crop species, and for that ZFN to mediate a double stranded break in the endogenous genome of that crop through recognition of, binding to and cleavage of its desired target. It is also understood that, in this example, the target of the ZFN is a gene in an endogenous locus and conformation within the crop genome.

In order to assess whether engineered ZFNs have functionality against the predicted target gene in a genomic context, DNA-sequence based assays were deployed. ZFN-induced double-stranded DNA breaks are predicted to induce repair mechanisms such as non-homologous end-joining (NHEJ) (reviewed by Cahill et al., (2006) Mechanisms Front Biosci. 1(11): 1958-76). One outcome of NHEJ is that a proportion of the broken DNA strands will be repaired in an imperfect manner, resulting in small deletions, insertions or substitutions at the cleavage site. One skilled in the art may detect these changes in DNA sequence through a variety of methods.

A. PCR-Based Cloning and Sequencing

In one example, maize HiII cultured cells expressing ZFN proteins were isolated at 24 hours post-transformation, frozen and subjected to genomic DNA extraction using the Qiagen (Valencia, Calif.) Plant DNeasy extraction kit as per the manufacturer's recommendations. PCR amplification was carried out using oligonucleotide primers specific for the target gene and flanking the predicted cleavage site of the ZFN. A forward orientation PCR primer (5'-GGAAGCAT-TATTCCAATTTGATGATAATGG-3') (SEQ ID NO:135) and reverse orientation PCR primer (5'-CCCAAGTGTC-GAGGTTGTCAATATGTTAC-3') (SEQ ID NO:136) specific for the targeted IPP2-K gene paralog were used in combination to amplify purified genomic DNA under the following conditions: 25 ul reaction volume containing 20 ng gDNA template, 20 pmol each primer, 1% DMSO and 10 units Accuprime Pf polymerase (Invitrogen, Carlsbad, Calif.)

in the enzyme manufacturer's buffer. Amplification products of the expected size resulted from amplification cycles consisting of 95° C.-1', (95° C.-30", 61° C.-30", 72° C.-1')×30, 72° C.-5', 4° C.-hold.

The amplified fragments were directly cloned into vector pCR2.1 (Invitrogen, Carlsbad, Calif.) using the TA cloning kit from Invitrogen (Carlsbad, Calif.). Isolated cloned fragments were sequenced with the CEQ Dye Terminator Cycle Sequencing Kit from Beckman Coulter (Fullerton, Calif.) as per the manufacturer's recommendations in a 96-well format. In this experiment, the ZFN proteins are predicted to bind to 2 short IPP2-K gene-specific sequences to create a heterodimeric nuclease that cleaves the ds-DNA as shown in FIG. 66.

Analysis of sequencing results from multiple clones revealed that clone #127 contained a small deletion at precisely the predicted cleavage site of the ZFN, indicating that the NHEJ mechanism had mediated an imperfect repair of the DNA sequence at that site (FIG. 67).

These results demonstrate the ability of these engineered ZFNs to induce targeted, double stranded breaks in a specific manner at an endogenous gene locus within a crop species.

B. Massively Parallel Sequencing Analysis

In another example, a combination of PCR and massively-parallel pyrosequencing methods were applied to interrogate the genomes of multiple cell samples expressing different ZFN proteins targeted against this same sequence. Three variants of a forward orientation PCR primer (5'-XXXCAC-CAAGTTGTATTGCCTTCTCA-3') (SEQ ID NO:137) in which XXX=GGG, CCC, or GGC and three variants of a reverse orientation PCR primer (5'-XXXATAGGCT-TGAGCCAAGCAATCTT-3') (SEQ ID NO:138) in which XXX=GCC, CCG or CGG were synthesized (IDT, Coralville, Iowa). The 3-bp tags at the 5'-end of each primer serve as an identifier key and indicate which cell sample the amplicon originated from. Primer pairs with matching identifier tags (keys) were used in combination to amplify purified genomic DNA derived from maize cell samples under the following conditions: 50 ul reaction volume containing 40 ng gDNA template, 20 pmol each primer, 1% DMSO and 10 units Accuprime Pf polymerase (Invitrogen, Carlsbad, Calif.) in the enzyme manufacturer's buffer. Amplification products of the expected size resulted from amplification cycles consisting of 95° C.-1', (95° C.-30", 65° C.-30", 72° C.-1')×30, 4° C.-hold and were purified using Qiagen's (Valencia, Calif.) MinElute PCR purification kit as per the manufacturer's recommendations.

Massively parallel pyrosequencing reactions (also known as 454 sequencing) were performed directly on PCR products as described in (Margulies et al. (2005) Nature 437: 376-380) by 454 Life Sciences (Branford, Conn.). Analysis of 454 sequencing results was carried out by identifying sequence reads containing deletions of the expected size and position within the DNA molecule.

Results of these analyses indicated the presence of multiple small deletions at the expected cleavage site for these ZFNs, as shown in FIG. 68. These deletions are precisely localized to the ZFN target site and indicate that ds breaks, induced by the ZFN, were generated in the genome and subsequently repaired by NHEJ. These results further demonstrate the ability of these engineered ZFNs to induce targeted, double stranded breaks in a specific manner at an endogenous gene locus within a crop species.

Example 18

Donor DNA Design for Targeted Integration

In this example, donor DNA is understood to include double-stranded DNA molecules that are delivered into plant cells and incorporated into the nuclear genome. The mechanism by which this incorporation takes place may be via homology-independent non-homologous end joining (NHEJ; reviewed by Cahill et al., (2006) Mechanisms Front Biosci. 1: 1958-76) or another similar mechanism at the site of a double stranded break in the nuclear DNA. Such NHEJ-driven, ligation-like incorporation of donor DNA into the genome is referred to as random integration, since the integration position of the donor DNA is primarily determined by the presence of a double stranded DNA break. In this mechanism, donor DNA integration into the genome is not dependent on either the nucleotide sequence of the genome at the site of the break or the nucleotide sequence of the donor itself. Therefore, during random integration, the "address" in the genome at which the donor DNA is incorporated is not specified nor predicted based on the sequence of the donor DNA. Random integration is the primary mechanism by which transgenesis of donor DNA occurs during standard plant transformation via either *Agrobacterium*- or biolistic-mediated DNA delivery into living plant cells.

In contrast to random integration, donor DNA may also incorporate into the genome via targeted integration. Targeted integration is understood to occur at the site of a double-stranded break (position) via homology-dependent mechanisms such as homology-dependent single stranded annealing or homologous recombination (reviewed in van den Bosch et al. (2002) Biol Chem. 383(6): 873-892). In the case of homology-dependent DNA break repair, donor DNA that contains nucleotide sequence with identity or similarity to the DNA at the break site may incorporate at that site. Therefore, the "address" at which the donor DNA integrates into the genome is dependent on nucleotide sequence identity or sequence similarity between the genome and donor DNA molecules. In plant systems, repair of double-stranded breaks in DNA is known to utilize both NHEJ and homology-dependent pathways (reviewed in Puchta (2005) J. Exp. Bot. 56: 1-14).

In this example, we describe the design and construction of donor DNA molecules to be integrated into the genome via targeted integration at the site of a double stranded break induced by sequence-specific ZFN proteins. Different ZFN proteins may induce double-stranded breaks at different nucleotides in the target gene sequence; the specific site of the induced double stranded break is referred to as the position.

As described in Example 13, we have characterized the nucleotide sequence of a target gene, IPP2K from maize. Subsequently, we designed ZFN proteins to bind to specific bases of that target gene (Example 14) and validated their binding/cleavage activity at that sequence within the target gene in both heterologous systems and against the endogenous gene in maize cells (Examples 15-17). Here, we describe the construction of various donor molecules designed to incorporate into the maize genome at the position of the ZFN-mediated double stranded break in the IPP2K gene via targeted integration. One skilled in the art might construct a donor DNA molecule designed to incorporate into a ZFN-induced double stranded break via homology-driven targeted integration at any position in any genome for which nucleotide sequence is known and that sequence is predicted to contain a double stranded break.

In one embodiment described herein, the donor DNA molecule comprises an autonomous herbicide-tolerance gene expression cassette bounded by segments of nucleotide sequence identical to that of the target gene, IPP2K at the targeted position. In this embodiment, the autonomous herbicide tolerance cassette is understood to include a complete promoter-transcription unit (PTU) containing a promoter, herbicide tolerance gene, and terminator sequence known to be functional in plant cells. One skilled in the art may select any promoter, gene and terminator combination to constitute the autonomous PTU. Also included on this plasmid construct are DNA fragments with sequence identity to the target gene in maize (IPP2K) at the position indicated. These fragments serve as the "homology flanks" of the donor DNA and direct incorporation of this donor into the target gene at the specified position via targeted integration. The homology flanks are placed both upstream and downstream of the PTU in the correct 5'- to 3'-orientation relative to the PTU. One skilled in the art may envision homology flanks of varying size and orientation in a donor DNA construction.

In another embodiment described herein, the donor DNA molecule comprises a plasmid construction containing a non-autonomous herbicide-tolerance gene expression cassette bounded by segments of nucleotide sequence identical to that of IPP2K at the target position. In this embodiment, the non-autonomous herbicide tolerance cassette is understood to include an incomplete promoter-transcription unit (PTU) that lacks a functional promoter. The non-autonomous PTU does contain an herbicide tolerance gene, and terminator sequence known to be functional in plant cells. One skilled in the art may select any gene and terminator combination to constitute a non-autonomous PTU. In this example of a non-autonomous donor, expression of the herbicide tolerance gene is dependent on incorporation of the donor segment into a genomic location proximal to a functional promoter that may drive expression of that gene. One might envision the relatively rare situation in which the donor will incorporate via random integration into a genetic locus where a serendipitous promoter resides and is available to drive expression of the herbicide tolerance gene. Alternatively, based on the presence of homology flanks of DNA fragments of the appropriate length with sequence identity to the target gene at a specified position in maize within the donor DNA construction, precise targeted integration of the donor DNA into the target gene at the specified position may occur (as described for the autonomous donor) and therefore exploit the endogenous promoter of said target gene. In this embodiment, the homology flanks are placed both upstream and downstream of the PTU in the correct 5'- to 3'-orientation relative to the PTU. One skilled in the art may envision homology flanks of varying size and orientation in a donor DNA construction.

In both embodiments described herein (autonomous and non-autonomous donor design), the plasmid constructions typically contain additional elements to enable cloning, expression of the herbicide tolerance gene, and subsequent analysis. Such elements include bacterial origins of replication, engineered restriction sites, etc. and are described below. One skilled in the art may envision the utilization of different elements comprising a donor DNA molecule.

A. Bacterial Strains and Culture Conditions

*Escherichia coli* strains (One Shot® Top 10 Chemically Competent Cells; MAX Efficiency® DH5α™ Chemically Competent Cells, Invitrogen Life Technologies, Carlsbad, Calif.), were grown at 37° C., 16 hrs using Luria-Bertani broth (LB: 10 g/L Bacto-tryptone, 10 g/L NaCl, 5 g/L Bacto-yeast extract), LB agar (LB broth plus 15 g/L Bacto-agar), or Terrific broth (TB: 12 g/L Bacto-tryptone, 24 g/L Bacto-yeast extract, 0.4% v/v glycerol, 17 mM $KH_2PO_4$, 72 mM $K_2HPO_4$). Liquid cultures were shaken at 200 rpm. Chloramphenicol (50 µg/ml), kanamycin (50 µg/ml), or ampicillin (100 µg/ml) were added to the media as required. All antibiotics, culture media and buffer reagents used in this study were purchased from Sigma-Aldrich Corporation (St. Louis, Mo.) or Difco Laboratories (Detroit, Mich.).

B. Plasmid Backbone Position-1

A plasmid backbone containing homology flanks for position-1 of IPP2K was engineered to allow for the integration of any donor DNA sequence into the corresponding target site of the IPP2K gene. One skilled in the art may envision plasmid backbones using various cloning sites, modular design elements and sequence homologous to any target sequence within the genome of interest. The plasmid backbone exemplified here originated with the base plasmid vector pBC SK(–) phagemid (3.4 Kbp) (Stratagene, La Jolla, Calif.). A four-step synthesis as described below was used to construct the position-1 plasmid backbone.

In step #1, the base plasmid was prepared. Three µg pBC SK(–) were linearized using 10 units of Spe I and 10 units of Not I (New England Biolabs, Beverly, Mass.) restriction endonucleases for 1 hr at 37° C. Restricted DNA was electrophoresed at 100 V for 1 hr in a 1.0% TAE (0.04 M Tris-acetate, 0.002 M EDTA) agarose gel supplemented with 0.5% ethidium bromide (Sigma-Aldrich Corporation, St. Louis, Mo.). DNA fragments were visualized with UV light and fragment size estimated by comparison with 1 Kbp DNA ladder (Invitrogen Life Technologies, Carlsbad, Calif.). The 3.4 Kbp Spe I/Not I digested subcloning vector, pBC SK(–) was gel-excised and purified according to the manufacturer's directions using QIAQUICK™ Gel Extraction Kit (QIAGEN Inc., Valencia, Calif.).

In step#2, 5'- & 3'-homology flanks from IPP2K position-1 were isolated. The following oligonucleotide primers were synthesized by Integrated DNA Technologies, Inc. (Coralville, Iowa) under conditions of standard desalting and diluted with water to a concentration of 0.125 µg/ul:

(SEQ ID NO: 143)
5'- GCGGCCGCGTCTCACCGCGGCTTGGGGATTGGATACGGAGCT -3'

(SEQ ID NO: 144)
5'- ACTAGTGATATGGCCCCACAGGAGTTGCTCATGACTTG -3'

(SEQ ID NO: 145)
5'- ACTAGTCCAGAACTGGTTGAGTCGGTCAAACAAGATTGCT -3'

(SEQ ID NO: 146)
5'- GTCGACCTTGATGCTACCCATTGGGCTGTTGT -3'

PCR amplification reactions were carried out using reagents provided by TaKaRa Biotechnology Inc., Seta 3-4-1, Otsu, Shiga, 520-2193, Japan and consisted of the following: Five µl 10× LA PCR™ Buffer II ($Mg^{2+}$), 20 ng double-stranded gDNA template (maize HiII), 10 pmol forward oligonucleotide primer, 10 pmol reverse oligonucleotide primer, 8 µl dNTP mix (2.5 mM each), 33.5 µl $H_2O$, 0.5 µl (2.5 units) TaKaRa LA Taq™ DNA polymerase, 1 drop of mineral oil. PCR reactions were performed using a Perkin-Elmer Cetus, 48-sample DNA Thermal Cycler (Norwalk, Conn.) under the following cycle conditions: 94° C., 4 min/1 cycle; 98° C. 20 sec, 65° C. 1 min, 68° C. 1 min/30 cycles; 72° C., 5 min/1 cycle; 4°/hold. Fifteen µl of each PCR reaction was electrophoresed at 100 V for 1 hr in a 1.0% TAE agarose gel supplemented with 0.5% ethidium bromide. Amplified fragments were visualized with UV light and fragment size estimated by comparison with 1 Kbp DNA ladder. Expected amplification products were diagnosed by the presence of either a DNA fragments of 0.821 Kbp (5'-homology flank) or 0.821 Kbp (3'-homology flank).

These fragments were gel-excised and purified according to manufacturer's directions using QIAQUICK™ Gel Extraction Kit (QIAGEN Inc., Valencia, Calif.). Purified fragments were then cloned into pCR2.1 plasmid using TOPO TA Cloning® Kit (with pCR®2.1 vector) and One Shot® TOP10 Chemically competent *E. coli* cells (Invitrogen Life Technologies, Carlsbad, Calif.) according to manufacturer's protocol.

Individual colonies were inoculated into a 14 ml Falcon Tube (Becton-Dickinson, Franklin Lakes, N.J.) containing 2 ml TB supplemented with 50 µl/ml kanamycin and incubated for 16 hrs at 37° C. with shaking at 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three µg of isolated plasmid from 5'-homology flank clone plasmids was digested with 10 units Spe I and Not I. Three prime-homology flank clone plasmids were digested with 10 units Spe I and 20 units Sal I (New England Biolabs, Beverly, Mass.). All plasmid digestions were incubated for 1 hr at 37° C. Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp DNA ladder. Expected plasmid clones were diagnosed by the presence of inserted DNA fragments of 0.821 Kbp (5'-homology flank) or 0.821 Kbp (3'-homology flank) in addition to the 3.9 Kbp pCR® 2.1 vector.

Double-stranded sequencing reactions of plasmid clones were performed as described by manufacturer using CEQ™ DTCS-Quick Start Kit (Beckman-Coulter, Palo Alto, Calif.). Reactions were purified using Performa DTR Gel Filtration Cartridges (Edge BioSystems, Gaithersburg, Md.) as described by manufacturer protocols. Sequence reactions were analyzed on a Beckman-Coulter CEQ™ 2000 XL DNA Analysis System and nucleotide characterization performed using Sequencher™ version 4.1.4 (Gene Codes Corporation, Ann Arbor, Mich.). The sequence of the 0.821 Kbp fragment corresponding to the position-1 5'-homology flank derived from IPP2K is shown in FIG. 87 (SEQ ID NO:171). The sequence of the 0.821 Kbp fragment corresponding to the position-1 3'-homology flank derived from IPP2K is shown in FIG. 88 (SEQ ID NO:172).

In step #3 position-1 5'-homology flanks were ligated into the base plasmid. Restricted fragments corresponding to clones that contained the correct position-1 5'-homology flank sequence were gel-excised and purified according to the manufacturer's directions using QIAQUICK™ Gel Extraction Kit (QIAGEN Inc., Valencia, Calif.). Fragments corresponding to the position-1 5'-homology flank (0.821 Kbp) were then ligated to purified base plasmid digested with Spe I/Not I (step #1) at a 1:5 vector:insert ratio using 500 units T4 DNA Ligase (Invitrogen Life Technologies, Carlsbad, Calif.) in a reaction volume of 20 µl under conditions of 16 hr incubation in a 16° C. water bath. Five µl of the ligation reaction was subsequently transformed *E. coli* One Shot® Top 10 Chemically Competent Cells, (Invitrogen Life Technologies, Carlsbad, Calif.) and plated under selection conditions described by the manufacturer. Individual colonies were inoculated into a 14 ml Falcon Tube (Becton-Dickinson, Franklin Lakes, N.J.) containing 2 ml TB supplemented with 50 µl/ml kanamycin and incubated for 16 hrs at 37° C. shaking 200 rpm.

Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three µg of isolated plasmid DNA was digested with 10 units Spe I and Not I. (New England Biolabs, Beverly, Mass.) and incubated for 1 hr at 37° C. Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp DNA ladder. Expected plasmid clones were diagnosed by the presence of an inserted DNA fragment of 0.821 Kbp (5'-homology flank) in addition to the 3.4 Kbp base plasmid.

In step#4, position-1 3'-homology flanks were ligated into the step #3 product. Three µg of the engineering product described in step #3 was linearized using 10 units of Spe I and 20 units of Sal I (New England Biolabs, Beverly, Mass.) restriction endonucleases for 1 hr at 37° C. Restricted DNA was electrophoresed at 100 V for 1 hr in a 1.0% TAE (0.04 M Tris-acetate, 0.002 M EDTA) agarose gel supplemented with 0.5% ethidium bromide (Sigma-Aldrich Corporation, St. Louis, Mo.). DNA fragments were visualized with UV light and fragment size estimated by comparison with 1 Kbp DNA ladder (Invitrogen Life Technologies, Carlsbad, Calif.). The ~4.2 Kbp Spe I/Sal I digested product from step #3 was gel-excised and purified according to the manufacturer's using QIAQUICK™ Gel Extraction Kit (QIAGEN Inc., Valencia, Calif.).

Isolated fragments of the 3'-homology flank donor (0.821 Kbp) generated in step #2 were subsequently combined with step #3 product that was digested with Spe I/Sal I and purified as described above in a 20 µl ligation reaction using a 1:5 vector:insert ratio and 500 units T4 DNA Ligase (Invitrogen Life Technologies, Carlsbad, Calif.). Ligation reactions were incubated for 16 hr in a 16° C. water bath. Following the ligation, 5 µl of the ligation reaction was transformed into MAX Efficiency® DH5α™ Chemically Competent Cells (Invitrogen Life Technologies, Carlsbad, Calif.) as per the manufacturer's recommendations. Individual colonies inoculated into a 14 ml Falcon Tube (Becton-Dickinson, Franklin Lakes, N.J.) containing 2 ml TB supplemented with 50 µl/ml chloramphenicol.

Cultures were incubated for 16 hrs at 37° C. shaking 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three µg isolated plasmid was digested with 10 units Sal I and Not I. (New England Biolabs, Beverly, Mass.) and incubated for 1 hr at 37° C. Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp DNA ladder. Expected clones were diagnosed by the presence of two DNA fragments of 1.64 Kbp (insert) and 3.33 Kbp (base plasmid). The resulting plasmid was given the name pDAB7471 (FIG. 70).

C. Plasmid Backbone Position-2

A plasmid backbone containing homology flanks for position-2 of IPP2K was engineered to allow for the integration of any donor DNA sequence into the corresponding target site of the IPP2K gene. One skilled in the art may envision plasmid backbones using various cloning sites, modular design elements and sequence homologous to any target sequence within the genome of interest. The plasmid backbone exemplified here originated with the base plasmid vector pBC SK(−) phagemid (3.4 Kbp) (Stratagene, La Jolla, Calif.). A four-step synthesis as described below was used to construct the position-2 plasmid backbone.

In step #1, the base plasmid was prepared. Three μg pBC SK(-) were linearized using 10 units of Spe I and 10 units of Not I (New England Biolabs, Beverly, Mass.) restriction endonucleases for 1 hr at 37° C. Restricted DNA was electrophoresed at 100 V for 1 hr in a 1.0% TAE (0.04 M Tris-acetate, 0.002 M EDTA) agarose gel supplemented with 0.5% ethidium bromide (Sigma-Aldrich Corporation, St. Louis, Mo.). DNA fragments were visualized with UV light and fragment size estimated by comparison with 1 Kbp DNA ladder (Invitrogen Life Technologies, Carlsbad, Calif.). The 3.4 Kbp Spe I/Not I digested subcloning vector, pBC SK(-) was gel-excised and purified according to the manufacturer's directions using QIAQUICK™ Gel Extraction Kit (QIAGEN Inc., Valencia, Calif.).

In step #2, 5'- & 3'-homology flanks from IPP2K position-2 were isolated. The following oligonucleotide primers were synthesized by Integrated DNA Technologies, Inc. (Coralville, Iowa) under conditions of standard desalting and diluted with water to a concentration of 0.125 μg/μl:
5'-GCGGCCGCTAGATAGCAGATGCAGATTGCT-3' (SEQ ID NO: 147)
5'-ACTAGTATTGGCACCCAGGTGTTGGCTCA-3' (SEQ ID NO:148)
5'-ACTAGTCATGTCGATGGTGGGGTATGGT-TCAGATTCAG-3' (SEQ ID NO:149)
5'-GTCGACGTACAATGATTTCAGGTTACG-GCCTCAGGAC-3' (SEQ ID NO: 150)

PCR amplification reactions were carried out using reagents provided by TaKaRa Biotechnology Inc., Seta 3-4-1, Otsu, Shiga, 520-2193, Japan and consisted of the following: 5 μl 10×LA PCR™ Buffer II (Mg2+), 20 ng double-stranded gDNA template (maize Hill), 10 pmol forward oligonucleotide primer, 10 pmol reverse oligonucleotide primer, 8 μl dNTP mix (2.5 mM each), 33.5 μl H$_2$O, 0.5 μl (2.5 units) TaKaRa LA Taq™ DNA polymerase, 1 drop of mineral oil. PCR reactions were performed using a Perkin-Elmer Cetus, 48-sample DNA Thermal Cycler (Norwalk, Conn.) under the following cycle conditions: 94° C., 4 min/1 cycle; 98° C. 20 sec, 55° C. 1 min, 68° C. 1 min/30 cycles; 72° C., 5 min/1 cycle; 4° C./hold. Fifteen μl of each PCR reaction was electrophoresed at 100 V for 1 hr in a 1.0% TAE agarose gel supplemented with 0.5% ethidium bromide. Amplified fragments were visualized with UV light and fragment size estimated by comparison with 1 Kbp DNA ladder. Expected amplification products were diagnosed by the presence of either a DNA fragments of 0.855 Kbp (5'-homology flank) or 0.845 Kbp (3'-homology flank). These fragments were gel-excised and purified according to manufacturer's directions using QIAQUICK™ Gel Extraction Kit (QIAGEN Inc., Valencia, Calif.). Purified fragments were then cloned into pCR2.1 plasmid using TOPO TA Cloning® Kit (with pCR®2.1 vector) and One Shot® TOP10 Chemically competent E. coli cells (Invitrogen Life Technologies, Carlsbad, Calif.) according to manufacturer's protocol.

Individual colonies were inoculated into a 14 ml Falcon Tube (Becton-Dickinson, Franklin Lakes, N.J.) containing 2 ml TB supplemented with 50 μl/ml kanamycin and incubated for 16 hrs at 37° C. with shaking at 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three μg of isolated plasmid from 5'-homology flank clone plasmids was digested with 10 units Spe I and Not I. Three prime-homology flank clone plasmids were digested with 10 units Spe I and 20 units Sal I (New England Biolabs, Beverly, Mass.). All plasmid digestions were incubated for 1 hr at 37° C.

Restricted DNA was electrophoresed at 100V for 1 hr in a 1.0% TAE agarose gel supplemented with 0.5% ethidium bromide. Fragments were visualized with UV light and fragment size estimated by comparison with 1 Kbp DNA ladder. Expected plasmid clones were diagnosed by the presence of inserted DNA fragments of 0.855 Kbp (5'-homology flank) or 0.845 Kbp (3'-homology flank) in addition to the 3.9 Kbp pCR® 2.1 vector.

Double-stranded sequencing reactions of plasmid clones were performed as described by manufacturer using CEQ™ DTCS-Quick Start Kit (Beckman-Coulter, Palo Alto, Calif.). Reactions were purified using Performa DTR Gel Filtration Cartridges (Edge BioSystems, Gaithersburg, Md.) as described by manufacturer protocols. Sequence reactions were analyzed on a Beckman-Coulter CEQ™ 2000 XL DNA Analysis System and nucleotide characterization performed using Sequencher™ version 4.1.4 (Gene Codes Corporation, Ann Arbor, Mich.). The sequence of the 0.855 Kbp fragment corresponding to the position-2 5'-homology flank derived from IPP2K is shown in FIG. 89 (SEQ ID NO:139). The sequence of the 0.845 Kbp fragment corresponding to the position-2 3'-homology flank derived from IPP2K is shown in FIG. 90 (SEQ ID NO:140).

In step #3, position-1 5'-homology flanks were ligated into the base plasmid. Restricted fragments corresponding to clones that contained the correct position-2, 5'-homology flank sequence were gel-excised and purified according to the manufacturer's directions using QIAQUICK™ Gel Extraction Kit (QIAGEN Inc., Valencia, Calif.). Fragments corresponding to the position-1 5'-homology flank (0.855 Kbp) were then ligated to purified base plasmid digested with Spe I/Not I (step #1) at a 1:5 vector:insert ratio using 500 units T4 DNA Ligase (Invitrogen Life Technologies, Carlsbad, Calif.) in a reaction volume of 20 μl under conditions of 16 hr incubation in a 16° C. water bath.

Five μl of the ligation reaction was subsequently transformed E. coli One Shot® Top 10 Chemically Competent Cells, (Invitrogen Life Technologies, Carlsbad, Calif.) and plated under selection conditions described by the manufacturer. Individual colonies were inoculated into a 14 ml Falcon Tube (Becton-Dickinson, Franklin Lakes, N.J.) containing 2 ml TB supplemented with 50 μl/ml kanamycin and incubated for 16 hrs at 37° C. shaking 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three μg of isolated plasmid DNA was digested with 10 units Spe I and Not I. (New England Biolabs, Beverly, Mass.) and incubated for 1 hr at 37° C. Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp DNA ladder. Expected plasmid clones were diagnosed by the presence of an inserted DNA fragment of 0.855 Kbp (5'-homology flank) in addition to the 3.4 Kbp base plasmid.

In step #4, position-2 3'-homology flanks were ligated into the step #3 product. Three μg of the engineering product described in step #3 was linearized using 10 units of Spe I and 20 units of Sal I (New England Biolabs, Beverly, Mass.) restriction endonucleases for 1 hr at 37° C. Restricted DNA was electrophoresed at 100 V for 1 hr in a 1.0% TAE (0.04 M Tris-acetate, 0.002 M EDTA) agarose gel supplemented with 0.5% ethidium bromide (Sigma-Aldrich Corporation, St. Louis, Mo.). DNA fragments were visualized with UV light and fragment size estimated by comparison with 1 Kbp DNA ladder (Invitrogen Life Technologies, Carlsbad, Calif.). The 4.25 Kbp Spe I/Sal I digested product from step #3 was gel-excised and purified according to the manufacturer's directions using OIAOUICK™ Gel Extraction Kit (QIAGEN Inc., Valencia, Calif.).

Isolated fragments of the 3'-homology flank donor (0.845 Kbp) generated in step #2 were subsequently combined with step #3 product that was digested with Spe I/Sal I and purified as described above in a 20 µl ligation reaction using a 1:5 vector:insert ratio and 500 units T4 DNA Ligase (Invitrogen Life Technologies, Carlsbad, Calif.). Ligation reactions were incubated for 16 hr in a 16° C. water bath. Following the ligation, 5 µl of the ligation reaction was transformed into MAX Efficiency® DH5α™ Chemically Competent Cells (Invitrogen Life Technologies, Carlsbad, Calif.) as per the manufacturer's recommendations. Individual colonies were inoculated into a 14 ml Falcon Tube (Becton-Dickinson, Franklin Lakes, N.J.) containing 2 ml TB supplemented with 50 µl/ml chloramphenicol. Cultures were incubated for 16 hrs at 37° C. shaking 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three µg isolated plasmid was digested with 10 units Sal I and Not I (New England Biolabs, Beverly, Mass.) and incubated for 1 hr at 37° C. Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp DNA ladder. Expected clones were diagnosed by the presence of two DNA fragments of ~1.7 Kbp (insert) and 3.33 Kbp (base plasmid). The resulting plasmid was given the name pDAB7451 (FIG. 71).

D. Autonomous Herbicide-Tolerance Gene Expression Cassette Construction

An autonomous herbicide-tolerance gene expression cassette comprising a complete promoter-transcriptional unit (PTU) containing promoter, herbicide tolerance gene, and poly adenylation (polyA) termination sequences was constructed (FIG. 72). In this embodiment, the promoter sequence is derived from *O. sativa* actin 1 [McElroy et al. (Plant Cell 2, 163-171; 1990); GENBANK™ Accession S44221 and, GENBANK™ Accession X63830]. The herbicide-tolerance gene, comprises the PAT (phosphinothricin acetyl transferase) gene, which confers resistance to the herbicide bialaphos (a modified version of the PAT coding region originally derived from *Streptomyces viridochromogenes* (GENBANK™ Accession M22827; Wohlleben et al. Gene 70, 25-37; 1988). The modifications to the original sequence of the longest open reading frame of M22827 are substantial, and include altering the codon utilization pattern to optimize expression in plants. Except for the substitution of methionine for valine as the first encoded amino acid, and the addition of alanine as the second encoded amino acid, the protein encoded from the PAT open reading frame of pDAB3014 is identical to that encoded by the longest open reading frame of accession M22827. The rebuilt version of PAT is found under GenBank accession 143995. The terminator sequences are derived from *Z. mays* L. lipase [maize lipase cDNA clone of GENBANK™ Accession Number L35913, except that a C at position 1093 of L35913 is replaced with a G at position 2468 in pDAB3014. This maize sequence comprises the 3' untranslated region/transcription terminator region for the PAT gene].

The following oligonucleotide primers were synthesized by Integrated DNA Technologies, Inc. (Coralville, Iowa) under conditions of standard desalting and diluted with water to a concentration of 0.125 µg/µl:

```
                                          (SEQ ID NO: 151)
5'- ACTAGTTAACTGACCTCACTCGAGGTCATTCATATGCTTGA -3'

(SEQ ID NO: 152)
5'- ACTAGTGTGAATTCAGCACTTAAAGATCT -3'
```

PCR amplification reactions were carried out using reagents provided by TaKaRa Biotechnology Inc., Seta 3-4-1, Otsu, Shiga, 520-2193, Japan and consisted of the following: 5 µl 10× LA PCR™ Buffer II (Mg2$^+$), 20 ng double-stranded template [pDAB3014 plasmid DNA], 10 pmol forward oligonucleotide primer, 10 pmol reverse oligonucleotide primer, 8 µl dNTP mix (2.5 mM each), 33.5 µl H$_2$O, 0.5 µl (2.5 units) TaKaRa LA Taq™ DNA polymerase, 1 drop of mineral oil. PCR reactions were performed using a Perkin-Elmer Cetus, 48-sample DNA Thermal Cycler (Norwalk, Conn.) under the following cycle conditions: 94° C., 4 min/1 cycle; 98° C. 20 sec, 55° C. 1 min, 68° C. 3 min/30 cycles; 72° C., 5 min/1 cycle; 4° C./hold. Fifteen µl of each PCR reaction was electrophoresed at 100 V for 1 hr in a 1.0% TAE agarose gel supplemented with 0.5% ethidium bromide.

Amplified fragments were visualized with UV light and fragment size estimated by comparison with 1 Kbp DNA ladder. Expected amplification products were diagnosed by the presence of a DNA fragment of 2.3 Kbp. This fragment was gel-excised and purified according to manufacturer's directions using QIAQUICK™ Gel Extraction Kit (QIAGEN Inc., Valencia, Calif.). Purified fragment was then cloned into pCR2.1 plasmid using TOPO TA Cloning® Kit and transformed into One Shot® TOP10 Chemically competent *E. coli* cells (Invitrogen Life Technologies, Carlsbad, Calif.) according to manufacturer's protocol.

Individual colonies were inoculated into a 14 ml Falcon Tube (Becton-Dickinson, Franklin Lakes, N.J.) containing 2 ml TB supplemented with 50 µl/ml kanamycin and incubated for 16 hrs at 37° C. with shaking at 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three µg of isolated plasmid was digested with 10 units Spe I and Not I. All plasmid digestions were incubated for 1 hr at 37° C.

Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp DNA ladder. Expected plasmid clones were diagnosed by the presence of an inserted DNA fragment of 2.325 Kbp in addition to the 3.9 Kbp pCR® 2.1 vector. Double-stranded sequencing reactions of plasmid clones were performed as described by manufacturer using CEQT DTCS-Quick Start Kit (Beckman-Coulter, Palo Alto, Calif.). Reactions were purified using Performa DTR Gel Filtration Cartridges (Edge BioSystems, Gaithersburg, Md.) as described by manufacturer protocols. Sequence reactions were analyzed on a Beckman-Coulter CEQ™ 200 XL DNA Analysis System and nucleotide characterization was performed using Sequencher™ version 4.1.4 (Gene Codes Corporation, Ann Arbor, Mich.).

E. Autonomous Herbicide Tolerance Gene Cassette Insertion into Plasmid Backbone—Autonomous Donor In order to create a donor plasmid, the autonomous herbicide tolerance gene cassette described in Example 18D was inserted into plasmid backbone constructions described in Examples 18B and 18C. Restricted fragment derived from a clone that contained the expected 2.325 Kbp sequence described above (FIG. 72) was gel-excised and purified according to the manufacturer's directions using QIAQUICK™ Gel Extraction Kit (QIAGEN Inc., Valencia, Calif.).

This fragment was then combined in a ligation reaction with either purified pDAB7471 (position-1 plasmid backbone, FIG. 70) or pDAB 7451 (position-2 plasmid backbone FIG. 71) that had been digested with restriction enzyme Spe I and subsequently dephosphorylated. Ligation was carried out under the following conditions: 1:5 vector:insert ratio and 500 units T4 DNA Ligase (Invitrogen Life Technologies, Carlsbad, Calif.) in a reaction volume of 20 µl under conditions of 16 hr incubation in a 16° C. water bath. Five µl of the ligation reaction was subsequently transformed into 50 µl *E. coli* MAX Efficiency® DH5α™ Chemically Competent Cells, (Invitrogen Life Technologies, Carlsbad, Calif.) and plated under selection conditions described by the manufacturer.

Individual colonies were inoculated into a 14 ml Falcon Tube (Becton-Dickinson, Franklin Lakes, N.J.) containing 2 ml TB supplemented with 50 µl/ml chloramphenicol and incubated for 16 hrs at 37° C. shaking 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three µg of isolated plasmid DNA was digested with 10 units Spe I (New England Biolabs, Beverly, Mass.) and incubated for 1 hr at 37° C. Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp DNA ladder. Expected plasmid clones were diagnosed by the presence of DNA fragments of 2.325 Kbp and ~4.9 Kbp (pDAB7471 vector) or 2.325 Kbp and ~5.0 Kbp (pDAB7451 vector).

Figure 73:
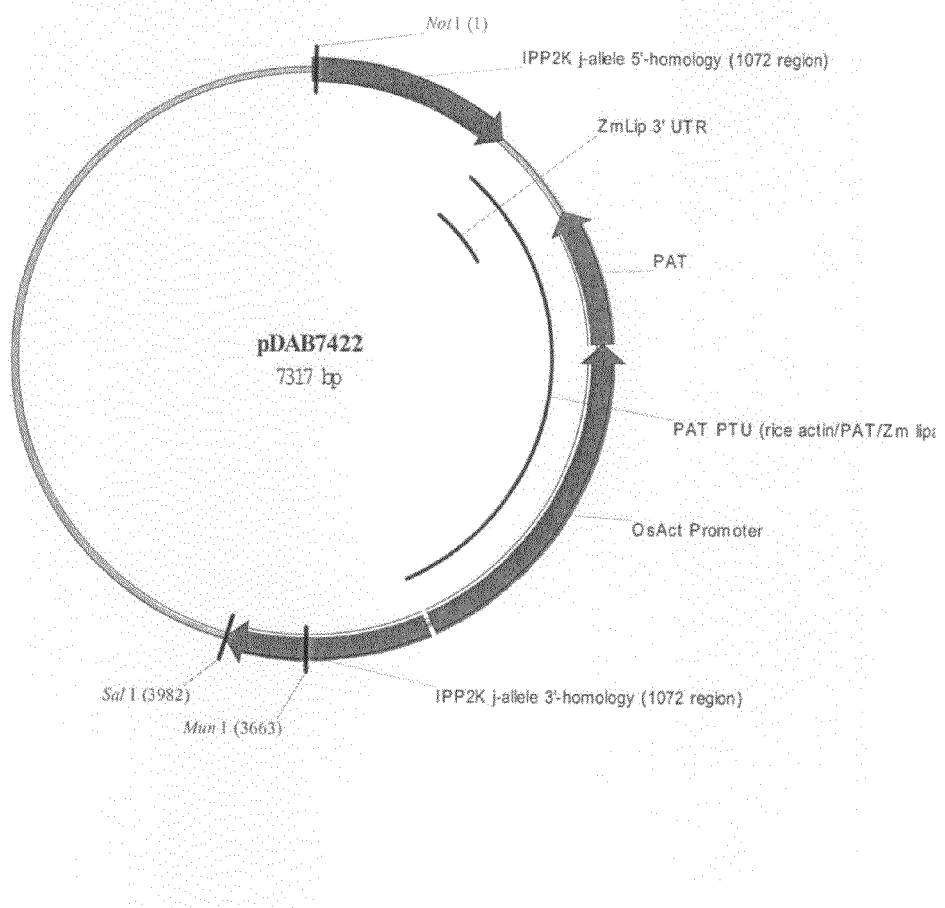
FIG. 73 depicts plasmid pDAB7422, constructed as described in Example 18E. The plasmid includes a complete promoter-transcriptional unit (PTU) containing a promoter, herbicide tolerance gene and poly adenylation (polyA) termination sequence inserted into a position-1 plasmid backbone.
Figure 74:
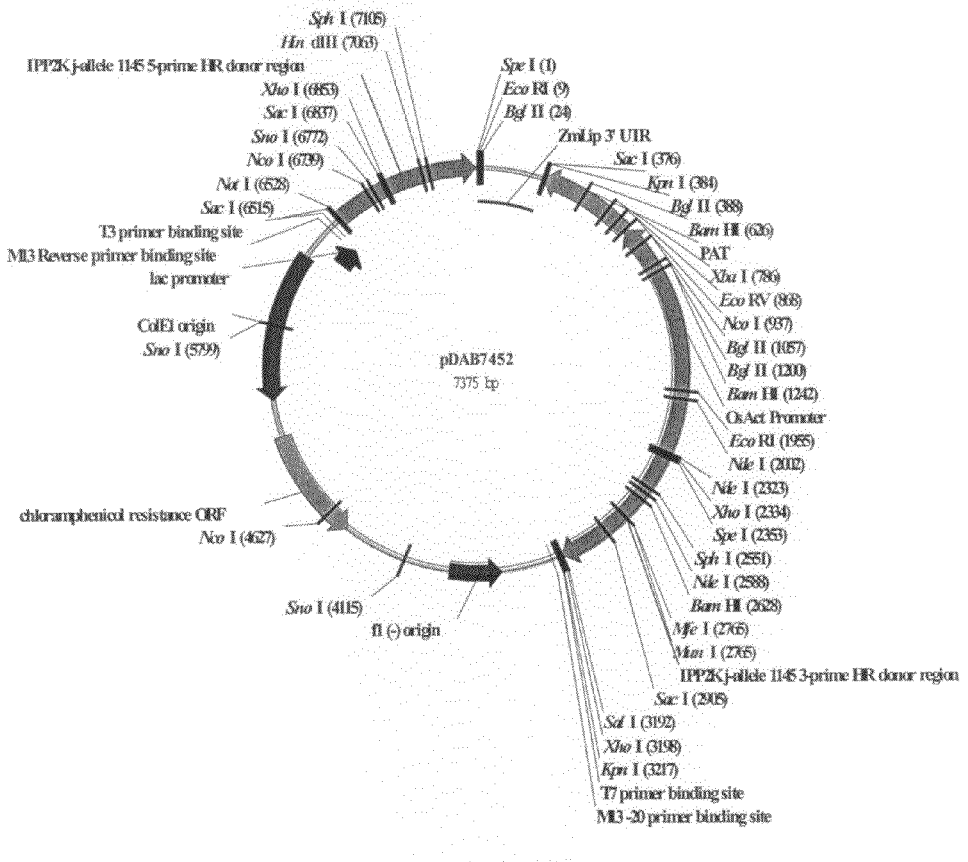
FIG. 74 depicts plasmid pDAB7452, constructed as described in Example 18E. The plasmid includes a complete promoter-transcriptional unit (PTU) containing a promoter, herbicide tolerance gene and poly adenylation (polyA) termination sequence inserted into a position-2 plasmid backbone.

The resulting plasmids were named pDAB7422 (position-1 autonomous donor) (FIG. 73) and pDAB7452 (position-2 autonomous donor) (FIG. 74), respectively.

F. Non-Autonomous Herbicide-Tolerance Gene Expression Cassette Construction

Figure 75:
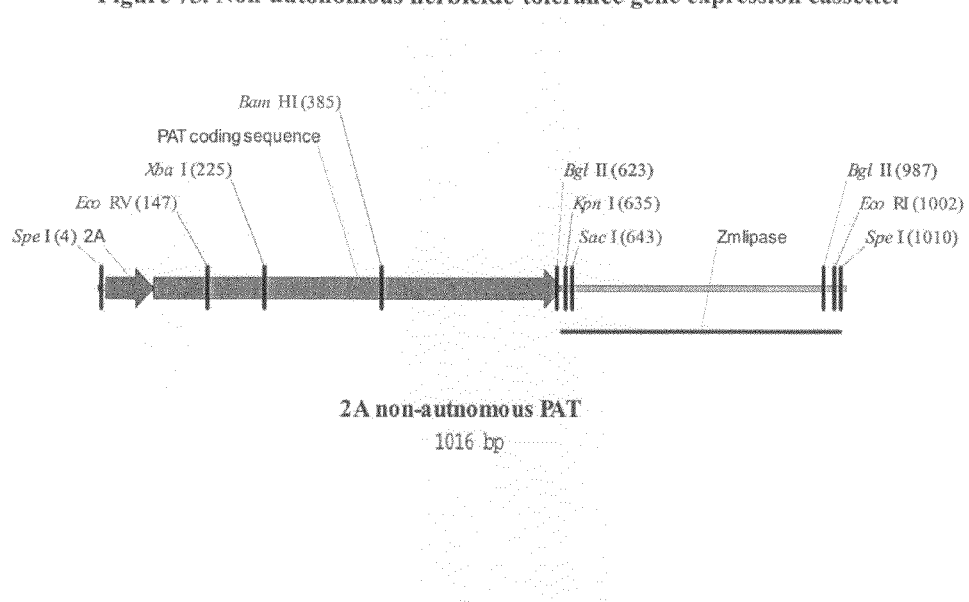
FIG. 75 is a schematic depicting an exemplary non-autonomous herbicide-tolerance gene expression cassette. This construction comprises an incomplete promoter-transcriptional unit (PTU) containing a herbicide tolerance gene and poly adenylation (polyA) termination sequence as described in Example 18F.

A non-autonomous herbicide-tolerance gene expression cassette comprising an incomplete promoter-transcriptional unit (PTU) was constructed (FIG. 75). In this embodiment, a strategy was used that exploits the functionality of a 2A sequence (Mattion, N. M., Hamish, E. C., Crowley, J. C. & Reilly, P. A. (1996) J. Virol. 70, 8124-8127) derived from the Thesoa assigna virus, a herbicide tolerance gene and poly adenylation (polyA) termination sequences, but no promoter. In this embodiment, the 2A translational termination signal sequence has been engineered to be translationally in-frame with the herbicide tolerance gene. In addition, the 2A/herbicide coding sequence has been engineered to coincide with the translational reading frame of the IPP2K gene target. The herbicide-tolerance gene comprises the PAT (phosphinothricin acetyl transferase) gene, which confers resistance to the herbicide bialaphos (a modified version of the PAT coding region originally derived from *Streptomyces viridochromogenes* (GENBANK™ Accession M22827; Wohlleben et al. Gene 70:25-37; 1988). The modifications to the original sequence of the longest open reading frame of M22827 are substantial, and include altering the codon utilization pattern to optimize expression in plants. Except for the substitution of methionine for valine as the first encoded amino acid, and the addition of alanine as the second amino acid, the protein encoded from the PAT open reading frame of pDAB3014 is identical to that encoded by the longest open reading frame of M22827 (which starts with GTG at position 244 of M22827). The rebuilt version of PAT is found under GENBANK™ accession 143995. The terminator sequences are derived from *Z. mays* L. lipase [maize lipase cDNA clone of GENBANK™ Accession Number L35913, except that a C at position 1093 of L35913 is replaced with a G at position 2468 in pDAB3014]. This maize sequence comprises the 3' untranslated region/transcription terminator region for the PAT gene.

The following oligonucleotide primers were synthesized by Integrated DNA Technologies, Inc. (Coralville, Iowa) under conditions of standard desalting and diluted with water to a concentration of 0.125 µg/µl:

(SEQ ID NO: 153)
5'- ACTAGTGGCGGCGGAGAGGGCAGAGGAAGTCTTCTAACATGC

GGTGACGTGGAGGAGAATCCCGGCCCTAGGATGGCTTCTCCGGAGAGGAG

ACCAGTTGA -3

(SEQ ID NO: 154)
5'- ACTAGTATGCATGTGAATTCAGCACTTAAAGATCT -3'

PCR amplification reactions were carried out using reagents provided by TaKaRa Biotechnology Inc. (Seta 3-4-1, Otsu, Shiga, 520-2193, Japan) and consisted of the following: 5 µl 10×LA PCR™ Buffer II (Mg2+), 20 ng double-stranded template (pDAB3014 plasmid DNA), 10 pmol forward oligonucleotide primer, 10 pmol reverse oligonucleotide primer, 8 µl dNTP mix (2.5 mM each), 33.5 µl H2O, 0.5 µl (2.5 units) TaKaRa LA Taq™ DNA polymerase, 1 drop of mineral oil. PCR reactions were performed using a Perkin-Elmer Cetus, 48-sample DNA Thermal Cycler (Norwalk, Conn.) under the following cycle conditions: 94° C., 4 min/1 cycle; 98° C. 20 sec, 55° C. 1 min, 68° C. 2 min/30 cycles; 72° C., 5 min/1 cycle; 4° C./hold. Fifteen µl of each PCR reaction was electrophoresed at 100 V for 1 hr in a 1.0% TAE agarose gel supplemented with 0.5% ethidium bromide. Amplified fragments were visualized with UV light and fragment size estimated by comparison with 1 Kbp DNA ladder. Expected amplification products were diagnosed by the presence of a DNA fragment of ~1 Kbp. This fragment was gel-excised and purified according to manufacturer's directions using QIAQUICK™ Gel Extraction Kit (QIAGEN Inc., Valencia, Calif.). Purified fragment were then cloned into pCR2.1 plasmid using TOPO TA Cloning® Kit transformed into One Shot® TOP10 chemically competent *E. coli* cells (Invitrogen Life Technologies, Carlsbad, Calif.) according to manufacturer's protocol.

Individual colonies were inoculated into a 14 ml Falcon Tube (Becton-Dickinson, Franklin Lakes, N.J.) containing 2 ml TB supplemented with 50 µl/ml kanamycin and incubated for 16 hrs at 37° C. with shaking at 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three μg of isolated plasmid was digested with 10 units Spe I. All plasmid digestions were incubated for 1 hr at 37° C. Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp DNA ladder. Expected plasmid clones were diagnosed by the presence of an inserted DNA fragment of 1.0 Kbp and 3.9 Kbp (pCR® 2.1 vector). Double-stranded sequencing reactions of plasmid clones were performed as described by manufacturer using CEQ™ DTCS-Quick Start Kit (Beckman-Coulter, Palo Alto, Calif.). Reactions were purified using Performa DTR Gel Filtration Cartridges (Edge BioSystems, Gaithersburg, Md.) as described by manufacturer protocols. Sequence reactions were analyzed on a Beckman-Coulter CEQ™ 2000 XL DNA Analysis System and nucleotide characterization performed using Sequencher™ version 4.1.4 (Gene Codes Corporation, Ann Arbor, Mich.).

G. Non-Autonomous Herbicide Tolerance Gene Cassette Insertion into Plasmid Backbone—Non-Autonomous Donor In order to create a donor plasmid, the non-autonomous herbicide-tolerance gene cassette described in Example 18F was inserted into the plasmid backbone constructions described in Examples 18B and 18C. Restricted fragment corresponding to a clone that contained the correct 1 Kbp sequence was gel-excised and purified according to the manufacturer's directions using QIAQUICK™ Gel Extraction Kit (QIAGEN Inc., Valencia, Calif.). This fragment was then combined in a ligation reaction with either purified pDAB7471 (position-1 plasmid backbone) (FIG. 70) or pDAB 7451 (position-2 plasmid backbone) (FIG. 71) that had been digested with restriction enzyme Spe I and subsequently dephosphorylated. Ligation was carried out under the following conditions: 1:5 vector:insert ratio and 500 units T4 DNA Ligase (Invitrogen Life Technologies, Carlsbad, Calif.) in a reaction volume of 20 μl under conditions of 16 hr incubation in a 16° C. water bath. Five μl of the ligation reaction was subsequently transformed into 50 μl *E. coli* MAX Efficiency® DH5α™ Chemically Competent Cells, (Invitrogen Life Technologies, Carlsbad, Calif.) and plated under selection conditions described by the manufacturer.

Figure 76:
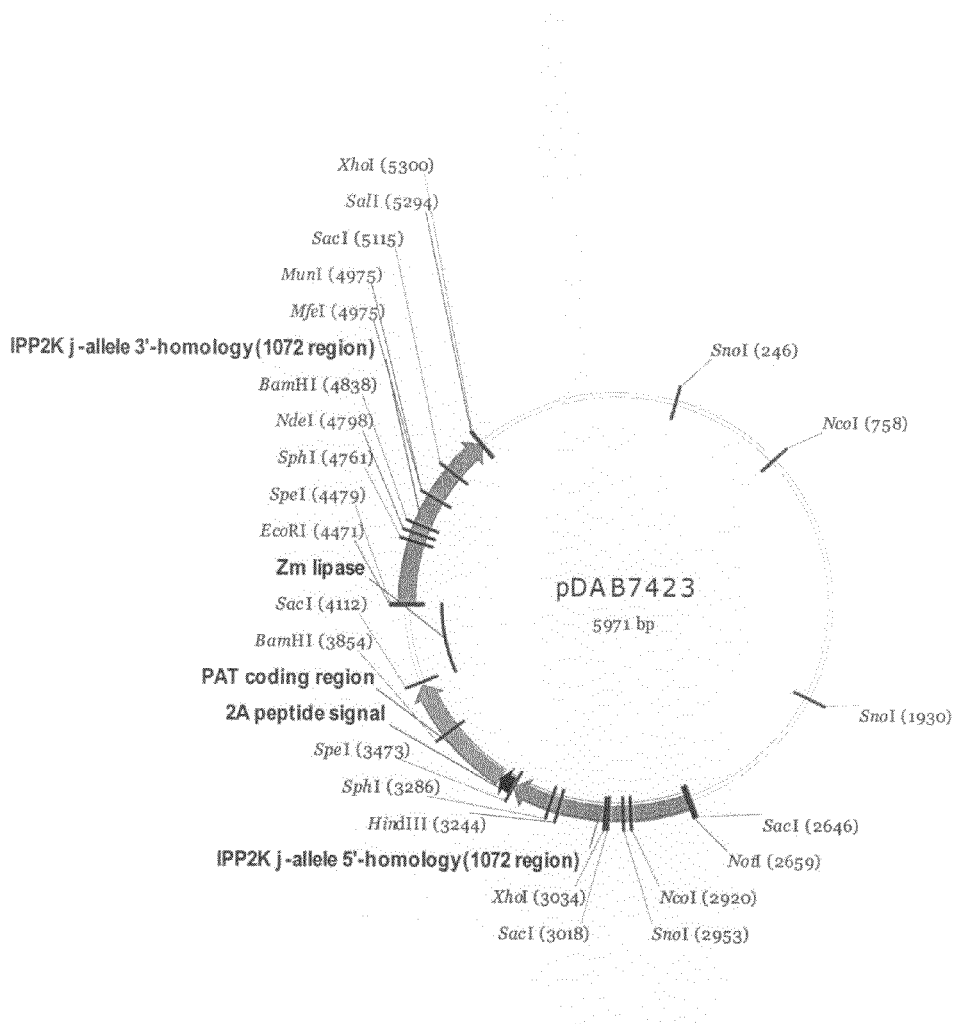
FIG. 76 depicts plasmid pDAB7423, constructed as described in Example 18G. This plasmid includes an incomplete promoter-transcriptional unit (PTU) containing an herbicide tolerance gene and poly adenylation (polyA) termination sequence inserted into a position-1 plasmid backbone.
Figure 77:
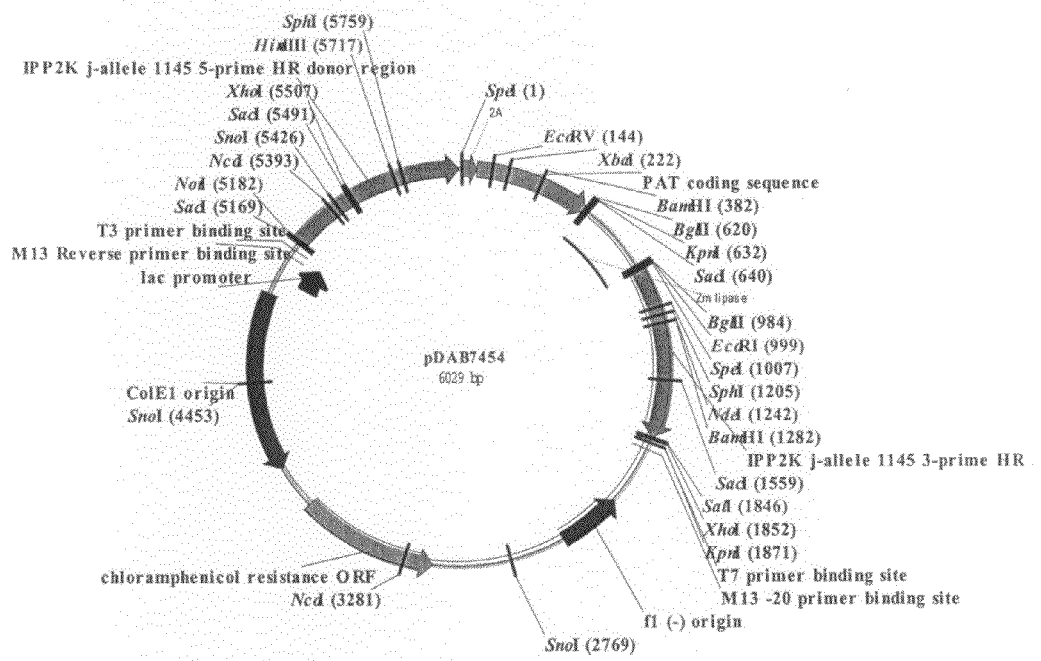
FIG. 77 depicts plasmid pDAB7454, constructed as described in Example 18G. The plasmid includes an incomplete promoter-transcriptional unit (PTU) containing an herbicide tolerance gene and poly adenylation (polyA) termination sequence inserted into a position-2 plasmid backbone as described in Example 18G.

Individual colonies were inoculated into a 14 ml Falcon Tube (Becton-Dickinson, Franklin Lakes, N.J.) containing 2 ml TB supplemented with 50 μl/ml chloramphenicol and incubated for 16 hrs at 37° C. shaking 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three μg of isolated plasmid DNA was digested with 10 units Spe I (New England Biolabs, Beverly, Mass.) and incubated for 1 hr at 37° C. Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp DNA ladder. Expected plasmid clones were diagnosed by the presence of DNA fragments 1.0 Kbp and 4.96 Kbp (pDAB7471 vector) or 1.0 Kbp and ~5.0 Kbp (pDAB7451 vector). The resulting plasmids were named pDAB7423 (position-1 non-autonomous donor) (FIG. 76) and pDAB7454 (position-2 non-autonomous donor) (FIG. 77), respectively.

H. Position 1 ZFN+HR Donor Sequences: Combination Plasmid.

As an alternative strategy to the delivery of two separate plasmids into a plant cell (e.g. one plasmid containing ZFN elements and a second containing the herbicide tolerance donor sequences), single plasmids were engineered containing all necessary elements illustrated in this patent. The combination plasmids described in this example contains both the ZFNs designed to target and generate double-strand breaks at the specified IPP2K locus as well as the autonomous PAT PTU and/or non-autonomous 2A/PAT PTU and donor flanks designed to integrate into those break sites.

Gateway® technology, which uses lambda phage-based site-specific recombination (Landy, A. (1989) *Ann. Rev. Biochem.* 58:913) was utilized to convert vectors pDAB7422 and pDAB7423 (described in examples 6E and 6G) into Gateway® destination vectors. Once converted, plasmids containing ZFN expression cassettes (housed in Gateway® Entry vectors) can be mobilized easily to the destination vector creating a ZFN/donor combination plasmid. One μg of each such plasmid was digested with 10 units Not I (New England Biolabs, Beverly, Mass.) for 1 hr at 37° C. Not I restriction endonuclease was heat-inactivated at 65° C. for 15 min and fragment ends subsequently dephosphorylated at 37° C. for 1 hr using 3 units of shrimp alkaline phosphatase (SAP) (Roche Diagnostics GmbH, Mannheim, Germany). Restricted DNA was electrophoresed at 100 V for 1 hr in a 1.0% TAE agarose gel supplemented with 0.5% ethidium bromide. Vector fragments (pDB7422=7.317 Kbp, pDAB7423=5.971 Kbp) were visualized with UV light, size estimated by comparison with 1 Kbp DNA ladder, gel-excised and subsequently purified according to the manufacturer's directions using QIAQUICK™ Gel Extraction Kit (QIAGEN Inc., Valencia, Calif.).

This vector fragment was then combined with a 2.274 Kbp Not I fragment containing Gateway® Technology elements attR1, ccdB, $Cm^R$, and attR2 in a ligation reaction carried out under the following conditions: 1:5 vector:insert ratio and 500 units T4 DNA Ligase (Invitrogen Life Technologies, Carlsbad, Calif.) in a reaction volume of 20 μl under conditions of 16 hr incubation in a 16° C. water bath. Five μl of the ligation reaction was subsequently transformed into 50 μl *E. coli* One Shot® ccdB Survival™ Chemically Competent Cells, (Invitrogen Life Technologies, Carlsbad, Calif.) and plated under selection conditions described by the manufacturer.

Figure 78:
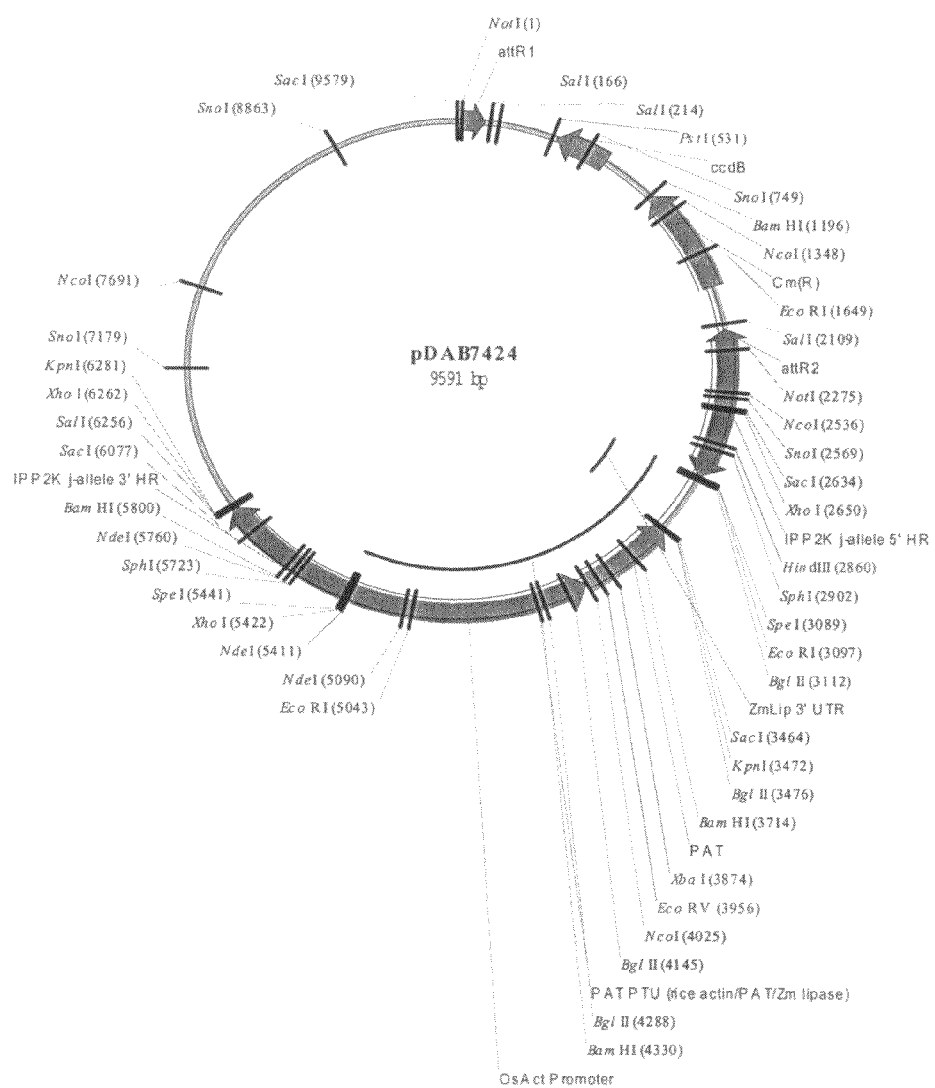
FIG. 78 depicts plasmid pDAB 7424 (an exemplary Gateway®-adapted position-1 autonomous donor), constructed as described in Example 18H.
Figure 79:
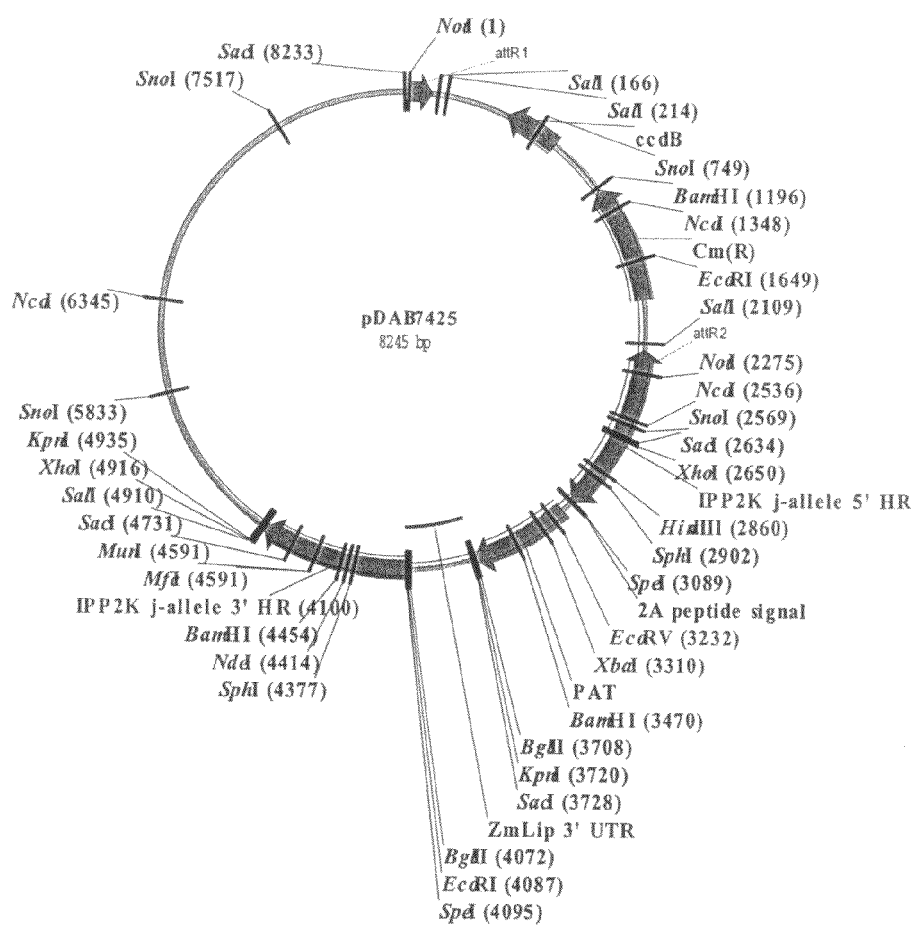
FIG. 79 depicts plasmid pDAB 7425 (an exemplary Gateway®-adapted position-1 autonomous donor), constructed as described in Example 18H.

Individual colonies were inoculated into a 14 ml Falcon Tube (Becton-Dickinson, Franklin Lakes, N.J.) containing 2 ml TB supplemented with 50 μl/ml chloramphenicol and incubated for 16 hrs at 37° C. shaking 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three μg of isolated plasmid DNA was digested with 10 units EcoRI I (New England BioLabs, Inc., Beverly, Mass.) and incubated for 1 hr at 37° C. Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp DNA ladder. Expected plasmid clones were diagnosed by the presence of DNA fragments of 1.448 Kbp, 1.946 Kbp, and 6.197 Kbp for the autonomous PAT PTU position-1 HR donor and 5.807 Kbp and 2.438 Kbp for the non-autonomous PAT position-1 HR donor. The resulting plasmids were named pDAB7424 (Gateway® adapted position-1 autonomous donor) (FIG. 78) and pDAB7425 (Gateway® adapted position-1 non-autonomous donor) (FIG. 79), respectively.

Figure 80:
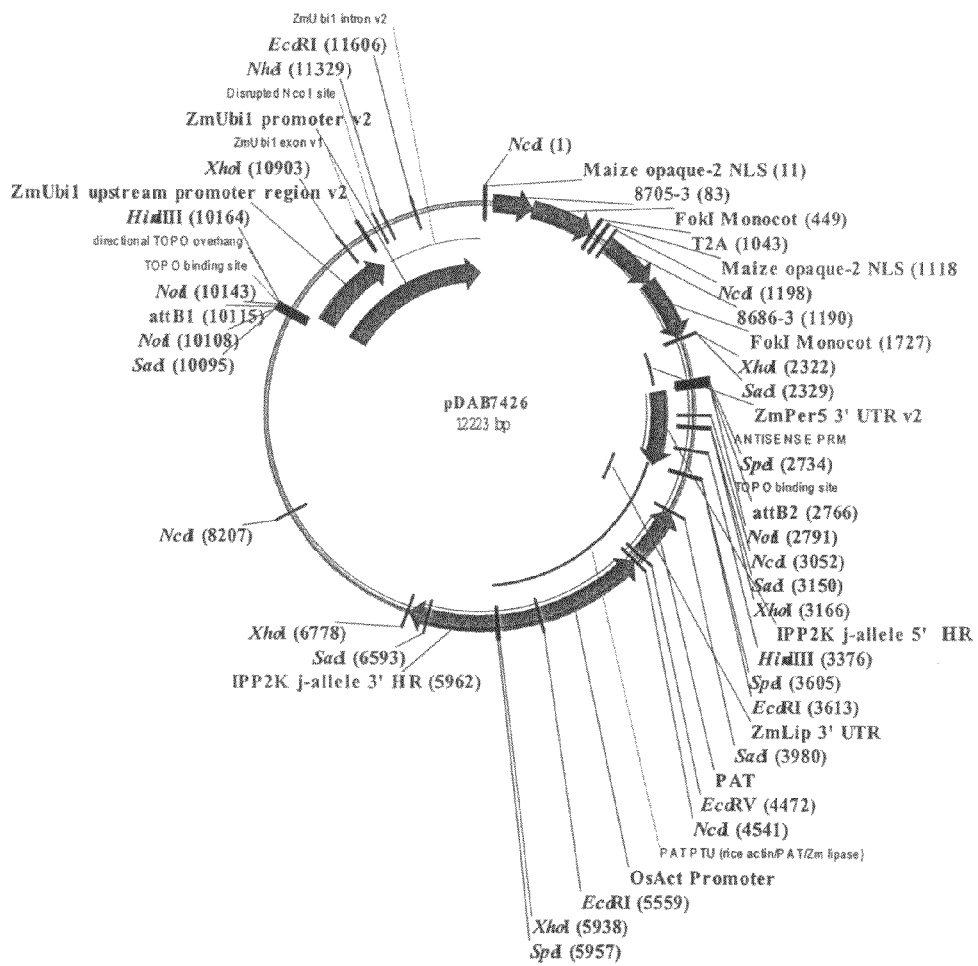
FIG. 80 depicts plasmid pDAB 7426, constructed as described in Example 18H. pDAB 7426 is a combination plasmid containing the position-1 autonomous donor with a ZFN-expression cassette.
Figure 81:
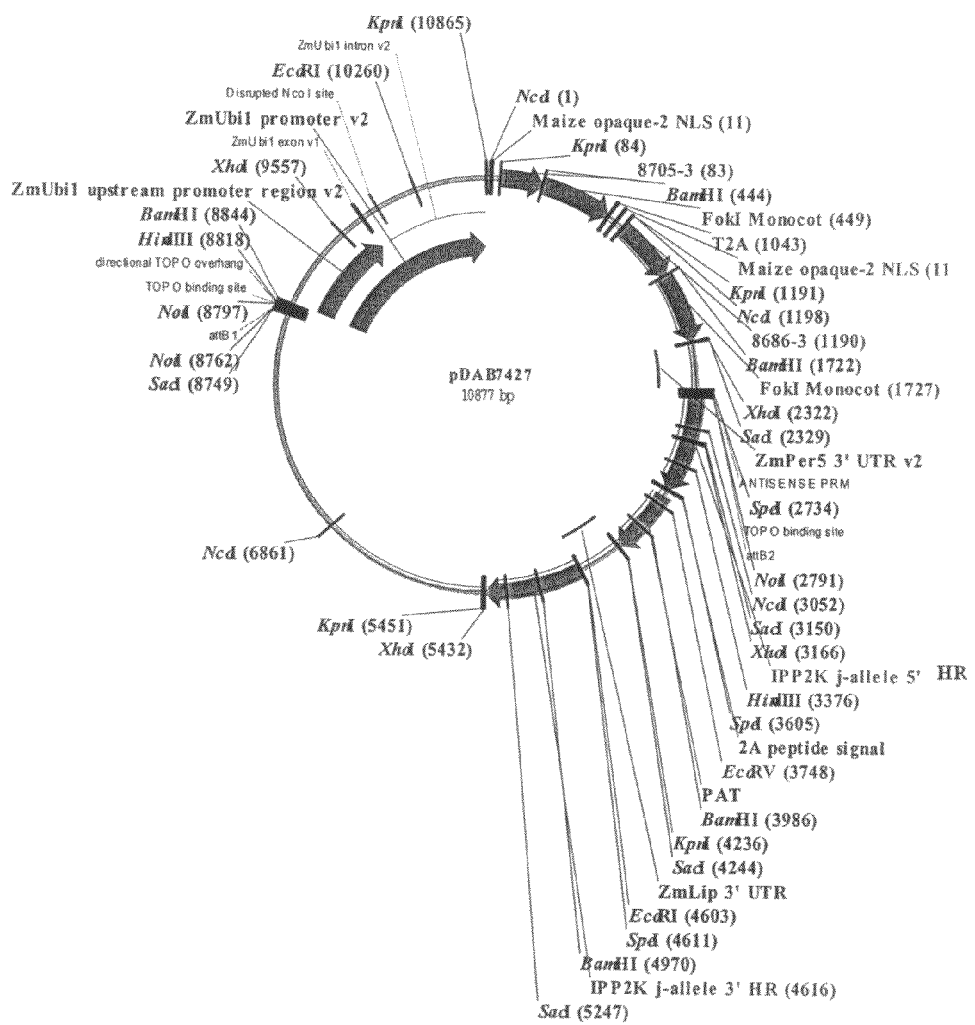
FIG. 81 depicts plasmid pDAB 7427, constructed as described in Example 18H. pDAB 7427 is a combination plasmid containing the position-1 autonomous donor with a ZFN-expression cassette.

As a result of these cloning manipulations, the plasmids pDAB7424 & pDAB7425 were designated as Gateway® destination vectors. pDAB7412 has functionality as a Gateway® entry vector containing the following elements: ZmUbi1v.2/ZFN12/Zm Per5 3' UTR. To transfer a ZFN expression cassette (Gateway® entry vector) into either autonomous or non-autonomous donor molecule (Gateway® destination vector), a LR Clonase™ II (Invitrogen Life Technologies, Carlsbad, Calif.) reaction was performed as outlined by the manufacturer at a ratio of 50 ng (Entry vector): 150 ng/µl (Destination vector). The resulting positive combination plasmids were named pDAB7426 (position-1 autonomous HR donor/ZFN12) (FIG. 80) & pDAB7427 (non-autonomous HR donor/ZFN12) (FIG. 81).

Example 19

ZFN and Donor DNA Delivery into Plant Cells

In order to enable ZFN-mediated integration of donor DNA into the plant genome via targeted integration, it is understood that delivery of ZFN-encoding DNA followed by expression of functional ZFN protein in the plant cell is required. Also required is concomitant delivery of donor DNA into said plant cell, such that functional ZFN protein may induce double-stranded breaks at the target DNA which are then repaired via homology driven integration of the donor DNA into the target locus. One skilled in the art may envision that expression of functional ZFN protein may be achieved by several methods, including, but not limited to transgenesis of the ZFN-encoding construction, or transient expression of the ZFN-encoding construction. In both these cases, expression of functional ZFN protein and delivery of donor DNA in the plant cell is simultaneously achieved in order to drive targeted integration.

In the examples cited here, we demonstrate methods for the concomitant delivery of ZFN-encoding and donor DNA into plant cells. One skilled in the art might use any of a variety of DNA-delivery methods appropriate for plant cells, including, but not limited to, *Agrobacterium*-mediated transformation, biolistics-based DNA delivery or Whiskers™-mediated DNA delivery. In one embodiment described here, Whiskers™-mediated DNA delivery experiments were carried out using various combinations of donor DNA with ZFN-encoding DNA constructions. These combinations include 1) a single plasmid containing both ZFN-encoding sequence and donor DNA and 2) two distinct plasmids, one containing ZFN-encoding sequence and the other containing donor DNA. In another embodiment, biolistics-based DNA-delivery was carried out using various combinations of donor DNA with ZFN-encoding DNA constructions. One skilled in the art may deduce that these combinations might include 1) a single plasmid containing both ZFN-encoding sequence and donor DNA and 2) two distinct plasmids, one containing ZFN-encoding sequence and the other containing donor DNA.

A. Whiskers™-Mediated DNA Delivery

As described earlier herein, embryogenic Hi-II cell cultures of maize were produced, and were used as the source of living plant cells in which targeted integration is demonstrated. One skilled in the art may envision the utilization of cell cultures derived from a variety of plant species, or differentiated plant tissues derived from a variety of plant species, as the source of living plant cells in which targeted integration is demonstrated.

In this example, 12 ml PCV from a previously cryo-preserved cell line plus 28 ml of conditioned medium was subcultured into 80 ml of GN6 liquid medium (N6 medium (Chu et al., 1975), 2.0 mg/L 2, 4-D, 30 g/L sucrose, pH 5.8) in a 500 ml Erlenmeyer flask, and placed on a shaker at 125 rpm at 28° C. This step was repeated 2 times using the same cell line such that a total of 36 ml PCV was distributed across 3 flasks. After 24 hours the GN6 liquid media was removed and replaced with 72 ml GN6 S/M osmotic medium (N6 Medium, 2.0 mg/L 2,4-D, 30 g/L sucrose, 45.5 g/L sorbitol, 45.5 g/L mannitol, 100 mg/L myo-inositol, pH 6.0). The flask was incubated in the dark for 30-35 minutes at 28° C. with moderate agitation (125 rpm). During the incubation period, a 50 mg/ml suspension of silicon carbide whiskers (Advanced Composite Materials, LLC, Greer, S.C.) was prepared by adding 8.1 ml of GN6 S/M liquid medium to 405 mg of sterile, silicon carbide whiskers.

Following incubation in GN6 S/M osmotic medium, the contents of each flask were pooled into a 250 ml centrifuge bottle. After all cells in the flask settled to the bottom, contents volume in excess of approximately 14 ml of GN6 S/M liquid was drawn off and collected in a sterile 1-L flask for future use. The pre-wetted suspension of whiskers was mixed at maximum speed on a vortex for 60 seconds, and then added to the centrifuge bottle.

In one example, wherein a single plasmid containing both the ZFN-encoding sequence plus the donor DNA is being delivered into the plant cells, 170 µg of purified circular plasmid DNA was added to the bottle. In an alternative example, wherein two distinct plasmids were being co-delivered, one containing ZFN-encoding sequence and the other containing donor DNA, multiple strategies for DNA amounts were assessed. One strategy utilized 85 µg of donor DNA and 85 µg of zinc-finger encoding DNA. Other modifications utilized molar ratios of 10, 5, or 1-fold donor DNA to 1-fold zinc finger DNA, based on the size (in kilobase pairs) of the individual plasmids such that a total of 170 µg of DNA was added per bottle. In all cases of co-delivery, DNA was pre-pooled in a tube prior to being added to the centrifuge bottle. Once DNA was added, the bottle was immediately placed in a modified Red Devil 5400 commercial paint mixer (Red Devil Equipment Co., Plymouth, Minn.) and agitated for 10 seconds. Following agitation, the cocktail of cells, media, whiskers and DNA was added to the contents of a 1-L flask along with 125 ml fresh GN6 liquid medium to reduce the osmoticant. The cells were allowed to recover on a shaker set at 125 rpm for 2 hours. Six mL of dispersed suspension was filtered onto Whatman #4 filter paper (5.5 cm) using a glass cell collector unit connected to a house vacuum line such that 60 filters were obtained per bottle. Filters were placed onto 60×20 mm plates of GN6 solid medium (same as GN6 liquid medium except with 2.5 g/L Gelrite gelling agent) and cultured at 28° C. under dark conditions for 1 week.

B: Biolistics-Mediated DNA Delivery

In the examples cited here, embryogenic suspensions of maize were subcultured into GN6 liquid medium approximately 24 hours prior to experimentation as described earlier herein. The excess liquid medium was removed and approximately 0.4 PCV of cells were thinly spread in a circle 2.5 cm in diameter over the center of a 100×15 mm petri dish containing GN6 S/M media solidified with 2.5 g/L gelrite. The cells were cultured under dark conditions for 4 hours. To coat the biolistic particles with DNA, 3 mg of 1.0 micron diameter gold particles were washed once with 100% ethanol, twice with sterile distilled water and resuspended in 50 µl water in a siliconized Eppendorf tube. A total of 5 µg of plasmid DNA, 20 µl spermidine (0.1 M) and 50 µl calcium chloride (2.5 M) were added separately to the gold suspension and mixed on a vortex. The mixture was incubated at room temperature for 10 min, pelleted at 10,000 rpm in a benchtop microcentrifuge for 10 seconds, resuspended in 60 µl cold 100% ethanol, and 8-9 µl was distributed onto each macrocarrier.

Bombardment took place using the Biolistic PDS-1000/He™ system (Bio-Rad Laboratories, Hercules, Calif.). Plates containing the cells were placed on the middle shelf under conditions of 1100 psi and 27 inches of Hg vacuum, and were bombarded following the operational manual. Sixteen hours post-bombardment, the tissue was transferred in small clumps to GN6 (1H) medium and cultured for 2-3 weeks at 28° C. under dark conditions. Transfers continued every 2-4 weeks until putative transgenic isolates resulting from integration of donor DNA appeared. Identification, isolation and regeneration of putative donor DNA integration events generated via biolistic-mediated DNA delivery is identical to the process utilized for putative donor DNA integration events generated via Whiskers™-mediated DNA delivery and described below.

C. Identification and Isolation of Putative Targeted Integration Transgenic Events One week post-DNA delivery, filter papers were transferred to 60×20 mm plates of GN6 (1H) selection medium (N6 Medium, 2.0 mg/L 2,4-D, 30 g/L sucrose, 100 mg/L myo-inositol, 1.0 mg/L bialaphos from Herbiace (Meiji Seika, Japan), 2.5 g/L Gelrite, pH 5.8). These selection plates were incubated at 28° C. for one week in the dark.

Following 1 week of selection in the dark, the tissue was embedded onto fresh media by scraping half the cells from each plate into a tube containing 3.0 mL of GN6 agarose medium held at 37-38° C. (N6 medium, 2.0 mg/L 2,4-D, 30 g/L sucrose, 100 mg/L myo-inositol, 7 g/L SeaPlaque® agarose, pH 5.8, autoclaved for only 10 minutes at 12° C.) and 1 mg/L bialaphos from Herbiace.

The agarose/tissue mixture was broken up with a spatula, and subsequently 3 mL of agarose/tissue mixture was evenly poured onto the surface of a 100×15 mm petri dish containing GN6 (1H) medium. This process was repeated for both halves of each plate. Once all the tissue was embedded, plates were individually sealed with Nescofilm® or Parafilm M®, and cultured at 28° C. under dark conditions for up to 10 weeks. Putatively transformed isolates that grew under these selection conditions were removed from the embedded plates and transferred to fresh selection medium in 60×20 mm plates. If sustained growth was evident after approximately 2 weeks, an event was deemed to be resistant to the applied herbicide (bialaphos) and an aliquot of cells was subsequently harvested into 2 mL Eppendorf tubes for genotype analysis.

One skilled in the art might utilize a gene encoding any appropriate selectable marker in the donor DNA and apply comparable selection conditions to living cells. For example, an alternative selectable marker gene such as AAD-1, as described in WO 2005/107437 A2, could be implemented as a donor for selection and recovery of integrated events in maize cells as described herein.

Example 20

Screening for Targeted Integration Events Via PCR Genotyping

In this example, PCR genotyping is understood to include, but not be limited to, polymerase-chain reaction (PCR) amplification of genomic DNA derived from isolated maize callus tissue predicted to contain donor DNA embedded in the genome, followed by standard cloning and sequence analysis of PCR amplification products. Methods of PCR genotyping have been well described (for example, Rios, G. et al. (2002) *Plant J.* 32:243-253) and may be applied to genomic DNA derived from any plant species or tissue type, including cell cultures.

One skilled in the art may devise strategies for PCR-genotyping that include (but are not limited to) amplification of specific sequences in the plant genome, amplification of multiple specific sequences in the plant genome, amplification of non-specific sequences in the plant genome, or combinations thereof. Amplification may be followed by cloning and sequencing, as described in this example, or by direct sequence analysis of amplification products. One skilled in the art might envision alternative methods for analysis of the amplification products generated herein.

In one embodiment described herein, oligonucleotide primers specific for the gene target are employed in PCR amplifications. In another embodiment described herein, oligonucleotide primers specific for donor DNA sequences are employed in PCR amplifications. Another embodiment includes a combination of oligonucleotide primers that bind to both gene target sequence and donor DNA sequence. One skilled in the art may devise additional combinations of primers and amplification reactions to interrogate the genome.

A. Genomic DNA Extraction

Genomic DNA (gDNA) was extracted from isolated, herbicide-tolerant, maize cells described in Example 19 and utilized as template for PCR genotyping experiments. gDNA was extracted from approximately 100-300 µl packed cell volume (PCV) of herbicide-tolerant HiII callus that were isolated as described above according to the manufacturer's protocols detailed in the DNeasy® 96 Plant Kit (QIAGEN Inc., Valencia, Calif.). Genomic DNA was eluted in 100 µl of kit-supplied elution buffer yielding final concentrations of 20-200 ng/µl and subsequently analyzed via PCR-based genotyping methods outlined below.

B. Primer Design for PCR Genotyping

One skilled in the art might use a variety of strategies for the design and implementation of PCR-based genotypying. Oligonucleotide primers designed to anneal to the gene target, donor DNA sequences and/or combinations of the two are feasible. In order to design oligonucleotide primers that can anneal to the IPP2K gene target in regions not encompassed by the homology flanks constructed into the donor DNA molecules, plasmid clones containing additional gene target sequence data were characterized via DNA sequencing. Double-stranded sequencing reactions of plasmid clones were performed as described by manufacturer using CEQT DTCS-Quick Start Kit (Beckman-Coulter, Palo Alto, Calif.). Reactions were purified using Performa DTR Gel Filtration Cartridges (Edge BioSystems, Gaithersburg, Md.) as described by manufacturer protocols. Sequence reactions were analyzed on a Beckman-Coulter CEQ™ 2000 XL DNA Analysis System and nucleotide characterization performed using Sequencher™ version 4.1.4 (Gene Codes Corporation, Ann Arbor, Mich.). These sequences correspond to regions of the IPP2K gene upstream (5'-) and downstream (3'-) of the ZFN targeted regions and are described in FIG. 91 (SEQ ID NO:141) and FIG. 92 (SEQ ID NO: 142).

In the examples presented here, all oligonucleotide primers were synthesized by Integrated DNA Technologies, Inc. (Coralville, Iowa) under conditions of standard desalting and diluted with water to a concentration of 100 µM. The following set of forward and reverse oligonucleotide primers were designed to anneal to gDNA sequences specific for the IPP2K gene target that lie outside the boundaries of the donor DNA sequences. These oligonucleotides are as follows:

```
                                            (SEQ ID NO: 153)
   5'-TGGACGGAGCGAGAGCCAGAATTCGACGCT G-3'

(SEQ ID NO: 154)
   5'-GTGCAAGAATGTATTGGGAATCAACCTGAT G-3'
```

A second set of forward and reverse oligonucleotide primers were also designed to anneal to gDNA sequence specific for the IPP2K gene target outside the boundaries of the donor DNA sequences, yet nested within the first pair:

```
                                            (SEQ D NO: 155)
   5'-CTGTGGTACCAGTACTAGTACCAGCATC-3'

(SEQ ID NO: 156)
   5'-TCT TGGATCAAGGCATCAAGC ATTCCAATCT-3'
```

Forward and reverse oligonucleotide primers were additionally designed to anneal specifically to donor DNA corresponding to coding region of the herbicide-tolerance gene:

```
   5'-TGGGTAACTGGCCTAACTGG-3'    (SEQ ID NO: 157)

5'-TGGAAGGCTAGGAACGCTTA-3'    (SEQ ID NO: 158)

5'-CCAGTTAGGCCAGTTACCCA-3'    (SEQ ID NO: 159)

5' TAAGCGTTCCTAGCCTTCCA-3'    (SEQ ID NO: 160)
```

C. Donor DNA—Specific PCR Amplification

Primary PCR amplification reactions were carried out using reagents provided by TaKaRa Biotechnology Inc., Seta 3-4-1, Otsu, Shiga, 520-2193, Japan and consisted of the following: 2.5 µl 10× Ex Taq PCR™ Buffer, 40-200 ng double-stranded genomic DNA template, 10 µM forward oligonucleotide primer, 10 µM reverse oligonucleotide primer, 2 µl dNTP mix (2.5 mM each), 16 µl H$_2$O, 0.5 µl (2.5 units) Ex Taq™ DNA polymerase. PCR reactions were performed using a Bio-Rad, 96-sample DNA Engine Tetrad2, Peltier Thermal Cycler (Hercules, Calif.) under the following cycle conditions: 94° C., 3 min/1 cycle; 94° C. 30 sec, 64° C. 30 sec, 72° C. 5 min/35 cycles; 72° C., 10 min/1 cycle; 4° C./hold.

Amplification products of the primary PCR reaction were subsequently re-amplified in a secondary PCR reaction comprised of the following: 2.5 µl 10× Ex Taq PCR™ Buffer, 2 µl template (1:100 dilution of 1° PCR reaction in H$_2$O), 10 µM forward oligonucleotide primer, 10 µM reverse oligonucleotide primer, 2 µl dNTP mix (2.5 mM each), 16 µl H$_2$O, 0.5 µl (2.5 units) Ex Taq™ DNA polymerase. PCR reactions were performed using a Bio-Rad, 96-sample DNA Engine Tetrad2, Peltier Thermal Cycler (Hercules, Calif.) under the following cycle conditions: 95° C., 1 min/1 cycle; 94° C. 15 sec, 61° C. 30 sec, 72° C. 30 sec/30 cycles; 72° C., 1 min/1 cycle; 4° C./hold. Ten µl of each amplified product was electrophoresed at 100 V for 1 hr in a 1.0% TAE agarose gel supplemented with 0.5% ethidium bromide. Amplified fragments were visualized with UV light and fragment size estimated by comparison with 1 Kbp Plus DNA ladder (Invitrogen Life Technologies, Carlsbad, Calif.). PCR products containing the expected fragment were diagnosed by the presence of a DNA fragment 0.317 Kbp, as shown in FIG. 82.

Example 21

Detection of Targeted Integration Events

Of the herbicide-tolerant events containing an integrated donor DNA molecule encoding an herbicide-tolerance gene cassette, it is expected that some proportion of said events are the product of targeted integration of donor DNA into the site of the ZFN-induced double-stranded break. In order to differentiate these targeted integration events from those derived from random integration of the herbicide-tolerance gene cassette, a PCR-based genotyping strategy using a combination of genome-specific and subsequent genome-specific plus donor-specific PCR primers was utilized.

A. Genome-Specific and Subsequent Genome/Donor Specific Amplification

In this embodiment, primary PCR reactions utilized oligonucleotide primers specific for the regions of the IPP2K gene target upstream and downstream of the donor integration region (e.g., FIGS. 92 and 93). Primary PCR amplification reactions were carried out using reagents provided by TaKaRa Biotechnology Inc., Seta 3-4-1, Otsu, Shiga, 520-2193, Japan and consisted of the following: 2.5 µl 10× Ex Taq PCR™ Buffer, 40-200 ng double-stranded maize gDNA template, 10 µM forward oligonucleotide primer, 10 µM reverse oligonucleotide primer, 2 µl dNTP mix (2.5 mM each), 16 µl H$_2$O, 0.5 µl (2.5 units) Ex Taq™ DNA polymerase. PCR reactions were performed using a Bio-Rad, 96-sample DNA Engine Tetrad2, Peltier Thermal Cycler (Hercules, Calif.) under the following cycle conditions: 94° C., 3 min/1 cycle; 94° C. 30 sec, 64° C. 30 sec, 72° C. 5 min/35 cycles; 72° C., 10 min/1 cycle; 4° C./hold.

The primary PCR reaction product was subsequently diluted 1:100 in H$_2$O and used as template DNA for two distinct secondary PCR reactions. In this embodiment, the secondary reactions utilize primers that bind in the IPP2K genomic region and the donor molecule, giving rise to an amplicon that spans the boundary of integration between genome and donor. The first reaction focused on the 5'-boundary between genome and donor. The second reaction focused on the 3'-boundary between donor and genome. Both reactions consisted of the following: 2.5 µl 10× Ex Taq PCR™ Buffer, 2 µl template [1:100 dilution of 1° PCR reaction], 10 µM forward oligonucleotide primer, 10 µM reverse oligonucleotide primer, 2 µl dNTP mix (2.5 mM each), 16 µl H$_2$O, 0.5 µl (2.5 units) Ex Taq™ DNA polymerase. PCR reactions were performed using a Bio-Rad, 96-sample DNA Engine Tetrad2, Peltier Thermal Cycler (Hercules, Calif.) under the following cycle conditions: 94° C., 3 min/1 cycle; 94° C. 30 sec, 60° C. 30 sec, 72° C. 2 min/35 cycles; 72° C., 10 min/1 cycle; 4° C./hold. Twenty µL of each 2° PCR reaction was electrophoresed at 100 V for 1 hr in a 1.0% TAE agarose gel supplemented with 0.5% ethidium bromide.

Figure 84:
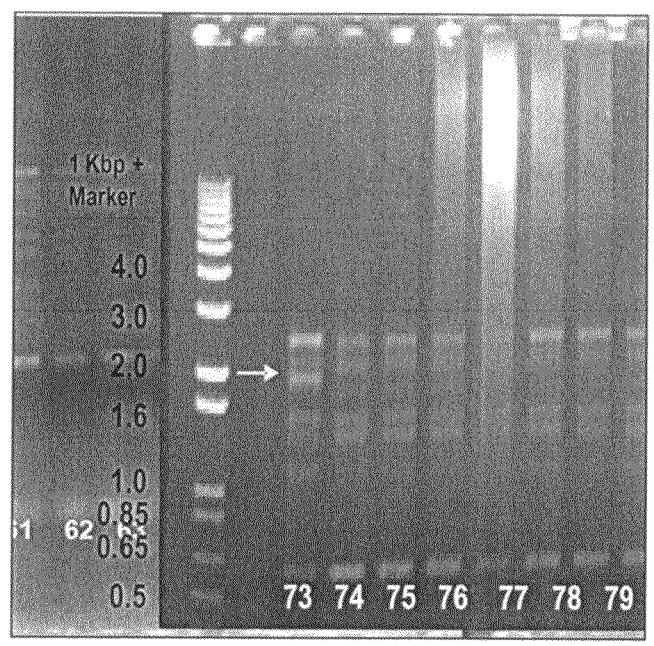
FIG. 84 depicts amplification of the 3'-boundary between donor-DNA and maize genomic sequences specific for IPP2K. Secondary PCR products derived from targeted integration of donor into the IPP2K gene were diagnosed by the presence of DNA fragments of 1.99 Kbp as described in Example 21A. HiII indicates a wild-type negative control.

Amplified fragments were visualized with UV light and fragment size estimated by comparison with 1 Kbp Plus DNA ladder (Invitrogen Life Technologies, Carlsbad, Calif.). PCR products derived from targeted integration of donor into the IPP2K gene were diagnosed by the presence of DNA fragments 1.65 Kbp (5'-boundary) (FIG. 83) or 1.99 Kbp (3'-boundary) (FIG. 84). These fragments were gel-excised and purified according to manufacturer's directions using QIAQUICK™ Gel Extraction Kit (QIAGEN Inc., Valencia, Calif.). Purified fragments were subsequently cloned into pCR2.1 plasmid using TOPO TA Cloning® Kit (with pCR®2.1 vector) and One Shot® TOP10 Chemically competent *E. coli* cells (Invitrogen Life Technologies, Carlsbad, Calif.) according to manufacturer's protocol.

Individual colonies were inoculated into a 14 ml Falcon Tube (Becton-Dickinson, Franklin Lakes, N.J.) containing 2 ml TB supplemented with 50 µl/ml kanamycin and incubated for 16 hrs at 37° C. with shaking at 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three μg of isolated plasmid was digested with 10 units Eco RI (New England Biolabs, Beverly, Mass.). All plasmid digestions were incubated for 1 hr at 37° C. Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp Plus DNA ladder (Invitrogen Life Technologies, Carlsbad, Calif.).

Expected plasmid clones were diagnosed by the presence of inserted DNA fragments of the appropriate size in addition to the 3.9 Kbp pCR® 2.1 vector. Double-stranded sequencing reactions of plasmid clones were performed as described by manufacturer using CEQT DTCS-Quick Start Kit (Beckman-Coulter, Palo Alto, Calif.). Reactions were purified using Performa DTR Gel Filtration Cartridges (Edge BioSystems, Gaithersburg, Md.) as described by manufacturer protocols. Sequence reactions were analyzed on a Beckman-Coulter CEQ™ 2000 XL DNA Analysis System and nucleotide characterization performed using Sequencher™ version 4.1.4 (Gene Codes Corporation, Ann Arbor, Mich.). Nucleotide alignments were performed using Vector NTi version 10.1 (Invitrogen Life Technologies, Carlsbad, Calif.).

Analysis of sequence data from a targeted integration event (event #073) was conducted as follows. Primary PCR products spanning the entire integration site of the genome were subjected to secondary amplification focused on either the 5'- or 3'-boundary between genome and donor. Alignment of cloned fragments corresponding to these secondary amplification products with the wild-type IPP2K genomic sequence as well as the expected sequence of a targeted integration event clearly indicated that the precise integration of donor DNA at the target site occurred.

Nucleotide sequence of the IPP2K genomic locus, the genome/donor boundary, nucleotide sequence of the donor regions corresponding to IPP2K homology flanks and nucleotide sequence of the herbicide tolerance cassette were all preserved in multiple cloned PCR products derived from this event. Therefore, this event represented a genome in which homology-driven repair of a ZFN-mediated double-stranded break and targeted integration of a donor DNA at a specific gene target occurred. Additional transformed events representing unique targeted integration occurrences have been obtained, demonstrating that the methods taught herein are reproducible in maize callus. One skilled in the art might apply these methods to any gene target in any species of plant for which targeted integration is deemed desirable.

B. Nested Genome/Donor Specific Amplification

In this embodiment, both primary and subsequent secondary PCR reactions utilized oligonucleotide primers specific for the regions of the IPP2K gene target upstream or downstream of the donor integration region (appendices V and VI) in combination with oligonucleotide primers specific for the donor sequence. In this example, primary PCR amplification reactions were carried out using reagents provided by TaKaRa Biotechnology Inc., Seta 3-4-1, Otsu, Shiga, 520-2193, Japan that consisted of the following: 2.5 μl 10× Ex Taq PCR™ Buffer, 40-200 ng double-stranded maize gDNA template, 10 μM forward oligonucleotide, 10 μM reverse oligonucleotide primer, 2 μl dNTP mix (2.5 mM each), 16 μl H$_2$O, 0.5 μl (2.5 units) Ex Taq™ DNA polymerase. PCR reactions were incubated using a Bio-Rad, 96-sample DNA Engine Tetrad2, Peltier Thermal Cycler (Hercules, Calif.) under the following cycle conditions: 94° C., 3 min/1 cycle; 94° C. 3 sec, 52° C. or 64° C. 30 sec, 72° C. 2 min/35 cycles; 72° C., 10 min/1 cycle; 4° C./hold.

The primary PCR reaction was then diluted 1:100 in H$_2$O and used as template DNA for a secondary PCR reaction. In this embodiment, the secondary reactions also utilize primers that bind in the IPP2K genomic region and the donor molecule, giving rise to an amplicon that spans the boundary of integration between genome and donor. The specific primers used determine whether the amplification is focused on either the 5'- or 3'-boundary between genome and donor. Reagents for these reactions consisted of the following: 2.5 μl 10× Ex Taq PCR™ Buffer, 2 μl template [1:100 dilution of 1° PCR reaction], 10 μM forward oligonucleotide primer, 10 μM reverse oligonucleotide primer, 2 μl dNTP mix (2.5 mM each), 16 μl H$_2$O, 0.5 μl (2.5 units) Ex Taq™ DNA polymerase. PCR reactions were performed using a Bio-Rad, 96-sample DNA Engine Tetrad2, Peltier Thermal Cycler (Hercules, Calif.) under the following cycle conditions: 94° C., 3 min/1 cycle; 94° C. 30 sec, 54° C. or 60° C. 30 sec, 72° C. 2 min/35 cycles; 72° C., 10 min/1 cycle; 4° C./hold. Twenty μl of each 2° PCR reaction was electrophoresed at 100 V for 1 hr in a 1.0% TAE agarose gel supplemented with 0.5% ethidium bromide.

Figure 85:
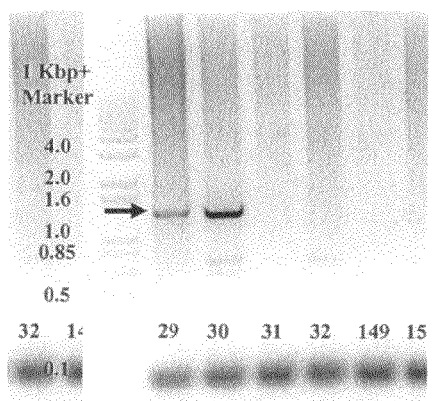
FIG. 85 depicts amplification of the upstream (5'-) boundary between genome and donor. PCR products derived from targeted integration of donor into the IPP2K gene (5'-boundary) were diagnosed by the presence of DNA fragments 1.35 Kbp in size as described in Example 21B. HiII indicates a wild-type negative control.
Figure 86:
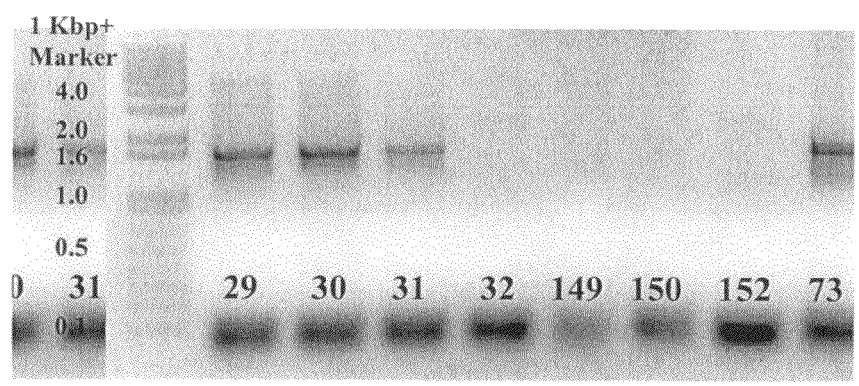
FIG. 86 depicts amplification of the downstream (3'-) boundary between donor and genome. PCR products derived from targeted integration of donor into the IPP2K gene (3'-boundary) were diagnosed by the presence of DNA fragments 1.66 Kbp in size as described in Example 21B. HiII indicates a wild-type negative control.

Amplified fragments were visualized with UV light and fragment size estimated by comparison with 1 Kbp Plus DNA ladder (Invitrogen Life Technologies, Carlsbad, Calif.). PCR products derived from targeted integration of donor into the IPP2K gene were diagnosed by the presence of DNA fragments 1.35 Kbp (5'-boundary) (FIG. 85) or 1.66 Kbp (3'-boundary) (FIG. 86). These fragments were gel-excised and purified according to manufacturer's directions using QIAQUICK™ Gel Extraction Kit (QIAGEN Inc., Valencia, Calif.). Purified fragments were subsequently cloned into pCR2.1 plasmid using TOPO TA Cloning® Kit (with pCR®2.1 vector) and One Shot® TOP10 Chemically competent E. coli cells (Invitrogen Life Technologies, Carlsbad, Calif.) according to manufacturer's protocol.

C. Nucleotide Sequence Analysis of Genotyping PCR Products

Individual colonies described in Example 21B were inoculated into a 14 ml Falcon Tube (Becton-Dickinson, Franklin Lakes, N.J.) containing 2 ml TB supplemented with 50 μl/ml kanamycin and incubated for 16 hrs at 37° C. with shaking at 200 rpm. Following incubation, 1.5 ml cells were transferred to a 1.7 ml Costar microcentrifuge tube (Fisher Scientific, Pittsburgh, Pa.) and pelleted at 16,000×g for 1 min. Supernatant was removed and plasmid DNA was isolated as described above using NucleoSpin® Plasmid Kit (BD Biosciences/Clontech/Macherey-Nagel, Palo Alto, Calif.). Three μg of isolated plasmid was digested with 10 units Eco RI (New England Biolabs, Beverly, Mass.). All plasmid digestions were incubated for 1 hr at 37° C. Restricted DNA was electrophoresed at 100 V for 1 hr in a 1.0% TAE agarose gel supplemented with 0.5% ethidium bromide. Fragments were visualized with UV light and fragment size estimated by comparison with 1 Kbp Plus DNA ladder (Invitrogen Life Technologies, Carlsbad, Calif.).

Plasmid clones were diagnosed by the presence of inserted DNA fragments in addition to the 3.9 Kbp pCR® 2.1 vector. Double-stranded sequencing reactions of plasmid clones were performed as described by manufacturer using CEQ™ DTCS-Quick Start Kit (Beckman-Coulter, Palo Alto, Calif.). Reactions were purified using Performa DTR Gel Filtration Cartridges (Edge BioSystems, Gaithersburg, Md.) as described by manufacturer protocols. Sequence reactions were analyzed on a Beckman-Coulter CEQ™ 2000 XL DNA Analysis System and nucleotide characterization performed using Sequencher™ version 4.1.4 (Gene Codes Corporation, Ann Arbor, Mich.). Nucleotide alignments were performed using Vector NTi version 10.1 (Invitrogen Life Technologies, Carlsbad, Calif.).

Sequence data encompassing the boundary between upstream (5'-) IPP2K genomic sequence and donor DNA derived from multiple targeted integration events was also obtained, including sequence data encompassing the boundary between donor DNA and downstream (3'-) IPP2K genomic sequence derived from multiple targeted integration events as well as sequence data including upstream (5'-) boundary sequences derived from a single transformed callus event (#114). The transformed targeted integration event (#114) was the result of integration of an autonomous donor into the IPP2K gene target.

In these analyses, both primary and secondary PCR amplification reactions focused on either the 5'- or 3'-boundary between genome and donor. Alignment of cloned fragments corresponding to these secondary amplification products with the wild-type IPP2K genomic sequence as well as the expected sequence of a targeted integration event revealed that the integration of donor DNA at the target site occurred. Nucleotide sequence of the IPP2K genomic locus, the genome/donor boundary, nucleotide sequence of the donor regions corresponding to IPP2K homology flanks and nucleotide sequence of the herbicide tolerance cassette were all preserved in multiple cloned PCR products derived from this event.

Therefore, this event represents a genome in which homology-driven repair of a ZFN-mediated double-stranded break at a specific gene target has occurred. Additional transformed events representing unique targeted integration occurrences have been obtained, demonstrating that the methods taught herein are reproducible in maize callus. One skilled in the art might apply these methods to any gene target in any species of plant for which targeted integration is deemed desirable.

Example 22

Regeneration of Fertile, Intact Plants from Maize Callus Tissue

Isolated calli of herbicide-tolerant maize cells derived from Hill cell culture may be regenerated into intact, fertile maize plants. One skilled in the art might regenerate intact, fertile maize plants from a variety of embryogenic maize cell cultures.

In this example, regeneration of isolated, bialophos-resistant HiII calli was initiated by transferring isolated callus tissue to a cytokinin-based induction medium, 28 (1H), containing MS salts and vitamins, 30.0 g/L sucrose, 5 mg/L benzylaminopurine, 0.25 mg/L 2,4-D, 1 mg/L bialaphos, and 2.5 g/L Gelrite; pH 5.7. Cells were allowed to grow in low light (13 μEm-2s-1) for one week followed by transfer to conditions of higher light (40 μEm-2s-1) for one week. Cells were then transferred to regeneration medium, 36 (1H), which is identical to the induction medium except that it lacks plant growth regulators. Small (3-5 cm) plantlets were excised with hand tools and placed into sterile 150×25-mm glass culture tubes containing SHGA medium (Schenk and Hildebrandt basal salts and vitamins, 1972, Can. J. Bot 50:199-204; 1 g/L myo-inositol, 10 g/L sucrose, 2.0 g/L Gelrite, pH 5.8).

Once plantlets developed a sufficiently large and differentiated root and shoot system, they were transplanted into 4-inch pots containing Metro-Mix 360 growing medium (Sun Gro Horticulture Canada Ltd.) and placed in a greenhouse. The plantlets were fully or partially covered with clear plastic cups for 2-7 days, then transplanted to 5-gallon pots containing a mixture consisting of 95% Metro-Mix 360 growing medium and 5% clay/loam soil and grown to maturity. Plants may be self-pollinated or cross-pollinated with an inbred line in order to produce T1 or F1 seed, respectively. One skilled in the art might self-pollinate regenerated plants or cross pollinate regenerated plants with a variety of germplasms in order to enable maize breeding.

Additional information related to targeted cleavage, targeted recombination and targeted integration can be found in United States Patent Application publications US-2003-0232410; US-2005-0026157; US-2005-0064474; US-2005-0208489; and US-2006-0188987; and in U.S. patent application Ser. No. 11/493,423, filed Jul. 26, 2006, the disclosures of which are incorporated by reference in their entireties for all purposes.

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A fusion protein comprising:
   (a) a cleavage half domain;
   (b) a zinc finger protein comprising a non-canonical (non-C2H2) zinc finger, wherein the non-canonical zinc finger has a helical portion involved in DNA binding and wherein at least one zinc finger comprises the sequence Cys-$(X^A)_{2-4}$-Cys-$(X^B)_{12}$-His-$(X^C)_{3-5}$-Cys-$(X^D)_{1-10}$ (SEQ ID NO:3), where $X^A$, $X^B$, $X^C$ and $X^D$ can be any amino acid and wherein
   (i) the zinc finger protein is engineered to bind to a target sequence;
   (ii) $(X^D)_{1-10}$ comprises an amino acid sequence selected from the group consisting of a G residue as the N-terminal residue of $(X^D)_{1-10}$; QKP; and QLV;
   (iii) $(X^C)_{3-5}$ comprises N-terminal T, L, A, Q, KE, KK, KQ, KI, KRI, SEGG, SSSN, IKR, IRT, ISS or IRR residues, and
   (iv) if $(X^C)_{3-5}$ consists of the amino acid residues TKI then the N-terminal residues of $(X^D)_{1-10}$ comprise GG, GL or GT; and
   (c) a ZC linker interposed between the cleavage half-domain and the zinc finger protein, wherein the ZC linker has the sequence GLRGS (SEQ ID NO:4) or GGLRGS (SEQ ID NO:5).

2. The fusion protein of claim 1, wherein the region of the zinc finger protein corresponding to His-$(X^C)_{3-5}$-Cys-$(X^D)_{1-10}$ consists of one of the amino acid sequences shown in Tables 1, 2, 3, or 4.

3. The fusion protein of claim 1, wherein $X^D$ comprises the sequence QLV or QKP.

4. The fusion protein of claim 3, wherein the sequence QLV or QKP are the 3 C-terminal amino acid residues of the zinc finger.

5. The fusion protein of claim 1, wherein $(X^D)_{1-10}$ comprises 1, 2 or 3 Gly (G) residues.

6. A fusion protein comprising a zinc finger protein comprising a plurality of zinc fingers, wherein at least one of the zinc fingers comprises a CCHC zinc finger according to claim 1.

7. The fusion protein of claim 6, wherein the zinc finger protein comprises 3, 4, 5 or 6 zinc fingers.

8. The fusion protein of claim 6, wherein finger 2 comprises the CCHC zinc finger.

9. The fusion protein of claim 6, wherein the C-terminal zinc finger comprises the CCHC finger.

10. The fusion protein of claim 6, wherein at least two zinc fingers comprise the CCHC zinc finger.

11. The fusion protein of claim 6, wherein the zinc finger protein comprises any of the sequences shown in Table 8 and is engineered to bind to a target sequence in an IPP2-K gene.

12. A polynucleotide encoding a fusion protein according to claim 1.

13. A plant cell comprising a fusion protein according to claim 1.

14. The plant cell of claim 13, wherein the cell is present in a seed.

15. The plant cell of claim 14, wherein seed is a corn seed.

16. The plant cell of claim 13, wherein IPP2-K is partially or fully inactivated.

17. The plant cell of claim 14, wherein the levels of phytic acid in the seed are reduced.

18. The plant cell of claim 13, wherein metabolically available levels of phosphorous in the cell are increased.

* * * * *

SEQUENCE LISTING

```
<160> NUMBER OF SEQ ID NOS: 201

<210> SEQ ID NO 1
<211> LENGTH: 25
<212> TYPE: PRT
<213> ORGANISM: Artificial Sequence
<220> FEATURE:
<223> OTHER INFORMATION: zinc finger motif
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(5)
<223> OTHER INFORMATION: Xaa = any amino acid
      Xaa can be present or absent
<220> FEATURE:
```

```
<221> NAME/KEY: MISC_FEATURE
<222> LOCATION: (7)..(18)
<223> OTHER INFORMATION: Xaa = any amino acid
<220> FEATURE:
<221> NAME/KEY: MISC_FEATURE
<222> LOCATION: (20)..(22)
<223> OTHER INFORMATION: Xaa = any amino acid
<220> FEATURE:
<221> NAME/KEY: MISC_FEATURE
<222> LOCATION: (23)..(24)
<223> OTHER INFORMATION: Xaa = any amino acid
      Xaa can be present or absent

<400> SEQUENCE: 1

Cys Xaa Xaa Xaa Xaa Cys Xaa Xaa Xaa Xaa Xaa Xaa Xaa Xaa Xaa
1               5                  10                  15

Xaa Xaa His Xaa Xaa Xaa Xaa Xaa His
            20                  25

<210> SEQ ID NO 2
<211> LENGTH: 6
<212> TYPE: PRT
<213> ORGANISM: Artificial Sequence
<220> FEATURE:
<223> OTHER INFORMATION: zinc finger motif
<220> FEATURE:
<221> NAME/KEY: MISC_FEATURE
<222> LOCATION: (2)..(2)
<223> OTHER INFORMATION: Xaa = any amino acid (A, K, or T are preferred)
<220> FEATURE:
<221> NAME/KEY: MISC_FEATURE
<222> LOCATION: (3)..(3)
<223> OTHER INFORMATION: Xaa = any amino acid (Q, E, or R are preferred)
<220> FEATURE:
<221> NAME/KEY: MISC_FEATURE
<222> LOCATION: (6)..(6)
<223> OTHER INFORMATION: Xaa = any amino acid (G is preferred)

<400> SEQUENCE: 2

His Xaa Xaa Arg Cys Xaa
1               5

<210> SEQ ID NO 3
<211> LENGTH: 35
<212> TYPE: PRT
<213> ORGANISM: Artificial Sequence
<220> FEATURE:
<223> OTHER INFORMATION: zinc finger motif
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(5)
<223> OTHER INFORMATION: Xaa = any amino acid
      Xaa can be present or absent
<220> FEATURE:
<221> NAME/KEY: MISC_FEATURE
<222> LOCATION: (7)..(18)
<223> OTHER INFORMATION: Xaa = any amino acid
<220> FEATURE:
<221> NAME/KEY: MISC_FEATURE
<222> LOCATION: (20)..(22)
<223> OTHER INFORMATION: Xaa = any amino acid
<220> FEATURE:
<221> NAME/KEY: MISC_FEATURE
<222> LOCATION: (23)..(24)
<223> OTHER INFORMATION: Xaa = any amino acid
      Xaa can be present or absent
<220> FEATURE:
<221> NAME/KEY: MISC_FEATURE
<222> LOCATION: (26)..(26)
<223> OTHER INFORMATION: Xaa = any amino acid
```

```
<220> FEATURE:
<221> NAME/KEY: MISC_FEATURE
<222> LOCATION: (27)..(35)
<223> OTHER INFORMATION: Xaa = any amino acid
      Xaa can be present or absent

<400> SEQUENCE: 3

Cys Xaa Xaa Xaa Xaa Cys Xaa Xaa Xaa Xaa Xaa Xaa Xaa Xaa Xaa
1               5                   10                  15

Xaa Xaa His Xaa Xaa Xaa Xaa Xaa Cys Xaa Xaa Xaa Xaa Xaa Xaa
            20                  25                  30

Xaa Xaa Xaa
        35

<210> SEQ ID NO 4
<211> LENGTH: 5
<212> TYPE: PRT
<213> ORGANISM: Artificial Sequence
<220> FEATURE:
<223> OTHER INFORMATION: ZC linker

<400> SEQUENCE: 4

Gly Leu Arg Gly Ser
1               5

<210> SEQ ID NO 5
<211> LENGTH: 6
<212> TYPE: PRT
<213> ORGANISM: Artificial Sequence
<220> FEATURE:
<223> OTHER INFORMATION: ZC linker

<400> SEQUENCE: 5

Gly Gly Leu Arg Gly Ser
1               5

<210> SEQ ID NO 6
<211> LENGTH: 1199
<212> TYPE: DNA
<213> ORGANISM: Zea mays

<400> SEQUENCE: 6
atggagatgg atggggttct gcaagccgcg gatgccaagg actgggttta caaggggaa       60
ggcgccgcga atctcatcct cagctacacc ggctcgtcgc cctccatggt aagcgctgag    120
taggttctta ctgagcgtgc acgcatcgat cacttgactt taggggctca atgtgtgatt    180
cacgggtgcc gcggcgccat tcgagctcca gatccagtac cgctcgagca agtgataaaa    240
catggagcag ggacgatcac gtggtcactt gaaaattacg tgaggtccgg ggcgacgatg    300
tacggcgcg cgaactctca aacactcaca caaccaaaac cgcttcgtgt tcgtctttgt    360
tccaagcgac tgtgtgagtg tttgagagtt cgccagcgcg acatcgcccg atctgacaaa    420
ttaagctttc gttgcttttc catgattgtg cattttgtga gcatgcactg aatactatga    480
tggatatgtt tggaggaagc attattccaa tttgatgata agggtgttat ttacacttgt    540
tttcagcttg gcaaggtact gcggctcaag aagattctaa aaaacaagtc gcagcgggca    600
ccgagttgta ttgtattctc aagtcatgag caactcctgt ggggccatat cccagaactg    660
gttgagtcgg tcaaacaaga ttgcttggct caagcctatg cagtgcatgt tatgagccaa    720
cacctgggtg ccaatcatgt cgatggtggg gtatggttca gattcagttc atttatgtcc    780
tgttattgtg atttttgattg gtaacatatt gacaacctcg acacttggga tcagattcag    840
```

-continued

```
ttcacttatg gaagaaattg gagaattgtt ataatttatc tataatcacc cctactgaaa        900
tagaaataac atggcatcaa tgtgcatgct attggatttt gacacgaata tgctttattc        960
tatcatatgt tggtaattcc agcaggcagc aggcactact ctttggatcc acgtgacttg       1020
acaaagaaat catgccatct ttccacaatg caggtccgtg tacgtgtttc tagggatttt       1080
ctggagcttg tcgaaaagaa tgttcttagc agccgtcctg ctgggagagt aaatgcaagt       1140
tcaattgata acactgctga tgccgctctt ctaatagcag accactcttt attttctgg        1199
```

<210> SEQ ID NO 7
<211> LENGTH: 50
<212> TYPE: DNA
<213> ORGANISM: Zea mays

<400> SEQUENCE: 7

```
caactcctgt ggggccatat cccagaactg gttgagtcgg tcaaacaaga                    50
```

<210> SEQ ID NO 8
<211> LENGTH: 12
<212> TYPE: DNA
<213> ORGANISM: Zea mays

<400> SEQUENCE: 8

```
ctgtggggcc at                                                             12
```

<210> SEQ ID NO 9
<211> LENGTH: 18
<212> TYPE: DNA
<213> ORGANISM: Zea mays

<400> SEQUENCE: 9

```
cttgaccaac tcagccag                                                       18
```

<210> SEQ ID NO 10
<211> LENGTH: 59
<212> TYPE: DNA
<213> ORGANISM: Zea mays

<400> SEQUENCE: 10

```
aagtcatgag caactcctgt ggggccatat cccagaactg gttgagtcgg tcaaacaag          59
```

<210> SEQ ID NO 11
<211> LENGTH: 53
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 11

```
aagtcatgag caactcctgt ggggccaaga actggttgag tcggtcaaac aag               53
```

<210> SEQ ID NO 12
<211> LENGTH: 12
<212> TYPE: PRT
<213> ORGANISM: Artificial Sequence
<220> FEATURE:
<223> OTHER INFORMATION: zinc finger motif

<400> SEQUENCE: 12

```
His Thr Lys Ile His Leu Arg Gly Ser Gln Leu Val
1               5                   10
```

```
<210> SEQ ID NO 13
<211> LENGTH: 12
<212> TYPE: PRT
<213> ORGANISM: Artificial Sequence
<220> FEATURE:
<223> OTHER INFORMATION: zinc finger motif

<400> SEQUENCE: 13

His Thr Lys Ile Cys Leu Arg Gly Ser Gln Leu Val
1               5                   10

<210> SEQ ID NO 14
<211> LENGTH: 12
<212> TYPE: PRT
<213> ORGANISM: Artificial Sequence
<220> FEATURE:
<223> OTHER INFORMATION: zinc finger motif

<400> SEQUENCE: 14

His Thr Lys Gly Cys Leu Arg Gly Ser Gln Leu Val
1               5                   10

<210> SEQ ID NO 15
<211> LENGTH: 12
<212> TYPE: PRT
<213> ORGANISM: Artificial Sequence
<220> FEATURE:
<223> OTHER INFORMATION: zinc finger motif

<400> SEQUENCE: 15

His Thr Lys Ala Cys Leu Arg Gly Ser Gln Leu Val
1               5                   10

<210> SEQ ID NO 16
<211> LENGTH: 12
<212> TYPE: PRT
<213> ORGANISM: Artificial Sequence
<220> FEATURE:
<223> OTHER INFORMATION: zinc finger motif

<400> SEQUENCE: 16

His Thr Lys Val Cys Leu Arg Gly Ser Gln Leu Val
1               5                   10

<210> SEQ ID NO 17
<211> LENGTH: 12
<212> TYPE: PRT
<213> ORGANISM: Artificial Sequence
<220> FEATURE:
<223> OTHER INFORMATION: zinc finger motif

<400> SEQUENCE: 17

His Thr Lys Leu Cys Leu Arg Gly Ser Gln Leu Val
1               5                   10

<210> SEQ ID NO 18
<211> LENGTH: 12
<212> TYPE: PRT
<213> ORGANISM: Artificial Sequence
<220> FEATURE:
<223> OTHER INFORMATION: zinc finger motif

<400> SEQUENCE: 18

His Thr Lys Ser Cys Leu Arg Gly Ser Gln Leu Val
1               5                   10

<210> SEQ ID NO 19
```

-continued

```
<211> LENGTH: 12
<212> TYPE: PRT
<213> ORGANISM: Artificial Sequence
<220> FEATURE:
<223> OTHER INFORMATION: zinc finger motif

<400> SEQUENCE: 19

His Thr Lys Asn Cys Leu Arg Gly Ser Gln Leu Val
1               5                   10

<210> SEQ ID NO 20
<211> LENGTH: 12
<212> TYPE: PRT
<213> ORGANISM: Artificial Sequence
<220> FEATURE:
<223> OTHER INFORMATION: zinc finger motif

<400> SEQUENCE: 20

His Thr Lys Lys Cys Leu Arg Gly Ser Gln Leu Val
1               5                   10

<210> SEQ ID NO 21
<211> LENGTH: 12
<212> TYPE: PRT
<213> ORGANISM: Artificial Sequence
<220> FEATURE:
<223> OTHER INFORMATION: zinc finger motif

<400> SEQUENCE: 21

His Thr Lys Arg Cys Leu Arg Gly Ser Gln Leu Val
1               5                   10

<210> SEQ ID NO 22
<211> LENGTH: 14
<212> TYPE: PRT
<213> ORGANISM: Artificial Sequence
<220> FEATURE:
<223> OTHER INFORMATION: zinc finger motif

<400> SEQUENCE: 22

His Thr Lys Ile Gly Gly Cys Leu Arg Gly Ser Gln Leu Val
1               5                   10

<210> SEQ ID NO 23
<211> LENGTH: 13
<212> TYPE: PRT
<213> ORGANISM: Artificial Sequence
<220> FEATURE:
<223> OTHER INFORMATION: zinc finger motif

<400> SEQUENCE: 23

His Thr Lys Ile Cys Gly Leu Arg Gly Ser Gln Leu Val
1               5                   10

<210> SEQ ID NO 24
<211> LENGTH: 14
<212> TYPE: PRT
<213> ORGANISM: Artificial Sequence
<220> FEATURE:
<223> OTHER INFORMATION: zinc finger motif

<400> SEQUENCE: 24

His Thr Lys Ile Cys Gly Gly Leu Arg Gly Ser Gln Leu Val
1               5                   10

<210> SEQ ID NO 25
<211> LENGTH: 14
```

```
<212> TYPE: PRT
<213> ORGANISM: Artificial Sequence
<220> FEATURE:
<223> OTHER INFORMATION: zinc finger motif

<400> SEQUENCE: 25

His Thr Lys Ile Gly Cys Gly Leu Arg Gly Ser Gln Leu Val
1               5                   10

<210> SEQ ID NO 26
<211> LENGTH: 15
<212> TYPE: PRT
<213> ORGANISM: Artificial Sequence
<220> FEATURE:
<223> OTHER INFORMATION: zinc finger motif

<400> SEQUENCE: 26

His Thr Lys Ile Gly Cys Gly Gly Leu Arg Gly Ser Gln Leu Val
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: zinc finger motif

<400> SEQUENCE: 27

His Leu Lys Gly Asn Cys Leu Arg Gly Ser Gln Leu Val
1               5                   10

<210> SEQ ID NO 28
<211> LENGTH: 13
<212> TYPE: PRT
<213> ORGANISM: Artificial Sequence
<220> FEATURE:
<223> OTHER INFORMATION: zinc finger motif

<400> SEQUENCE: 28

His Leu Lys Gly Asn Cys Pro Ala Gly Ser Gln Leu Val
1               5                   10

<210> SEQ ID NO 29
<211> LENGTH: 13
<212> TYPE: PRT
<213> ORGANISM: Artificial Sequence
<220> FEATURE:
<223> OTHER INFORMATION: zinc finger motif

<400> SEQUENCE: 29

His Ser Glu Gly Gly Cys Leu Arg Gly Ser Gln Leu Val
1               5                   10

<210> SEQ ID NO 30
<211> LENGTH: 13
<212> TYPE: PRT
<213> ORGANISM: Artificial Sequence
<220> FEATURE:
<223> OTHER INFORMATION: zinc finger motif

<400> SEQUENCE: 30

His Ser Glu Gly Gly Cys Pro Gly Gly Ser Gln Leu Val
1               5                   10

<210> SEQ ID NO 31
<211> LENGTH: 13
<212> TYPE: PRT
```

```
<213> ORGANISM: Artificial Sequence
<220> FEATURE:
<223> OTHER INFORMATION: zinc finger motif

<400> SEQUENCE: 31

His Ser Ser Ser Asn Cys Leu Arg Gly Ser Gln Leu Val
1               5                   10

<210> SEQ ID NO 32
<211> LENGTH: 13
<212> TYPE: PRT
<213> ORGANISM: Artificial Sequence
<220> FEATURE:
<223> OTHER INFORMATION: zinc finger motif

<400> SEQUENCE: 32

His Ser Ser Ser Asn Cys Thr Ile Gly Ser Gln Leu Val
1               5                   10

<210> SEQ ID NO 33
<211> LENGTH: 15
<212> TYPE: PRT
<213> ORGANISM: Artificial Sequence
<220> FEATURE:
<223> OTHER INFORMATION: zinc finger motif

<400> SEQUENCE: 33

His Thr Lys Ile Cys Gly Gly Gly Leu Arg Gly Ser Gln Leu Val
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: zinc finger motif

<400> SEQUENCE: 34

His Thr Lys Ile Gly Cys Gly Gly Gly Leu Arg Gly Ser Gln Leu Val
1               5                   10                  15

<210> SEQ ID NO 35
<211> LENGTH: 14
<212> TYPE: PRT
<213> ORGANISM: Artificial Sequence
<220> FEATURE:
<223> OTHER INFORMATION: zinc finger motif

<400> SEQUENCE: 35

His Thr Lys Ile Gly Gly Cys Leu Arg Gly Ser Gln Leu Val
1               5                   10

<210> SEQ ID NO 36
<211> LENGTH: 15
<212> TYPE: PRT
<213> ORGANISM: Artificial Sequence
<220> FEATURE:
<223> OTHER INFORMATION: zinc finger motif

<400> SEQUENCE: 36

His Thr Lys Ile Gly Gly Cys Gly Leu Arg Gly Ser Gln Leu Val
1               5                   10                  15

<210> SEQ ID NO 37
<211> LENGTH: 16
<212> TYPE: PRT
<213> ORGANISM: Artificial Sequence
```

```
<220> FEATURE:
<223> OTHER INFORMATION: zinc finger motif

<400> SEQUENCE: 37

His Thr Lys Ile Gly Gly Cys Gly Gly Leu Arg Gly Ser Gln Leu Val
1               5                   10                  15

<210> SEQ ID NO 38
<211> LENGTH: 13
<212> TYPE: PRT
<213> ORGANISM: Artificial Sequence
<220> FEATURE:
<223> OTHER INFORMATION: zinc finger motif

<400> SEQUENCE: 38

His Thr Lys Arg Cys Gly Leu Arg Gly Ser Gln Leu Val
1               5                   10

<210> SEQ ID NO 39
<211> LENGTH: 14
<212> TYPE: PRT
<213> ORGANISM: Artificial Sequence
<220> FEATURE:
<223> OTHER INFORMATION: zinc finger motif

<400> SEQUENCE: 39

His Thr Lys Arg Cys Gly Gly Leu Arg Gly Ser Gln Leu Val
1               5                   10

<210> SEQ ID NO 40
<211> LENGTH: 15
<212> TYPE: PRT
<213> ORGANISM: Artificial Sequence
<220> FEATURE:
<223> OTHER INFORMATION: zinc finger motif

<400> SEQUENCE: 40

His Thr Lys Arg Cys Gly Gly Gly Leu Arg Gly Ser Gln Leu Val
1               5                   10                  15

<210> SEQ ID NO 41
<211> LENGTH: 13
<212> TYPE: PRT
<213> ORGANISM: Artificial Sequence
<220> FEATURE:
<223> OTHER INFORMATION: zinc finger motif

<400> SEQUENCE: 41

His Thr Lys Arg Gly Cys Leu Arg Gly Ser Gln Leu Val
1               5                   10

<210> SEQ ID NO 42
<211> LENGTH: 14
<212> TYPE: PRT
<213> ORGANISM: Artificial Sequence
<220> FEATURE:
<223> OTHER INFORMATION: zinc finger motif

<400> SEQUENCE: 42

His Thr Lys Arg Gly Cys Gly Leu Arg Gly Ser Gln Leu Val
1               5                   10

<210> SEQ ID NO 43
<211> LENGTH: 15
<212> TYPE: PRT
<213> ORGANISM: Artificial Sequence
<220> FEATURE:
```

<223> OTHER INFORMATION: zinc finger motif

<400> SEQUENCE: 43

His Thr Lys Arg Gly Cys Gly Gly Leu Arg Gly Ser Gln Leu Val
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: zinc finger motif

<400> SEQUENCE: 44

His Thr Lys Arg Gly Cys Gly Gly Gly Leu Arg Gly Ser Gln Leu Val
1               5                   10                  15

<210> SEQ ID NO 45
<211> LENGTH: 14
<212> TYPE: PRT
<213> ORGANISM: Artificial Sequence
<220> FEATURE:
<223> OTHER INFORMATION: zinc finger motif

<400> SEQUENCE: 45

His Thr Lys Arg Gly Gly Cys Leu Arg Gly Ser Gln Leu Val
1               5                   10

<210> SEQ ID NO 46
<211> LENGTH: 15
<212> TYPE: PRT
<213> ORGANISM: Artificial Sequence
<220> FEATURE:
<223> OTHER INFORMATION: zinc finger motif

<400> SEQUENCE: 46

His Thr Lys Arg Gly Gly Cys Gly Leu Arg Gly Ser Gln Leu Val
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: zinc finger motif

<400> SEQUENCE: 47

His Thr Lys Arg Gly Gly Cys Gly Gly Leu Arg Gly Ser Gln Leu Val
1               5                   10                  15

<210> SEQ ID NO 48
<211> LENGTH: 14
<212> TYPE: PRT
<213> ORGANISM: Artificial Sequence
<220> FEATURE:
<223> OTHER INFORMATION: zinc finger motif

<400> SEQUENCE: 48

His Leu Lys Gly Asn Cys Gly Leu Arg Gly Ser Gln Leu Val
1               5                   10

<210> SEQ ID NO 49
<211> LENGTH: 15
<212> TYPE: PRT
<213> ORGANISM: Artificial Sequence
<220> FEATURE:
<223> OTHER INFORMATION: zinc finger motif

```
<400> SEQUENCE: 49

His Leu Lys Gly Asn Cys Gly Gly Leu Arg Gly Ser Gln Leu Val
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: zinc finger motif

<400> SEQUENCE: 50

His Leu Lys Gly Asn Cys Gly Gly Gly Leu Arg Gly Ser Gln Leu Val
1               5                   10                  15

<210> SEQ ID NO 51
<211> LENGTH: 13
<212> TYPE: PRT
<213> ORGANISM: Artificial Sequence
<220> FEATURE:
<223> OTHER INFORMATION: zinc finger motif

<400> SEQUENCE: 51

His Lys Glu Arg Cys Gly Leu Arg Gly Ser Gln Leu Val
1               5                   10

<210> SEQ ID NO 52
<211> LENGTH: 13
<212> TYPE: PRT
<213> ORGANISM: Artificial Sequence
<220> FEATURE:
<223> OTHER INFORMATION: zinc finger motif

<400> SEQUENCE: 52

His Thr Arg Arg Cys Gly Leu Arg Gly Ser Gln Leu Val
1               5                   10

<210> SEQ ID NO 53
<211> LENGTH: 13
<212> TYPE: PRT
<213> ORGANISM: Artificial Sequence
<220> FEATURE:
<223> OTHER INFORMATION: zinc finger motif

<400> SEQUENCE: 53

His Ala Gln Arg Cys Gly Leu Arg Gly Ser Gln Leu Val
1               5                   10

<210> SEQ ID NO 54
<211> LENGTH: 14
<212> TYPE: PRT
<213> ORGANISM: Artificial Sequence
<220> FEATURE:
<223> OTHER INFORMATION: zinc finger motif

<400> SEQUENCE: 54

His Lys Lys Phe Tyr Cys Gly Leu Arg Gly Ser Gln Leu Val
1               5                   10

<210> SEQ ID NO 55
<211> LENGTH: 14
<212> TYPE: PRT
<213> ORGANISM: Artificial Sequence
<220> FEATURE:
<223> OTHER INFORMATION: zinc finger motif
```

```
<400> SEQUENCE: 55

His Lys Lys His Tyr Cys Gly Leu Arg Gly Ser Gln Leu Val
1               5                   10

<210> SEQ ID NO 56
<211> LENGTH: 14
<212> TYPE: PRT
<213> ORGANISM: Artificial Sequence
<220> FEATURE:
<223> OTHER INFORMATION: zinc finger motif

<400> SEQUENCE: 56

His Lys Lys Tyr Thr Cys Gly Leu Arg Gly Ser Gln Leu Val
1               5                   10

<210> SEQ ID NO 57
<211> LENGTH: 14
<212> TYPE: PRT
<213> ORGANISM: Artificial Sequence
<220> FEATURE:
<223> OTHER INFORMATION: zinc finger motif

<400> SEQUENCE: 57

His Lys Lys Tyr Tyr Cys Gly Leu Arg Gly Ser Gln Leu Val
1               5                   10

<210> SEQ ID NO 58
<211> LENGTH: 14
<212> TYPE: PRT
<213> ORGANISM: Artificial Sequence
<220> FEATURE:
<223> OTHER INFORMATION: zinc finger motif

<400> SEQUENCE: 58

His Lys Gln Tyr Tyr Cys Gly Leu Arg Gly Ser Gln Leu Val
1               5                   10

<210> SEQ ID NO 59
<211> LENGTH: 14
<212> TYPE: PRT
<213> ORGANISM: Artificial Sequence
<220> FEATURE:
<223> OTHER INFORMATION: zinc finger motif

<400> SEQUENCE: 59

His Leu Leu Lys Lys Cys Gly Leu Arg Gly Ser Gln Leu Val
1               5                   10

<210> SEQ ID NO 60
<211> LENGTH: 14
<212> TYPE: PRT
<213> ORGANISM: Artificial Sequence
<220> FEATURE:
<223> OTHER INFORMATION: zinc finger motif

<400> SEQUENCE: 60

His Gln Lys Phe Pro Cys Gly Leu Arg Gly Ser Gln Leu Val
1               5                   10

<210> SEQ ID NO 61
<211> LENGTH: 14
<212> TYPE: PRT
<213> ORGANISM: Artificial Sequence
<220> FEATURE:
<223> OTHER INFORMATION: zinc finger motif

<400> SEQUENCE: 61
```

```
His Gln Lys Lys Leu Cys Gly Leu Arg Gly Ser Gln Leu Val
1               5                   10
```

<210> SEQ ID NO 62
<211> LENGTH: 14
<212> TYPE: PRT
<213> ORGANISM: Artificial Sequence
<220> FEATURE:
<223> OTHER INFORMATION: zinc finger motif

<400> SEQUENCE: 62

```
His Gln Ile Arg Gly Cys Gly Leu Arg Gly Ser Gln Leu Val
1               5                   10
```

<210> SEQ ID NO 63
<211> LENGTH: 15
<212> TYPE: PRT
<213> ORGANISM: Artificial Sequence
<220> FEATURE:
<223> OTHER INFORMATION: zinc finger motif

<400> SEQUENCE: 63

```
His Ile Lys Arg Gln Ser Cys Gly Leu Arg Gly Ser Gln Leu Val
1               5                   10                  15
```

<210> SEQ ID NO 64
<211> LENGTH: 15
<212> TYPE: PRT
<213> ORGANISM: Artificial Sequence
<220> FEATURE:
<223> OTHER INFORMATION: zinc finger motif

<400> SEQUENCE: 64

```
His Ile Arg Arg Tyr Thr Cys Gly Leu Arg Gly Ser Gln Leu Val
1               5                   10                  15
```

<210> SEQ ID NO 65
<211> LENGTH: 15
<212> TYPE: PRT
<213> ORGANISM: Artificial Sequence
<220> FEATURE:
<223> OTHER INFORMATION: zinc finger motif

<400> SEQUENCE: 65

```
His Ile Ser Ser Lys Lys Cys Gly Leu Arg Gly Ser Gln Leu Val
1               5                   10                  15
```

<210> SEQ ID NO 66
<211> LENGTH: 15
<212> TYPE: PRT
<213> ORGANISM: Artificial Sequence
<220> FEATURE:
<223> OTHER INFORMATION: zinc finger motif

<400> SEQUENCE: 66

```
His Lys Ile Gln Lys Ala Cys Gly Leu Arg Gly Ser Gln Leu Val
1               5                   10                  15
```

<210> SEQ ID NO 67
<211> LENGTH: 15
<212> TYPE: PRT
<213> ORGANISM: Artificial Sequence
<220> FEATURE:
<223> OTHER INFORMATION: zinc finger motif

<400> SEQUENCE: 67

-continued

His Lys Arg Ile Tyr Thr Cys Gly Leu Arg Gly Ser Gln Leu Val
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: zinc finger motif

<400> SEQUENCE: 68

His Leu Lys Gly Gln Asn Cys Gly Leu Arg Gly Ser Gln Leu Val
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: zinc finger motif

<400> SEQUENCE: 69

His Leu Lys Lys Asp Gly Cys Gly Leu Arg Gly Ser Gln Leu Val
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: zinc finger motif

<400> SEQUENCE: 70

His Leu Lys Tyr Thr Pro Cys Gly Leu Arg Gly Ser Gln Leu Val
1               5                   10                  15

<210> SEQ ID NO 71
<211> LENGTH: 12
<212> TYPE: PRT
<213> ORGANISM: Artificial Sequence
<220> FEATURE:
<223> OTHER INFORMATION: zinc finger motif

<400> SEQUENCE: 71

His Thr Lys Arg Cys Gly Arg Gly Ser Gln Leu Val
1               5                   10

<210> SEQ ID NO 72
<211> LENGTH: 14
<212> TYPE: PRT
<213> ORGANISM: Artificial Sequence
<220> FEATURE:
<223> OTHER INFORMATION: zinc finger motif

<400> SEQUENCE: 72

His Thr Lys Ile Gly Cys Gly Gly Arg Gly Ser Gln Leu Val
1               5                   10

<210> SEQ ID NO 73
<211> LENGTH: 13
<212> TYPE: PRT
<213> ORGANISM: Artificial Sequence
<220> FEATURE:
<223> OTHER INFORMATION: zinc finger motif

<400> SEQUENCE: 73

His Leu Lys Gly Asn Cys Gly Arg Gly Ser Gln Leu Val

```
<210> SEQ ID NO 74
<211> LENGTH: 13
<212> TYPE: PRT
<213> ORGANISM: Artificial Sequence
<220> FEATURE:
<223> OTHER INFORMATION: zinc finger motif

<400> SEQUENCE: 74

His Leu Lys Gly Asn Cys Gly Gly Gly Ser Gln Leu Val
1               5                   10

<210> SEQ ID NO 75
<211> LENGTH: 11
<212> TYPE: PRT
<213> ORGANISM: Artificial Sequence
<220> FEATURE:
<223> OTHER INFORMATION: zinc finger motif

<400> SEQUENCE: 75

His Ile Arg Thr Cys Thr Gly Ser Gln Lys Pro
1               5                   10

<210> SEQ ID NO 76
<211> LENGTH: 12
<212> TYPE: PRT
<213> ORGANISM: Artificial Sequence
<220> FEATURE:
<223> OTHER INFORMATION: zinc finger motif

<400> SEQUENCE: 76

His Ile Arg Thr Cys Gly Thr Gly Ser Gln Lys Pro
1               5                   10

<210> SEQ ID NO 77
<211> LENGTH: 12
<212> TYPE: PRT
<213> ORGANISM: Artificial Sequence
<220> FEATURE:
<223> OTHER INFORMATION: zinc finger motif

<400> SEQUENCE: 77

His Ile Arg Thr Gly Cys Thr Gly Ser Gln Lys Pro
1               5                   10

<210> SEQ ID NO 78
<211> LENGTH: 13
<212> TYPE: PRT
<213> ORGANISM: Artificial Sequence
<220> FEATURE:
<223> OTHER INFORMATION: zinc finger motif

<400> SEQUENCE: 78

His Ile Arg Thr Gly Cys Gly Thr Gly Ser Gln Lys Pro
1               5                   10

<210> SEQ ID NO 79
<211> LENGTH: 11
<212> TYPE: PRT
<213> ORGANISM: Artificial Sequence
<220> FEATURE:
<223> OTHER INFORMATION: zinc finger motif

<400> SEQUENCE: 79

His Ile Arg Arg Cys Thr Gly Ser Gln Lys Pro
1               5                   10
```

```
<210> SEQ ID NO 80
<211> LENGTH: 12
<212> TYPE: PRT
<213> ORGANISM: Artificial Sequence
<220> FEATURE:
<223> OTHER INFORMATION: zinc finger motif

<400> SEQUENCE: 80

His Ile Arg Arg Gly Cys Thr Gly Ser Gln Lys Pro
1               5                   10

<210> SEQ ID NO 81
<211> LENGTH: 11
<212> TYPE: PRT
<213> ORGANISM: Artificial Sequence
<220> FEATURE:
<223> OTHER INFORMATION: zinc finger motif

<400> SEQUENCE: 81

His Thr Lys Ile His Thr Gly Ser Gln Lys Pro
1               5                   10

<210> SEQ ID NO 82
<211> LENGTH: 11
<212> TYPE: PRT
<213> ORGANISM: Artificial Sequence
<220> FEATURE:
<223> OTHER INFORMATION: zinc finger motif

<400> SEQUENCE: 82

His Thr Lys Ile Cys Thr Gly Ser Gln Lys Pro
1               5                   10

<210> SEQ ID NO 83
<211> LENGTH: 11
<212> TYPE: PRT
<213> ORGANISM: Artificial Sequence
<220> FEATURE:
<223> OTHER INFORMATION: zinc finger motif

<400> SEQUENCE: 83

His Thr Lys Arg Cys Thr Gly Ser Gln Lys Pro
1               5                   10

<210> SEQ ID NO 84
<211> LENGTH: 11
<212> TYPE: PRT
<213> ORGANISM: Artificial Sequence
<220> FEATURE:
<223> OTHER INFORMATION: zinc finger motif

<400> SEQUENCE: 84

His Ala Gln Arg Cys Thr Gly Ser Gln Lys Pro
1               5                   10

<210> SEQ ID NO 85
<211> LENGTH: 12
<212> TYPE: PRT
<213> ORGANISM: Artificial Sequence
<220> FEATURE:
<223> OTHER INFORMATION: zinc finger motif

<400> SEQUENCE: 85

His Thr Lys Ile Cys Gly Thr Gly Ser Gln Lys Pro
1               5                   10
```

```
<210> SEQ ID NO 86
<211> LENGTH: 12
<212> TYPE: PRT
<213> ORGANISM: Artificial Sequence
<220> FEATURE:
<223> OTHER INFORMATION: zinc finger motif

<400> SEQUENCE: 86

His Thr Lys Arg Cys Gly Thr Gly Ser Gln Lys Pro
1               5                   10

<210> SEQ ID NO 87
<211> LENGTH: 12
<212> TYPE: PRT
<213> ORGANISM: Artificial Sequence
<220> FEATURE:
<223> OTHER INFORMATION: zinc finger motif

<400> SEQUENCE: 87

His Ala Gln Arg Cys Gly Thr Gly Ser Gln Lys Pro
1               5                   10

<210> SEQ ID NO 88
<211> LENGTH: 12
<212> TYPE: PRT
<213> ORGANISM: Artificial Sequence
<220> FEATURE:
<223> OTHER INFORMATION: zinc finger motif

<400> SEQUENCE: 88

His Thr Lys Ile His Leu Arg Gly Ser Gln Leu Val
1               5                   10

<210> SEQ ID NO 89
<211> LENGTH: 7
<212> TYPE: PRT
<213> ORGANISM: Artificial Sequence
<220> FEATURE:
<223> OTHER INFORMATION: zinc finger motif

<400> SEQUENCE: 89

His Ala Gln Arg Cys Gly Gly
1               5

<210> SEQ ID NO 90
<211> LENGTH: 8
<212> TYPE: PRT
<213> ORGANISM: Artificial Sequence
<220> FEATURE:
<223> OTHER INFORMATION: zinc finger motif

<400> SEQUENCE: 90

His Ala Gln Arg Cys Gly Gly Gly
1               5

<210> SEQ ID NO 91
<211> LENGTH: 8
<212> TYPE: PRT
<213> ORGANISM: Artificial Sequence
<220> FEATURE:
<223> OTHER INFORMATION: zinc finger motif

<400> SEQUENCE: 91

His Thr Lys Ile Cys Gly Gly Gly
1               5
```

-continued

```
<210> SEQ ID NO 92
<211> LENGTH: 8
<212> TYPE: PRT
<213> ORGANISM: Artificial Sequence
<220> FEATURE:
<223> OTHER INFORMATION: zinc finger motif

<400> SEQUENCE: 92

His Thr Lys Arg Cys Gly Gly Gly
1               5

<210> SEQ ID NO 93
<211> LENGTH: 6
<212> TYPE: PRT
<213> ORGANISM: Artificial Sequence
<220> FEATURE:
<223> OTHER INFORMATION: zinc finger motif

<400> SEQUENCE: 93

His Ala Gln Arg Cys Gly
1               5

<210> SEQ ID NO 94
<211> LENGTH: 7
<212> TYPE: PRT
<213> ORGANISM: Artificial Sequence
<220> FEATURE:
<223> OTHER INFORMATION: zinc finger motif

<400> SEQUENCE: 94

Cys Cys His Thr Lys Ile His
1               5

<210> SEQ ID NO 95
<211> LENGTH: 7
<212> TYPE: PRT
<213> ORGANISM: Artificial Sequence
<220> FEATURE:
<223> OTHER INFORMATION: zinc finger motif

<400> SEQUENCE: 95

Cys Cys His Thr Lys Ile His
1               5

<210> SEQ ID NO 96
<211> LENGTH: 7
<212> TYPE: PRT
<213> ORGANISM: Artificial Sequence
<220> FEATURE:
<223> OTHER INFORMATION: zinc finger motif

<400> SEQUENCE: 96

Cys Cys His Thr Lys Ile Cys
1               5

<210> SEQ ID NO 97
<211> LENGTH: 10
<212> TYPE: PRT
<213> ORGANISM: Artificial Sequence
<220> FEATURE:
<223> OTHER INFORMATION: zinc finger motif

<400> SEQUENCE: 97

Cys Cys His Thr Lys Arg Cys Gly Gly Gly
1               5                   10

<210> SEQ ID NO 98
```

```
<211> LENGTH: 8
<212> TYPE: PRT
<213> ORGANISM: Artificial Sequence
<220> FEATURE:
<223> OTHER INFORMATION: zinc finger motif

<400> SEQUENCE: 98

Cys Cys His Ala Gln Arg Cys Gly
1               5

<210> SEQ ID NO 99
<211> LENGTH: 8
<212> TYPE: PRT
<213> ORGANISM: Artificial Sequence
<220> FEATURE:
<223> OTHER INFORMATION: zinc finger motif

<400> SEQUENCE: 99

Cys Cys His Ile Arg Thr Gly Cys
1               5

<210> SEQ ID NO 100
<211> LENGTH: 7
<212> TYPE: PRT
<213> ORGANISM: Artificial Sequence
<220> FEATURE:
<223> OTHER INFORMATION: zinc finger motif

<400> SEQUENCE: 100

Cys Cys His Thr Lys Ile His
1               5

<210> SEQ ID NO 101
<211> LENGTH: 8
<212> TYPE: PRT
<213> ORGANISM: Artificial Sequence
<220> FEATURE:
<223> OTHER INFORMATION: zinc finger motif

<400> SEQUENCE: 101

Cys Cys His Ile Arg Thr Gly Cys
1               5

<210> SEQ ID NO 102
<211> LENGTH: 7
<212> TYPE: PRT
<213> ORGANISM: Artificial Sequence
<220> FEATURE:
<223> OTHER INFORMATION: zinc finger motif

<400> SEQUENCE: 102

Cys Cys His Thr Lys Ile His
1               5

<210> SEQ ID NO 103
<211> LENGTH: 9
<212> TYPE: PRT
<213> ORGANISM: Artificial Sequence
<220> FEATURE:
<223> OTHER INFORMATION: zinc finger motif

<400> SEQUENCE: 103

Cys Cys His Ala Gln Arg Cys Gly Gly
1               5

<210> SEQ ID NO 104
<211> LENGTH: 29
```

```
<212> TYPE: DNA
<213> ORGANISM: Artificial Sequence
<220> FEATURE:
<223> OTHER INFORMATION: primer

<400> SEQUENCE: 104
atggagatgg atggggttct gcaagccgc                                       29

<210> SEQ ID NO 105
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 105

Asp Arg Ser Ala Leu Ser Arg
1               5

<210> SEQ ID NO 106
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 106

Arg Asn Asp Asp Arg Lys Lys
1               5

<210> SEQ ID NO 107
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 107

Arg Ser Asp Asn Leu Ser Thr
1               5

<210> SEQ ID NO 108
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 108

His Ser His Ala Arg Ile Lys
1               5

<210> SEQ ID NO 109
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 109

Arg Ser Asp Val Leu Ser Glu
1               5

<210> SEQ ID NO 110
<211> LENGTH: 7
<212> TYPE: PRT
<213> ORGANISM: Artificial Sequence
```

```
<220> FEATURE:
<223> OTHER INFORMATION: zinc finger binding domain

<400> SEQUENCE: 110

Gln Ser Gly Asn Leu Ala Arg
1               5

<210> SEQ ID NO 111
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 111

Arg Ser Asp Asn Leu Ala Arg
1               5

<210> SEQ ID NO 112
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 112

Thr Ser Gly Ser Leu Thr Arg
1               5

<210> SEQ ID NO 113
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 113

Thr Ser Gly Asn Leu Thr Arg
1               5

<210> SEQ ID NO 114
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 114

Arg Ser Asp His Leu Ser Glu
1               5

<210> SEQ ID NO 115
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 115

Gln Ser Ala Thr Arg Lys Lys
1               5

<210> SEQ ID NO 116
<211> LENGTH: 7
<212> TYPE: PRT
<213> ORGANISM: Artificial Sequence
<220> FEATURE:
```

```
<223> OTHER INFORMATION: zinc finger binding domain

<400> SEQUENCE: 116

Glu Arg Gly Thr Leu Ala Arg
1               5

<210> SEQ ID NO 117
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 117

Arg Ser Asp Ala Leu Thr Gln
1               5

<210> SEQ ID NO 118
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 118

Arg Ser Asp Ser Leu Ser Ala
1               5

<210> SEQ ID NO 119
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 119

Arg Ser Ala Ala Leu Ala Arg
1               5

<210> SEQ ID NO 120
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 120

Arg Ser Asp Asn Leu Ser Glu
1               5

<210> SEQ ID NO 121
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 121

Ala Ser Lys Thr Arg Thr Asn
1               5

<210> SEQ ID NO 122
<211> LENGTH: 7
<212> TYPE: PRT
<213> ORGANISM: Artificial Sequence
<220> FEATURE:
<223> OTHER INFORMATION: zinc finger binding domain
```

<400> SEQUENCE: 122

Asp Arg Ser His Leu Ala Arg
1               5

<210> SEQ ID NO 123
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 123

Arg Ser Asp His Leu Ser Thr
1               5

<210> SEQ ID NO 124
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 124

Gln Ser Gly Ser Leu Thr Arg
1               5

<210> SEQ ID NO 125
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 125

Gln Asn His His Arg Ile Asn
1               5

<210> SEQ ID NO 126
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 126

Thr Gly Ser Asn Leu Thr Arg
1               5

<210> SEQ ID NO 127
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 127

Asp Arg Ser Ala Leu Ala Arg
1               5

<210> SEQ ID NO 128
<211> LENGTH: 18
<212> TYPE: DNA
<213> ORGANISM: Artificial Sequence
<220> FEATURE:
<223> OTHER INFORMATION: IPP2K zinc finger target sequence

<400> SEQUENCE: 128
gaactggttg agtcggtc                                                18

<210> SEQ ID NO 129
<211> LENGTH: 18
<212> TYPE: DNA
<213> ORGANISM: Artificial Sequence
<220> FEATURE:
<223> OTHER INFORMATION: IPP2K zinc finger target sequence

<400> SEQUENCE: 129
gaactggttg agtcggtc                                                18

<210> SEQ ID NO 130
<211> LENGTH: 12
<212> TYPE: DNA
<213> ORGANISM: Artificial Sequence
<220> FEATURE:
<223> OTHER INFORMATION: IPP2K zinc finger target sequence

<400> SEQUENCE: 130
atggccccac ag                                                      12

<210> SEQ ID NO 131
<211> LENGTH: 15
<212> TYPE: DNA
<213> ORGANISM: Artificial Sequence
<220> FEATURE:
<223> OTHER INFORMATION: IPP2K zinc finger target sequence

<400> SEQUENCE: 131
ggcacccagg tgttg                                                   15

<210> SEQ ID NO 132
<211> LENGTH: 18
<212> TYPE: DNA
<213> ORGANISM: Artificial Sequence
<220> FEATURE:
<223> OTHER INFORMATION: IPP2K zinc finger target sequence

<400> SEQUENCE: 132
gtcgatggtg gggtatgg                                                18

<210> SEQ ID NO 133
<211> LENGTH: 18
<212> TYPE: PRT
<213> ORGANISM: Artificial Sequence
<220> FEATURE:
<223> OTHER INFORMATION: NLS derived from maize op-2

<400> SEQUENCE: 133

Arg Lys Arg Lys Glu Ser Asn Arg Glu Ser Ala Arg Arg Ser Arg Tyr
1               5                   10                  15

Arg Lys

<210> SEQ ID NO 134
<211> LENGTH: 18
<212> TYPE: PRT
<213> ORGANISM: Artificial Sequence
<220> FEATURE:
<223> OTHER INFORMATION: 2A sequence from Thosea asigna virus

<400> SEQUENCE: 134

Glu Gly Arg Gly Ser Leu Leu Thr Cys Gly Asp Val Glu Glu Asn Pro
1               5                   10                  15

Gly Pro

<210> SEQ ID NO 135
<211> LENGTH: 30
<212> TYPE: DNA
<213> ORGANISM: Artificial Sequence
<220> FEATURE:
<223> OTHER INFORMATION: primer

<400> SEQUENCE: 135
ggaagcatta ttccaatttg atgataatgg                               30

<210> SEQ ID NO 136
<211> LENGTH: 29
<212> TYPE: DNA
<213> ORGANISM: Artificial Sequence
<220> FEATURE:
<223> OTHER INFORMATION: primer

<400> SEQUENCE: 136
cccaagtgtc gaggttgtca atatgttac                                29

<210> SEQ ID NO 137
<211> LENGTH: 26
<212> TYPE: DNA
<213> ORGANISM: Artificial Sequence
<220> FEATURE:
<223> OTHER INFORMATION: primer

<400> SEQUENCE: 137
ssscaccaag ttgtattgcc ttctca                                   26

<210> SEQ ID NO 138
<211> LENGTH: 26
<212> TYPE: DNA
<213> ORGANISM: Artificial Sequence
<220> FEATURE:
<223> OTHER INFORMATION: primer

<400> SEQUENCE: 138
sssataggct tgagccaagc aatctt                                   26

<210> SEQ ID NO 139
<211> LENGTH: 855
<212> TYPE: DNA
<213> ORGANISM: Artificial Sequence
<220> FEATURE:
<223> OTHER INFORMATION: position-1 3'-homology flank sequence

<400> SEQUENCE: 139
gcggccgcta gatagcagat gcagattgct tgcttctctg gtttgatttt tggagtcacc    60
atttctgttt ggttcgtgtg cctcagtgtc tgacagcagc agatcctcga tggagatgga   120
tggggttctg caagccgcgg atgccaagga ctgggtttac aagggggaag cgccgcgaa    180 tctcatcctc agctacaccg gcacgtcgcc ctccatggta agcgctgagt aggttcttac   240
tgagtgtgca cgcatcgatc acttgacttt aggggctcaa tgtgtgattc acgggtgccg   300
ccattcgagc tccagatcca gtatcgctcg agcaagtgat aaaacatgga gcagggacga   360
tcacgtggtc acttgaaaat tatgtgaggt ccggggcgac gatgtacggc gcggcgaact   420
ctcaaacact cacacagcca aaaccgcttc gtgttcgtct ttgttccaag cgaccgtgtg   480
gtgtgtttgt agtagttcgc cggcgccgca catcgtcgcc ccggatctga caaattaagc   540

```
tttcgttgct tttccacgat tgtgcatttt ctgagcatgc actgaatact atgatggata    600
tgtttggagg aagcattatt ccaatttgat gataatggtg ttatttacac ttgttttcag    660
cttggcaagg tactgcggct caagaagatt ctaaaaaaca agttgcagcg ggcaccaagt    720
tgtattgcct tctcaagtca tgagcaactc ctgtggggcc atatcccaga actggttgag    780
tcggtcaaac aagattgctt ggctcaagcc tatgcagtgc atgttatgag ccaacacctg    840
ggtgccaata ctagt                                                     855
```

<210> SEQ ID NO 140
<211> LENGTH: 845
<212> TYPE: DNA
<213> ORGANISM: Artificial Sequence
<220> FEATURE:
<223> OTHER INFORMATION: position-2 3'-homology flank sequence

<400> SEQUENCE: 140

```
actagtcatg tcgatggtgg ggtatggttc agattcagtt catttatgtc ctgttattgt     60
gattttgatt ggtaacatat tgacaacctc gacacttggg atcagattca gttcacttat    120
ggaagaaatt ggagaattgt gataatttat ctataatcac ccctactgaa atagaaataa    180
catgacatca atgtgcatgc tattggattt tgacacgaat atgctttatt ctatcatatg    240
ttggtaattc cagcaggcag caggcactac tctttggatc cacgtgactt gacaaagaaa    300
tcatgccatc tttccacaat gcaggtccgt gtacgtgttt ctagggattt tctggagctt    360
gtcgaaaaga atgttcttag cagccgtcct gctgggagag taaatgcaag ttcaattgat    420
aacactgctg atgccgctct tctaatagca gaccactctt tattttctgg tacgtactct    480
atccctcttc ttaccataat ctgaatcttg ttaaggttta aaatatacga ttgattaagt    540
aaaatccaga gctctattca tatctcacgc actgatgttt tgatgaaacg cttgcagcaa    600
gacggttgcc tgttatttct atttgcatta gacaaacagt cacctttgtt tataaaggtc    660
tttgaatttg cagttcttat aggtttaagt ttgcaactgt tacttacaac agcccaatgg    720
gtagcatcaa gattgttttt ttcagtgatt cataacttaa ctcttggtta aaccgctaga    780
acatggttgg tgtcttaaaa tgcaactggt cctgaggccg taacctgaaa tcattgtacg    840
tcgac                                                                845
```

<210> SEQ ID NO 141
<211> LENGTH: 484
<212> TYPE: DNA
<213> ORGANISM: Artificial Sequence
<220> FEATURE:
<223> OTHER INFORMATION: Upstream 5'-IPP2K genomic sequence of the ZFN
      targeted regions

<400> SEQUENCE: 141

```
tggacggagc gagagccaga attcgacgct ggcggcggcg cgtcgccaat acgcagcgcg     60
gatgtggagc cacatgcaaa cgtgtgtccg cccgcgtggc gtccactctc cctccacgtt    120
tcggcgtcct cgtcgccttc ctgggaaatc tccagctact gcccactgcc ccttcccttc    180
agtccctttc cccgggctgt ggtaccagta ctagtaccag catctcttca ggctccacca    240
agcgcagaca ccgcagcagc ggcagcagca cgatccggtg accccccgcc gcgtccagcc    300
tgctcctccg gtgatcgccg gactggcggg gtaggaacca gcggagcgca gcccgcctcc    360
ttccgctggt aagagtgacg cccgcccgct cctcccttcg ctcgcttcct tgctcttccg    420
attctggcgt accagtctca ccgcggcttg gggatttgat gcggagctag ttaaccagca    480
``` gagc                                                                484

<210> SEQ ID NO 142
<211> LENGTH: 729
<212> TYPE: DNA
<213> ORGANISM: Artificial Sequence
<220> FEATURE:
<223> OTHER INFORMATION: Downstream 3'-IPP2K genomic sequence of the ZFN
      targeted regions

<400> SEQUENCE: 142
attgtttttt tcagtgattc ataacttaac tcttggttaa accgctagaa catggttggt    60
gtcttaaaat gcaactggtc ctgaggccgt aacctgaaat cattgtactt ttctctcatt   120
tctttagata tttccaaaac tctacattag atgatttatg tttgcttact tagtcttttct  180
taatctcagg caatcctaag ggtagcagct gcatagctgt agagataaag gtactttgca   240
agcttcctct tttattctta tttttcattt cttatgtata tttctcctca accatttgac   300
ttcttttcgg catgctctac cttgcaggcc aaatgtgggt ttctgccatc atcagaatat   360
atatcagaag ataatactat caagaaacta gtaacgagat ataagatgca tcagcacctc   420
aaatttatc agggtgaggt gtgtagattg gaatgcttga tgccttgatc caagataaaa    480
ttccactctc ttttgcgcac ttaaaaaaca tccatcgatg atacaaactt gatcaaaata   540
ccttaaggct tgttatttac ggcactgttg taatattata ccgtctcttg cttttttgaca  600
tcaggttgat tcccaataca ttcttgcaca catttcagat atcgaagact agtgagtaca   660
atcctcttga tctattttct gggtcaaaag agagaatatg catggccatc aagtcccttt   720
tctcaactc                                                          729

<210> SEQ ID NO 143
<211> LENGTH: 42
<212> TYPE: DNA
<213> ORGANISM: Artificial Sequence
<220> FEATURE:
<223> OTHER INFORMATION: primer

<400> SEQUENCE: 143
gcggccgcgt ctcaccgcgg cttggggatt ggatacggag ct                      42

<210> SEQ ID NO 144
<211> LENGTH: 38
<212> TYPE: DNA
<213> ORGANISM: Artificial Sequence
<220> FEATURE:
<223> OTHER INFORMATION: primer

<400> SEQUENCE: 144
actagtgata tggccccaca ggagttgctc atgacttg                           38

<210> SEQ ID NO 145
<211> LENGTH: 40
<212> TYPE: DNA
<213> ORGANISM: Artificial Sequence
<220> FEATURE:
<223> OTHER INFORMATION: primer

<400> SEQUENCE: 145
actagtccag aactggttga gtcggtcaaa caagattgct                         40

<210> SEQ ID NO 146
<211> LENGTH: 32
<212> TYPE: DNA

<210> SEQ ID NO 147
<211> LENGTH: 30
<212> TYPE: DNA
<213> ORGANISM: Artificial Sequence
<220> FEATURE:
<223> OTHER INFORMATION: primer

<400> SEQUENCE: 146
gtcgaccttg atgctaccca ttgggctgtt gt                                   32

<210> SEQ ID NO 147
<211> LENGTH: 30
<212> TYPE: DNA
<213> ORGANISM: Artificial Sequence
<220> FEATURE:
<223> OTHER INFORMATION: primer

<400> SEQUENCE: 147
gcggccgcta gatagcagat gcagattgct                                      30

<210> SEQ ID NO 148
<211> LENGTH: 29
<212> TYPE: DNA
<213> ORGANISM: Artificial Sequence
<220> FEATURE:
<223> OTHER INFORMATION: primer

<400> SEQUENCE: 148
actagtattg gcacccaggt gttggctca                                       29

<210> SEQ ID NO 149
<211> LENGTH: 38
<212> TYPE: DNA
<213> ORGANISM: Artificial Sequence
<220> FEATURE:
<223> OTHER INFORMATION: primer

<400> SEQUENCE: 149
actagtcatg tcgatggtgg ggtatggttc agattcag                             38

<210> SEQ ID NO 150
<211> LENGTH: 37
<212> TYPE: DNA
<213> ORGANISM: Artificial Sequence
<220> FEATURE:
<223> OTHER INFORMATION: primer

<400> SEQUENCE: 150
gtcgacgtac aatgatttca ggttacggcc tcaggac                              37

<210> SEQ ID NO 151
<211> LENGTH: 41
<212> TYPE: DNA
<213> ORGANISM: Artificial Sequence
<220> FEATURE:
<223> OTHER INFORMATION: primer

<400> SEQUENCE: 151
actagttaac tgacctcact cgaggtcatt catatgcttg a                         41

<210> SEQ ID NO 152
<211> LENGTH: 29
<212> TYPE: DNA
<213> ORGANISM: Artificial Sequence
<220> FEATURE:
<223> OTHER INFORMATION: primer

<400> SEQUENCE: 152
actagtgtga attcagcact taaagatct                                       29

<210> SEQ ID NO 153
<211> LENGTH: 101
<212> TYPE: DNA
<213> ORGANISM: Artificial Sequence
<220> FEATURE:
<223> OTHER INFORMATION: primer

<400> SEQUENCE: 153
actagtggcg gcggagaggg cagaggaagt cttctaacat gcggtgacgt ggaggagaat    60
cccggcccta ggatggcttc tccggagagg agaccagttg a    101

<210> SEQ ID NO 154
<211> LENGTH: 35
<212> TYPE: DNA
<213> ORGANISM: Artificial Sequence
<220> FEATURE:
<223> OTHER INFORMATION: primer

<400> SEQUENCE: 154
actagtatgc atgtgaattc agcacttaaa gatct    35

<210> SEQ ID NO 155
<211> LENGTH: 28
<212> TYPE: DNA
<213> ORGANISM: Artificial Sequence
<220> FEATURE:
<223> OTHER INFORMATION: primer

<400> SEQUENCE: 155
ctgtggtacc agtactagta ccagcatc    28

<210> SEQ ID NO 156
<211> LENGTH: 31
<212> TYPE: DNA
<213> ORGANISM: Artificial Sequence
<220> FEATURE:
<223> OTHER INFORMATION: primer

<400> SEQUENCE: 156
tcttggatca aggcatcaag cattccaatc t    31

<210> SEQ ID NO 157
<211> LENGTH: 20
<212> TYPE: DNA
<213> ORGANISM: Artificial Sequence
<220> FEATURE:
<223> OTHER INFORMATION: primer

<400> SEQUENCE: 157
tgggtaactg gcctaactgg    20

<210> SEQ ID NO 158
<211> LENGTH: 20
<212> TYPE: DNA
<213> ORGANISM: Artificial Sequence
<220> FEATURE:
<223> OTHER INFORMATION: primer

<400> SEQUENCE: 158
tggaaggcta ggaacgctta    20

<210> SEQ ID NO 159
<211> LENGTH: 20
<212> TYPE: DNA

```
<213> ORGANISM: Artificial Sequence
<220> FEATURE:
<223> OTHER INFORMATION: primer

<400> SEQUENCE: 159
ccagttaggc cagttaccca                                              20

<210> SEQ ID NO 160
<211> LENGTH: 20
<212> TYPE: DNA
<213> ORGANISM: Artificial Sequence
<220> FEATURE:
<223> OTHER INFORMATION: primer

<400> SEQUENCE: 160
taagcgttcc tagccttcca                                              20

<210> SEQ ID NO 161
<211> LENGTH: 31
<212> TYPE: DNA
<213> ORGANISM: Artificial Sequence
<220> FEATURE:
<223> OTHER INFORMATION: primer

<400> SEQUENCE: 161
cttggcaagg tactgcggct caagaagatt c                                 31

<210> SEQ ID NO 162
<211> LENGTH: 26
<212> TYPE: DNA
<213> ORGANISM: Artificial Sequence
<220> FEATURE:
<223> OTHER INFORMATION: primer

<400> SEQUENCE: 162
atgaagaaag acagggaatg aaggac                                       26

<210> SEQ ID NO 163
<211> LENGTH: 32
<212> TYPE: DNA
<213> ORGANISM: Artificial Sequence
<220> FEATURE:
<223> OTHER INFORMATION: primer

<400> SEQUENCE: 163
atgaagaaag acagggaatg aaggaccgcc ac                                32

<210> SEQ ID NO 164
<211> LENGTH: 28
<212> TYPE: DNA
<213> ORGANISM: Artificial Sequence
<220> FEATURE:
<223> OTHER INFORMATION: primer

<400> SEQUENCE: 164
catggagggc gacgagccgg tgtagctg                                     28

<210> SEQ ID NO 165
<211> LENGTH: 27
<212> TYPE: DNA
<213> ORGANISM: Artificial Sequence
<220> FEATURE:
<223> OTHER INFORMATION: primer

<400> SEQUENCE: 165
atcgacatga ttggcaccca ggtgttg                                      27
```

-continued

<210> SEQ ID NO 166
<211> LENGTH: 31
<212> TYPE: DNA
<213> ORGANISM: Artificial Sequence
<220> FEATURE:
<223> OTHER INFORMATION: primer

<400> SEQUENCE: 166
tttcgacaag ctccagaaaa tccctagaaa c                                    31

<210> SEQ ID NO 167
<211> LENGTH: 28
<212> TYPE: DNA
<213> ORGANISM: Artificial Sequence
<220> FEATURE:
<223> OTHER INFORMATION: primer

<400> SEQUENCE: 167
acaagctcca gaaatccct agaaacac                                          28

<210> SEQ ID NO 168
<211> LENGTH: 32
<212> TYPE: DNA
<213> ORGANISM: Artificial Sequence
<220> FEATURE:
<223> OTHER INFORMATION: primer

<400> SEQUENCE: 168
ttcgacaagc tccagaaaat ccctagaaac ac                                   32

<210> SEQ ID NO 169
<211> LENGTH: 29
<212> TYPE: DNA
<213> ORGANISM: Artificial Sequence
<220> FEATURE:
<223> OTHER INFORMATION: primer

<400> SEQUENCE: 169
tgctaagaac attcttttcg acaagctcc                                        29

<210> SEQ ID NO 170
<211> LENGTH: 32
<212> TYPE: DNA
<213> ORGANISM: Artificial Sequence
<220> FEATURE:
<223> OTHER INFORMATION: primer

<400> SEQUENCE: 170
gaacattctt ttcgacaagc tccagaaaat cc                                   32

<210> SEQ ID NO 171
<211> LENGTH: 30
<212> TYPE: DNA
<213> ORGANISM: Artificial Sequence
<220> FEATURE:
<223> OTHER INFORMATION: primer

<400> SEQUENCE: 171
tggacggagc gagagccaga attcgacgct                                       30

<210> SEQ ID NO 172
<211> LENGTH: 31
<212> TYPE: DNA
<213> ORGANISM: Artificial Sequence
<220> FEATURE:

```
<223> OTHER INFORMATION: primer

<400> SEQUENCE: 172
gtgcaagaat gtattgggaa tcaacctgat g                                  31

<210> SEQ ID NO 173
<211> LENGTH: 59
<212> TYPE: DNA
<213> ORGANISM: Zea mays

<400> SEQUENCE: 173
aagtcatgag caactcctgt ggggccatat cccagaactg gttgagtcgg tcaaacaag    59

<210> SEQ ID NO 174
<211> LENGTH: 53
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 174
aagtcatgag caactcctgt ggggccaaga actggttgag tcggtcaaac aag          53

<210> SEQ ID NO 175
<211> LENGTH: 55
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 175
aagtcatgag caactcctgt ggggccataa gaactggttg agtcggtcaa acaag        55

<210> SEQ ID NO 176
<211> LENGTH: 54
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 176
aagtcatgag caactcctgt ggggccatag aactggttga gtcggtcaaa caag          54

<210> SEQ ID NO 177
<211> LENGTH: 56
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 177
aagtcatgag caactcctgt ggggccatac agaactggtt gagtcggtca acaag         56

<210> SEQ ID NO 178
<211> LENGTH: 57
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 178
```
aagtcatgag caactcctgt ggggccatac cagaactggt tgagtcggtc aaacaag        57

<210> SEQ ID NO 179
<211> LENGTH: 52
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 179
aagtcatgag caactcctgt ggggccagaa ctggttgagt cggtcaaaca ag        52

<210> SEQ ID NO 180
<211> LENGTH: 57
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 180
aagtcatgag caactcctgt ggggccatat cagaactggt tgagtcggtc aaacaag        57

<210> SEQ ID NO 181
<211> LENGTH: 54
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 181
aagtcatgag caactcctgt ggggccatag aactggttga gtcggtcaaa caag        54

<210> SEQ ID NO 182
<211> LENGTH: 54
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 182
aagtcatgag caactcctgt ggggccatag aactggttga gtcggtcaaa caag        54

<210> SEQ ID NO 183
<211> LENGTH: 57
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 183
aagtcatgag caactcctgg tggggccata cagaactggt tgagtcggtc aaacaag        57

<210> SEQ ID NO 184
<211> LENGTH: 54
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 184
aagtcatgag caactcctgt ggggccatag aactggttga gtcggtcaaa caag        54

<210> SEQ ID NO 185
<211> LENGTH: 53
<212> TYPE: DNA
<213> ORGANISM: Artificial Sequence
<220> FEATURE:
<223> OTHER INFORMATION: Maize IPP2K gene sequence with ZFN-mediated mutation

<400> SEQUENCE: 185
aagcatgagc aactcctgtg gggccataga actggttgag tcggtcaaac aag    53

<210> SEQ ID NO 186
<211> LENGTH: 56
<212> TYPE: DNA
<213> ORGANISM: Artificial Sequence
<220> FEATURE:
<223> OTHER INFORMATION: Maize IPP2K gene sequence with ZFN-mediated mutation

<400> SEQUENCE: 186
aagtcatgag caactcctgt ggggccatac agaactggtt gagtcggtca acaag    56

<210> SEQ ID NO 187
<211> LENGTH: 57
<212> TYPE: DNA
<213> ORGANISM: Artificial Sequence
<220> FEATURE:
<223> OTHER INFORMATION: Maize IPP2K gene sequence with ZFN-mediated mutation

<400> SEQUENCE: 187
aagtcatgag caactcctgt ggggccatat cagaactggt tgagtcggtc aaacaag    57

<210> SEQ ID NO 188
<211> LENGTH: 54
<212> TYPE: DNA
<213> ORGANISM: Artificial Sequence
<220> FEATURE:
<223> OTHER INFORMATION: Maize IPP2K gene sequence with ZFN-mediated mutation

<400> SEQUENCE: 188
aagtcatgag caactcctgt ggggccatag aactggttga gtcggtcaaa caag    54

<210> SEQ ID NO 189
<211> LENGTH: 54
<212> TYPE: DNA
<213> ORGANISM: Artificial Sequence
<220> FEATURE:
<223> OTHER INFORMATION: Maize IPP2K gene sequence with ZFN-mediated mutation

<400> SEQUENCE: 189
aagtcatgag caactcctgt ggggccacag aactggttga gtcggtcaaa caag    54

<210> SEQ ID NO 190
<211> LENGTH: 54
<212> TYPE: DNA
<213> ORGANISM: Artificial Sequence
<220> FEATURE:
<223> OTHER INFORMATION: Maize IPP2K gene sequence with ZFN-mediated mutation

<400> SEQUENCE: 190
aagtcatgag caactcctgt ggggccatag aactggttga gtcggtcaaa caag    54

```
<210> SEQ ID NO 191
<211> LENGTH: 57
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 191
aagtcatgag caactcctgt ggggccatac cagaactggt tgagtcggtc aaacaag        57

<210> SEQ ID NO 192
<211> LENGTH: 54
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 192
aagtcatgag caactcctgt ggggccatag aactggttga gtcggtcaaa caag           54

<210> SEQ ID NO 193
<211> LENGTH: 55
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 193
aagtcatgag caactcctgt ggggccataa gaactggttg agtcggtcaa acaag          55

<210> SEQ ID NO 194
<211> LENGTH: 56
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 194
aagtcatgag caactcctgt ggggccatac agaactggtt gagtcggtca aacaag         56

<210> SEQ ID NO 195
<211> LENGTH: 56
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 195
aagtcatgag caactcctgt ggggccatat agaactggtt gagtcggtca aacaag         56

<210> SEQ ID NO 196
<211> LENGTH: 56
<212> TYPE: DNA
<213> ORGANISM: Artificial Sequence
<220> FEATURE:
<223> OTHER INFORMATION: Maize IPP2K gene sequence with ZFN-mediated
      mutation

<400> SEQUENCE: 196
aagtcatgag caactcctgt ggggccatac agaactggtt gagtcggtca aacaag         56
```

<210> SEQ ID NO 197
<211> LENGTH: 57
<212> TYPE: DNA
<213> ORGANISM: Artificial Sequence
<220> FEATURE:
<223> OTHER INFORMATION: Maize IPP2K gene sequence with ZFN-mediated mutation

<400> SEQUENCE: 197
aagtcatgag caactcctgt ggggccatac cagaactggt tgagtcggtc aaacaag        57

<210> SEQ ID NO 198
<211> LENGTH: 821
<212> TYPE: DNA
<213> ORGANISM: Artificial Sequence
<220> FEATURE:
<223> OTHER INFORMATION: position-1 5'-homology flank sequence

<400> SEQUENCE: 198
gcggccgcgt ctcaccgcgg cttggggatt ggatacggag ctagttaacc agcagagcta     60
gatagcagac gcagatcgct tgcttctctg gtttgatttt tggagtcacc atttctgttt    120
ggttcgtgtg cctcagtgtc tgacagcagc agatcctcga tggagatgga tggggttctg    180
caagccgcgg atgccaagga ctgggtttac aaggggaag gcgccgcgaa tctcatcctc     240
agctacaccg gcacgtcgcc ctccatggta agcgctgagt aggttcttac tgagtgtgca    300
cgcatcgatc acttgacttt aggggctcaa tgtgtgattc acgggtgccg ccattcgagc    360
tccagatcca gtatcgctcg agcaagtgat aaaacatgga gcagggacga tcacgtggtc    420
acttgaaaat tatgtgaggt ccggggcgac gatgtacggc gcggcgaact ctcaaacact    480
cacacagcca aaccgcttc gtgttcgtct ttgttccaag cgaccgtgtg gtgtgtttgt     540
agtagttcgc cggcgccgca catcgtcgcc ccgatctga caaattaagc tttcgttgct     600
tttccacgat tgtgcatttt ctgagcatgc actgaatact atgatggata tgtttggagg    660
aagcattatt ccaatttgat gataatggtg ttatttacac ttgttttcag cttggcaagg    720
tactgcggct caagaagatt ctaaaaaaca agttgcagcg ggcaccaagt tgtattgcct    780
tctcaagtca tgagcaactc ctgtggggcc atatcactag t                        821

<210> SEQ ID NO 199
<211> LENGTH: 821
<212> TYPE: DNA
<213> ORGANISM: Artificial Sequence
<220> FEATURE:
<223> OTHER INFORMATION: position-1 3'-homology flank sequence

<400> SEQUENCE: 199
actagtccag aactggttga gtcggtcaaa caagattgct tggctcaagc ctatgcagtg     60
catgttatga gccaacacct gggtgccaat catgtcgatg gtggggtatg gttcagattc    120
agttcattta tgtcctgtta ttgtgatttt gattggtaac atattgacaa cctcgacact    180
tgggatcaga ttcagttcac ttatggaaga aattggagaa ttgtgataat ttatctataa    240 tcaccccctac tgaaatagaa ataacatgac atcaatgtgc atgctattgg attttgacac   300
gaatatgctt tattctatca tatgttggta attccagcag gcagcaggca ctactctttg    360
gatccacgtg acttgacaaa gaaatcatgc catctttcca caatgcaggt ccgtgtacgt    420
gtttctaggg attttctgga gcttgtcgaa aagaatgttc ttagcagccg tcctgctggg    480
agagtaaatg caagttcaat tgataacact gctgatgccg ctcttctaat agcagaccac    540
tctttatttt ctggtacgta ctctatccct cttcttacca taatctgaat cttgttaagg    600

```
tttaaaatat atgattgatt aagtaaaatc cagagctcta ttcatatctc acgcactgat    660
gttttgatga aacgcttgca gcaagacggt tgcctgttat ttctatttgc attagacaaa    720
cagtcacctt tgtttataaa ggtctttgaa tttgcagttc ttataggttt aagtttgcaa    780
ctgttactta caacagccca atgggtagca tcaaggtcga c                        821

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
attatccgag tttaatagaa ctcggataat                                      30

<210> SEQ ID NO 201
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
cgagttcttg tacaccagta caagaactcg                                      30
```